United States Patent
Heo et al.

(10) Patent No.: US 11,367,836 B2
(45) Date of Patent: Jun. 21, 2022

(54) HETEROCYCLIC COMPOUND AND ORGANIC LIGHT EMITTING ELEMENT INCLUDING SAME

(71) Applicant: LG CHEM, LTD., Seoul (KR)

(72) Inventors: Dong Uk Heo, Daejeon (KR); Dong Hoon Lee, Daejeon (KR); Jungoh Huh, Daejeon (KR); Boonjae Jang, Daejeon (KR); Miyeon Han, Daejeon (KR); Junghoon Yang, Daejeon (KR); Heekyung Yun, Daejeon (KR)

(73) Assignee: LG CHEM, LTD., Seoul (KR)

( * ) Notice: Subject to any disclaimer, the term of this patent is extended or adjusted under 35 U.S.C. 154(b) by 384 days.

(21) Appl. No.: 16/606,707

(22) PCT Filed: Jun. 29, 2018

(86) PCT No.: PCT/KR2018/007430
§ 371 (c)(1),
(2) Date: Oct. 18, 2019

(87) PCT Pub. No.: WO2019/004791
PCT Pub. Date: Jan. 3, 2019

(65) Prior Publication Data
US 2020/0136055 A1 Apr. 30, 2020

(30) Foreign Application Priority Data
Jun. 30, 2017 (KR) .................. 10-2017-0083385

(51) Int. Cl.
*C07D 405/14* (2006.01)
*H01L 51/00* (2006.01)
(Continued)

(52) U.S. Cl.
CPC ........ *H01L 51/0067* (2013.01); *C07D 405/14* (2013.01); *C07D 409/14* (2013.01);
(Continued)

(58) Field of Classification Search
None
See application file for complete search history.

(56) References Cited

U.S. PATENT DOCUMENTS

| 7,014,925 | B2 * | 3/2006 | Thoms ................. C07D 221/20 252/301.16 |
| 2003/0168970 | A1 * | 9/2003 | Tominaga ........... H01L 51/0036 313/504 |

(Continued)

FOREIGN PATENT DOCUMENTS

| CN | 101440082 | 5/2009 |
| CN | 102786508 | 11/2012 |

(Continued)

*Primary Examiner* — Robert S Loewe
(74) *Attorney, Agent, or Firm* — Dentons US LLP

(57) ABSTRACT

Provided is a heterocyclic compound of Chemical Formula 1:

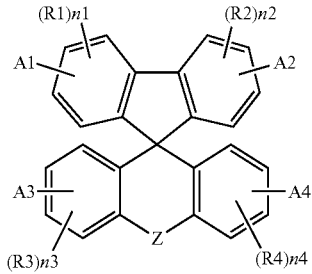

and an organic light emitting device including the same.

16 Claims, 1 Drawing Sheet

(51) Int. Cl.
*C07D 409/14* (2006.01)
*H01L 51/50* (2006.01)

(52) U.S. Cl.
CPC ...... *H01L 51/0072* (2013.01); *H01L 51/0073* (2013.01); *H01L 51/0074* (2013.01); *H01L 51/5072* (2013.01); *H01L 51/5092* (2013.01); *H01L 51/5096* (2013.01)

(56) References Cited

U.S. PATENT DOCUMENTS

| | | |
|---|---|---|
| 2015/0115241 A1 | 4/2015 | Zoellner et al. |
| 2015/0295181 A1* | 10/2015 | Mujica-Fernaud .... H05B 33/20 252/500 |
| 2016/0118599 A1 | 4/2016 | Jeong et al. |
| 2016/0293852 A1 | 10/2016 | Huh et al. |
| 2017/0162800 A1 | 6/2017 | Zoellner et al. |
| 2019/0355915 A1* | 11/2019 | Heo ................. C07D 311/96 |

FOREIGN PATENT DOCUMENTS

| | | |
|---|---|---|
| JP | 2009-191232 | 8/2009 |
| KR | 10-2015-0002740 | 1/2015 |
| KR | 10-2016-0019846 | 2/2016 |
| KR | 10-2016-0047670 | 5/2016 |
| KR | 10-2017-0071399 | 6/2017 |

\* cited by examiner

【FIG. 1】
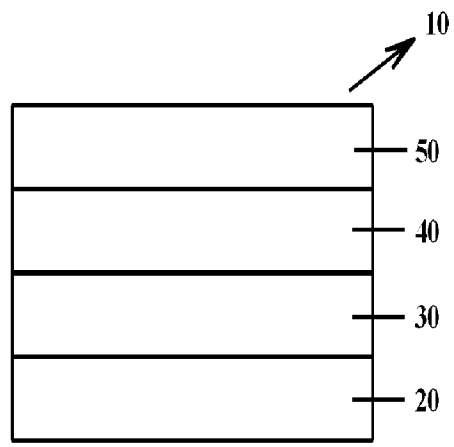
【FIG. 2】
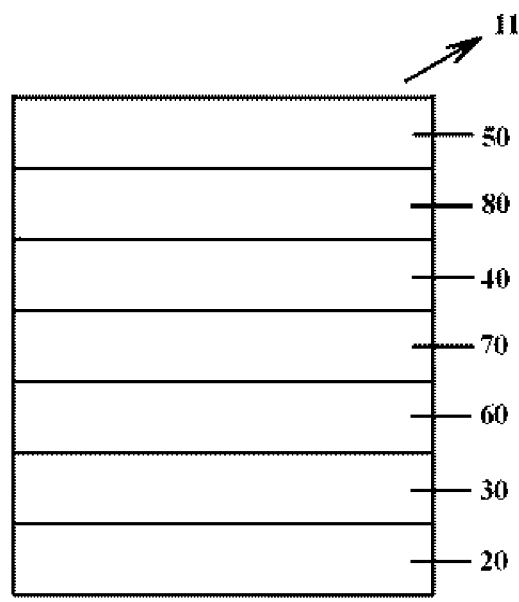

HETEROCYCLIC COMPOUND AND ORGANIC LIGHT EMITTING ELEMENT INCLUDING SAME

CROSS-REFERENCE TO RELATED APPLICATIONS

The present application is a National Stage Application of International Application No. PCT/KR2018/007430 filed on Jun. 29, 2018, which claims priority to and the benefits of Korean Patent Application No. 10-2017-0083385, filed with the Korean Intellectual Property Office on Jun. 30, 2017, the entire contents of which are incorporated herein by reference.

TECHNICAL FIELD

The present specification relates to a heterocyclic compound and an organic light emitting device including the same.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

BRIEF DESCRIPTION

Technical Problem

The present specification is directed to providing a heterocyclic compound and an organic light emitting device including the same.

Technical Solution

One embodiment of the present specification provides a heterocyclic compound of the following Chemical Formula 1:

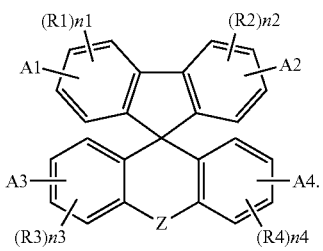

[Chemical Formula 1]

In Chemical Formula 1,

Z is O or S,

R1 to R4 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, n1 to n4 are the same as or different from each other and each independently an integer of 0 to 3, and when n1 to n4 are an integer of 2 or greater, substituents in the parentheses are the same as or different from each other, A1 is hydrogen or -L1-Ar1, A2 is hydrogen or -L2-Ar2, A3 is hydrogen or -L3-Ar3, and A4 is hydrogen or -L4-Ar4, L1 to L4 are the same as or different from each other, and each independently a direct bond; a substituted or unsubstituted arylene group; or a substituted or unsubstituted heteroarylene group, at least two of A1 to A4 are not hydrogen, A1 and A2 bond to a symmetric position of a core structure, A3 and A4 bond to a symmetric position of a core structure, and Ar1 and Ar3 are the same as or different from each other and each independently is the following Chemical Formula A, and Ar2 and Ar4 are the same as or different from each other and each independently is one selected from among the following Chemical Formulae C and D,

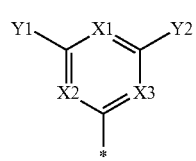

[Chemical Formula A]

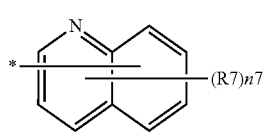

[Chemical Formula C]

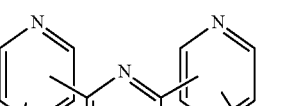

[Chemical Formula D]

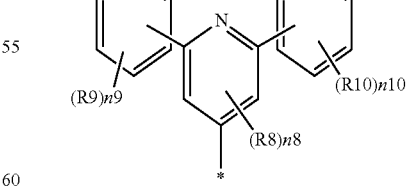

in Chemical Formulae A, C and D,

* is a bonding site,

X1 to X3 are the same as or different from each other and each independently N or CR5, and at least two of X1 to X3 are N, R5, R7 to R10, Y1 and Y2 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, and n9 and n10 are an integer of 0 to 4, n7 is an integer of 0 to 6, n8 is an integer of 0 to 2, and when n6 to n10 are an integer of 2 or greater, substituents in the parentheses are the same as or different from each other.

Another embodiment of the present specification provides an organic light emitting device including a first electrode; a second electrode provided opposite to the first electrode; and one or more organic material layers provided between the first electrode and the second electrode, wherein one or more layers of the organic material layers include the heterocyclic compound of Chemical Formula 1.

Advantageous Effects

A heterocyclic compound according to one embodiment of the present specification can be used as a material of an organic material layer of an organic light emitting device, and by using the same, efficiency can be enhanced, a low driving voltage can be obtained and/or lifetime properties can be enhanced in the organic light emitting device.

DESCRIPTION OF THE DRAWINGS

FIG. 1 illustrates an organic light emitting device (10) according to one embodiment of the present specification.

FIG. 2 illustrates an organic light emitting device (11) according to another embodiment of the present specification.

REFERENCE NUMERAL 10, 11: Organic Light Emitting Device
20: Substrate
30: First Electrode
40: Light Emitting Layer
50: Second Electrode
60: Hole Injection Layer
70: Hole Transfer Layer
80: Layer Carrying Out Electron Injection and Electron Transfer At The Same Time

DETAILED DESCRIPTION

Herein, the present specification will be described in more detail.

One embodiment of the present specification provides a heterocyclic compound of Chemical Formula 1.

The heterocyclic compound according to one embodiment of the present specification has a non-linear structure and is capable of enhancing efficiency, obtaining a low driving voltage and enhancing lifetime properties in an organic light emitting device. In addition, in the structure of the heterocyclic compound of Chemical Formula 1, molecular dipole moment can be designed close to nonpolar by substituents A1 to A4 having an electron deficient-structured substituent, and therefore, an amorphous layer can be formed when manufacturing an organic light emitting device including the heterocyclic compound of Chemical Formula 1. Accordingly, the organic light emitting device including the heterocyclic compound according to one embodiment of the present specification is capable of enhancing efficiency, obtaining a low driving voltage and enhancing lifetime properties.

In the present specification, a description of a certain part "including" certain constituents means capable of further including other constituents, and does not exclude other constituents unless particularly stated on the contrary.

In the present specification, a description of a certain member being placed "on" another member includes not only a case of the one member adjoining the another member but a case of still another member being present between the two members.

Examples of substituents in the present specification are described below, however, the substituents are not limited thereto.

In the present specification, the term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents can be the same as or different from each other.

In the present specification, the term "substituted or unsubstituted" means being substituted with one, two or more substituents selected from the group consisting of deuterium; a halogen group; a nitrile group; a nitro group; an imide group; an amide group; a carbonyl group; an ester group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted heteroaryl group, or being substituted with a substituent linking two or more substituents among the substituents illustrated above, or having no substituents. For example, "a substituent linking two or more substituents" can include a biphenyl group. In other words, a biphenyl group can be an aryl group, or interpreted as a substituent linking two phenyl groups.

In the present specification, examples of the halogen group can include fluorine, chlorine, bromine or iodine.

In the present specification, the number of carbon atoms of the imide group is not particularly limited, but is preferably from 1 to 30. Specifically, compounds having structures as below can be included, but the imide group is not limited thereto:

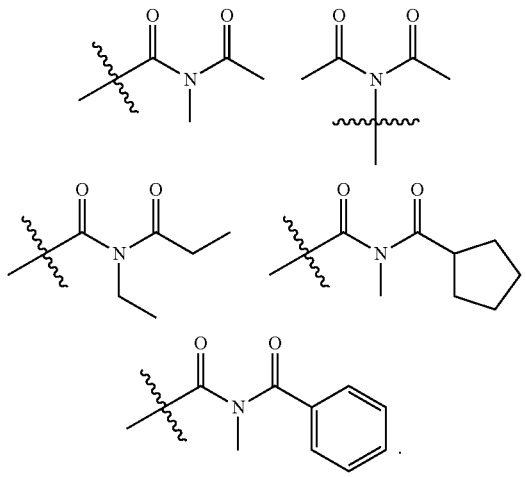

In the present specification, in the amide group, the nitrogen of the amide group can be substituted with a linear, branched or cyclic alkyl group having 1 to 30 carbon atoms or an aryl group having 6 to 30 carbon atoms. Specifically, compounds having the following structural formulae can be included, but the amide group is not limited thereto:

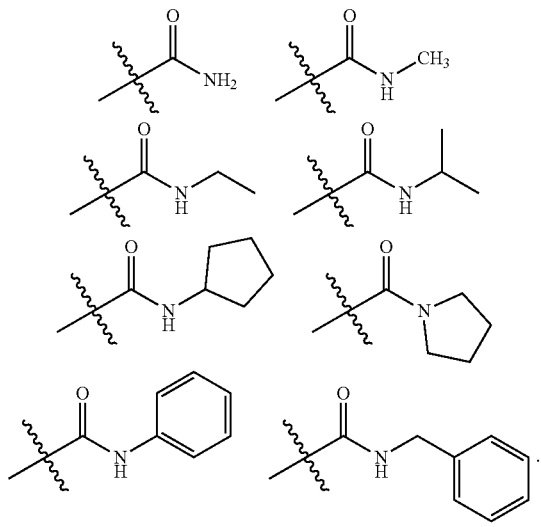

In the present specification, the number of carbon atoms of the carbonyl group is not particularly limited, but is preferably from 1 to 30. Specifically, compounds having structures as below can be included, but the carbonyl group is not limited thereto:

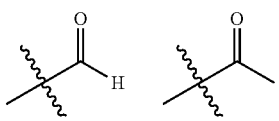

-continued

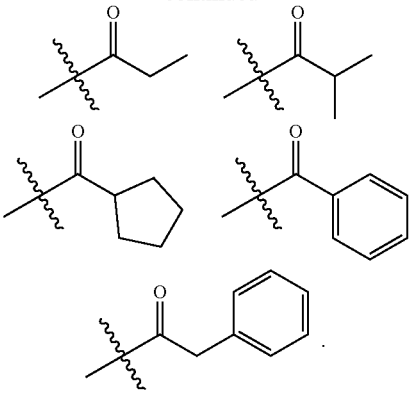

In the present specification, in the ester group, the oxygen of the ester group can be substituted with a linear, branched or cyclic alkyl group having 1 to 25 carbon atoms or an aryl group having 6 to 30 carbon atoms. Specifically, compounds having the following structural formulae can be included, however, the ester group is not limited thereto:

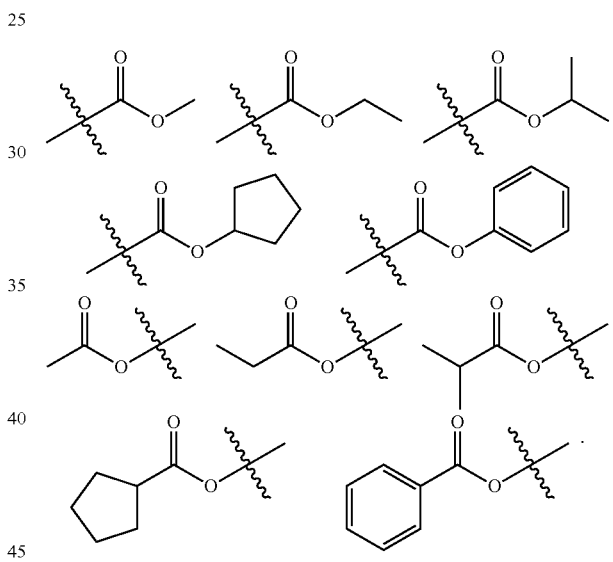

In the present specification, the alkyl group can be linear or branched, and although not particularly limited thereto, the number of carbon atoms is preferably from 1 to 30. Specifically, the number of carbon atoms is preferably from 1 to 20. More specifically, the number of carbon atoms is preferably from 1 to 10. Specific examples thereof can include a methyl group; an ethyl group; a propyl group; an n-propyl group; an isopropyl group; a butyl group; an n-butyl group; an isobutyl group; a tert-butyl group; a sec-butyl group; a 1-methylbutyl group; a 1-ethylbutyl group; a pentyl group; an n-pentyl group; an isopentyl group; a neopentyl group; a tert-pentyl group; a hexyl group; an n-hexyl group; a 1-methylpentyl group; a 2-methylpentyl group; a 4-methyl-2-pentyl group; a 3,3-dimethylbutyl group; a 2-ethylbutyl group; a heptyl group; an n-heptyl group; a 1-methylhexyl group; a cyclopentylmethyl group; a cyclohexylmethyl group; an octyl group; an n-octyl group; a tert-octyl group; a 1-methylheptyl group; a 2-ethylhexyl group; a 2-propylpentyl group; an n-nonyl group; a 2,2-dimethylheptyl group; a 1-ethylpropyl group; a 1,1-dimethylpropyl group; an isohexyl group; a 2-methylpentyl group; a 4-methylhexyl group; a 5-methylhexyl group and the like, but are not limited thereto.

In the present specification, the cycloalkyl group is not particularly limited, but preferably has 3 to 30 carbon atoms and more preferably has 3 to 20 carbon atoms. Specific examples thereof can include a cyclopropyl group; a cyclobutyl group; a cyclopentyl group; a 3-methylcyclopentyl group; a 2,3-dimethylcyclopentyl group; a cyclohexyl group; a 3-methylcyclohexyl group; a 4-methylcyclohexyl group; a 2,3-dimethylcyclohexyl group; a 3,4,5-trimethylcyclohexyl group; a 4-tert-butylcyclohexyl group; a cycloheptyl group; a cyclooctyl group and the like, but are not limited thereto.

In the present specification, the alkoxy group can be linear, branched or cyclic. The number of carbon atoms of the alkoxy group is not particularly limited, but is preferably from 1 to 30. Specifically, the number of carbon atoms is preferably 1 to 20. More specifically, the number of carbon atoms is preferably 1 to 10. Specific examples thereof can include a methoxy group; an ethoxy group; an n-propoxy group; an isopropoxy group; an i-propyloxy group; an n-butoxy group; an isobutoxy group; a tert-butoxy group; a sec-butoxy group; an n-pentyloxy group; a neopentyloxy group; an isopentyloxy group; an n-hexyloxy group; an 3,3-dimethylbutyloxy group; an 2-ethylbutyloxy group; an n-octyloxy group; an n-nonyloxy group; an n-decyloxy group; a benzyloxy group; a p-methylbenzyloxy group and the like, but are not limited thereto.

In the present specification, the amine group can be selected from the group consisting of —$NH_2$; an alkylamine group; an N-alkylarylamine group; an arylamine group; an N-arylheteroarylamine group; an N-alkylheteroarylamine group and a heteroarylamine group, and although not particularly limited thereto, the number of carbon atoms is preferably from 1 to 30. Specific examples of the amine group can include a methylamine group; a dimethylamine group; an ethylamine group; a diethylamine group; a phenylamine group; a naphthylamine group; a biphenylamine group; an anthracenylamine group; a 9-methylanthracenylamine group; a diphenylamine group; an N-phenylnaphthylamine group; a ditolylamine group; an N-phenyltolylamine group; a triphenylamine group; an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the alkylamine group, the N-arylalkylamine group, the alkylthioxy group, the alkylsulfoxy group and the N-alkylheteroarylamine group is the same as the examples of the alkyl group described above. Specifically, the alkylthioxy group can include a methylthioxy group; an ethylthioxy group; a tert-butylthioxy group; a hexylthioxy group; an octylthioxy group and the like, and the alkylsulfoxy group can include mesyl; an ethylsulfoxy group; a propylsulfoxy group; a butylsulfoxy group and the like, however, the alkylthioixy group and the alkylsulfoxy group are not limited thereto.

In the present specification, the alkenyl group can be linear or branched, and although not particularly limited thereto, the number of carbon atoms is preferably from 2 to 30. More specifically, the number of carbon atoms is preferably from 2 to 20. Specific examples thereof can include a vinyl group; a 1-propenyl group; an isopropenyl group; a 1-butenyl group; a 2-butenyl group; a 3-butenyl group; a 1-pentenyl group; a 2-pentenyl group; a 3-pentenyl group; a 3-methyl-1-butenyl group; a 1,3-butadienyl group; an allyl group; a 1-phenylvinyl-1-yl group; a 2-phenylvinyl-1-yl group; a 2,2-diphenylvinyl-1-yl group; a 2-phenyl-2-(naphthyl-1-yl)vinyl-1-yl group; a 2,2-bis(diphenyl-1-yl)vinyl-1-yl group; a stilbenyl group; a styrenyl group and the like, but are not limited thereto.

In the present specification, the silyl group can be a chemical formula of —$SiRaRbRc$, and Ra, Rb and Rc are the same as or different from each other, and can be each independently hydrogen; a substituted or unsubstituted alkyl group; or a substituted or unsubstituted aryl group. Specific examples of the silyl group can include a trimethylsilyl group; a triethylsilyl group; a t-butyldimethylsilyl group; a vinyldimethylsilyl group; a propyldimethylsilyl group; a triphenylsilyl group; a diphenylsilyl group; a phenylsilyl group and the like, but are not limited thereto.

In the present specification, the boron group can be —$BR_{100}R_{101}$, and $R_{100}$ and $R_{101}$ are the same as or different from each other, and can be each independently selected from the group consisting of hydrogen; deuterium; a halogen group; a nitrile group; a substituted or unsubstituted monocyclic or polycyclic cycloalkyl group having 3 to 30 carbon atoms; a substituted or unsubstituted linear or branched alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of the phosphine oxide group can include a diphenylphosphine oxide group; a dinaphthylphosphine oxide group and the like, but are not limited thereto.

In the present specification, the aryl group is not particularly limited, but preferably has 6 to 30 carbon atoms, and more preferably has 6 to 20 carbon atoms. The aryl group can be monocyclic or polycyclic.

When the aryl group is a monocyclic aryl group, the number of carbon atoms is not particularly limited, but is preferably from 6 to 30. More specifically, the number of carbon atoms is preferably from 6 to 20. More specifically, the number of carbon atoms is preferably from 6 to 20. Specific examples of the monocyclic aryl group can include a phenyl group; a biphenyl group; a terphenyl group and the like, but are not limited thereto.

When the aryl group is a polycyclic aryl group, the number of carbon atoms is not particularly limited, but is preferably from 10 to 30, and more specifically, is preferably from 10 to 20. Specific examples of the polycyclic aryl group can include a naphthyl group; an anthracenyl group; a phenanthryl group; a triphenyl group; a pyrenyl group; a phenalenyl group; a perylenyl group; a chrysenyl group; a fluorenyl group and the like, but are not limited thereto.

In the present specification, the fluorenyl group can be substituted, and adjacent groups can bond to each other to form a ring.

When the fluorenyl group is substituted,

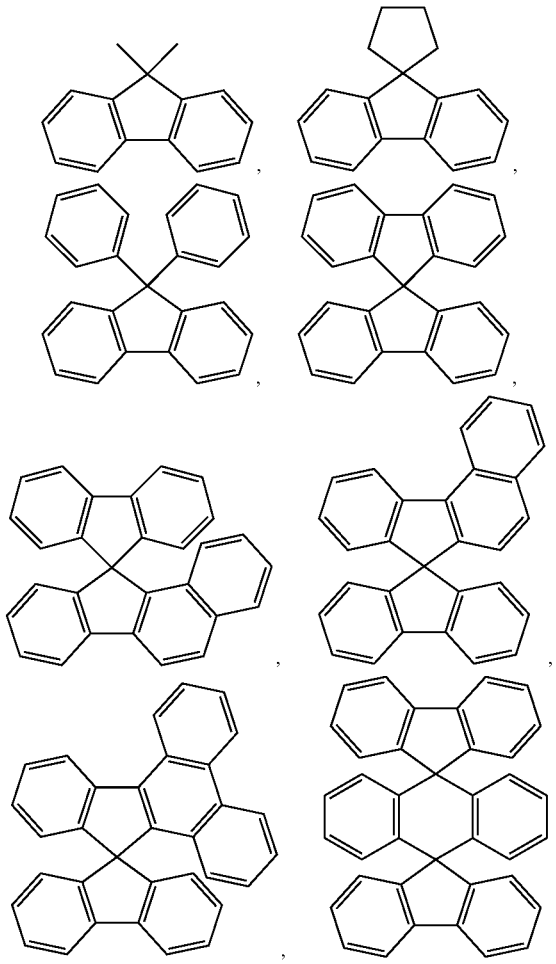

and the like can be included. However, the compound is not limited thereto.

In the present specification, an "adjacent" group can mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring can be interpreted as groups "adjacent" to each other.

In the present specification, the aryl group in the aryloxy group, the arylthioxy group, the arylsulfoxy group, the N-arylalkylamine group, the N-arylheteroarylamine group and the arylphosphine group is the same as the examples of the aryl group described above. Specific examples of the aryloxy group can include a phenoxy group; a p-tolyloxy group; an m-tolyloxy group; a 3,5-dimethylphenoxy group; a 2,4,6-trimethylphenoxy group; a p-tert-butylphenoxy group; a 3-biphenyloxy group; a 4-biphenyloxy group; a 1-naphthyloxy group; a 2-naphthyloxy group; a 4-methyl-1-naphthyloxy group; a 5-methyl-2-naphthyloxy group; a 1-anthryloxy group; a 2-anthryloxy group; a 9-anthryloxy group; a 1-phenanthryloxy group; a 3-phenanthryloxy group; a 9-phenanthryloxy group and the like. Specific examples of the arylthioxy group can include a phenylthioxy group; a 2-methylphenylthioxy group; a 4-tert-butylphenylthioxy group and the like, and specific examples of the arylsulfoxy group can include a benzenesulfoxy group; a p-toluenesulfoxy group and the like. However, the aryloxy group, the arylthioxy group and the arylsulfoxy group are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group can be a monocyclic aryl group or a polycyclic aryl group. The arylamine group including two or more aryl groups can include monocyclic aryl groups, polycyclic aryl groups, or both monocyclic aryl groups and polycyclic aryl groups. For example, the aryl group in the arylamine group can be selected from among the examples of the aryl group described above.

In the present specification, the heteroaryl group is a group including one or more atoms that are not carbon, that is, heteroatoms, and specifically, the heteroatom can include one or more atoms selected from the group consisting of O, N, Se, S and the like. The number of carbon atoms is not particularly limited, but is preferably from 2 to 30 and more preferably from 2 to 20, and the heteroaryl group can be monocyclic or polycyclic. Examples of the heteroaryl group can include a thiophene group; a furanyl group; a pyrrole group; an imidazolyl group; a thiazolyl group; an oxazolyl group; an oxadiazolyl group; a pyridyl group; a bipyridyl group; a pyrimidyl group; a triazinyl group; a triazolyl group; an acridyl group; a pyridazinyl group; a pyrazinyl group; a quinolinyl group; a quinazolinyl group; a quinoxalinyl group; a phthalazinyl group; a pyridopyrimidyl group; a pyridopyrazinyl group; a pyrazinopyrazinyl group; an isoquinolinyl group; an indolyl group; a carbazolyl group; a benzoxazolyl group; a benzimidazolyl group; a benzothiazolyl group; a benzocarbazolyl group; a benzothiophene group; a dibenzothiophene group; a benzofuranyl group; a phenanthrolinyl group; an isoxazolyl group; a thiadiazolyl group; a phenothiazinyl group; a dibenzofuranyl group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups can include monocyclic heteroaryl groups, polycyclic heteroaryl groups, or both monocyclic heteroaryl groups and polycyclic heteroaryl groups. For example, the heteroaryl group in the heteroarylamine group can be selected from among the examples of the heteroaryl group described above.

In the present specification, examples of the heteroaryl group in the N-arylheteroarylamine group and the N-alkylheteroarylamine group are the same as the examples of the heteroaryl group described above.

In the present specification, the arylene group means an aryl group having two bonding sites, that is, a divalent group. Descriptions on the aryl group provided above can be applied thereto except for each being a divalent group.

In the present specification, the heteroarylene group means a heteroaryl group having two bonding sites, that is, a divalent group. Descriptions on the heteroaryl group provided above can be applied thereto except for each being a divalent group.

According to one embodiment of the present specification, L1 to L4 are the same as or different from each other, and each independently a direct bond; a substituted or unsubstituted arylene group; or a substituted or unsubstituted heteroarylene group.

According to one embodiment of the present specification, L1 to L4 are the same as or different from each other, and each independently a direct bond; a substituted or unsubstituted arylene group having 6 to 30 carbon atoms; or a substituted or unsubstituted heteroarylene group having 2 to 30 carbon atoms.

According to one embodiment of the present specification, L1 to L4 are the same as or different from each other, and each independently a direct bond; an arylene group; or a heteroarylene group.

According to one embodiment of the present specification, L1 to L4 are the same as or different from each other, and each independently a direct bond; a substituted or unsubstituted phenylene group; a substituted or unsubstituted biphenylylene group; a substituted or unsubstituted naphthylene group; a substituted or unsubstituted terphenylene group; a substituted or unsubstituted quaterphenylene group; a substituted or unsubstituted anthracenylene group; a substituted or unsubstituted phenanthrenylene group; a substituted or unsubstituted triphenylenylene group; a substituted or unsubstituted pyrenylene group; a substituted or unsubstituted fluorenylene group; a substituted or unsubstituted spirocyclopentanefluorenylene group; a substituted or unsubstituted dibenzofuranylene group; a substituted or unsubstituted divalent dibenzothiophene group; a substituted or unsubstituted carbazolene group; a substituted or unsubstituted pyridylene group; a substituted or unsubstituted divalent furan group; or a substituted or unsubstituted divalent thiophene group.

According to one embodiment of the present specification, L1 to L4 are the same as or different from each other, and each independently a direct bond; a phenylene group; a biphenylylene group unsubstituted or substituted with a nitrile group; a naphthylene group; a terphenylene group; a quaterphenylene group; an anthracenylene group; a phenanthrenylene group; a triphenylenylene group; a pyrenylene group; a fluorenylene group unsubstituted or substituted with an alkyl group or an aryl group; a spirocyclopentanefluorenylene group; a dibenzofuranylene group; a divalent dibenzothiophene group; a carbazolene group unsubstituted or substituted with an aryl group; a pyridylene group; a divalent furan group; or a divalent thiophene group.

According to one embodiment of the present specification, L1 to L4 are the same as or different from each other, and can be each independently a direct bond or one of the following structural formulae:

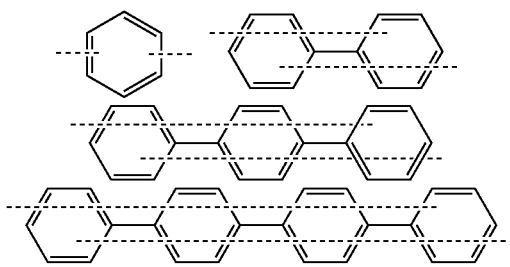

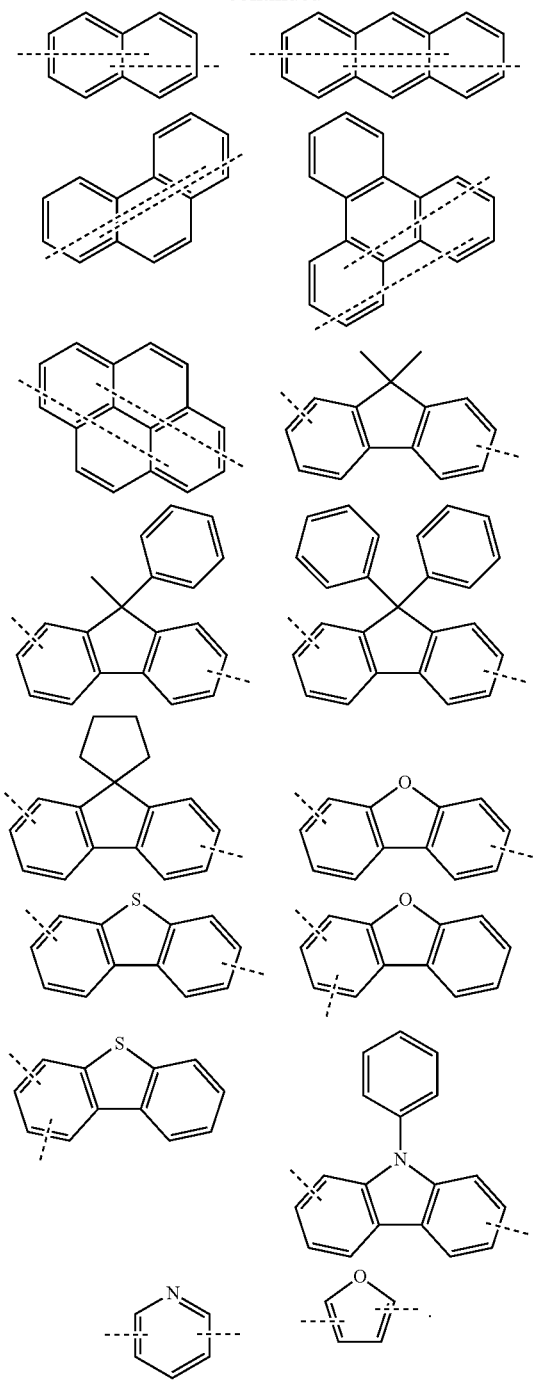

In the structures, ■ ■ ■ ■ ■ is a site bonding to a main chain.

According to one embodiment of the present specification, L1 to L4 are the same as or different from each other, and each independently a direct bond; a phenylene group; a biphenylylene group; a naphthylene group; or a pyridylene group.

According to one embodiment of the present specification, Ar1 and Ar3 are the same as or different from each other, and can be each independently one of the following Chemical Formula A:

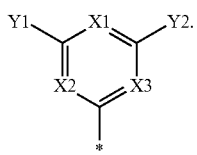

[Chemical Formula A]

In Chemical Formula A,

* is a bonding site,

X1 to X3 are the same as or different from each other and each independently N or CR5, and at least two of X1 to X3 are N, R5, Y1 and Y2 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group.

According to one embodiment of the present specification, R5 is hydrogen.

According to one embodiment of the present specification, Chemical Formula A can be one selected from among the following Chemical Formulae A-1 to A-4:

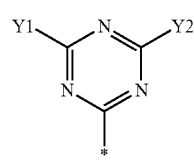

[Chemical Formula A-1]

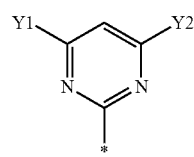

[Chemical Formula A-2]

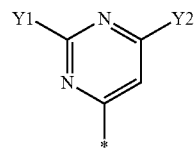

[Chemical Formula A-3]

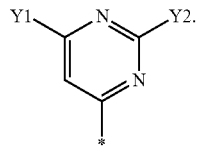

[Chemical Formula A-4]

In Chemical Formulae A-1 to A-4, the substituents have the same definitions as in Chemical Formula A.

According to one embodiment of the present specification, Y1 and Y2 are the same as or different from each other, and can be each independently a substituted or unsubstituted aryl group having 6 to 30 carbon atoms, or a substituted or unsubstituted heteroaryl group having 2 to 30 carbon atoms.

According to one embodiment of the present specification, Y1 and Y2 are the same as or different from each other, and can be each independently a substituted or unsubstituted aryl group having 6 to 20 carbon atoms, or a substituted or unsubstituted heteroaryl group having 2 to 20 carbon atoms.

According to one embodiment of the present specification, Y1 and Y2 are the same as or different from each other, and can be each independently a substituted or unsubstituted phenyl group; a substituted or unsubstituted biphenyl group; a substituted or unsubstituted naphthyl group; a substituted or unsubstituted terphenyl group; a substituted or unsubstituted quaterphenyl group; a substituted or unsubstituted anthracenyl group; a substituted or unsubstituted phenanthrenyl group; a substituted or unsubstituted triphenylenyl group; a substituted or unsubstituted pyrenyl group; a substituted or unsubstituted fluorenyl group; a substituted or unsubstituted spirocyclopentanefluorenyl group; a substituted or unsubstituted dibenzofuranyl group; a substituted or unsubstituted dibenzothiophene group; a substituted or unsubstituted carbazole group; a substituted or unsubstituted pyridyl group; a substituted or unsubstituted furan group; or a substituted or unsubstituted thiophene group.

According to one embodiment of the present specification, Y1 and Y2 are the same as or different from each other, and can be each independently a substituted or unsubstituted phenyl group; a substituted or unsubstituted naphthyl group; a substituted or unsubstituted pyridyl group; or a substituted or unsubstituted biphenyl group.

According to one embodiment of the present specification, Y1 and Y2 are the same as or different from each other, and can be each independently a phenyl group; a naphthyl group; a pyridyl group; or a biphenyl group.

According to one embodiment of the present specification, Ar2 and Ar4 are the same as or different from each other, and each can be independently selected from among the following Chemical Formulae C and D:

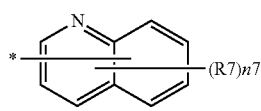

[Chemical Formula C]

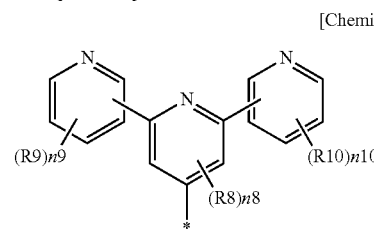

[Chemical Formula D]

In Chemical Formulae C and D,

* is a bonding site,

R7 to R10 are the same as or different from each other, and each independently hydrogen; deuterium; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; or a substituted or unsubstituted heteroaryl group, and n9 and n10 are an integer of 0 to 4, n7 is an integer of 0 to 6, n8 is an integer of 0 to 2, and when n7 to n10 are an integer of 2 or greater, substituents in the parentheses are the same as or different from each other.

According to one embodiment of the present specification, Chemical Formula C can be one selected from among the following Chemical Formulae C-1 to C-7:

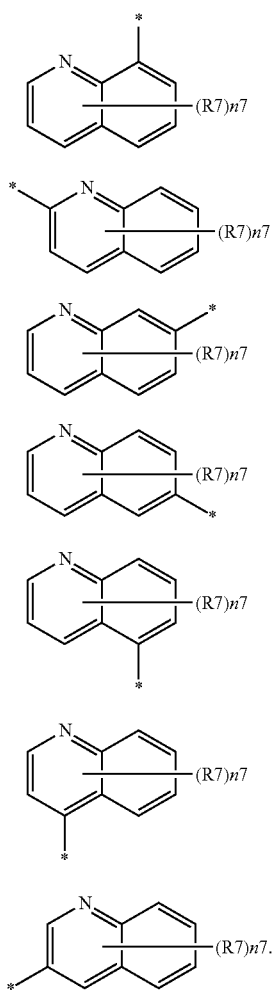

[Chemical Formula C-1]

[Chemical Formula C-2]

[Chemical Formula C-3]

[Chemical Formula C-4]

[Chemical Formula C-5]

[Chemical Formula C-6]

[Chemical Formula C-7]

In Chemical Formulae C-1 to C-7, the substituents have the same definitions as in Chemical Formula C.

According to one embodiment of the present specification, Chemical Formula D can be one selected from among the following Chemical Formulae D-1 to D-3:

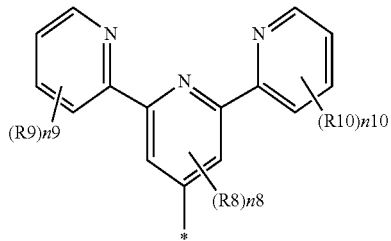

[Chemical Formula D-1]

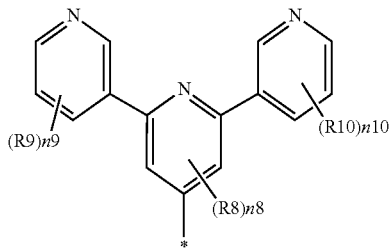

[Chemical Formula D-2]

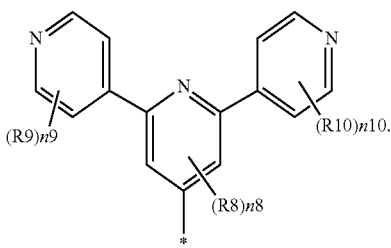

[Chemical Formula D-3]

In Chemical Formulae D-1 to D-3, the substituents have the same definitions as in Chemical Formula D.

According to one embodiment of the present specification, R1 to R4 can be hydrogen.

According to one embodiment of the present specification, R7 to R10 can be hydrogen.

According to one embodiment of the present specification, Z can be O.

According to one embodiment of the present specification, Z can be S.

According to one embodiment of the present specification, Chemical Formula 1 can be asymmetric based on a core structure.

According to one embodiment of the present specification, Chemical Formula 1 can be one of the following Chemical Formula 2 or 3:

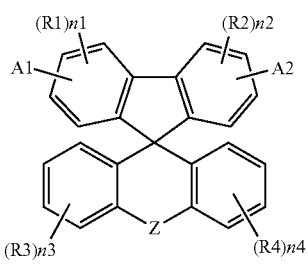

[Chemical Formula 2]

[Chemical Formula 3]

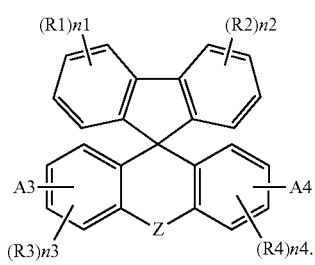

In Chemical Formulae 2 and 3,
A1 is -L1-Ar1, A2 is -L2-Ar2, A3 is -L3-Ar3, and A4 is -L4-Ar4, and
the substituents have the same definitions as in Chemical Formula 1.

According to one embodiment of the present specification, A1 and A2 are each hydrogen, A3 is -L3-Ar3, and A4 can be -L4-Ar4.

According to one embodiment of the present specification, A3 and A4 are each hydrogen, A1 is -L1-Ar1, and A2 can be -L2-Ar2.

According to one embodiment of the present specification, A1 and A2 can bond to a symmetric position of a core structure.

According to one embodiment of the present specification, A3 and A4 can bond to a symmetric position of a core structure.

In the present specification, the 'symmetric position' refers to a bonding position in a mirror-image position centered around a virtual baseline made by extending a line connecting Z of the core structure and a spiro bonding portion. For example, in the following structural formula, two *1s are in a symmetric position, and likewise, two *2s to *8s are each in a symmetric position:

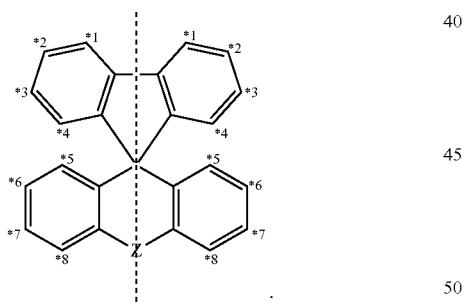

According to one embodiment of the present specification, Chemical Formula 1 can be one selected from among the following Chemical Formulae 1-1 to 1-8:

[Chemical Formula 1-1]

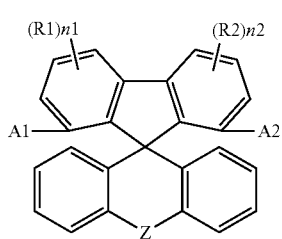

[Chemical Formula 1-2]

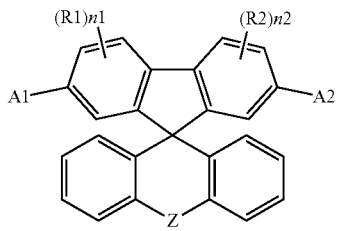

[Chemical Formula 1-3]

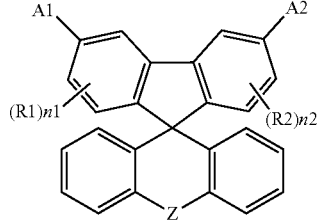

[Chemical Formula 1-4]

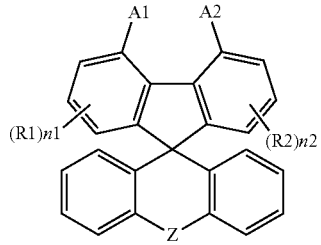

[Chemical Formula 1-5]

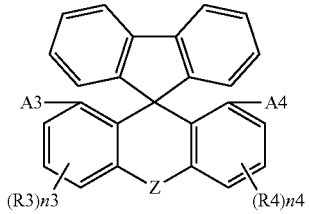

[Chemical Formula 1-6]

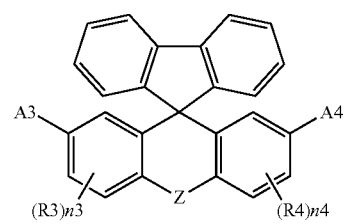

[Chemical Formula 1-7]

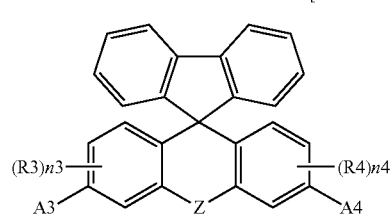

[Chemical Formula 1-8]
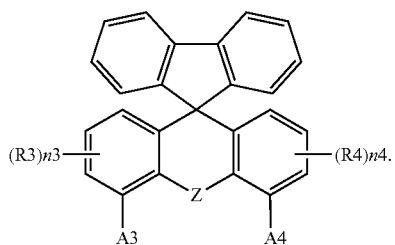
In Chemical Formulae 1-1 to 1-8, A1 is -L1-Ar1, A2 is -L2-Ar2, A3 is -L3-Ar3, and A4 is -L4-Ar4, and
the substituents have the same definitions as in Chemical Formula 1.
According to one embodiment of the present specification, Chemical Formula 1 can be one selected from among the following compounds:
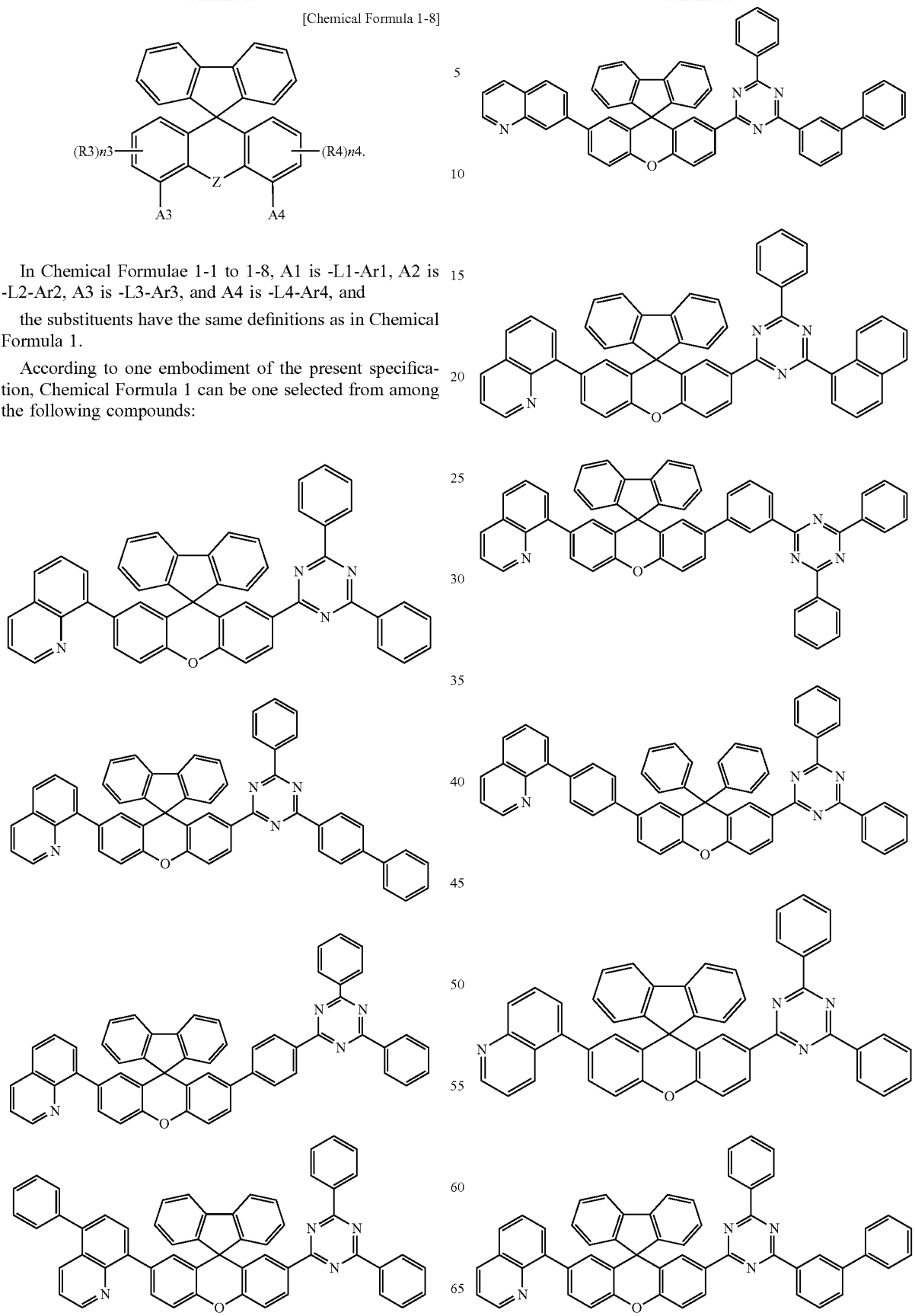

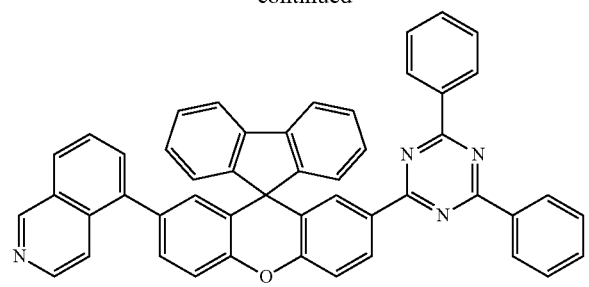
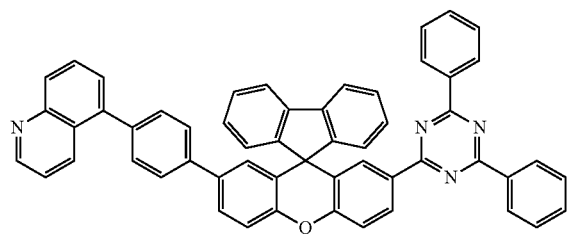
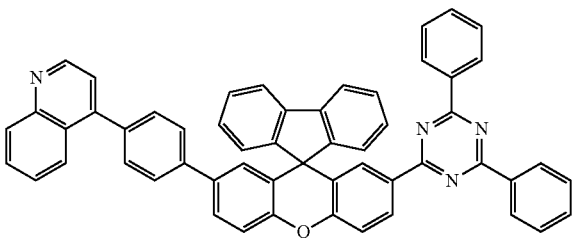
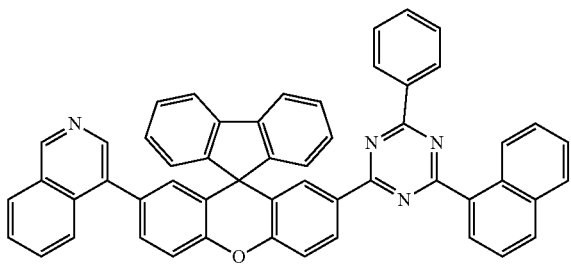
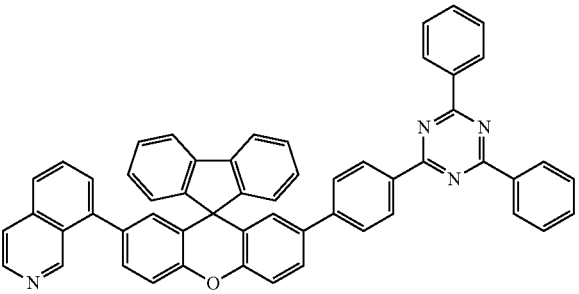
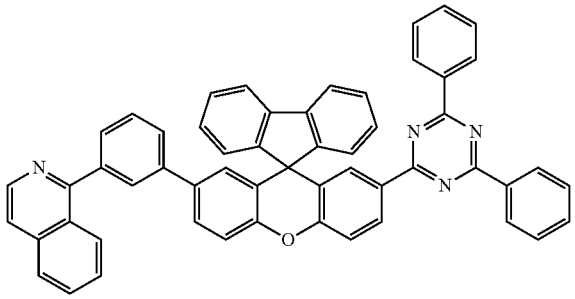
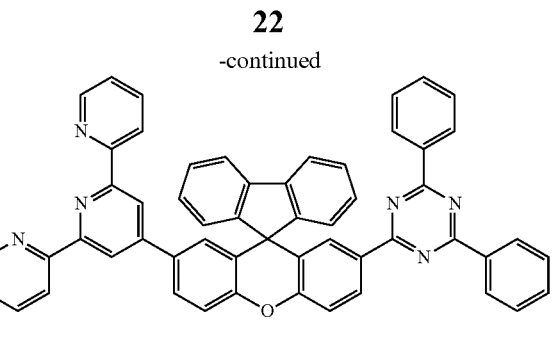
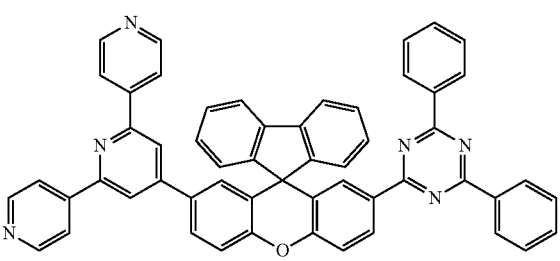
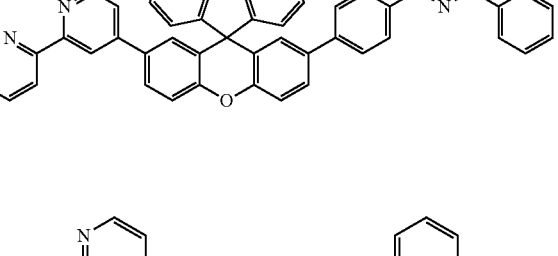
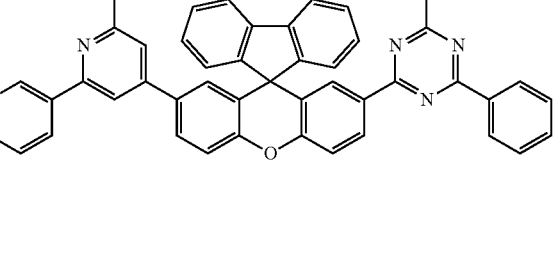
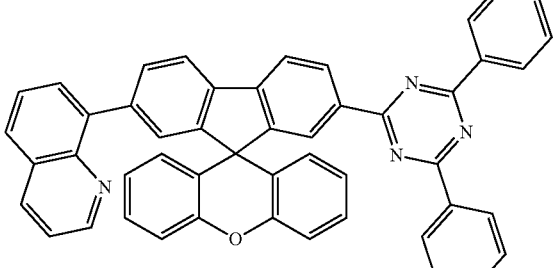

-continued
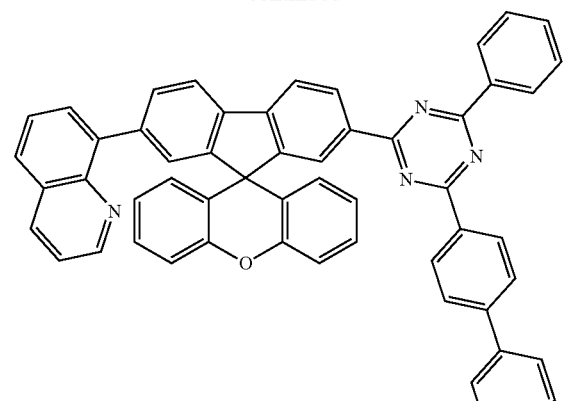
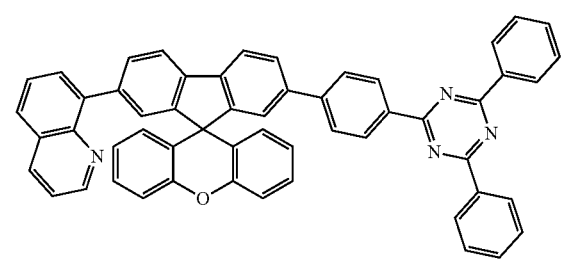
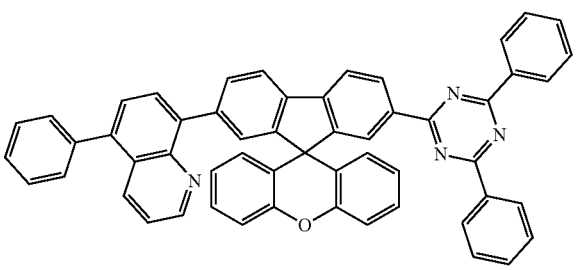
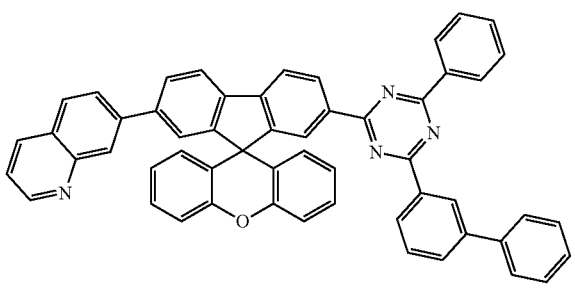
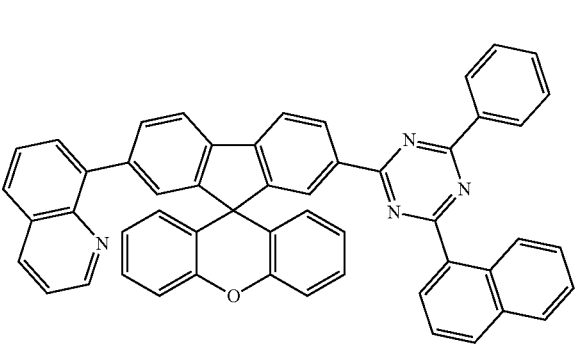
-continued
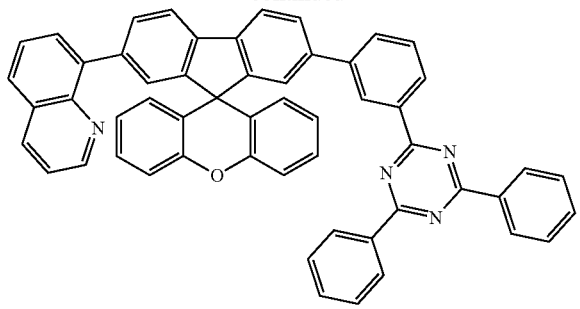
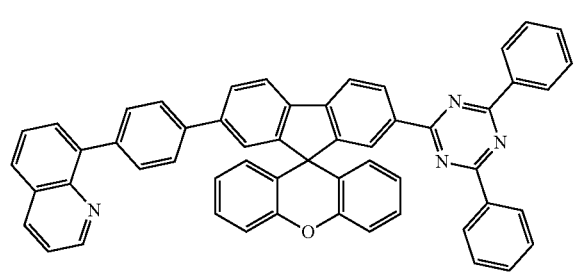
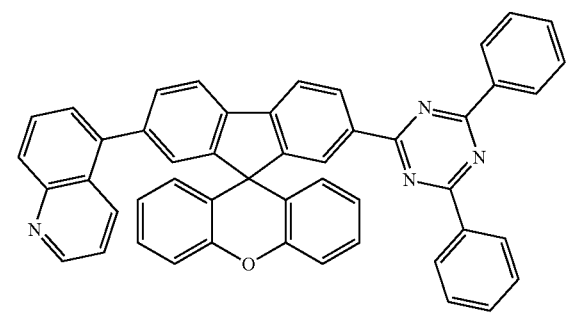
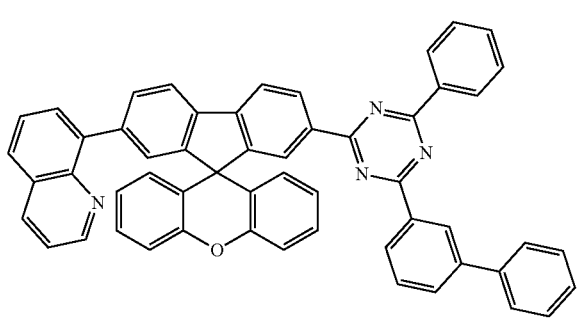
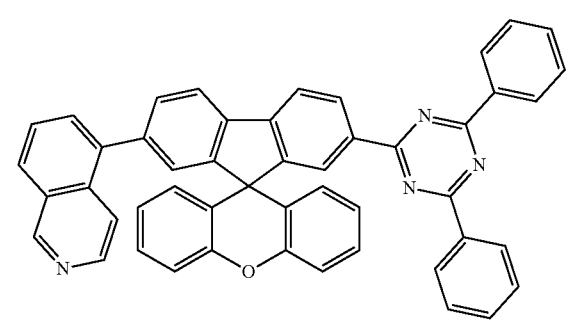

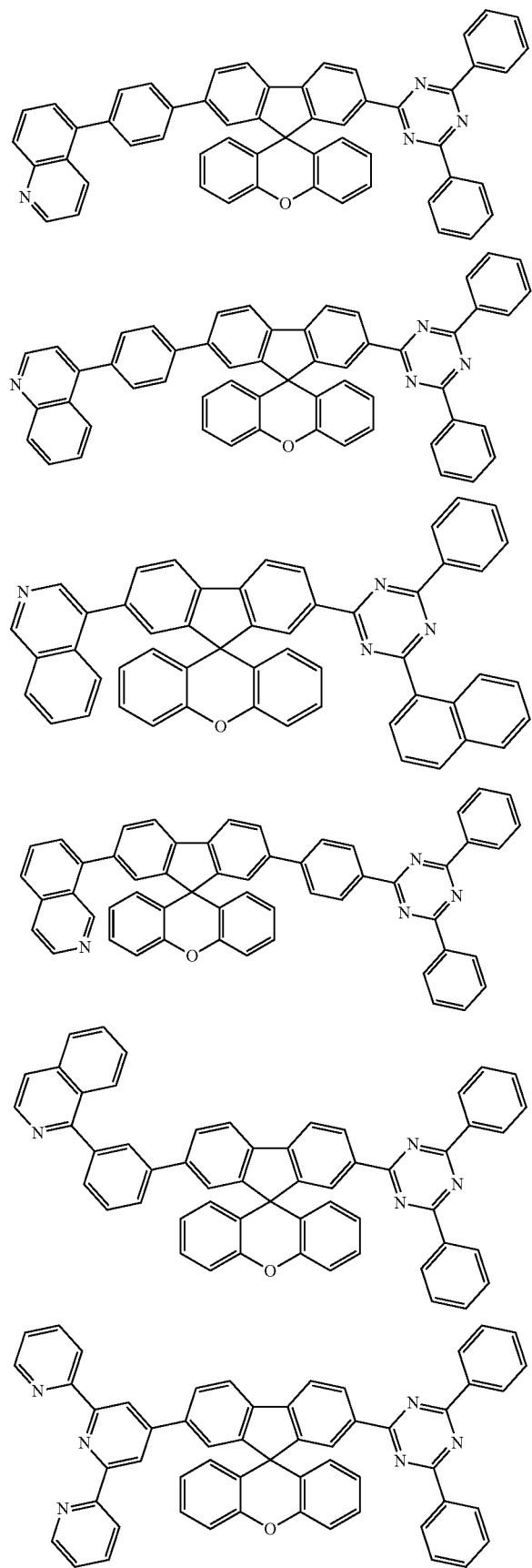
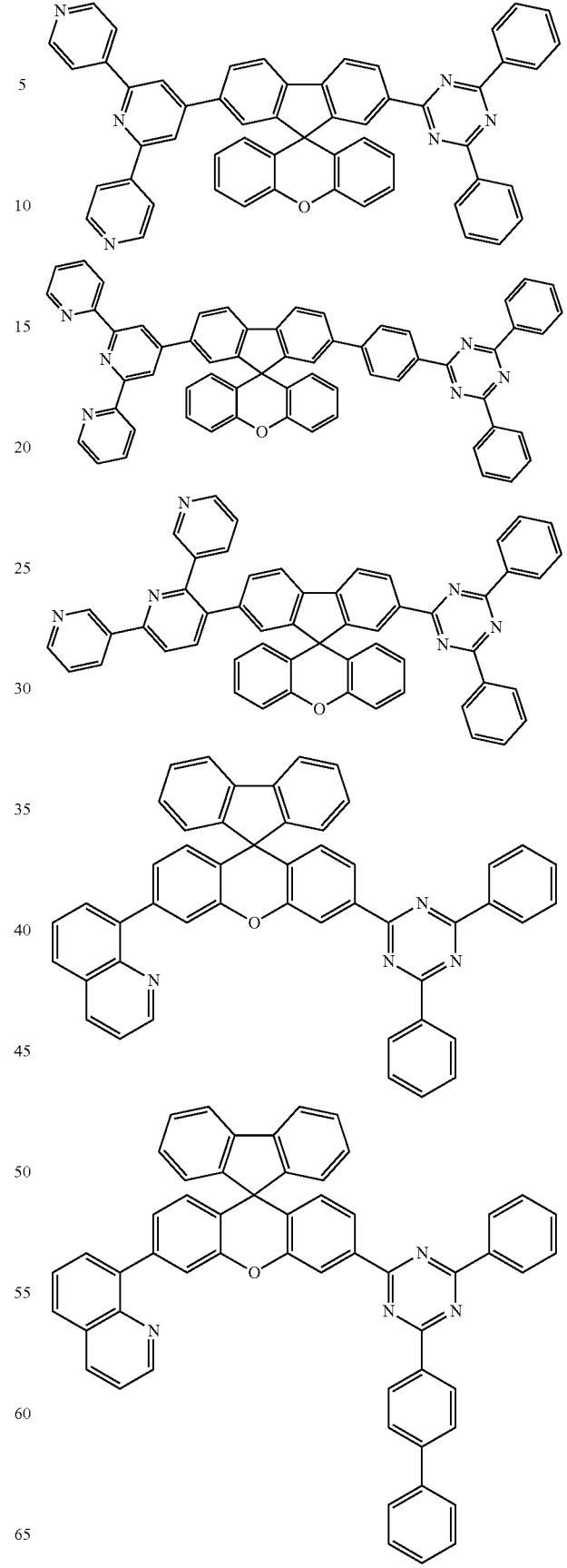

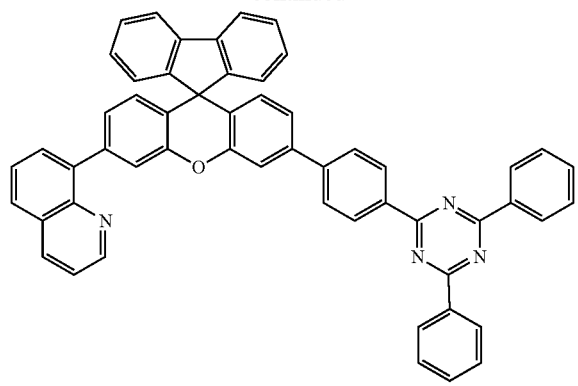
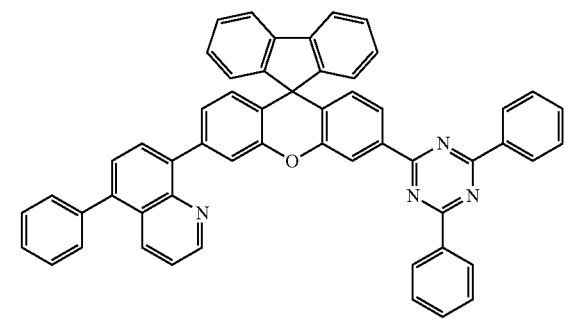
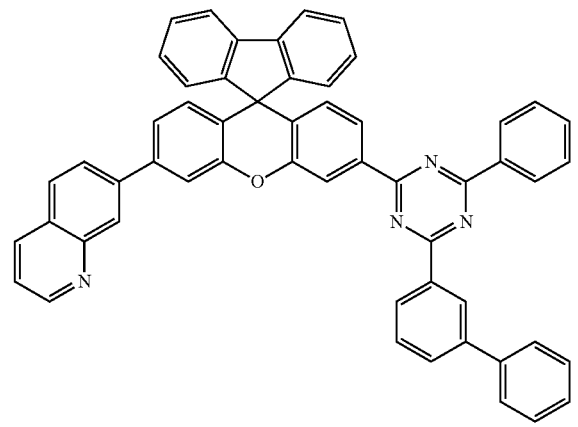
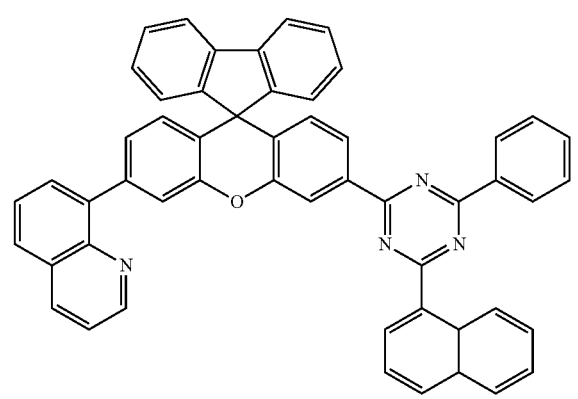
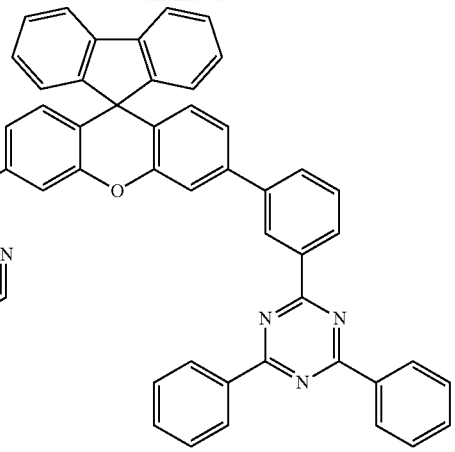
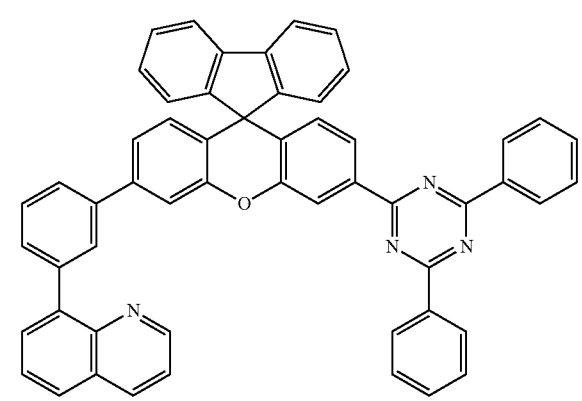
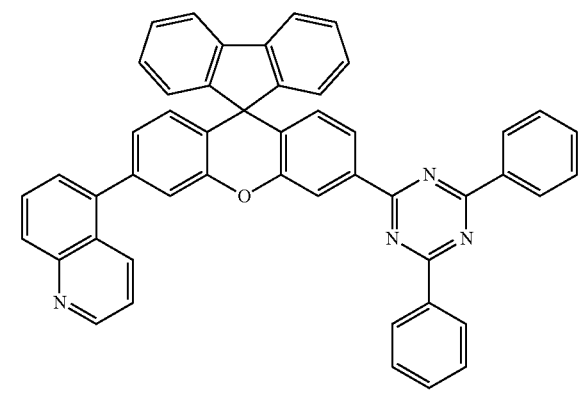
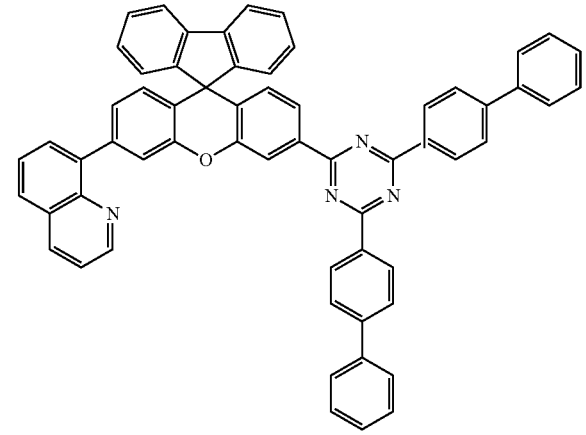

29
-continued
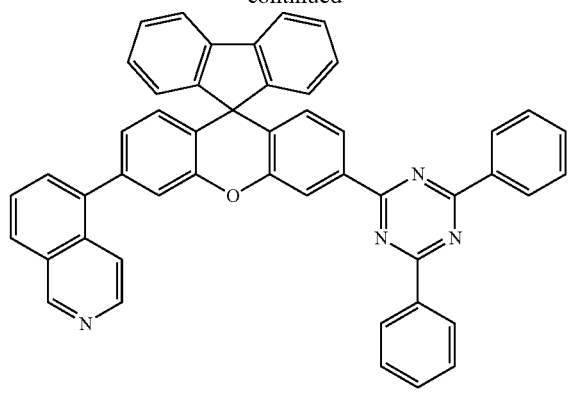
30
-continued
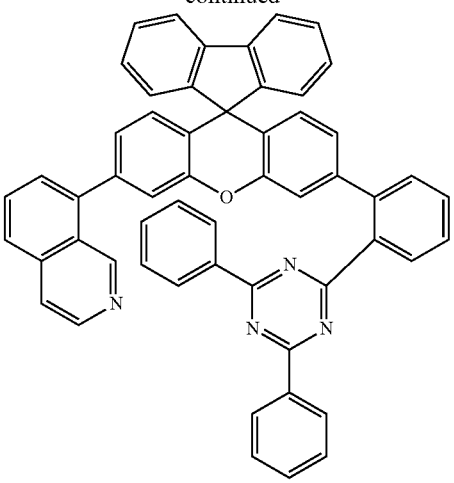
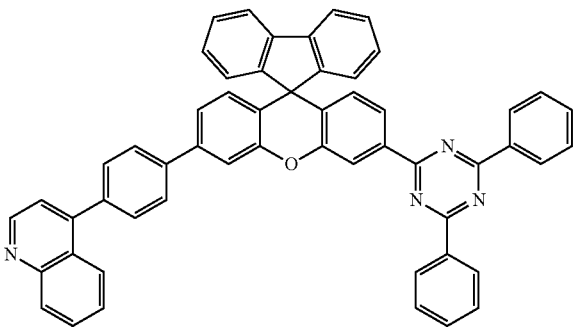
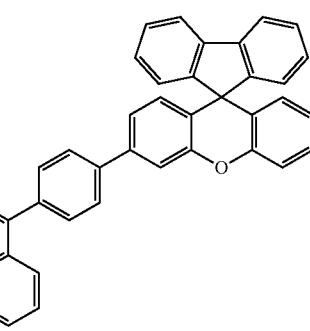
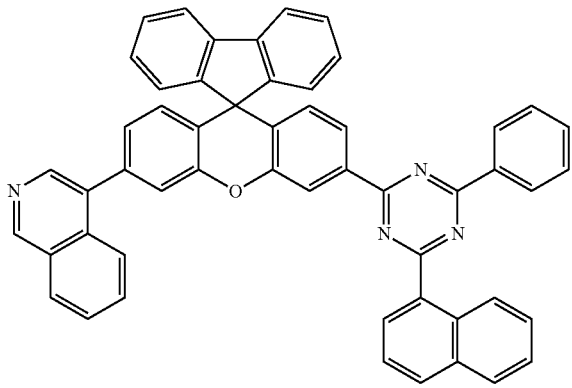
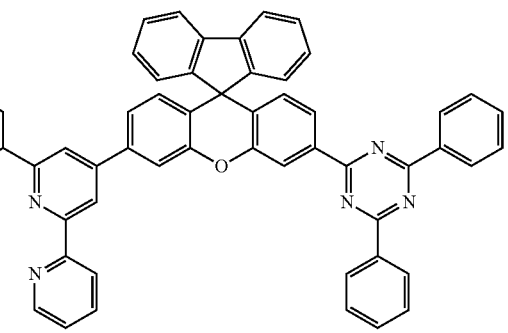
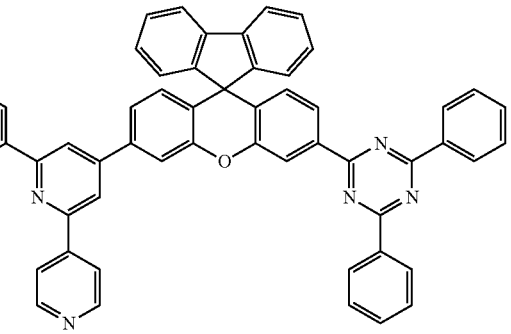

31
-continued
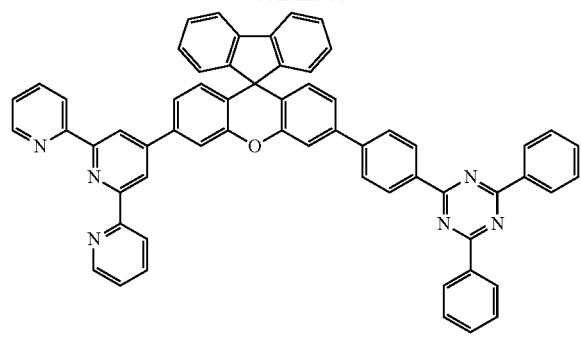
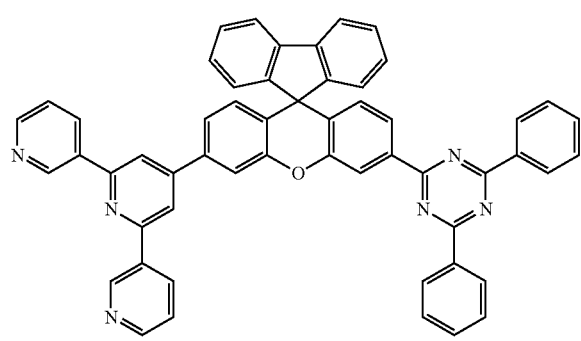
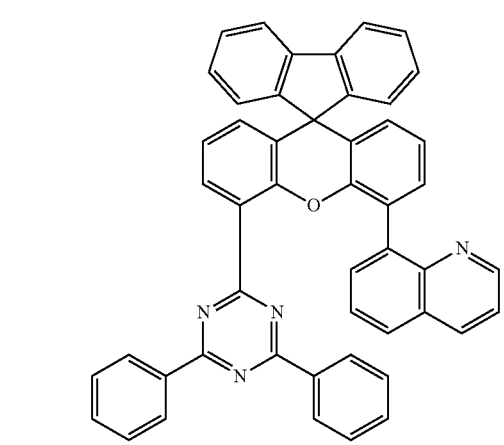
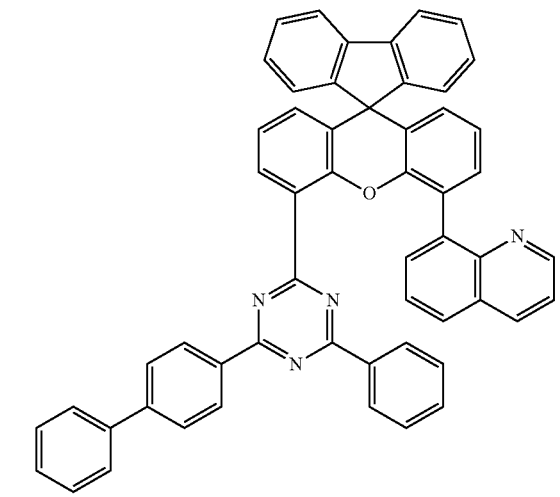
32
-continued
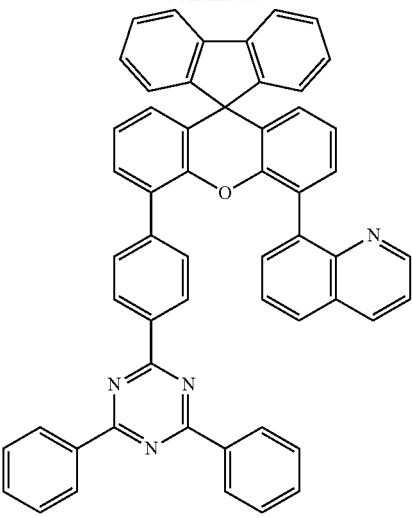
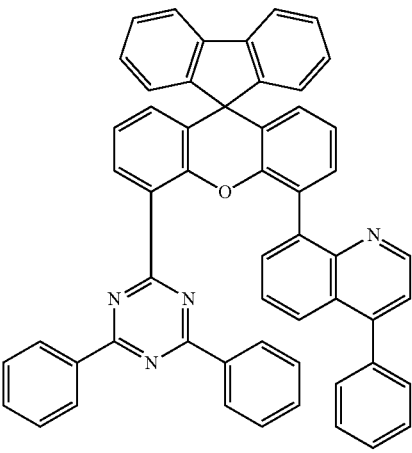
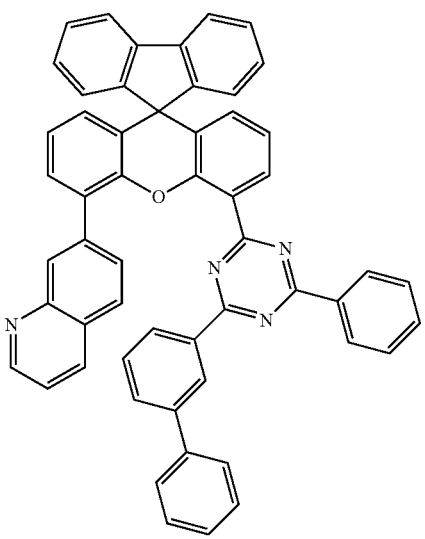

33
-continued
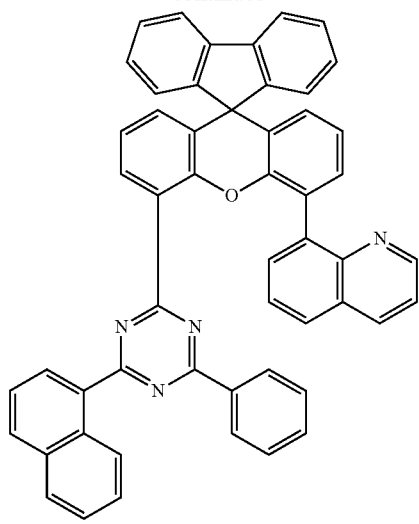
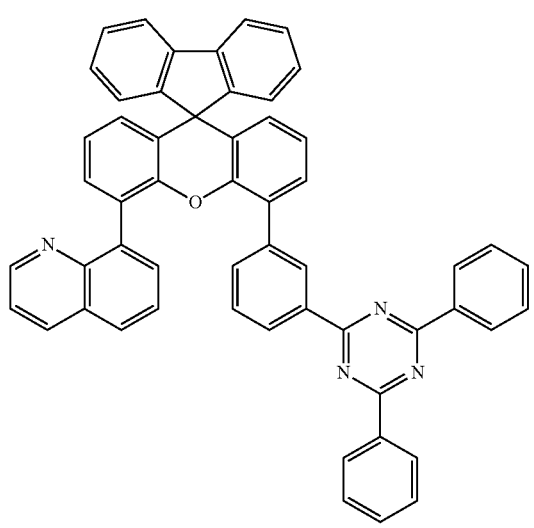
34
-continued
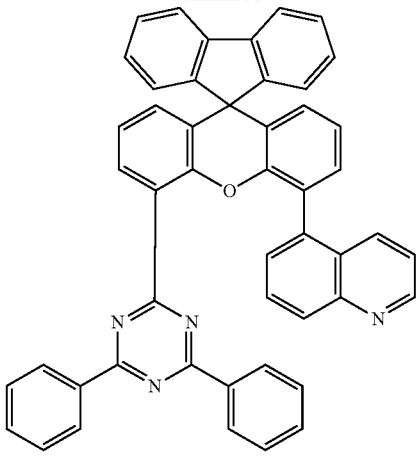
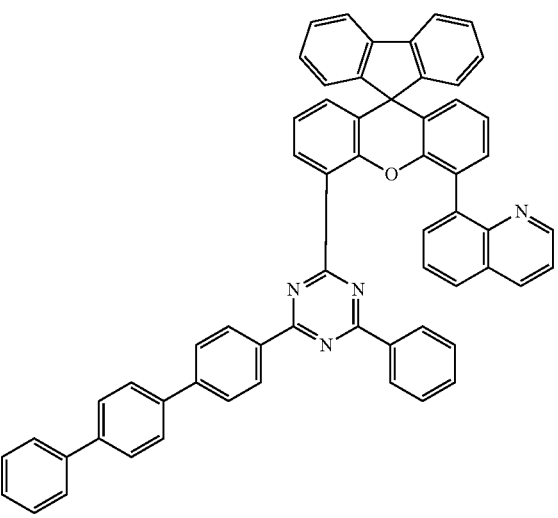
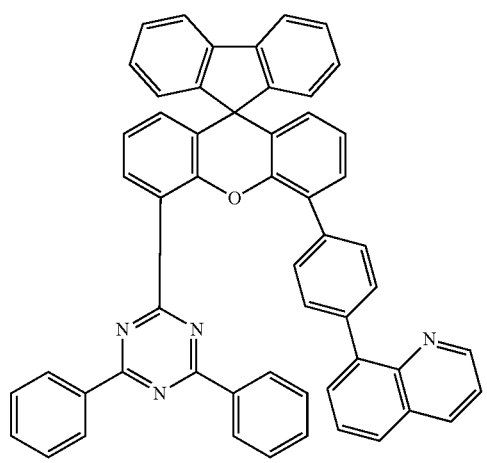
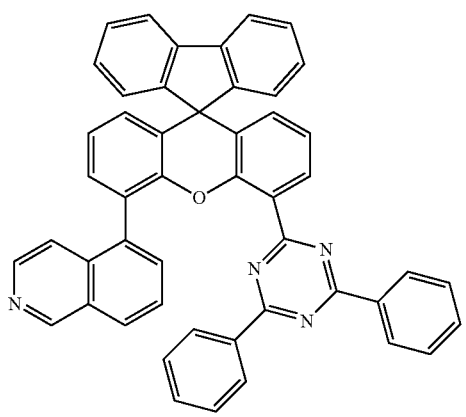

35
-continued
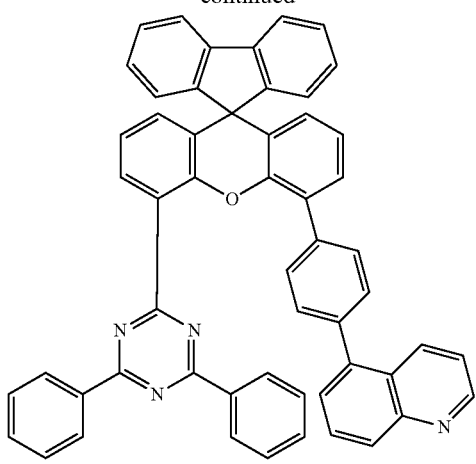
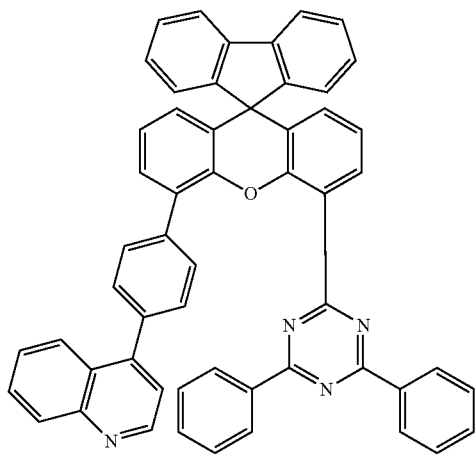
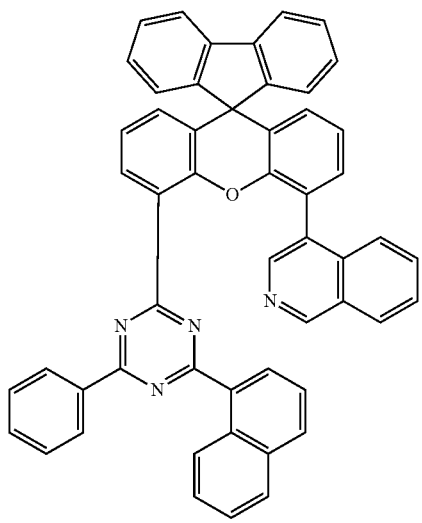
36
-continued
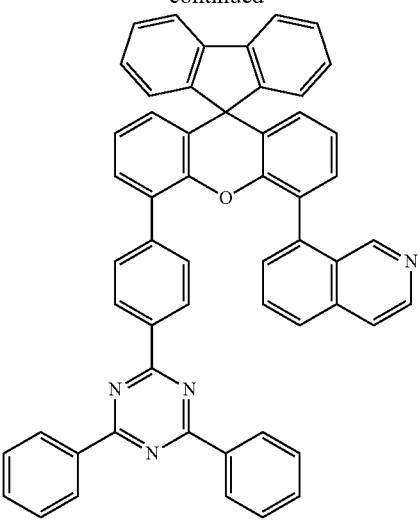
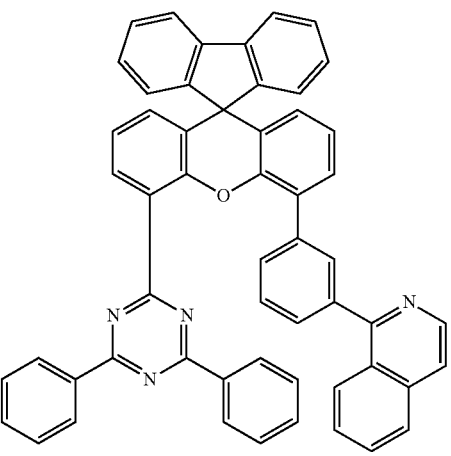
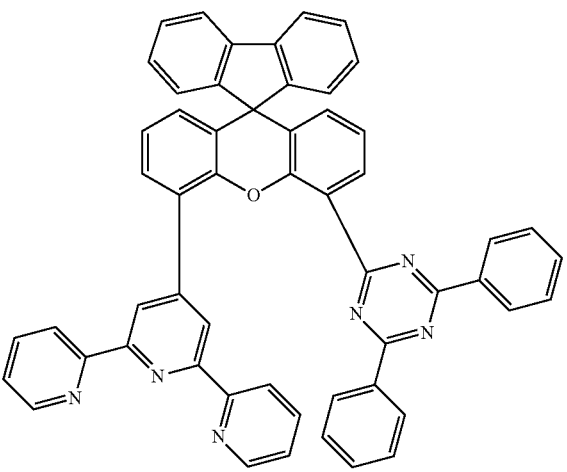

37
-continued
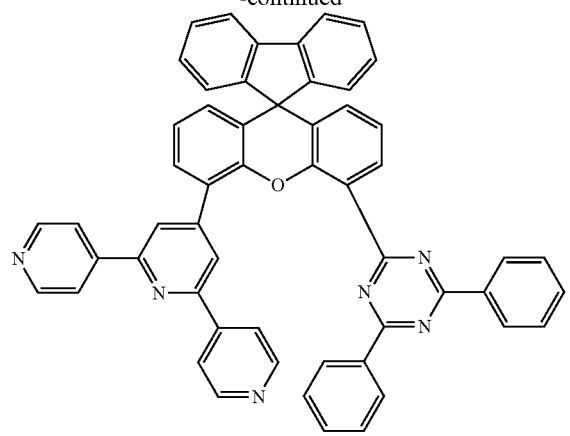
38
-continued
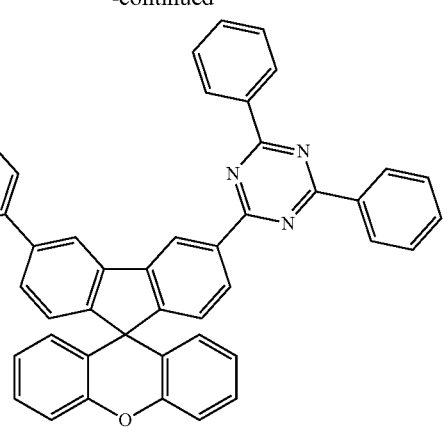
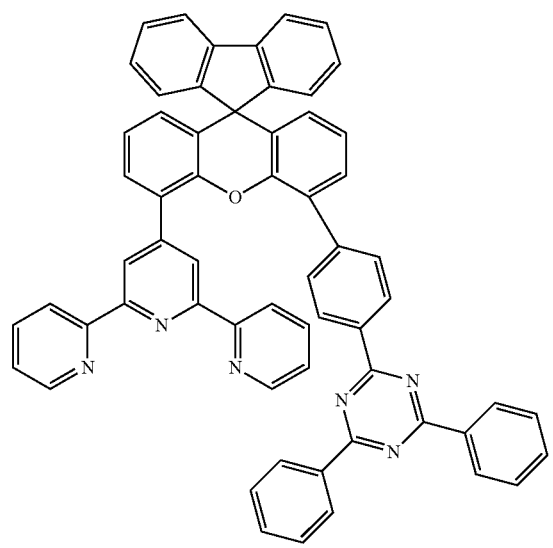
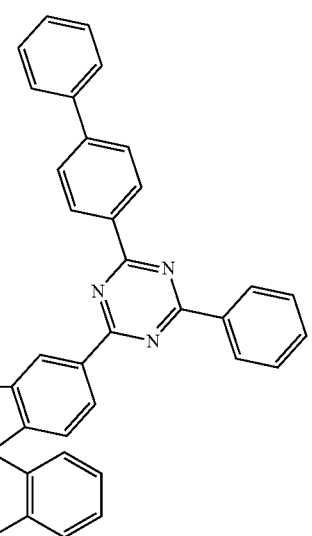
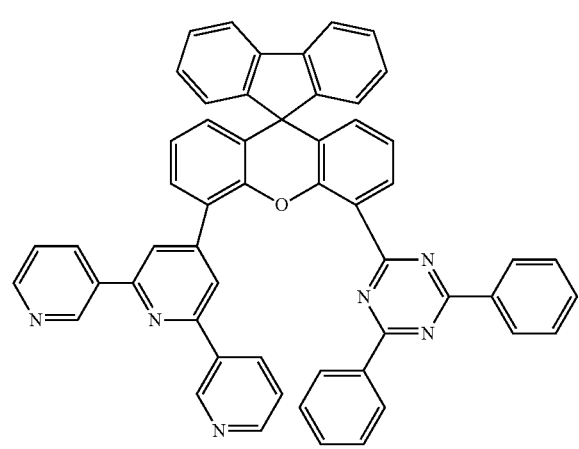
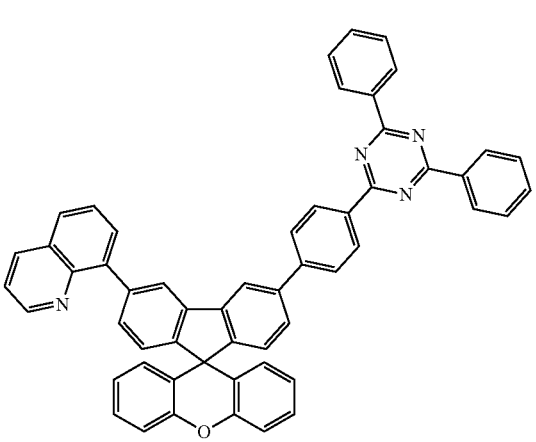

-continued
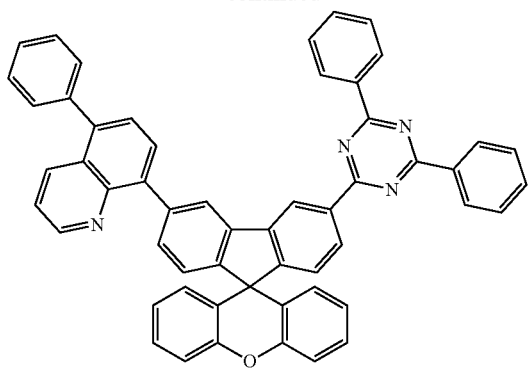
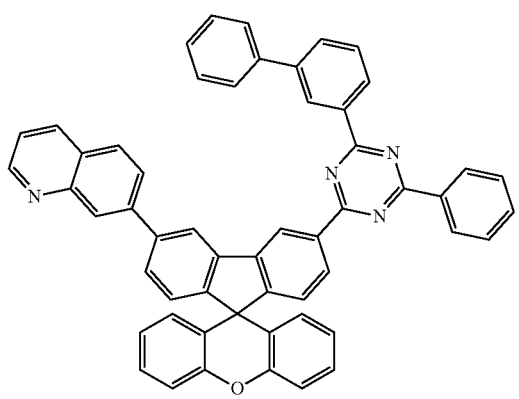
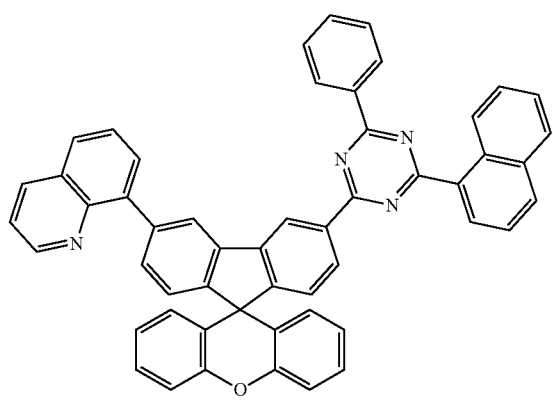
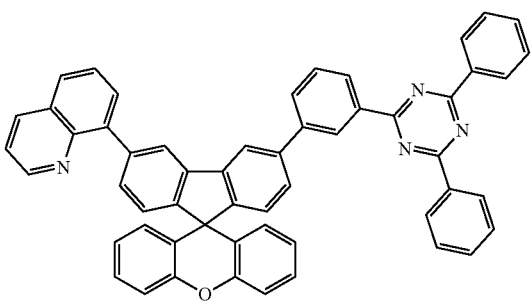
-continued
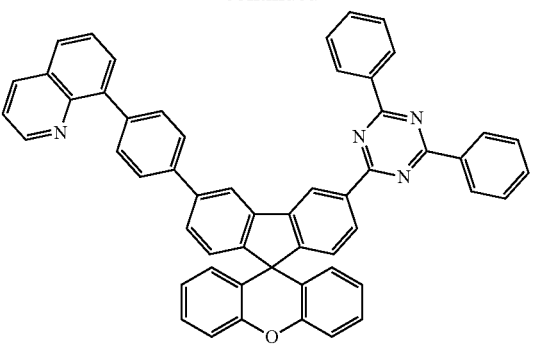
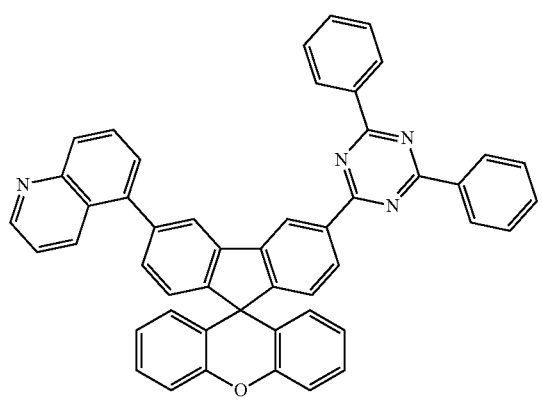
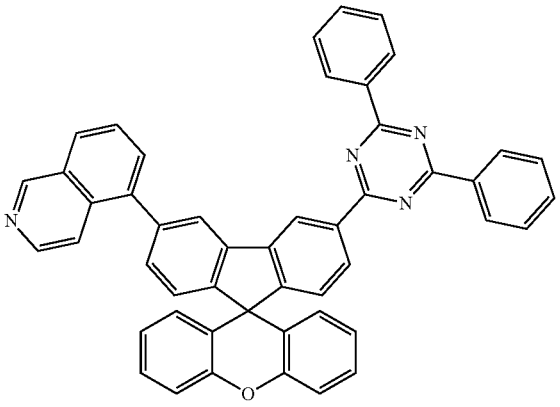

-continued
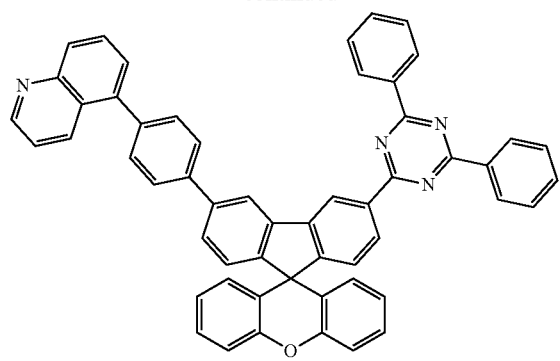
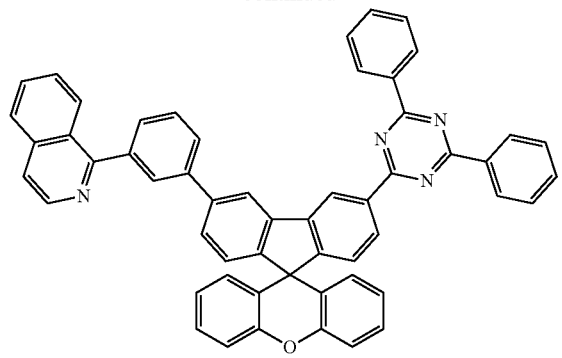
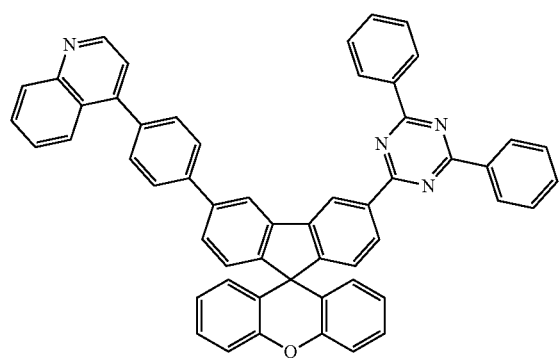
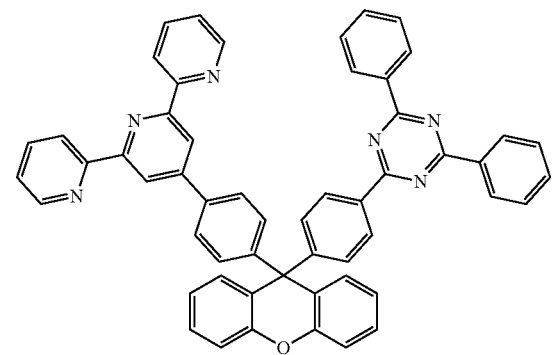
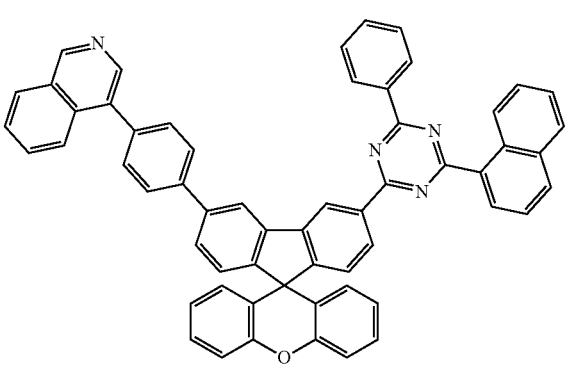
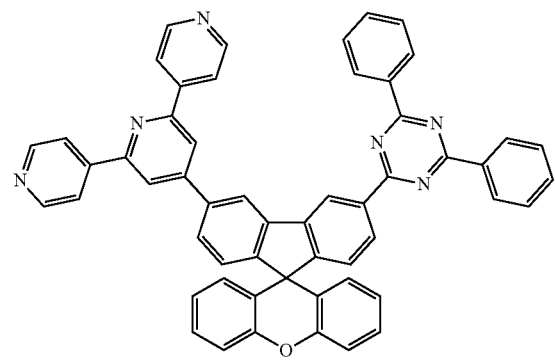
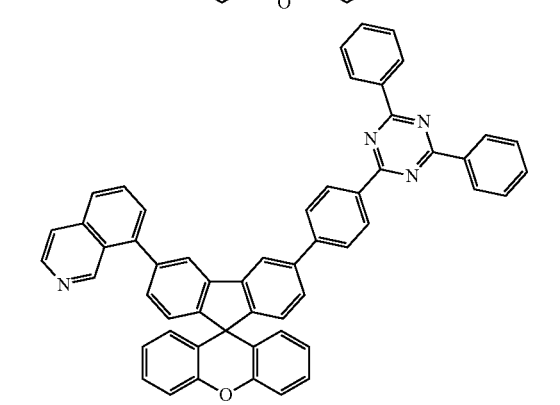
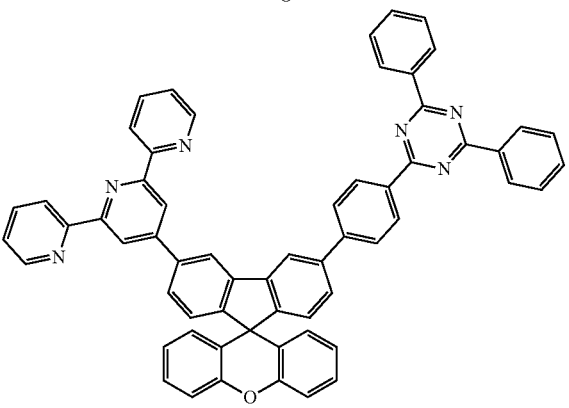

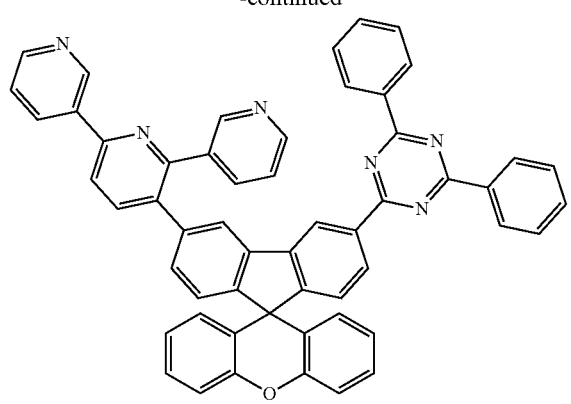
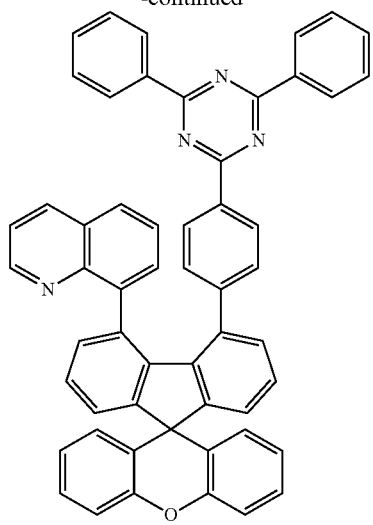
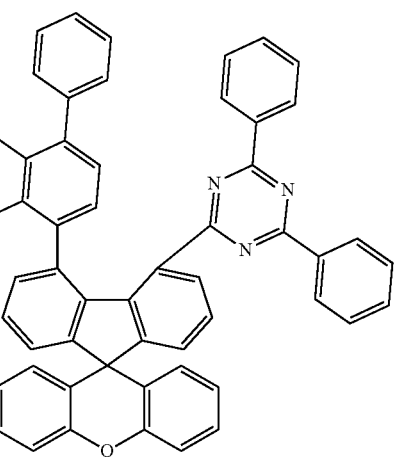
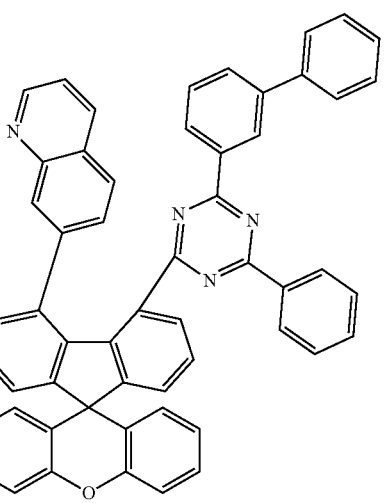

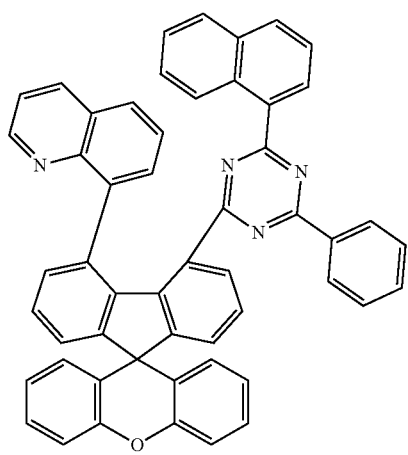
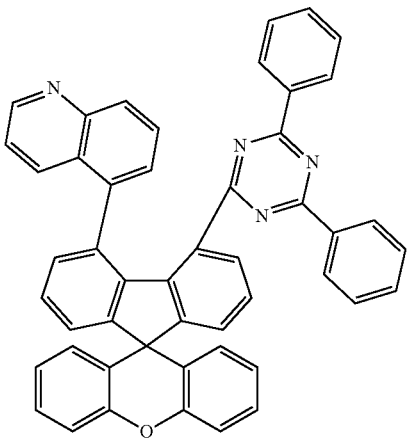
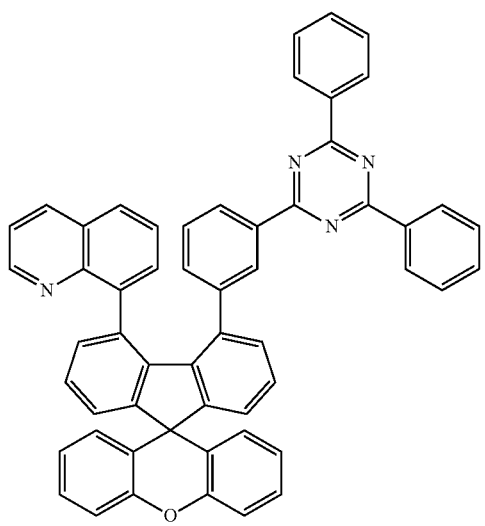
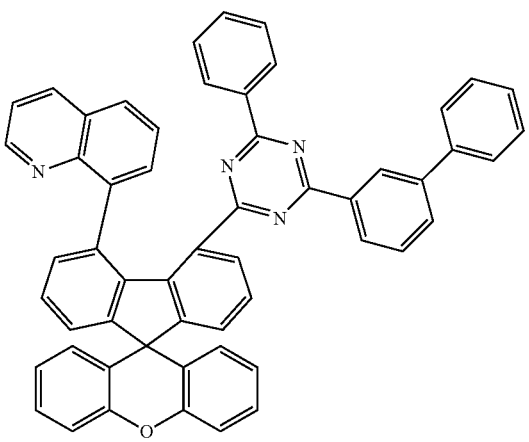
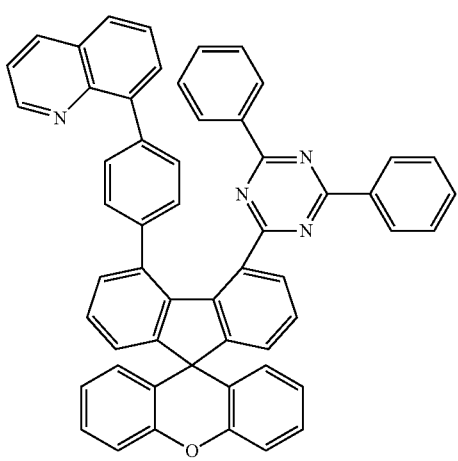
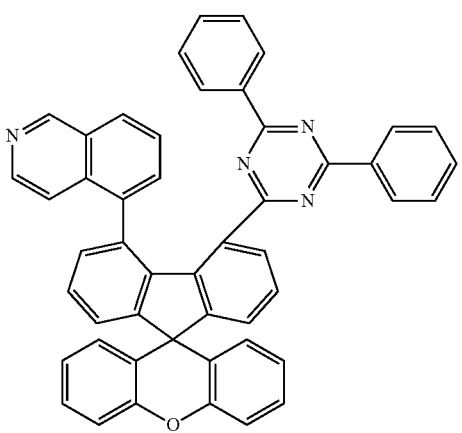

47
-continued
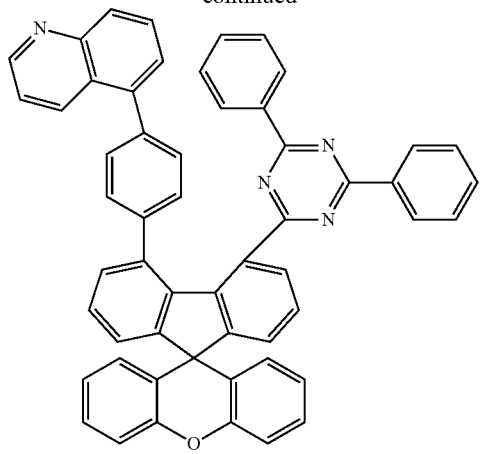
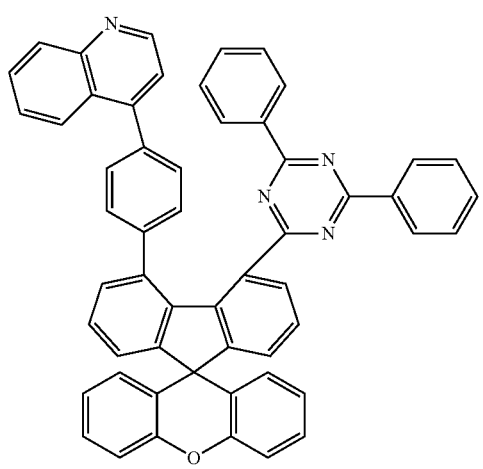
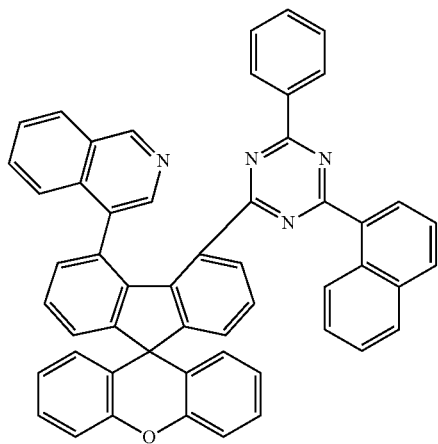
48
-continued
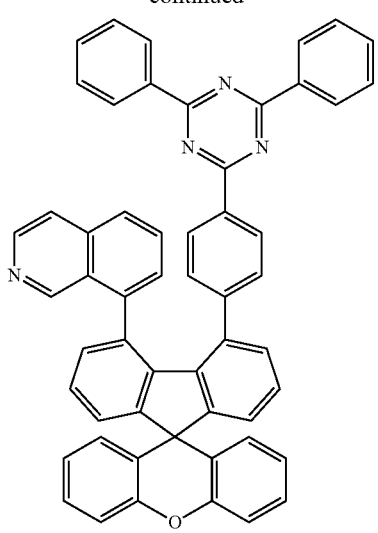
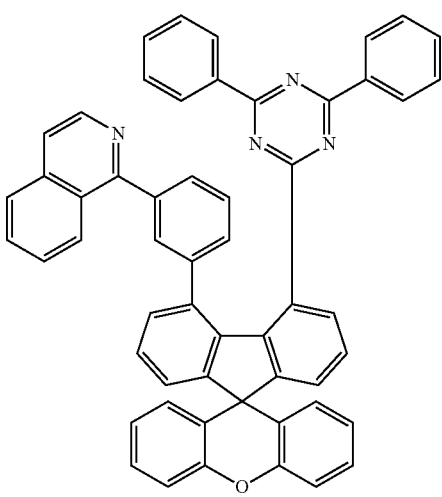
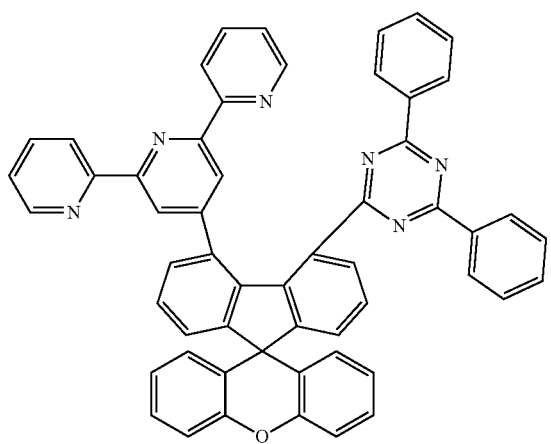

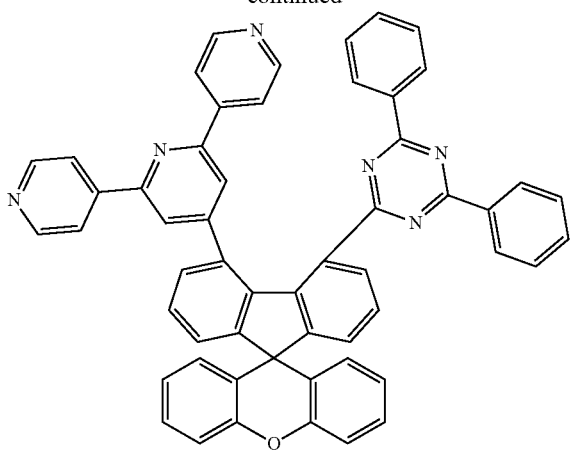
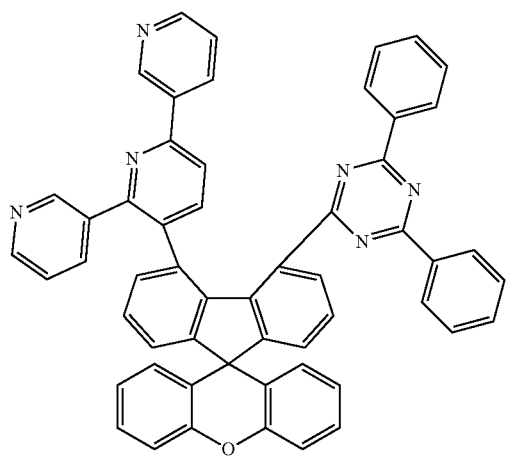
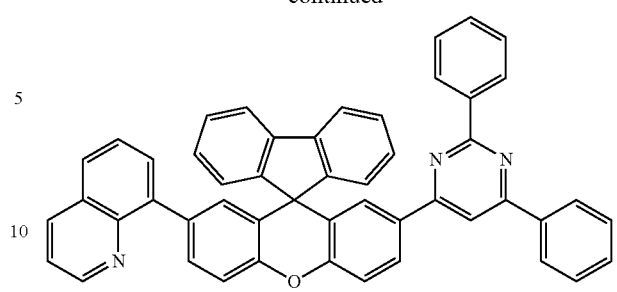
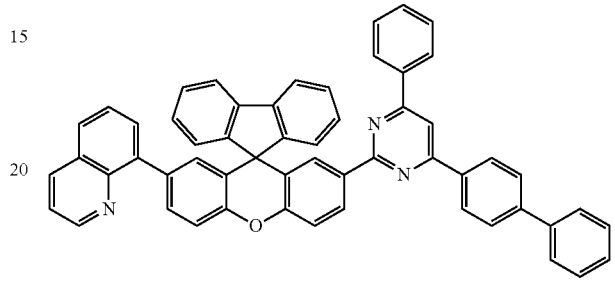
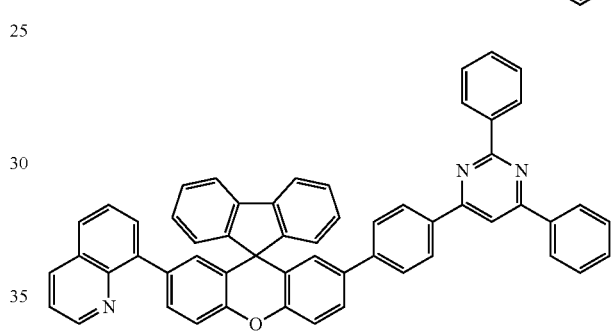
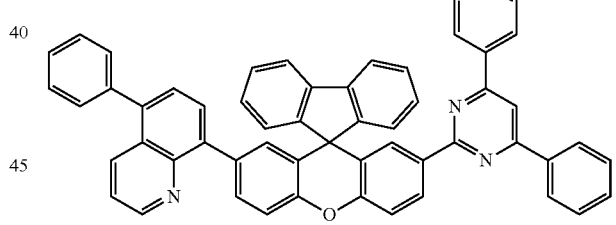
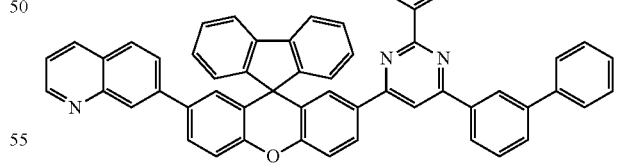
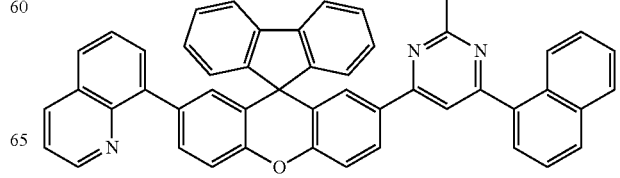

51
-continued
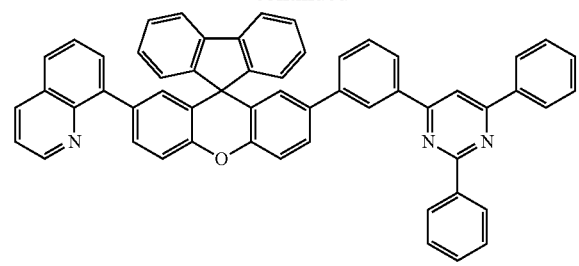
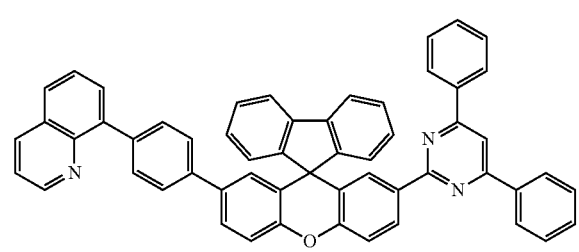
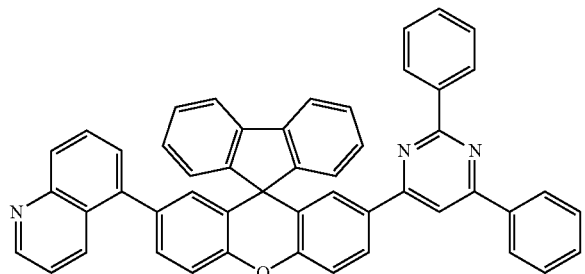
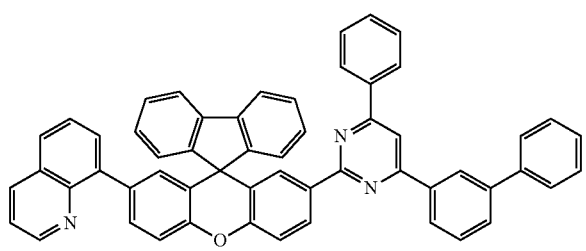
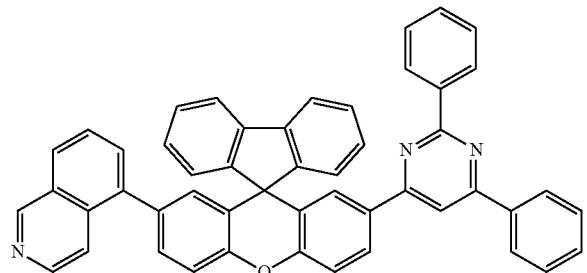
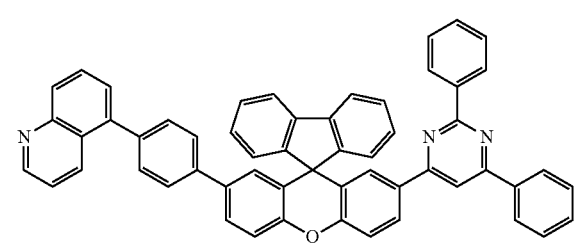
52
-continued
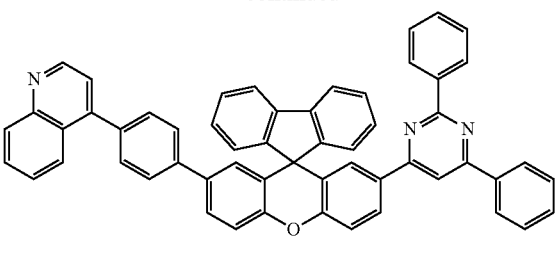
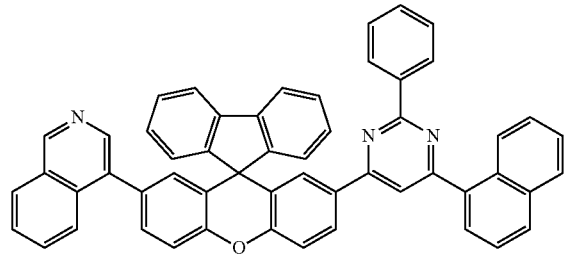
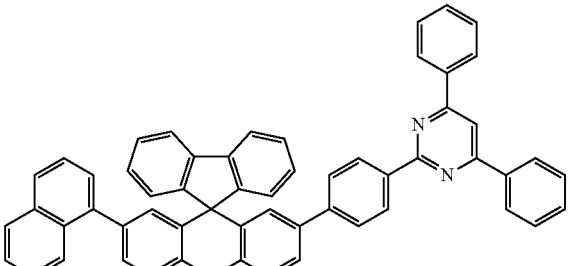
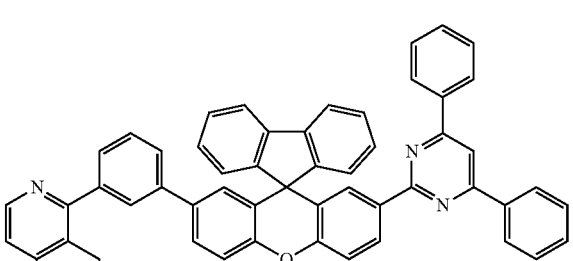
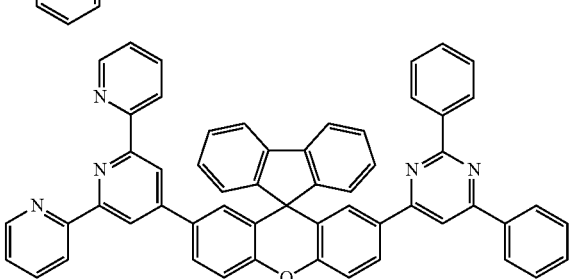
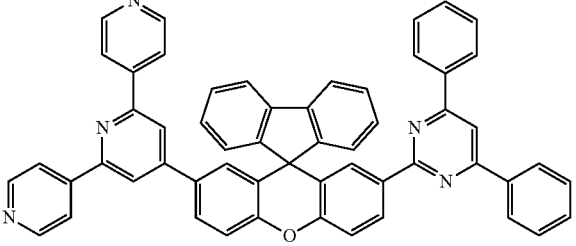

-continued
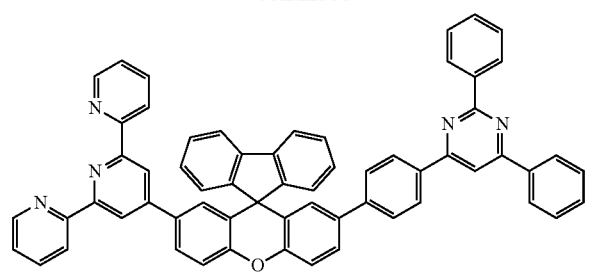
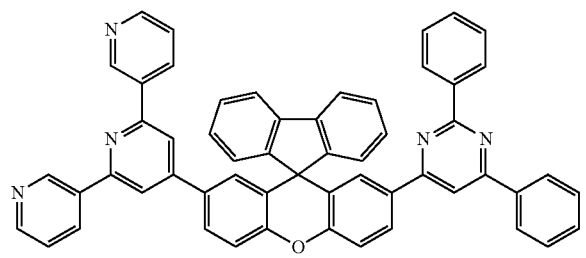
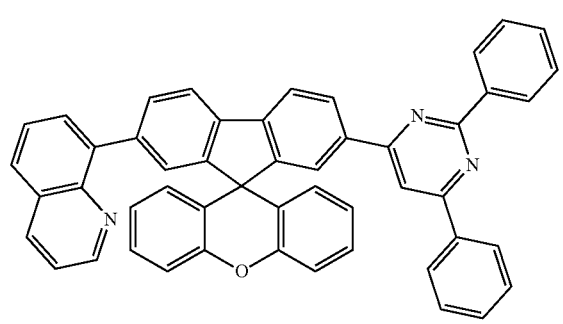
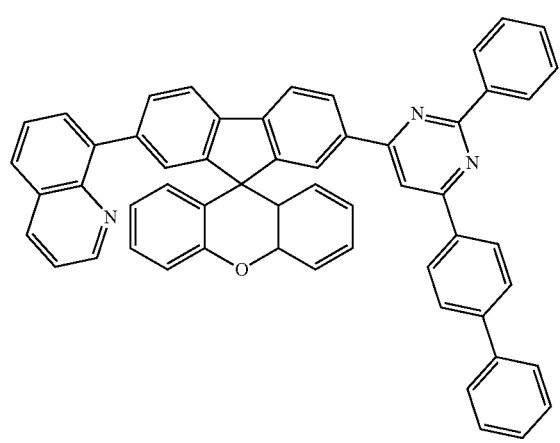
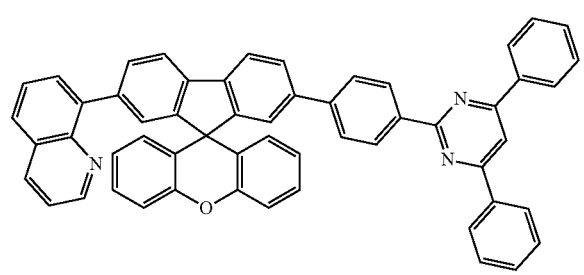
-continued
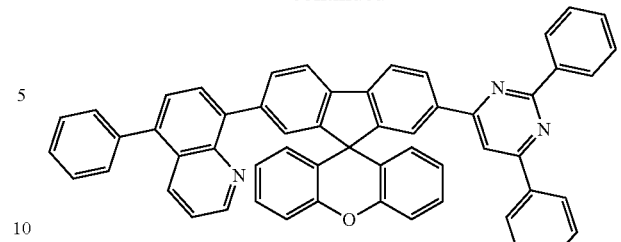
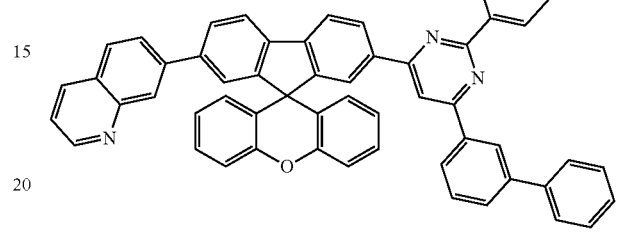
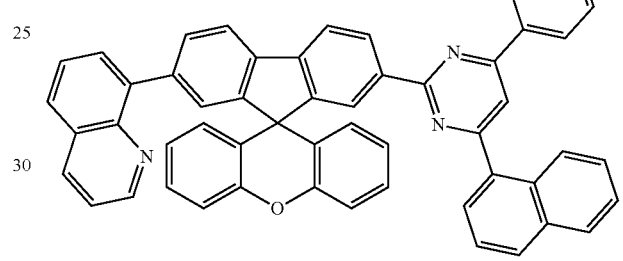
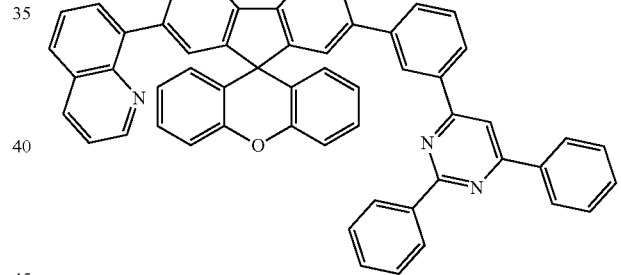
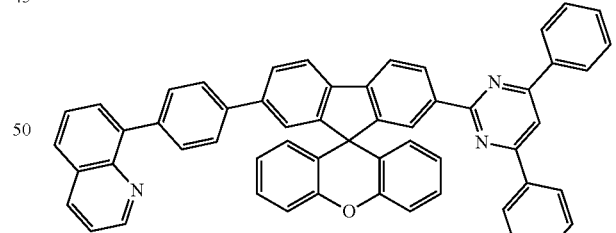
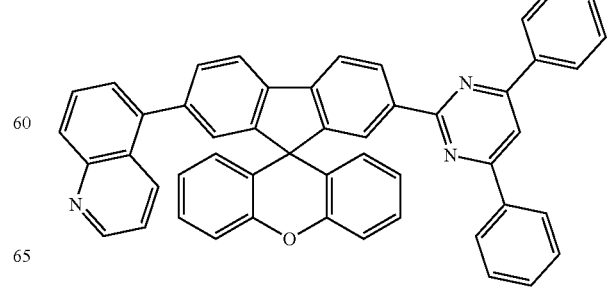

55
-continued
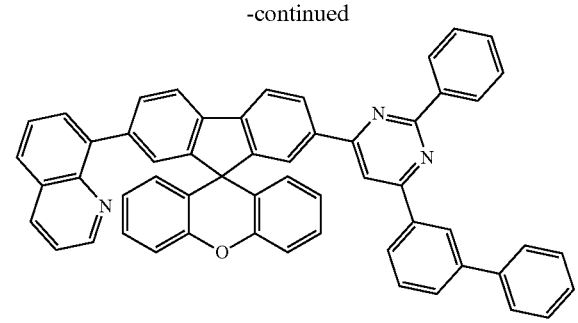
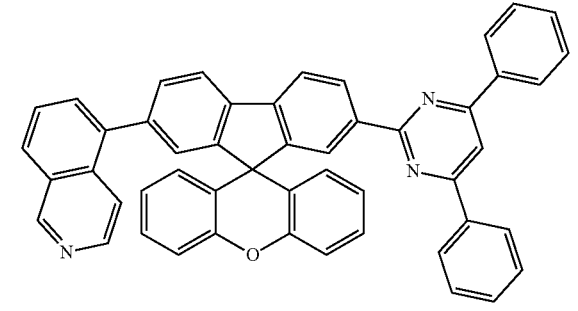
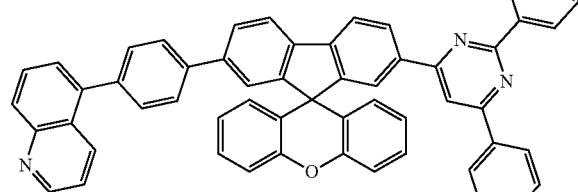
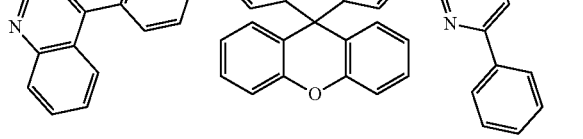
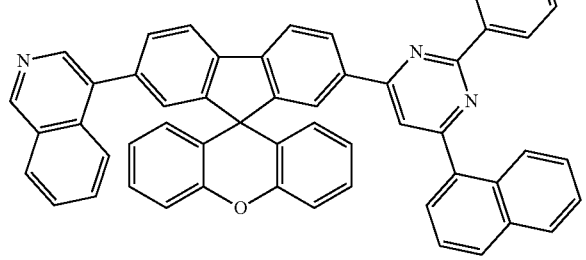
56
-continued
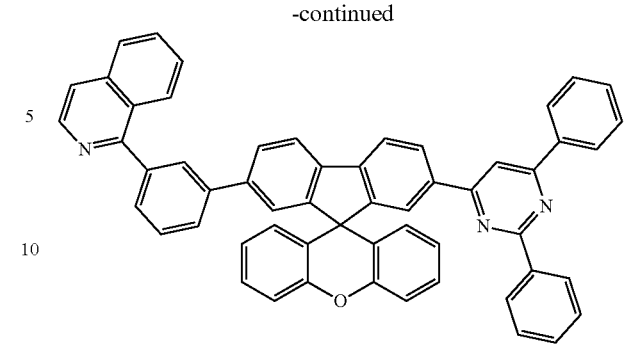
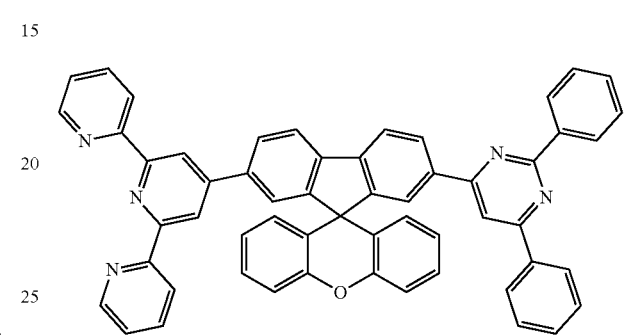
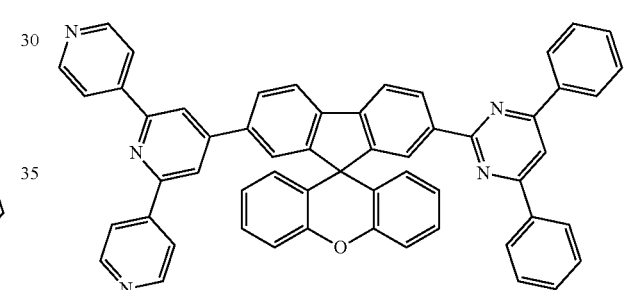
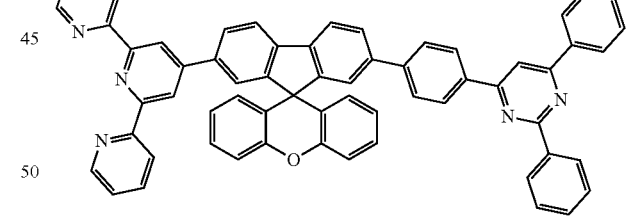
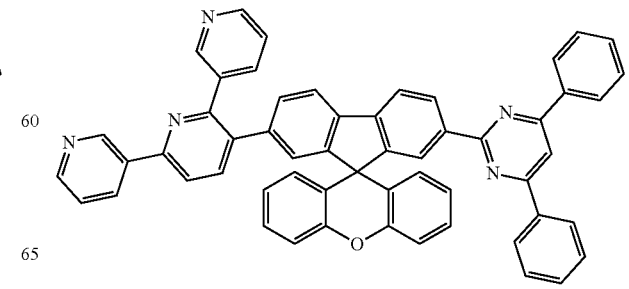

57
-continued
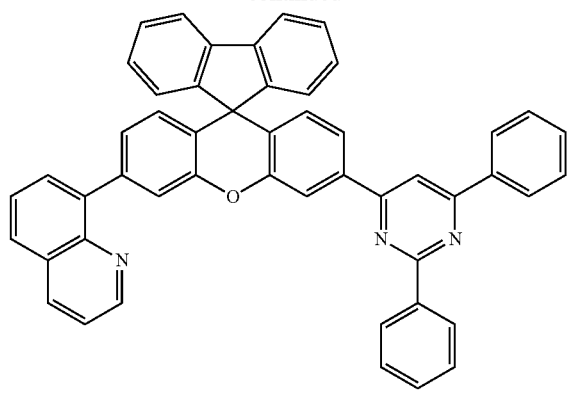
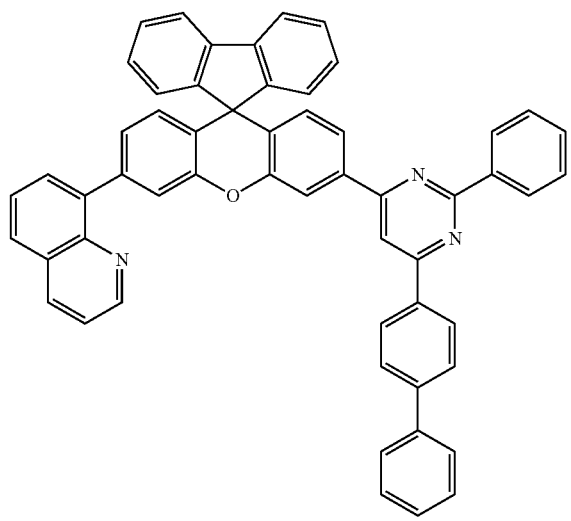
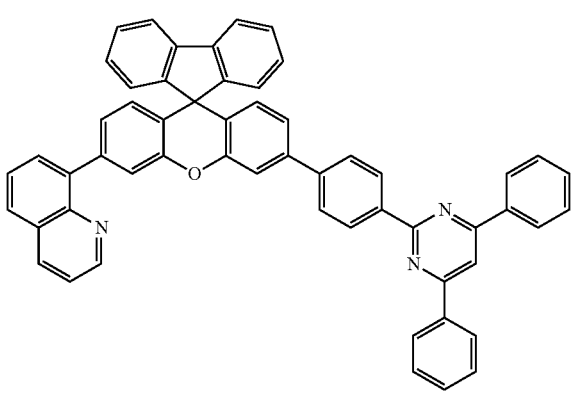
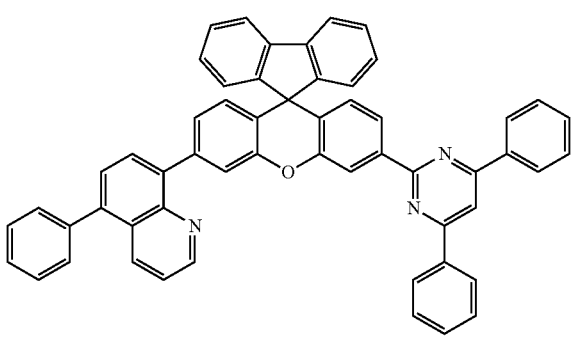
58
-continued
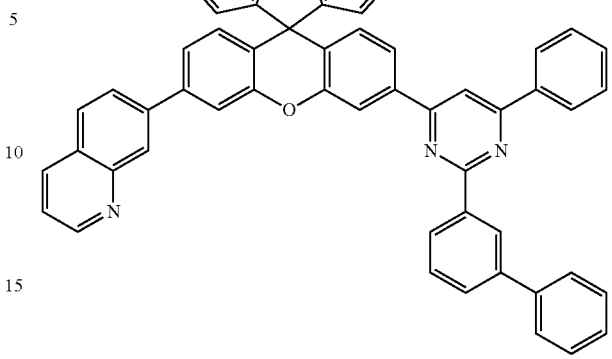
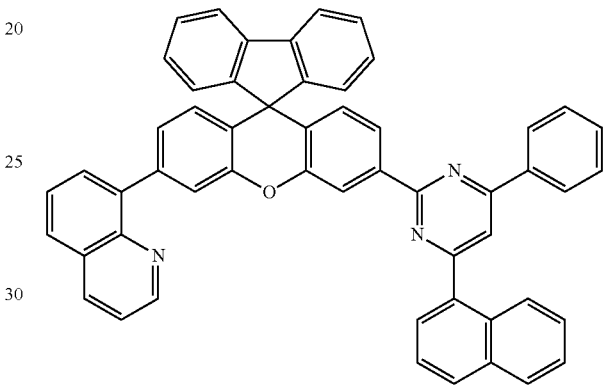
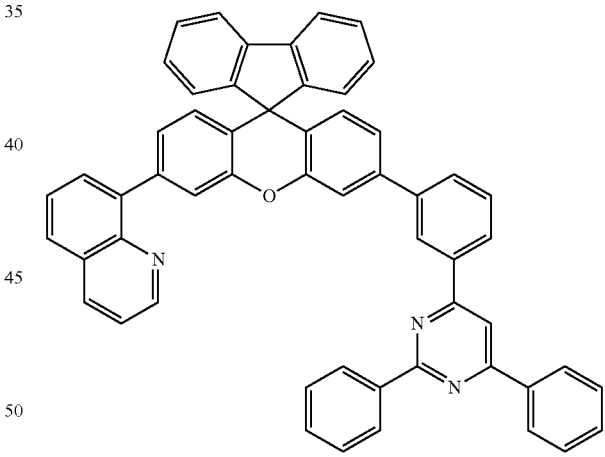
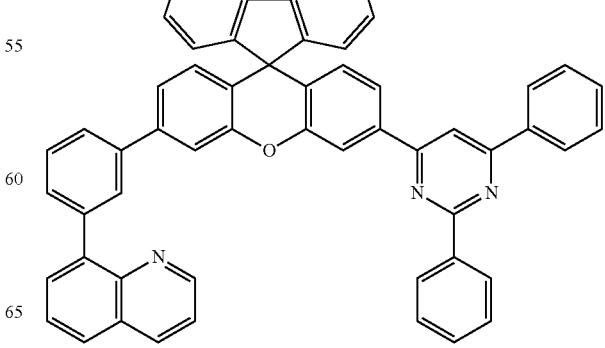

59
-continued
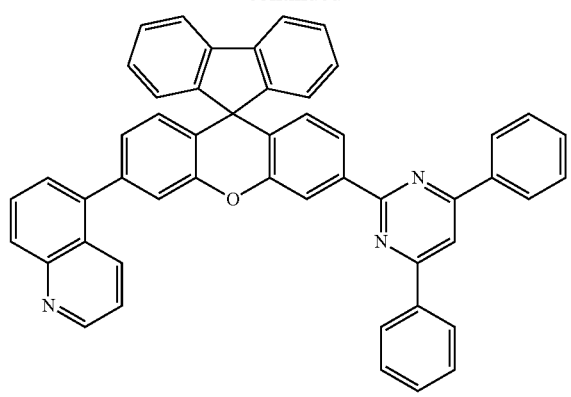
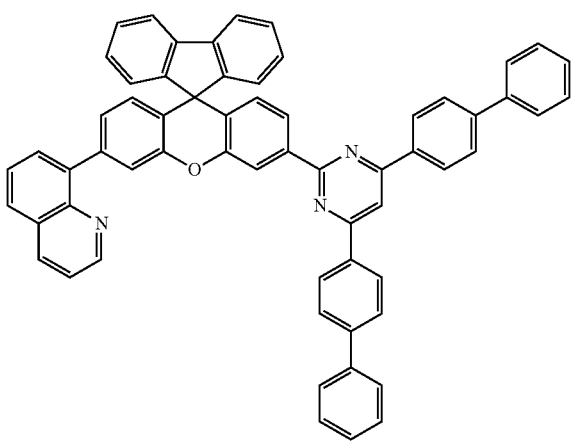
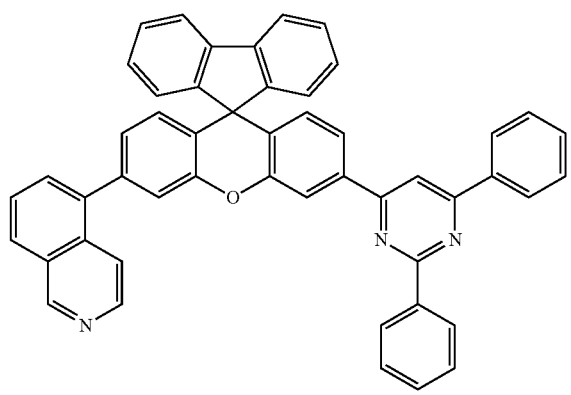
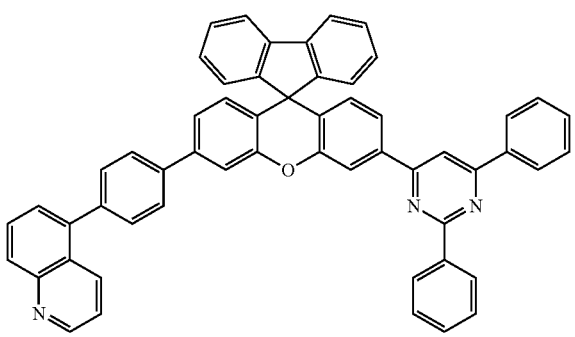
60
-continued
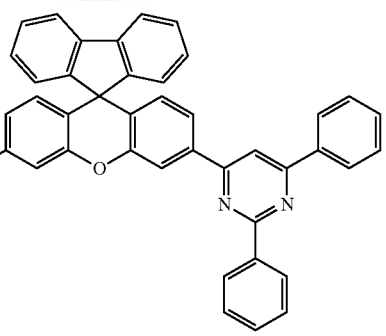
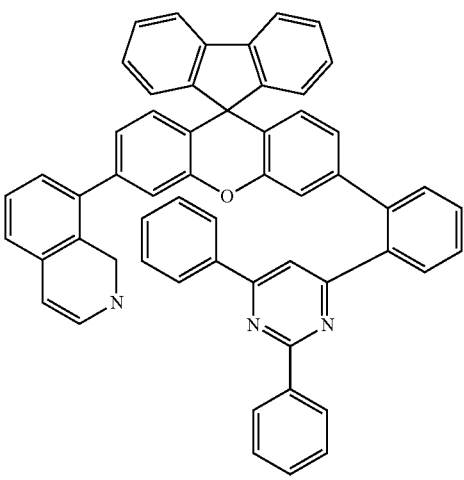
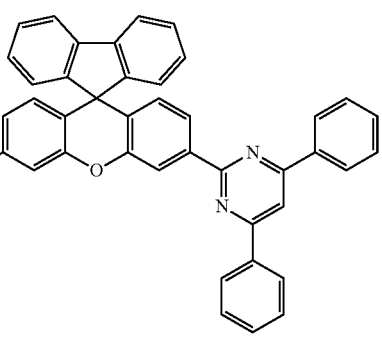

-continued
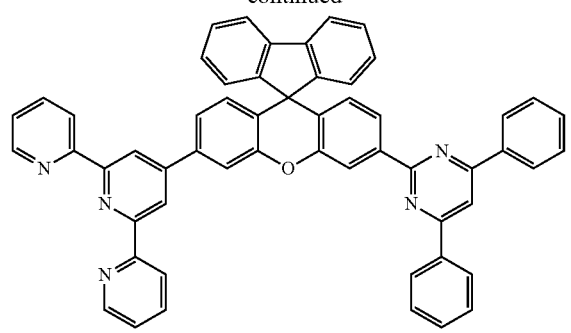
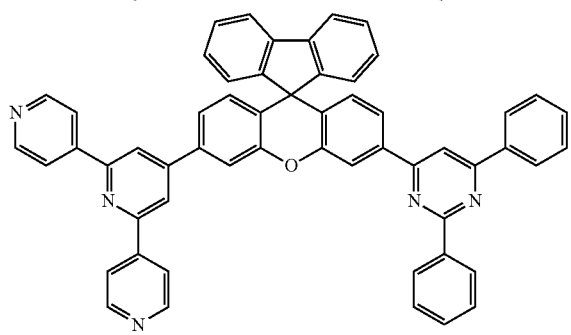
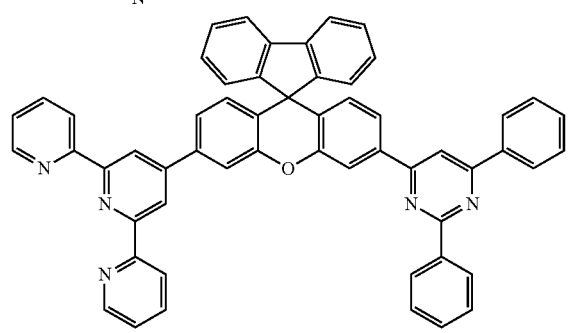
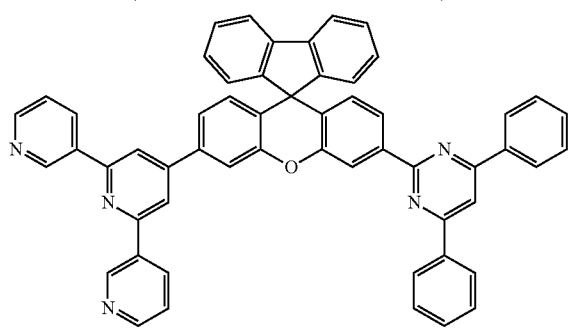
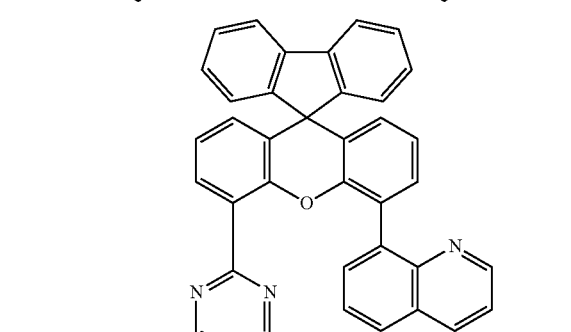
-continued
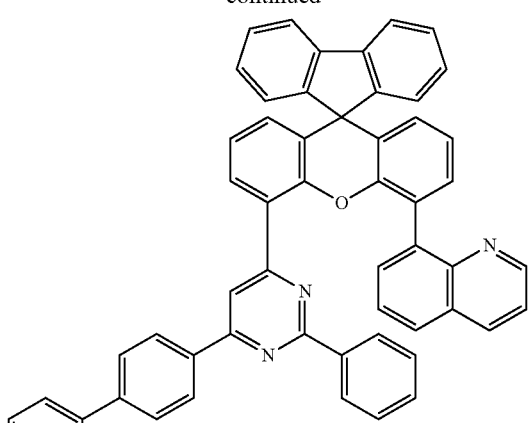
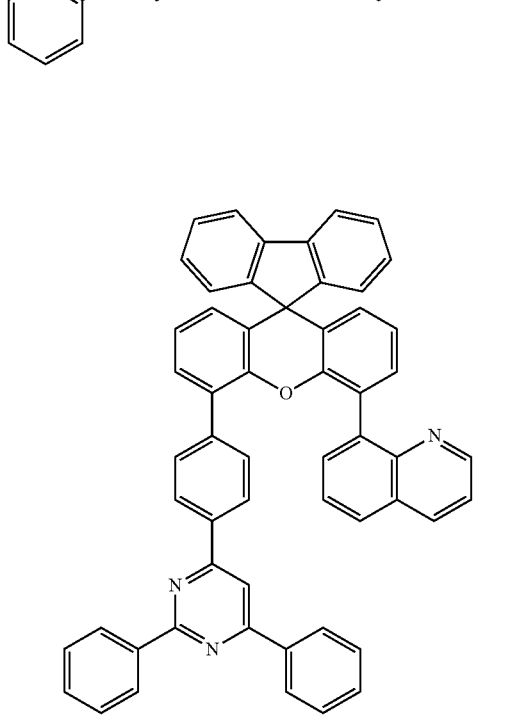
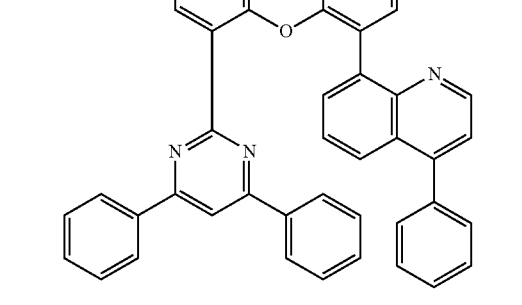

63
-continued
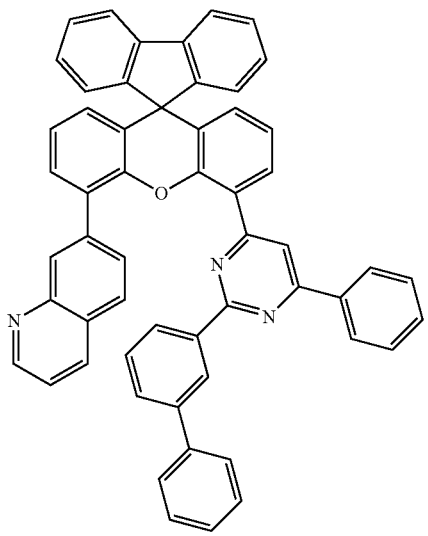
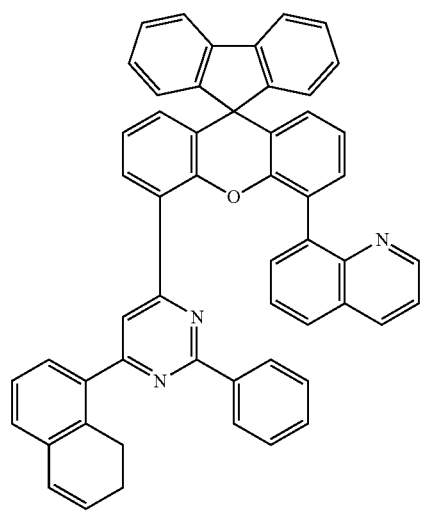
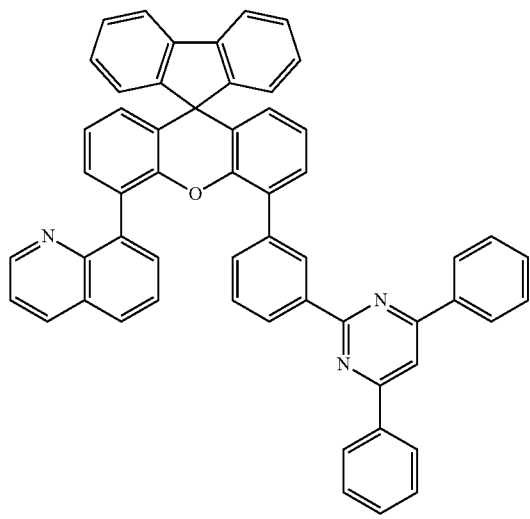
64
-continued
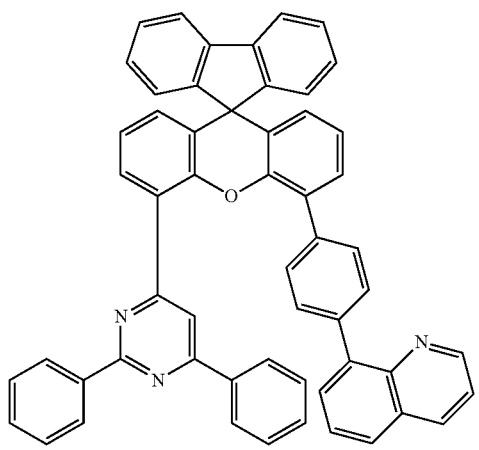
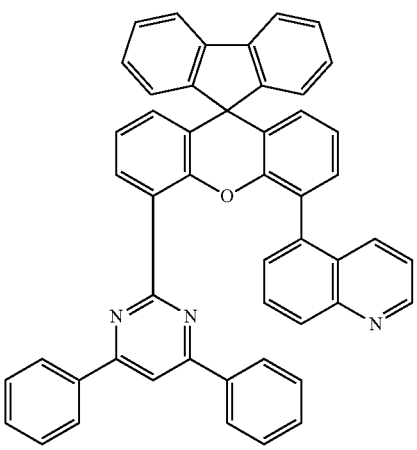
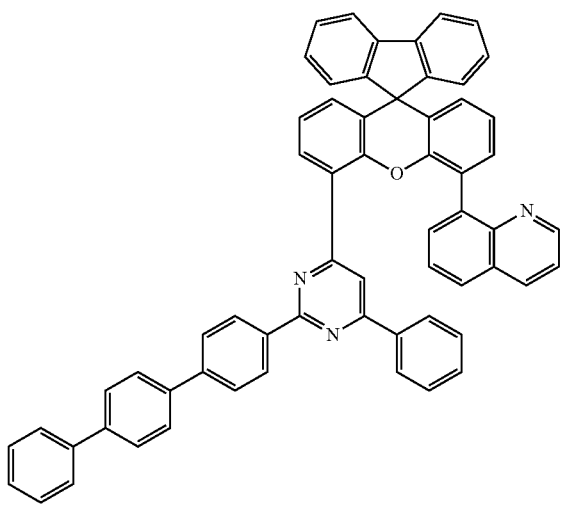

65
-continued
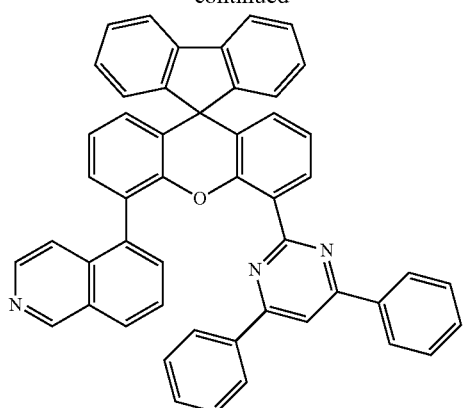
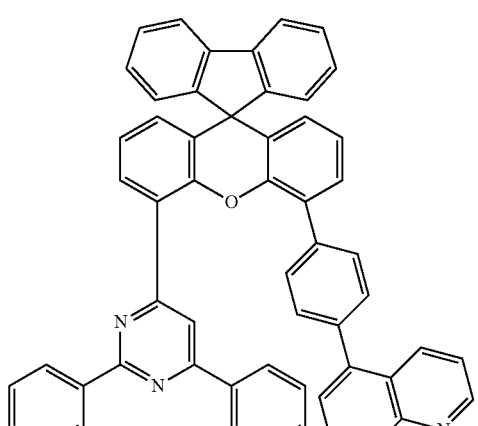
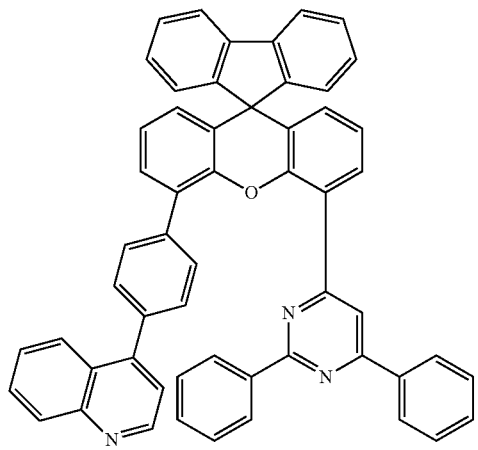
66
-continued
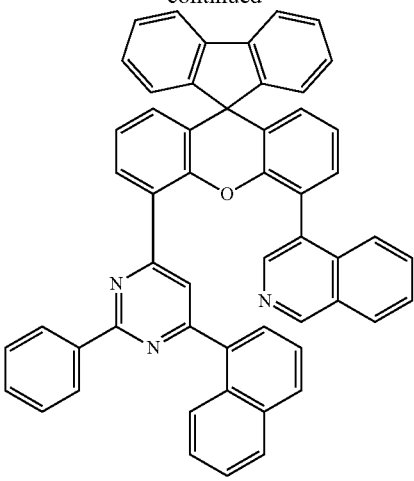
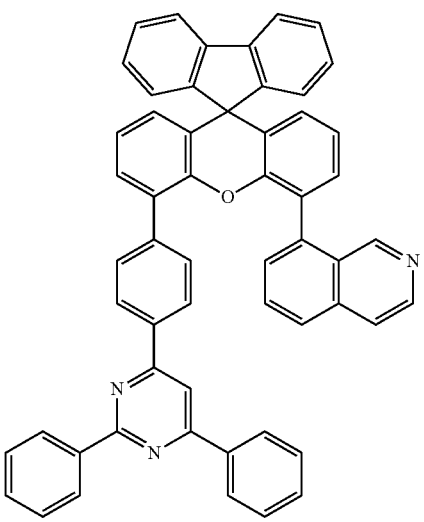
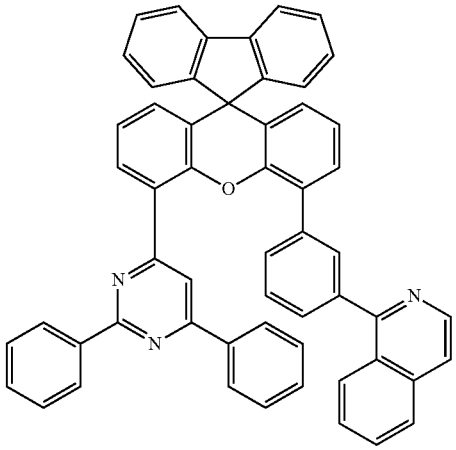

67
-continued
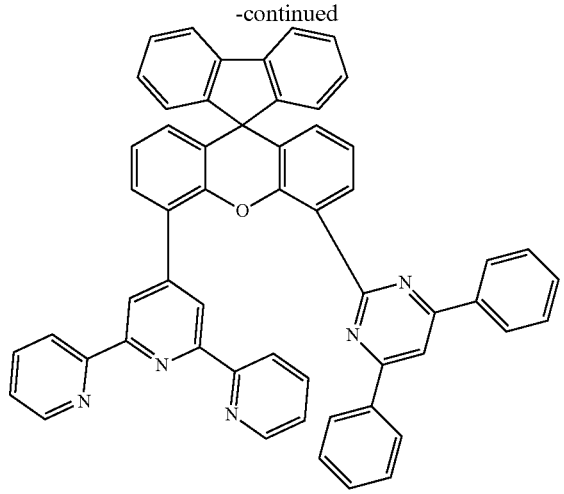
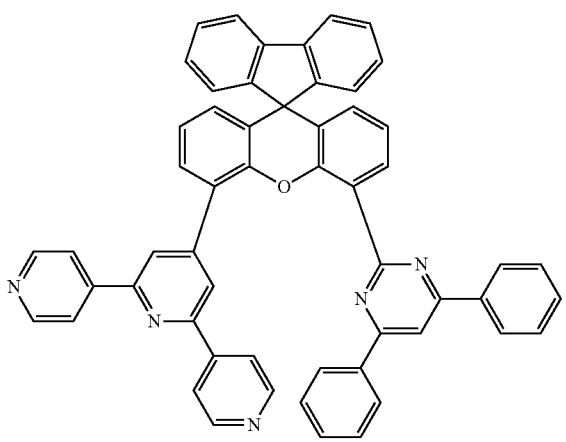
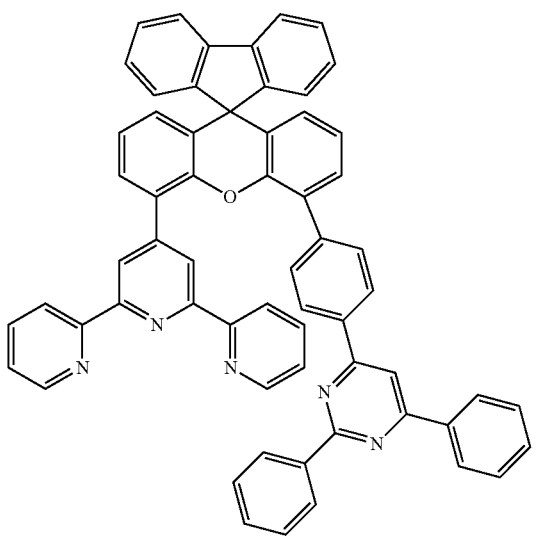
68
-continued
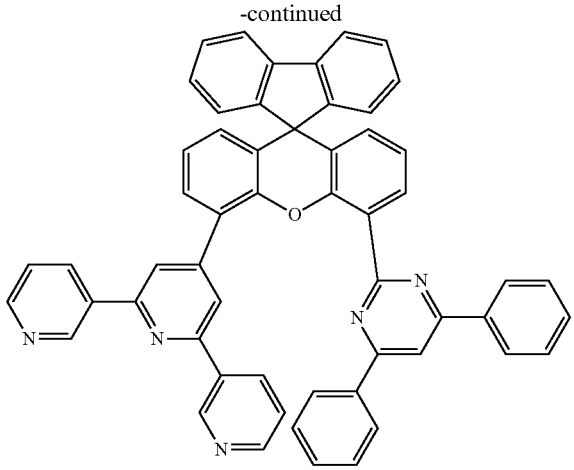
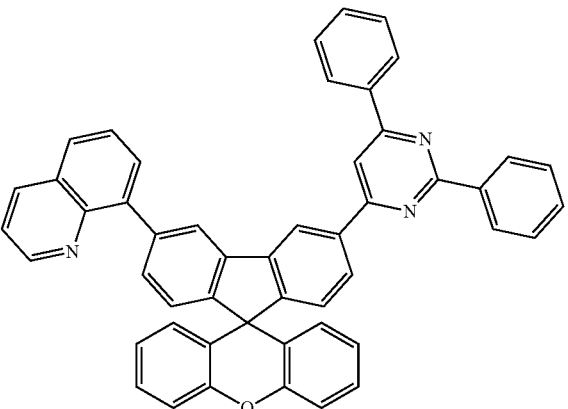
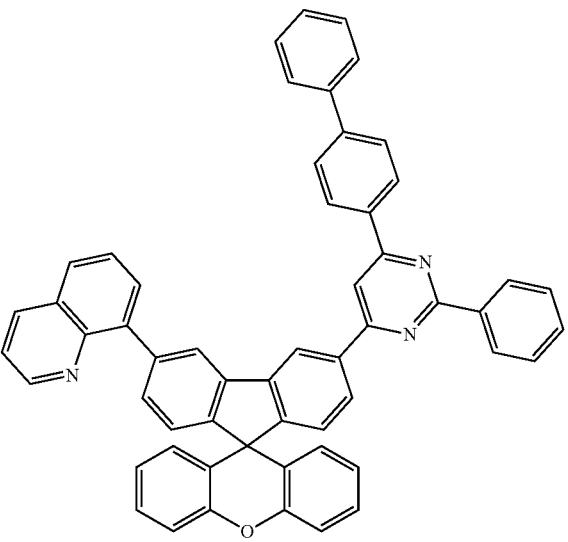

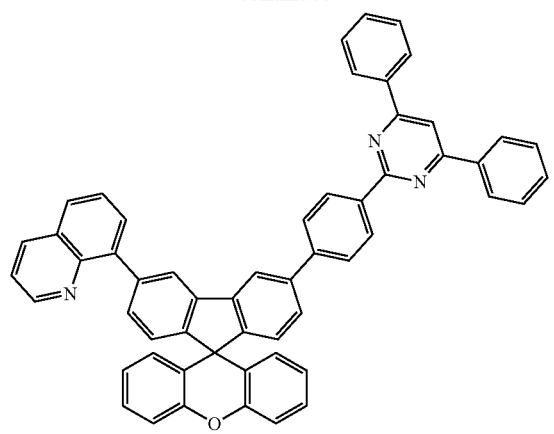
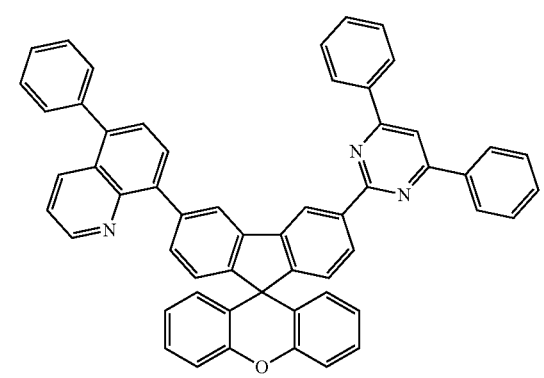
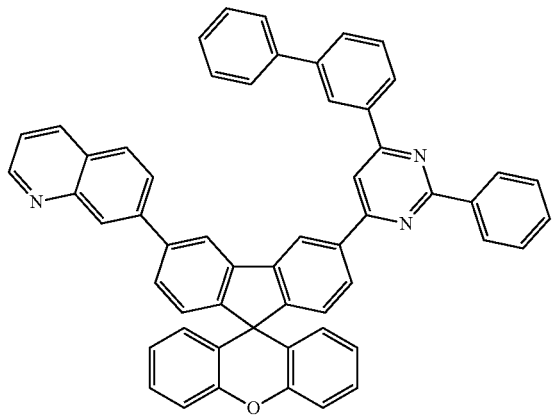
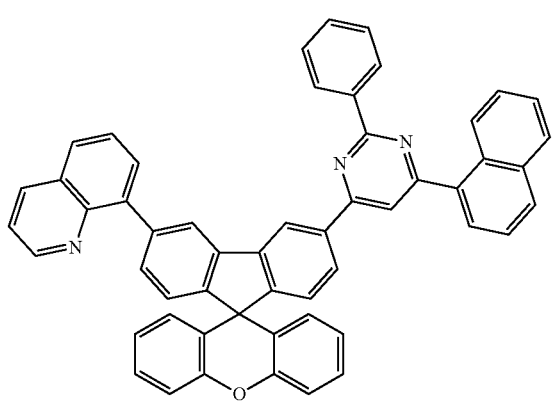
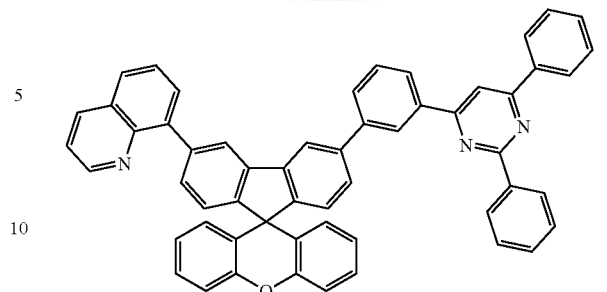
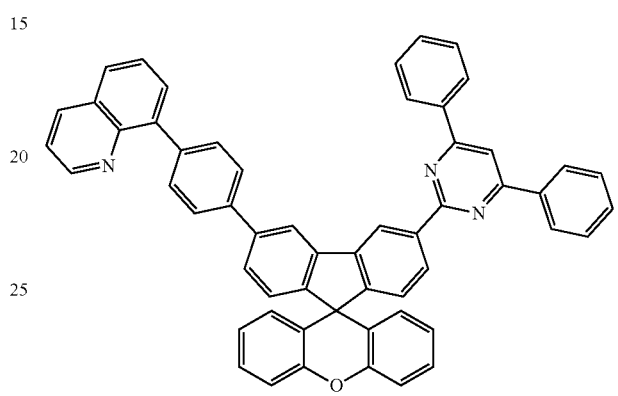
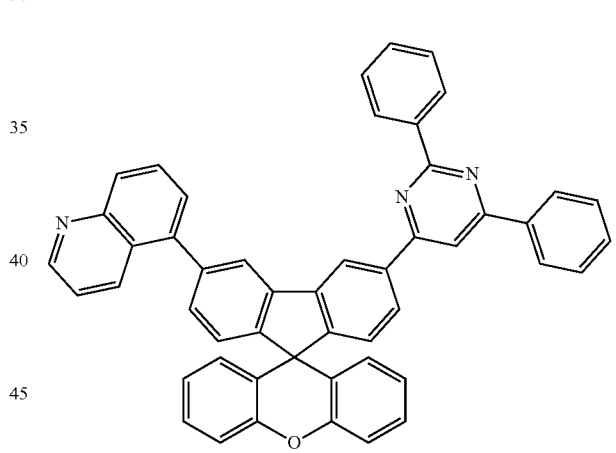
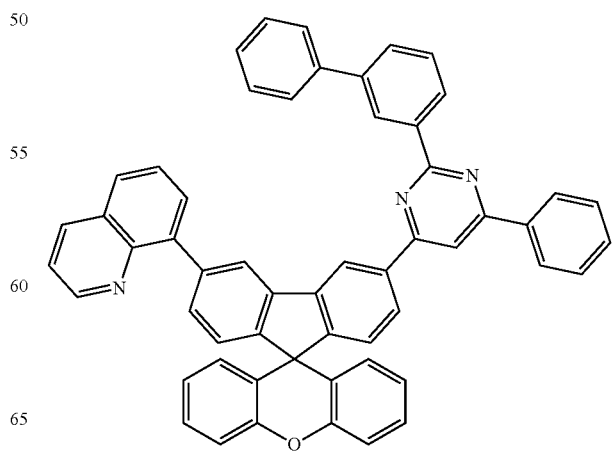

71
-continued
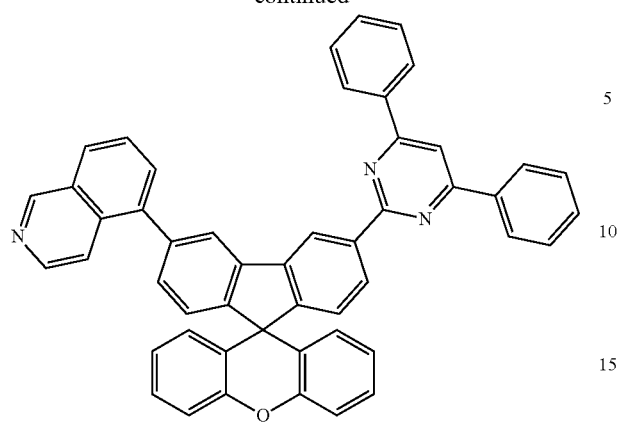
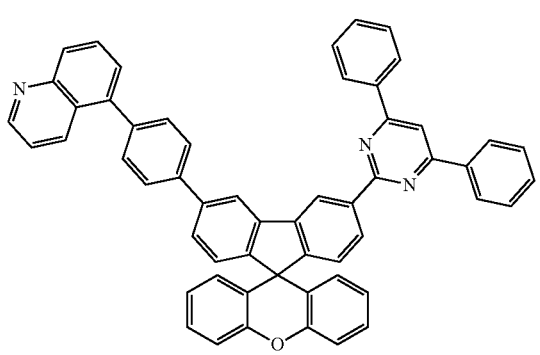
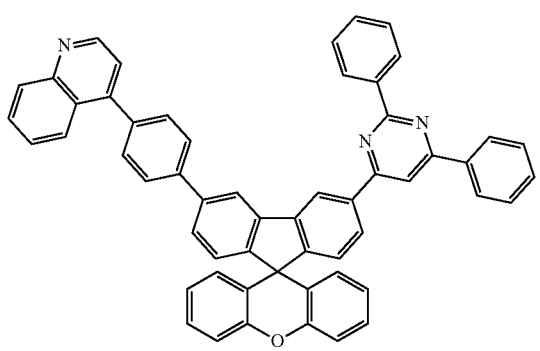
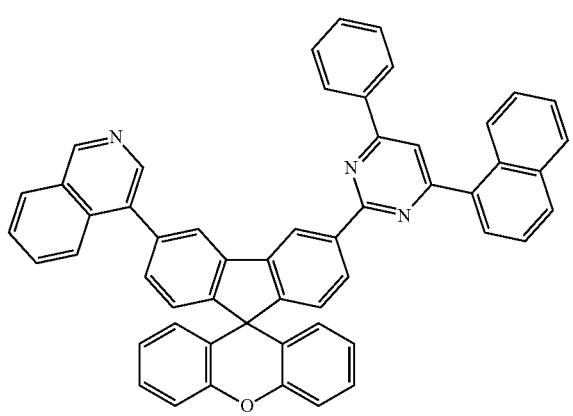
72
-continued
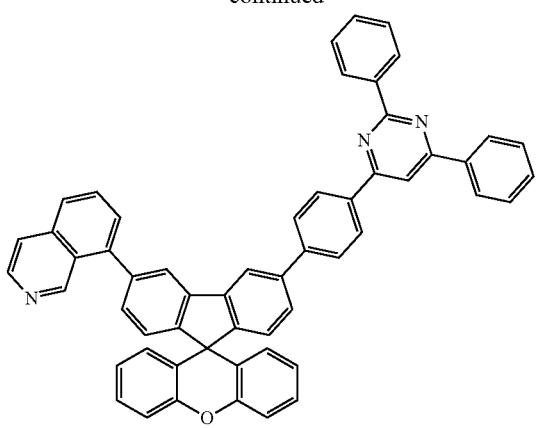
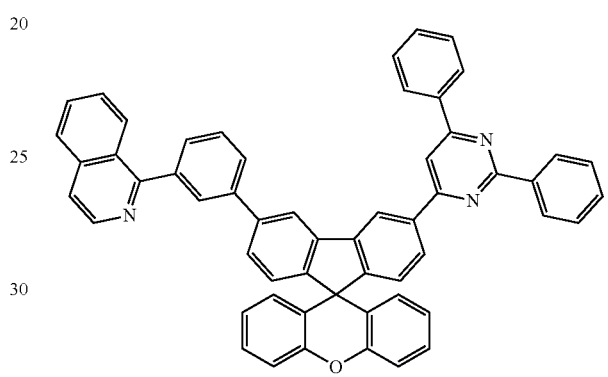
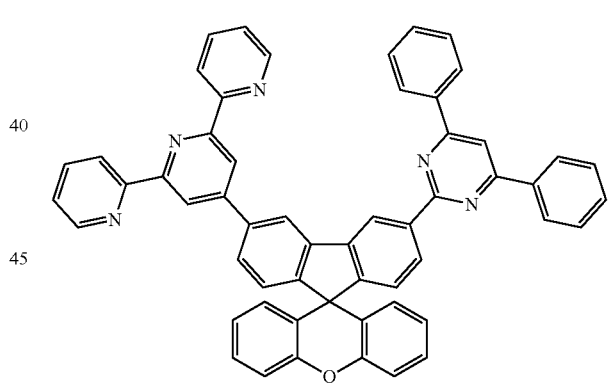
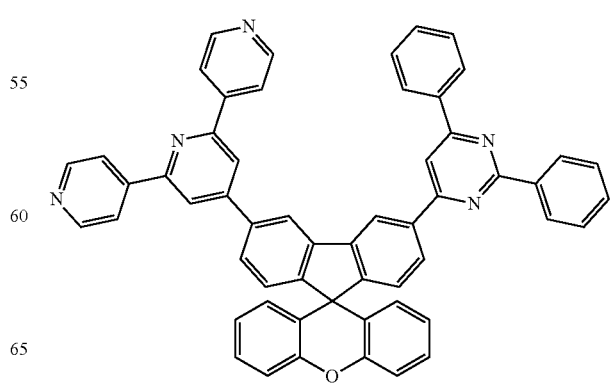

-continued
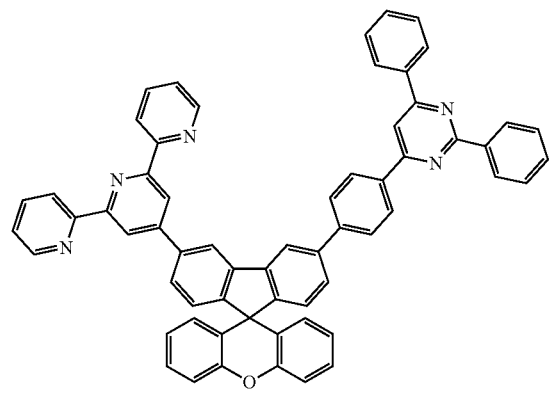
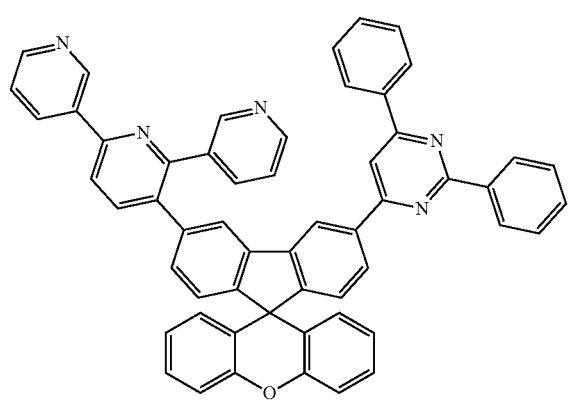
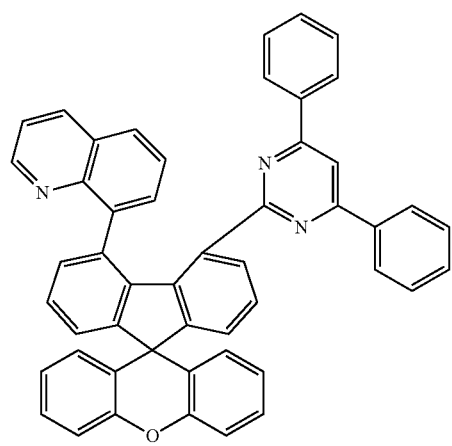
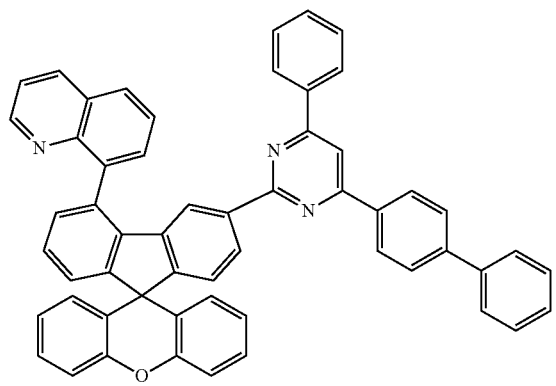
-continued
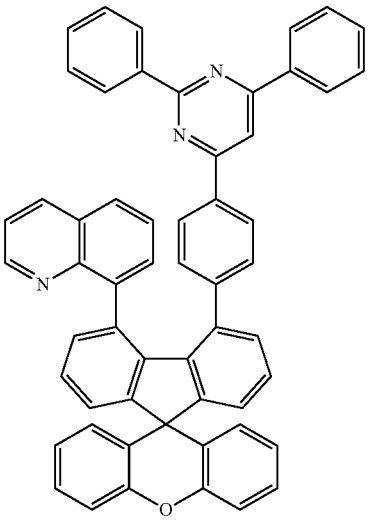
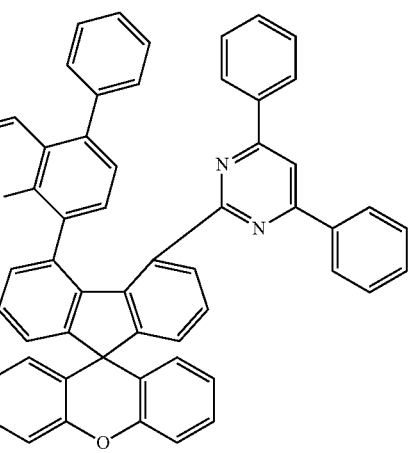
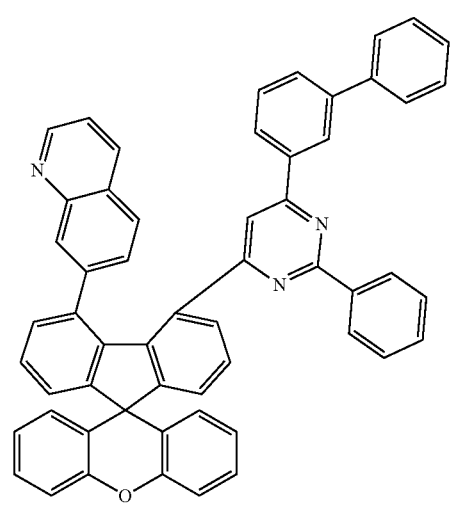

75
-continued
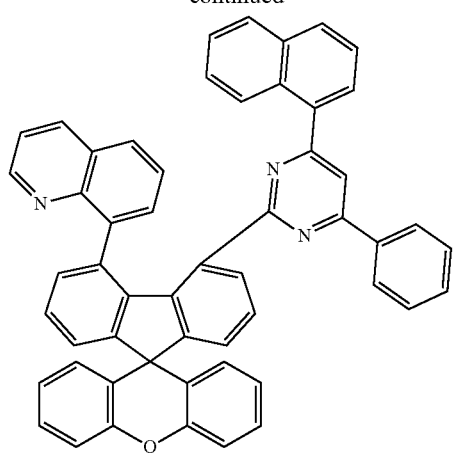
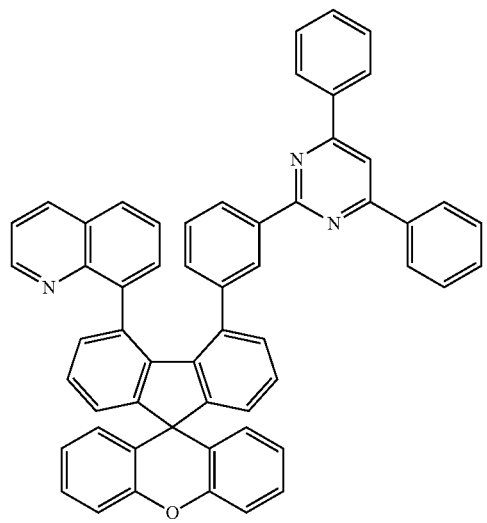
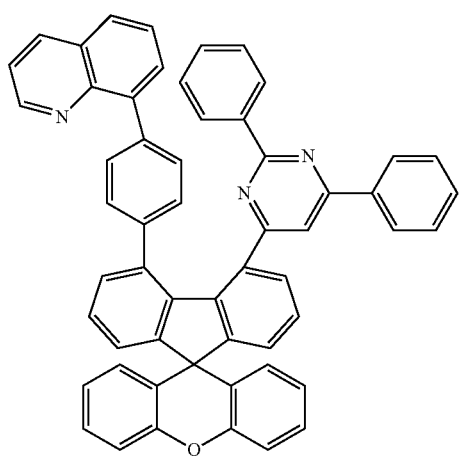
76
-continued
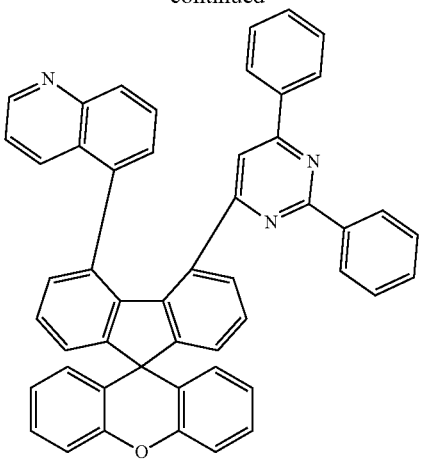
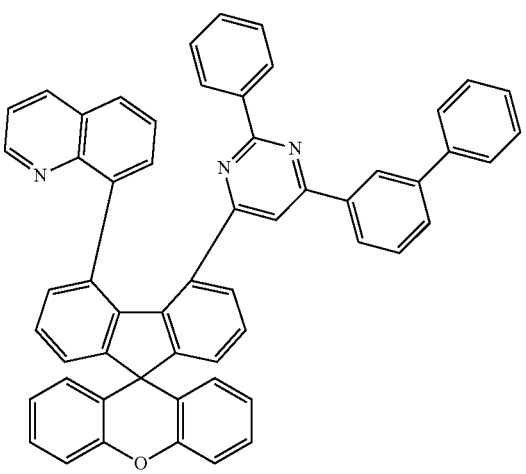
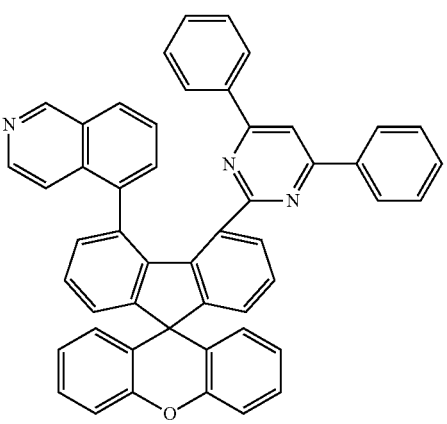

77
-continued
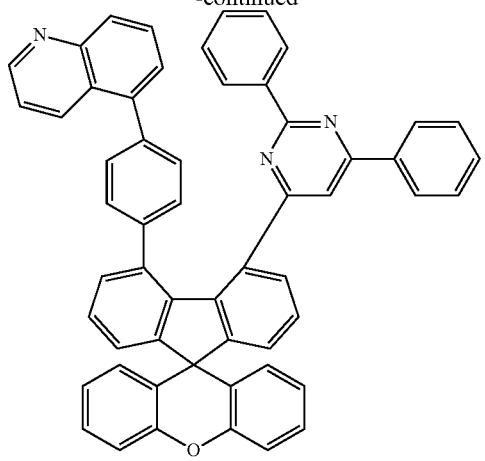
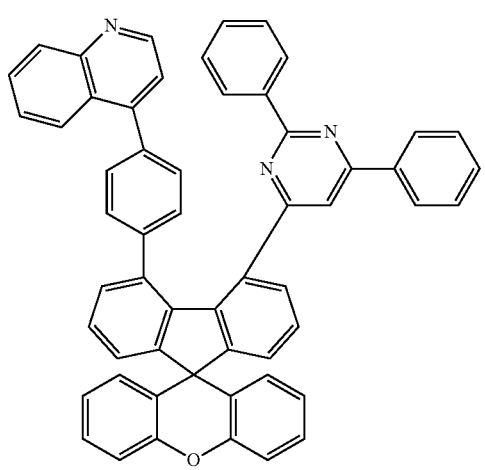
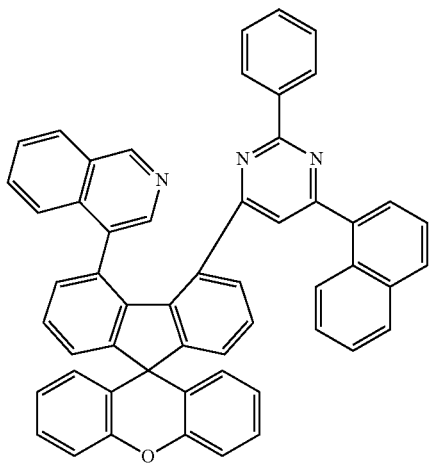
78
-continued
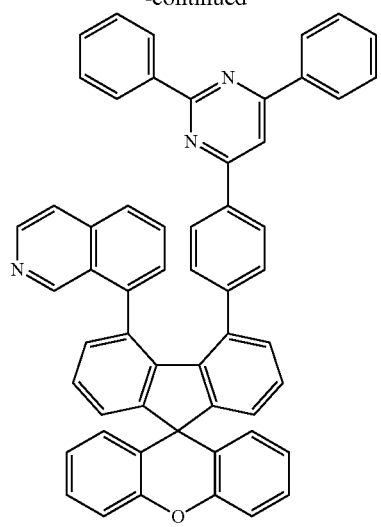
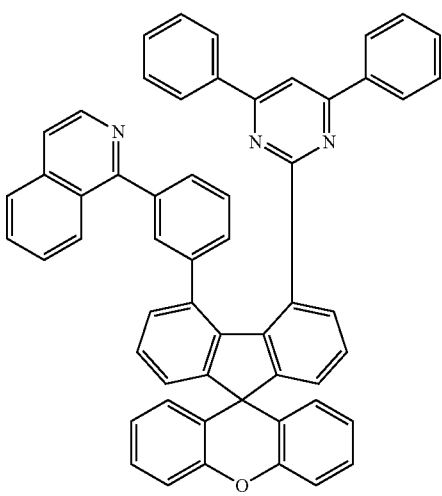
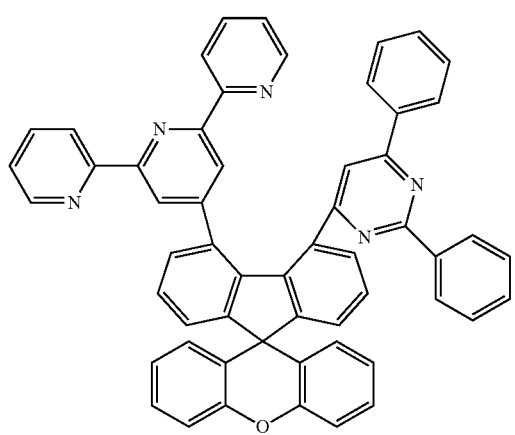

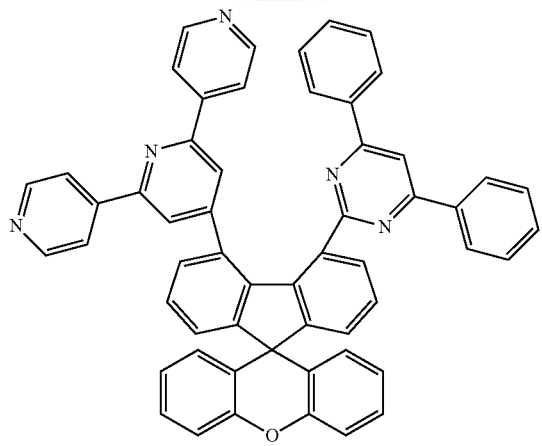
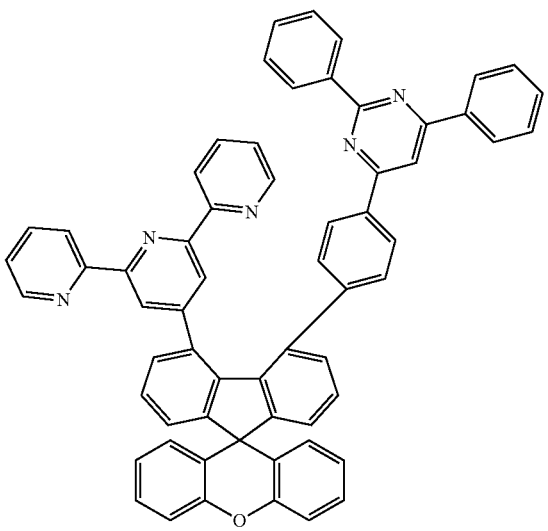
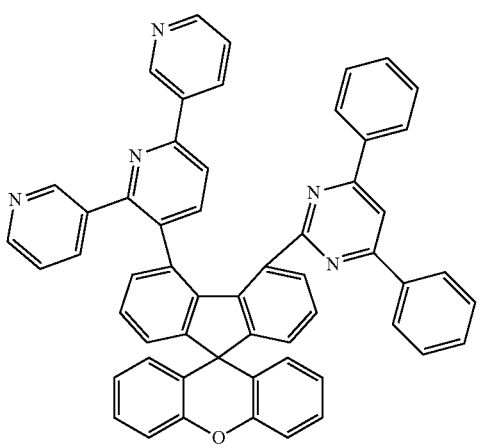
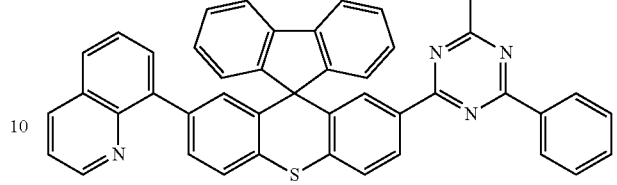
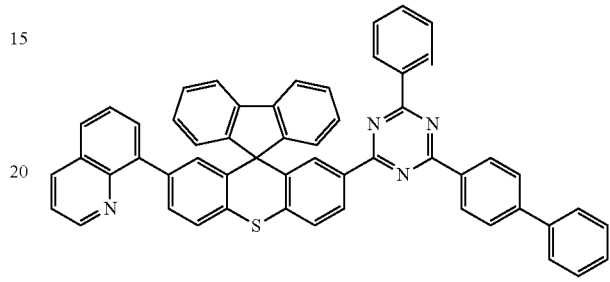
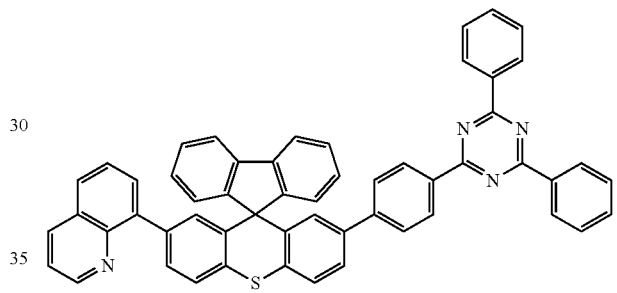
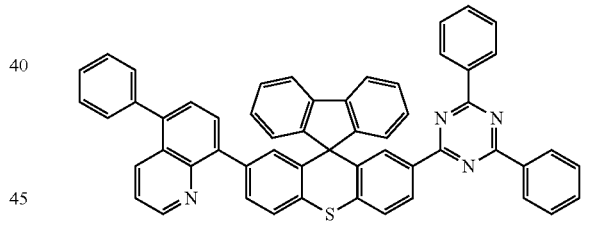
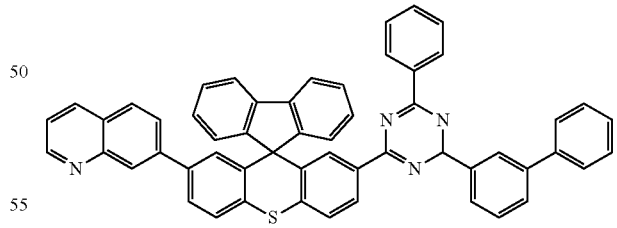
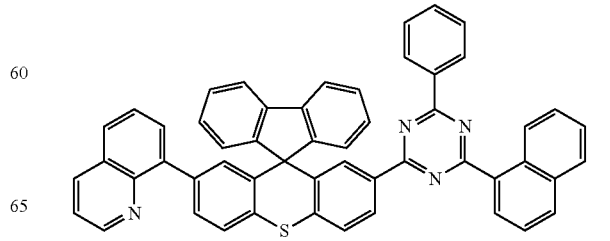

81
-continued
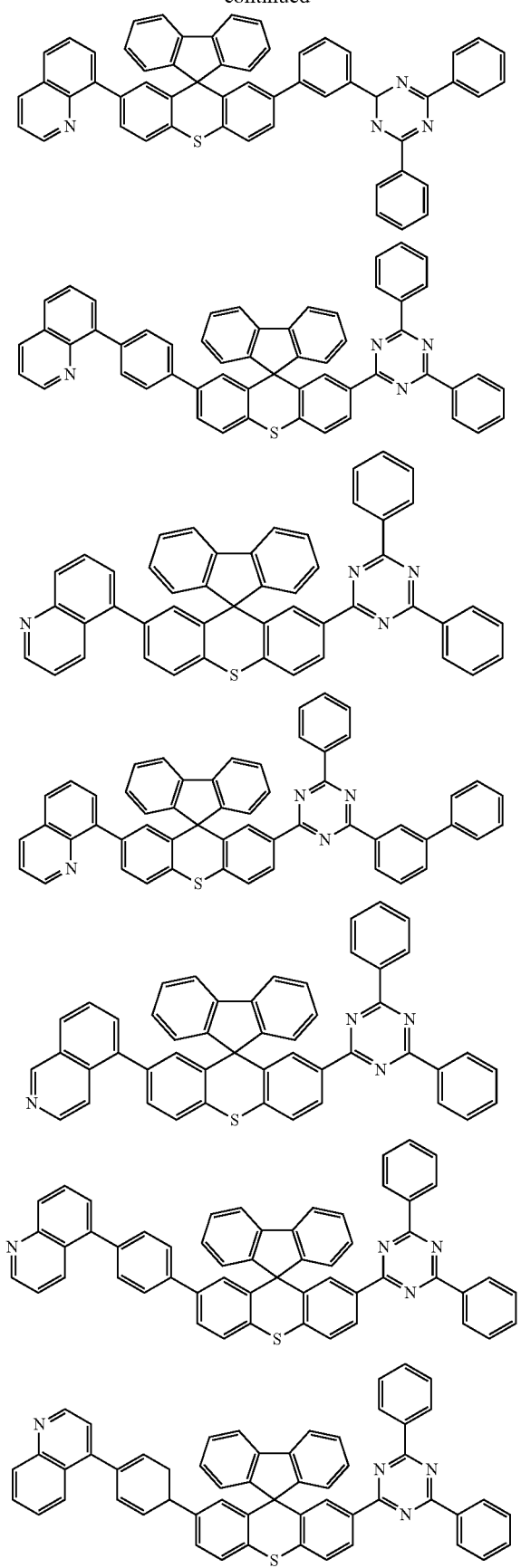
82
-continued
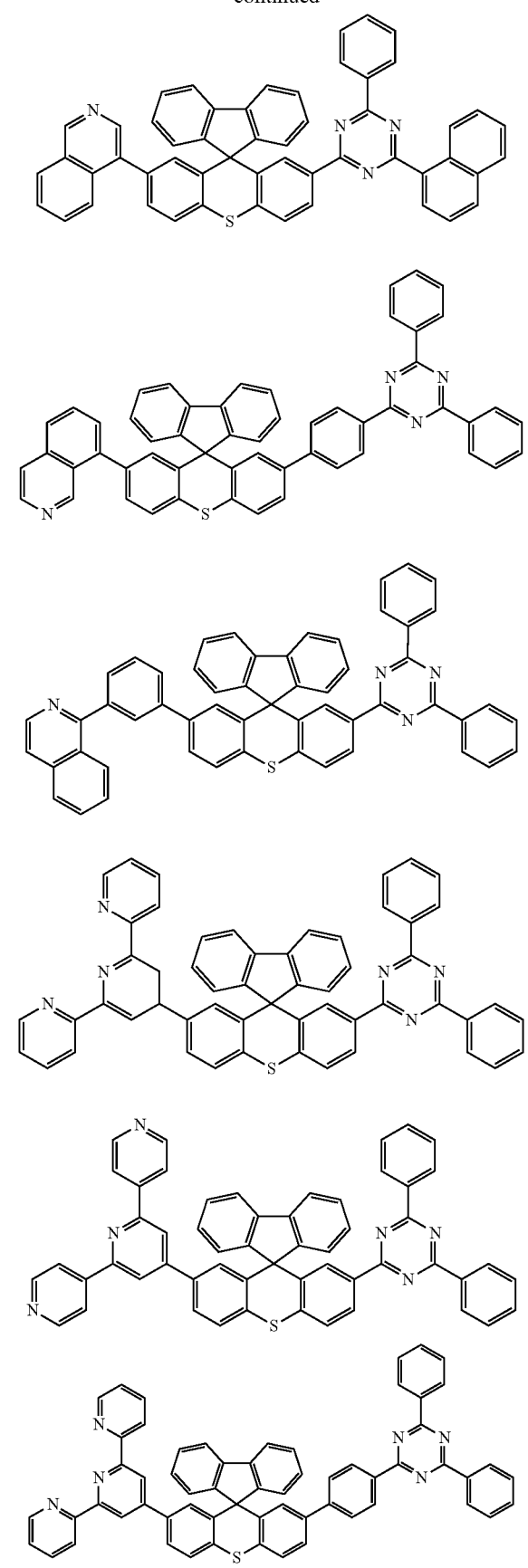

83
-continued
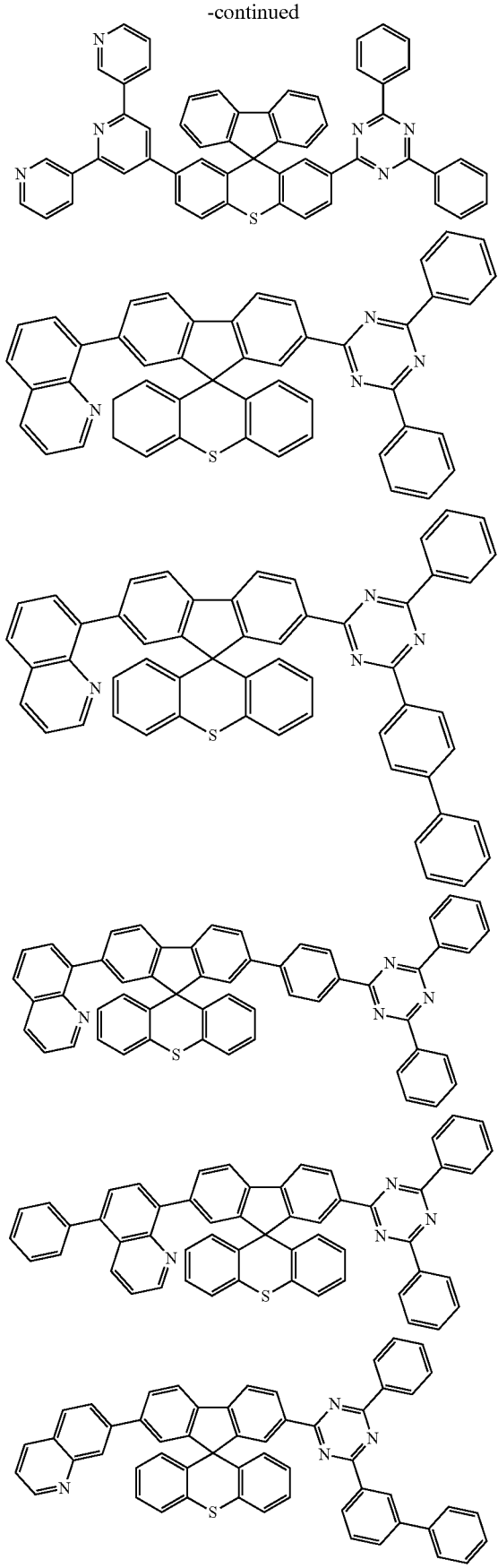
84
-continued
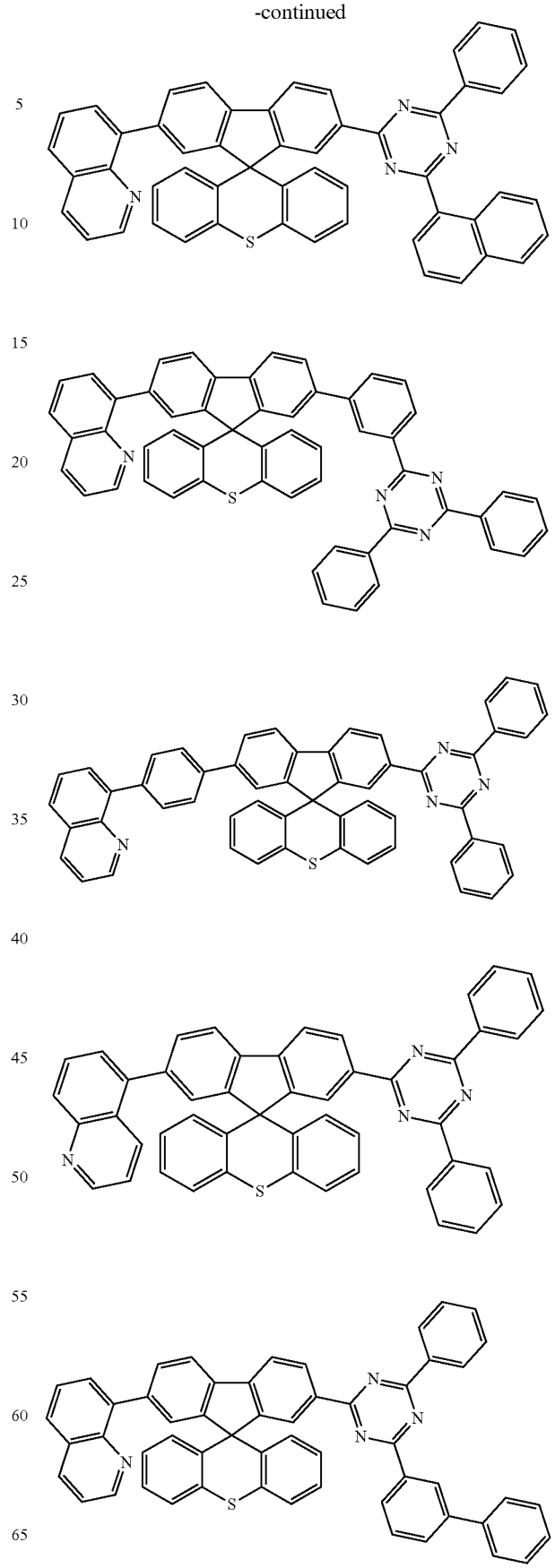

85
-continued
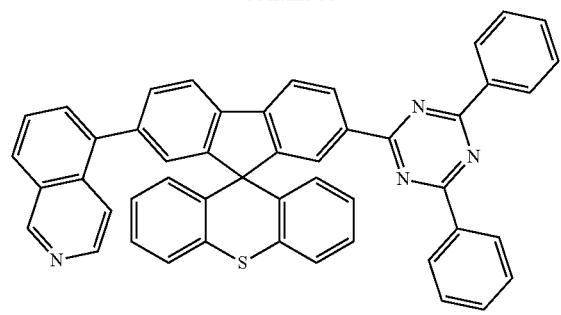
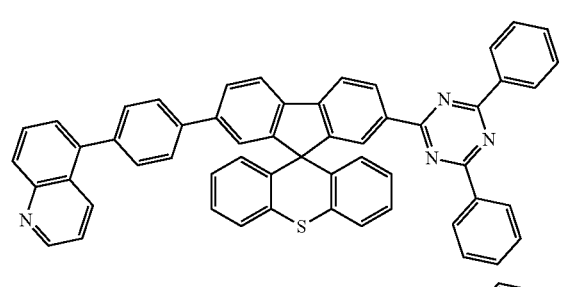
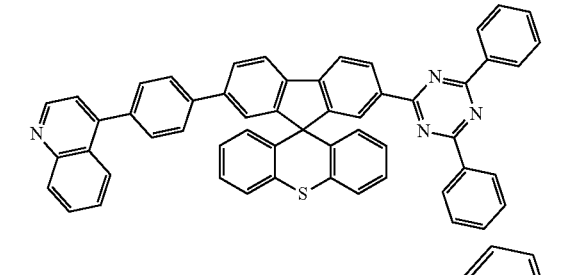
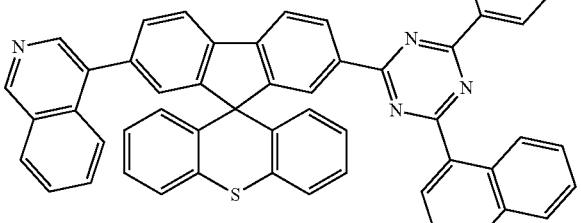
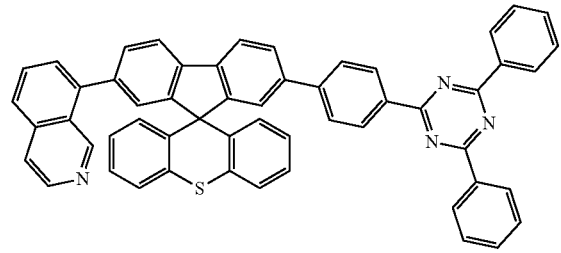
86
-continued
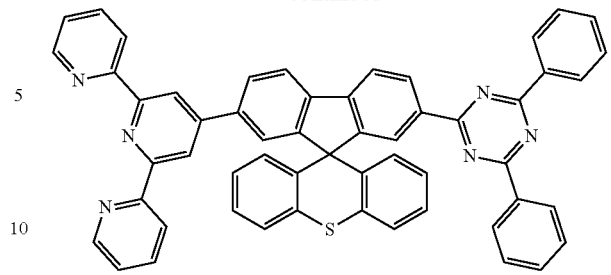
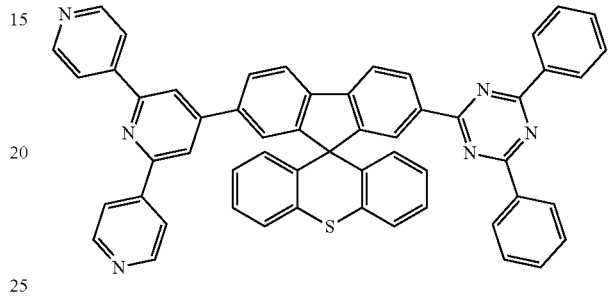
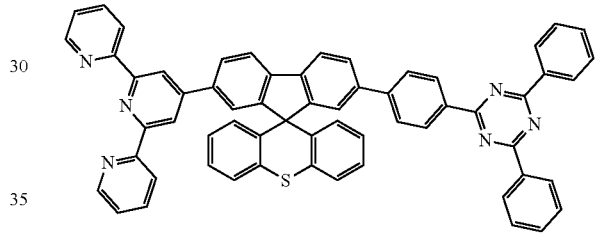
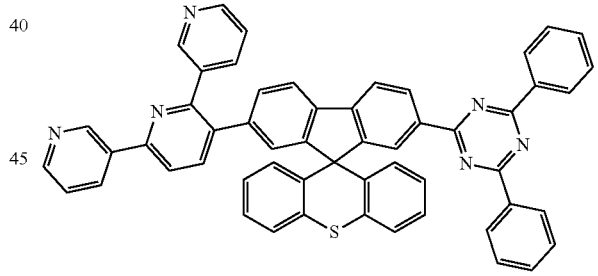
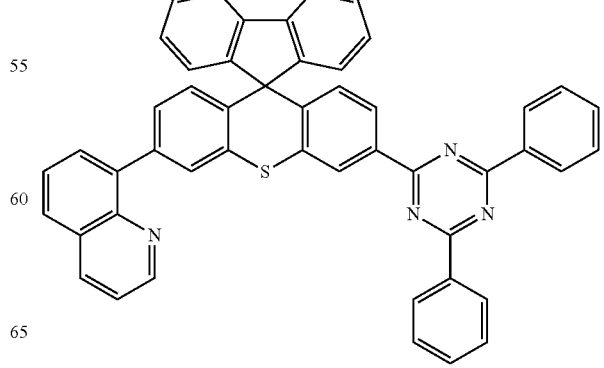

87
-continued
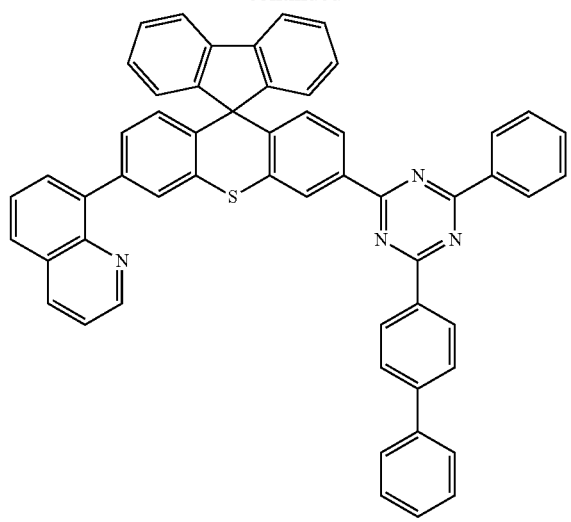
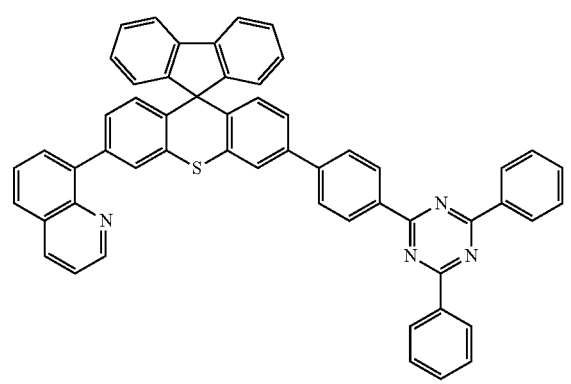
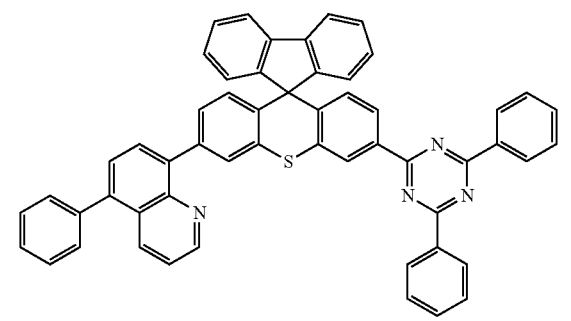
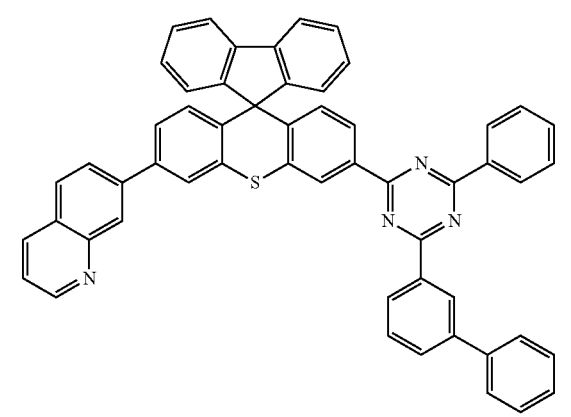
88
-continued
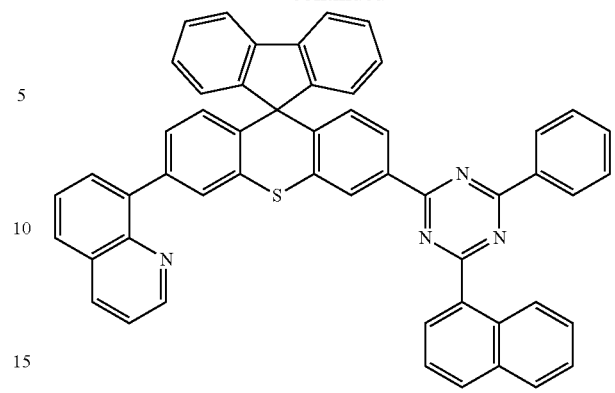
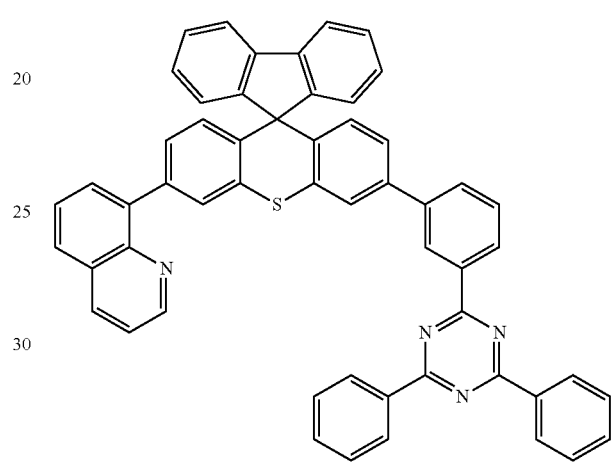
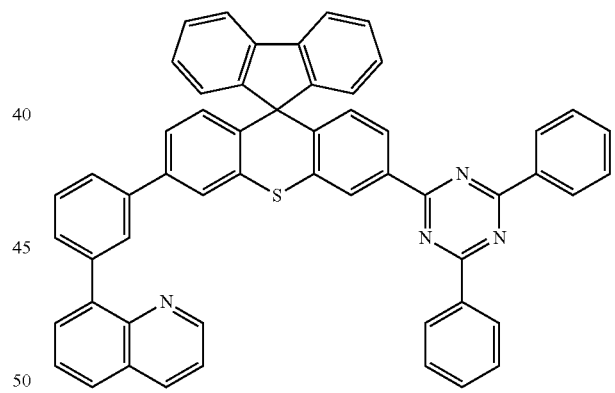
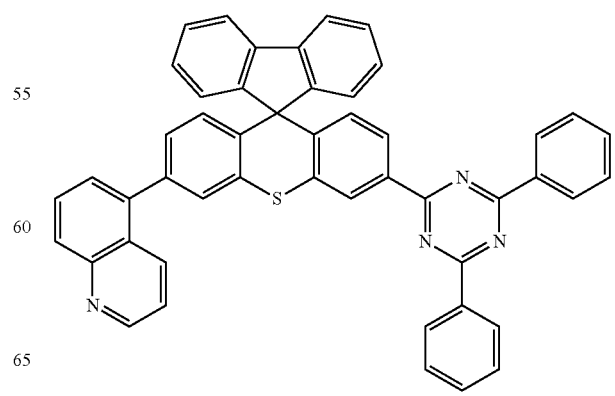

89
-continued
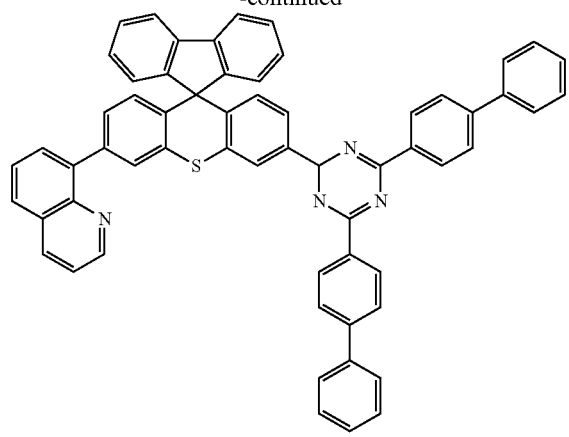
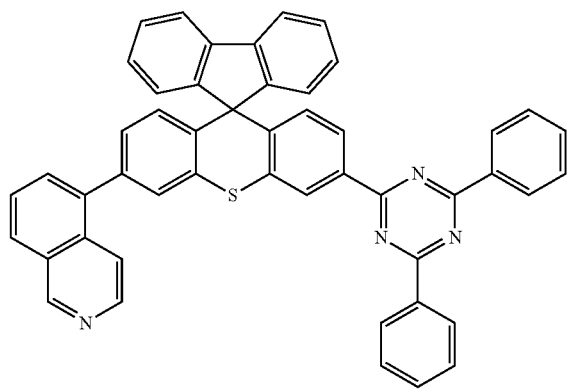
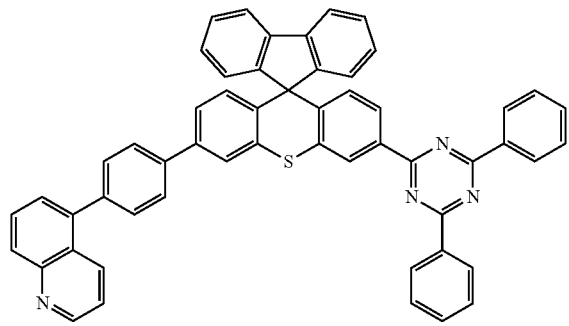
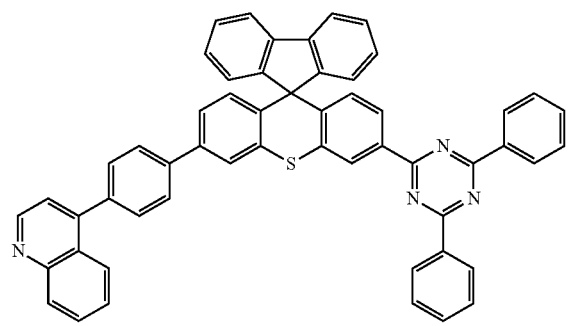
90
-continued
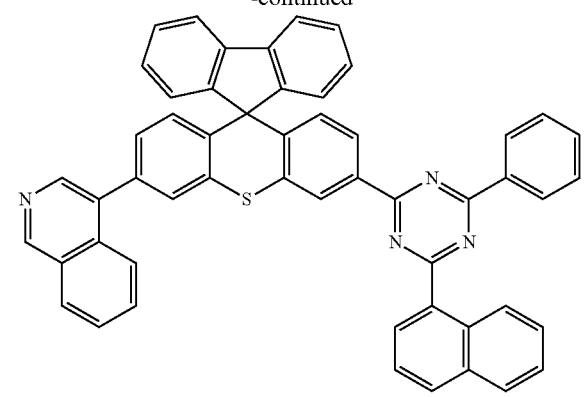
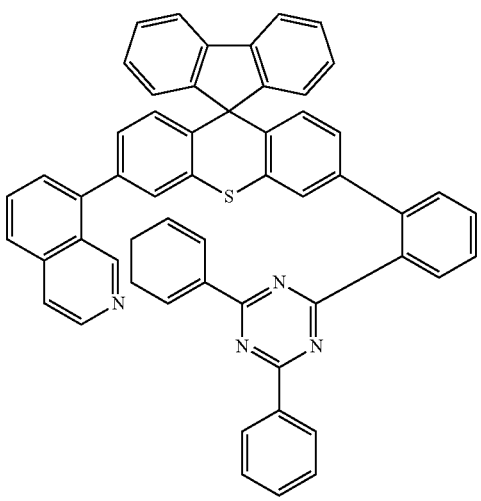
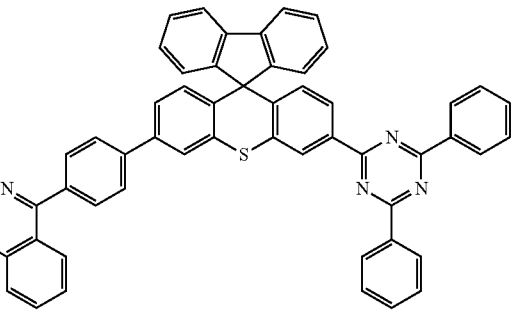
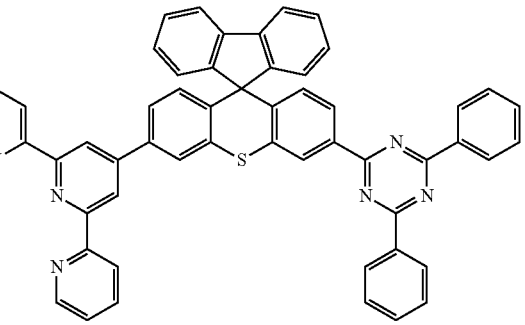

-continued
91
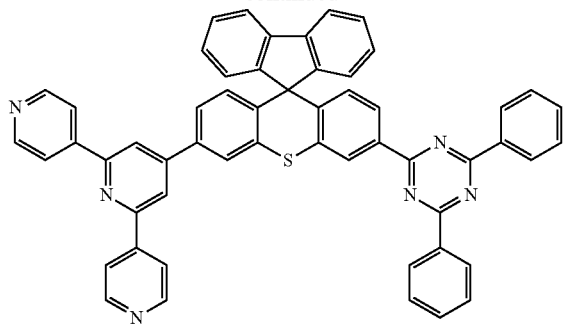
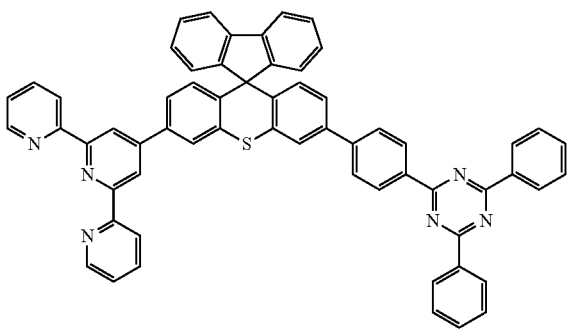
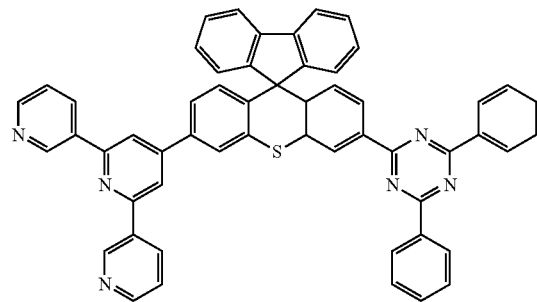
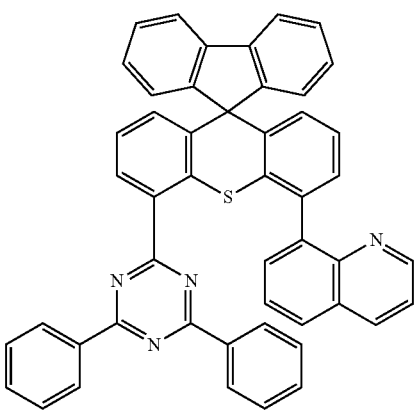
92
-continued
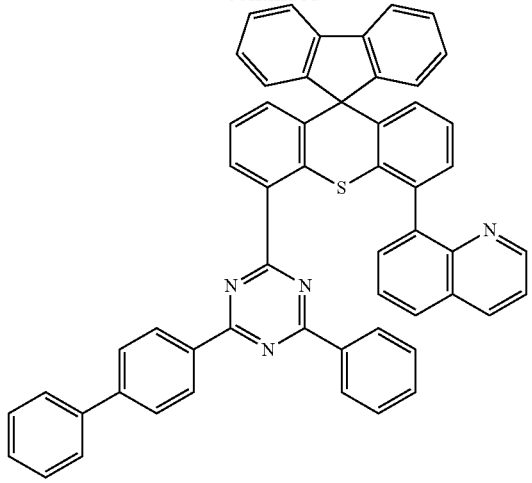
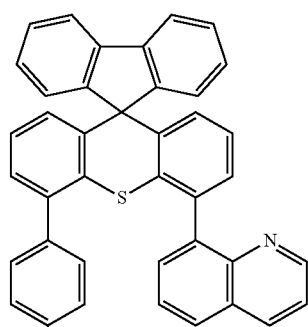
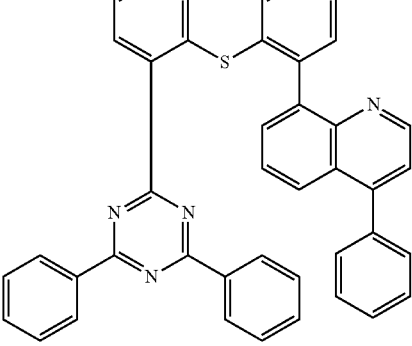

93
-continued
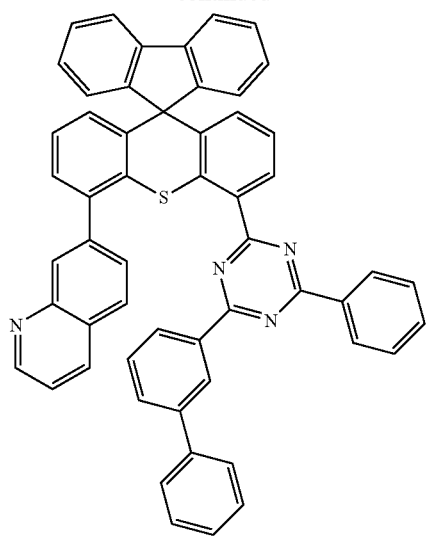
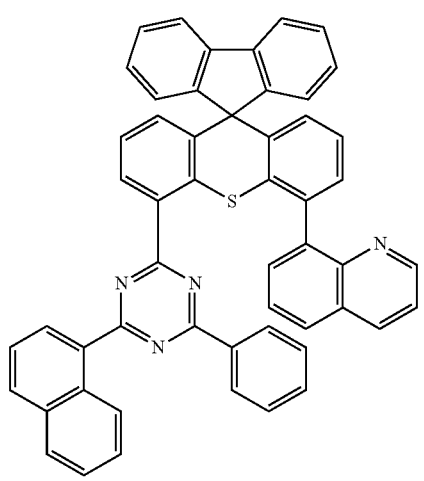
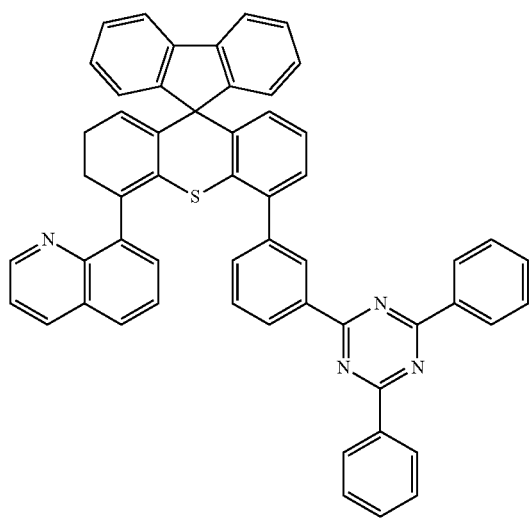
94
-continued
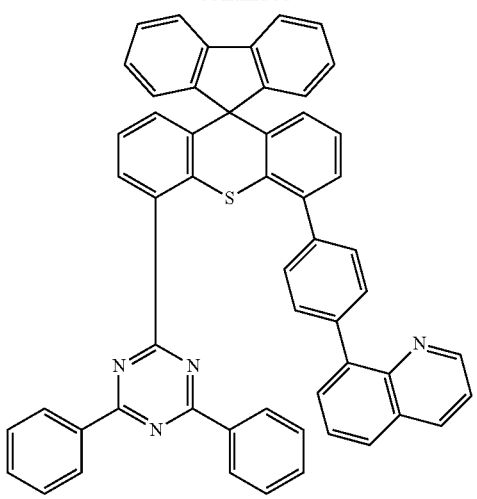
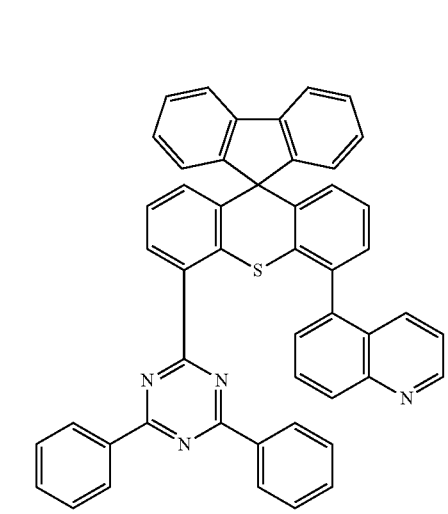
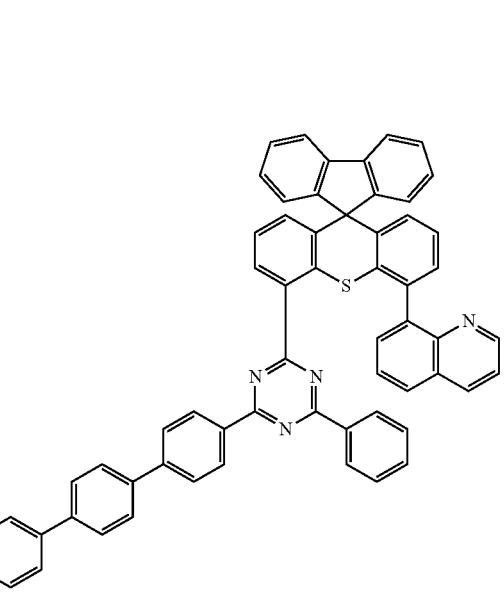

95
-continued
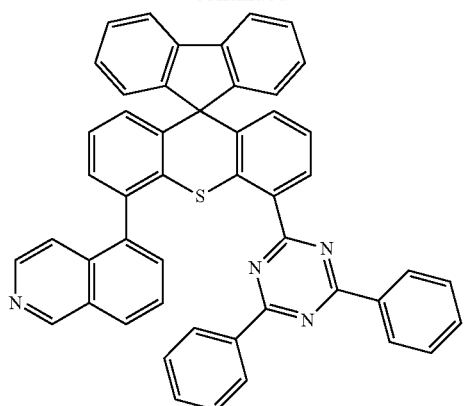
96
-continued
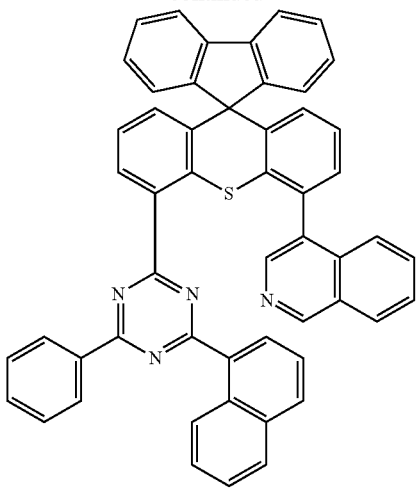
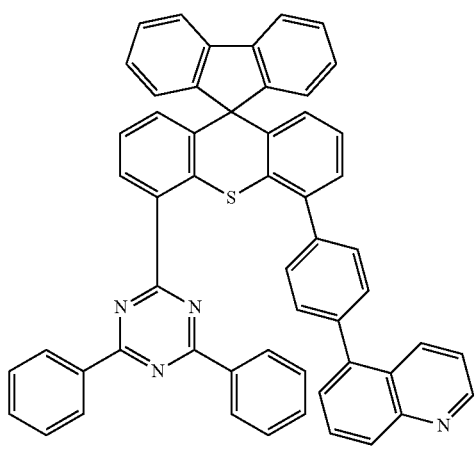
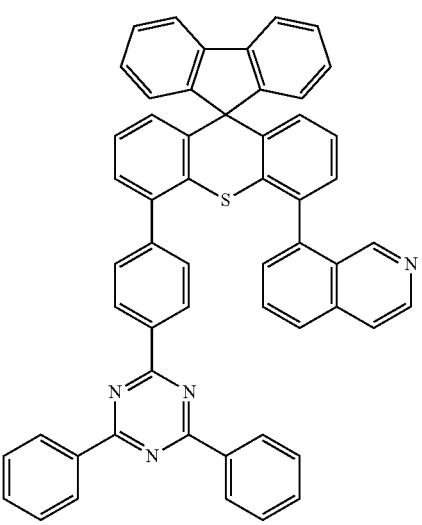
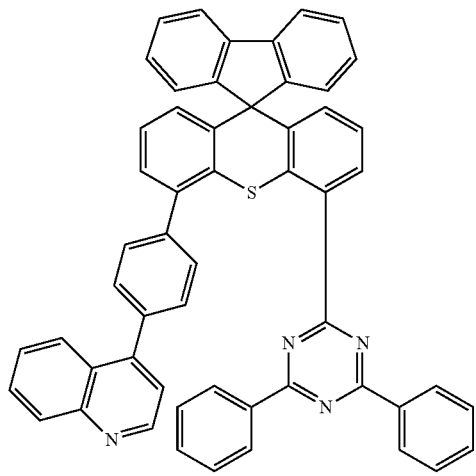
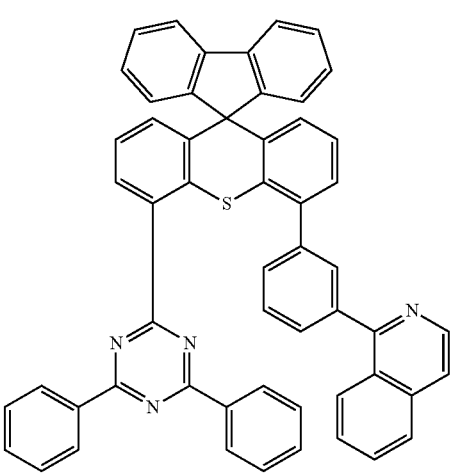

97
-continued
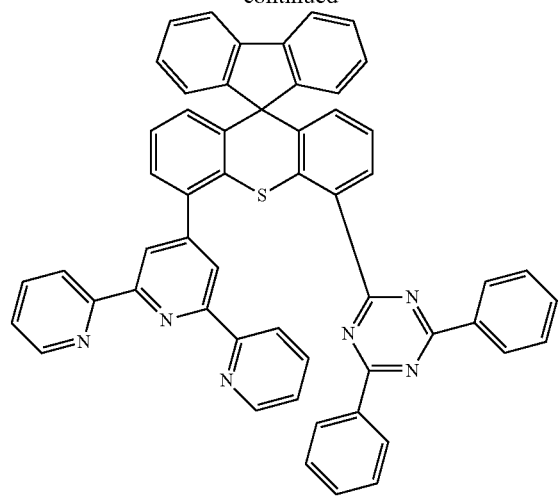
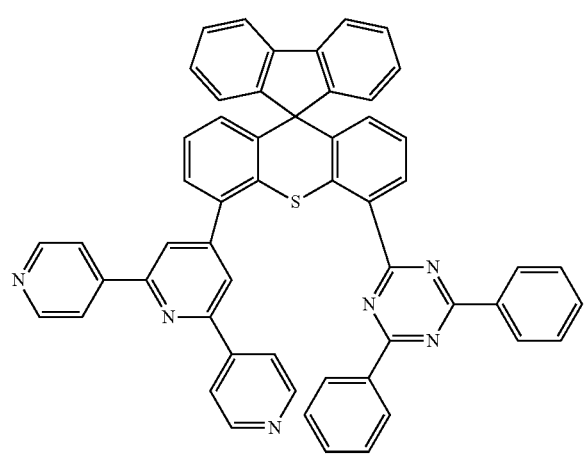
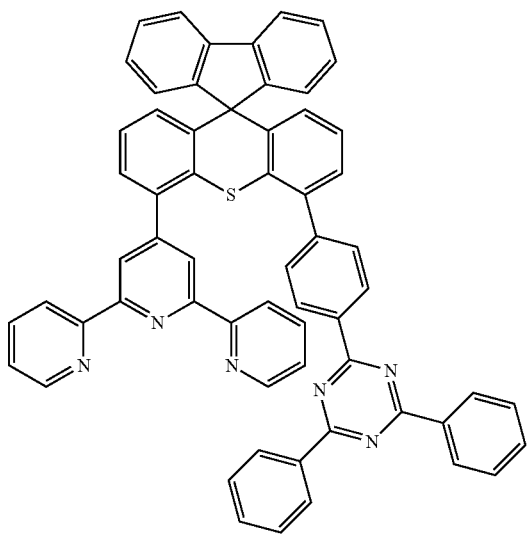
98
-continued
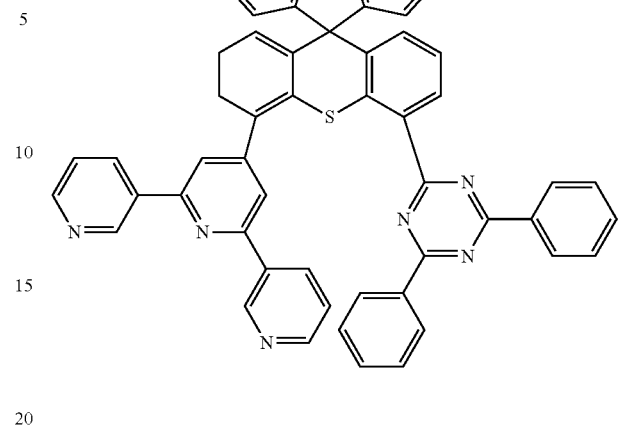
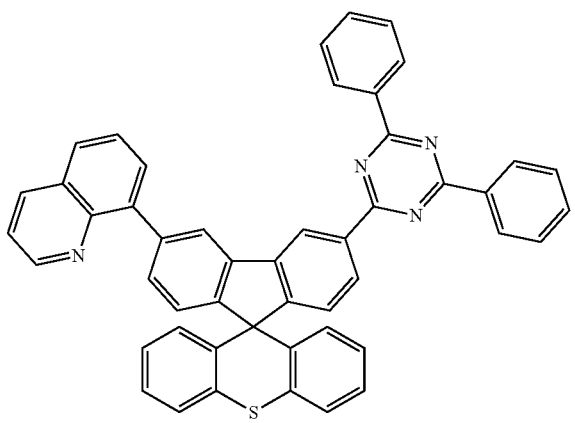
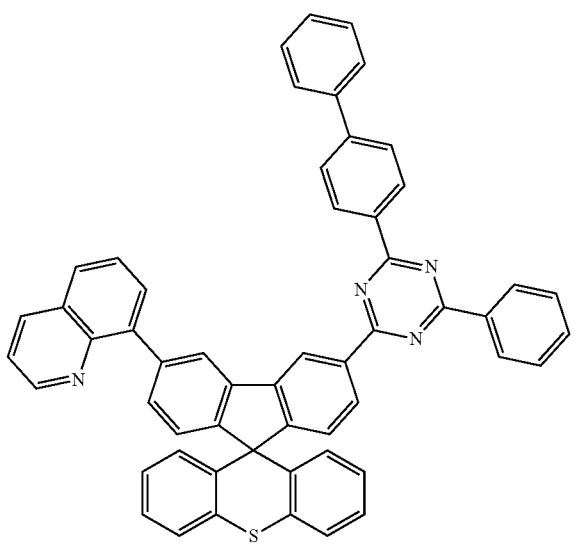

-continued
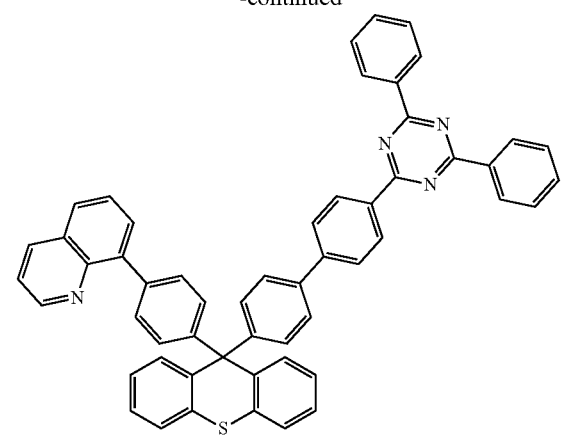
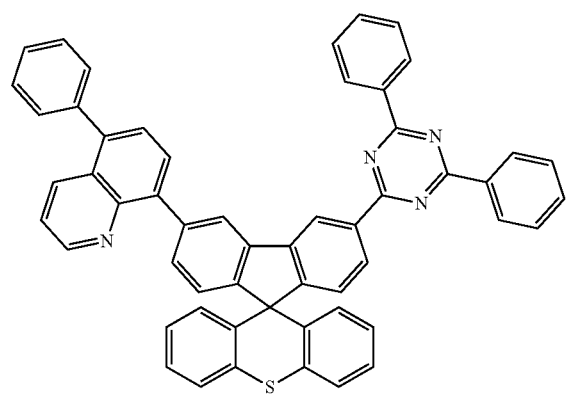
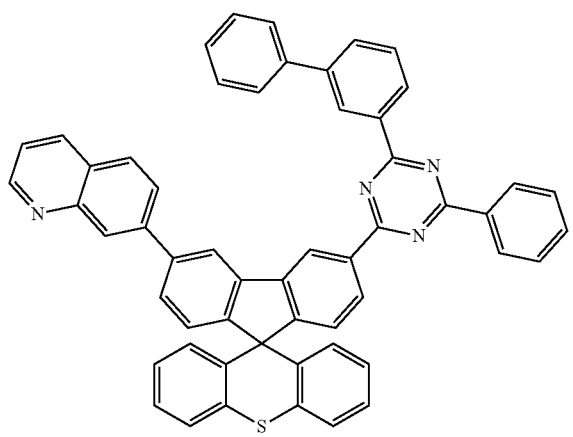
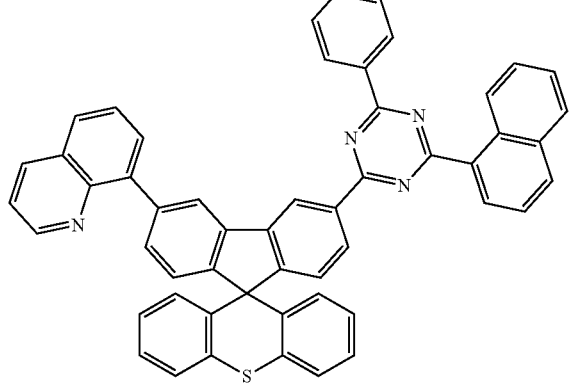
-continued
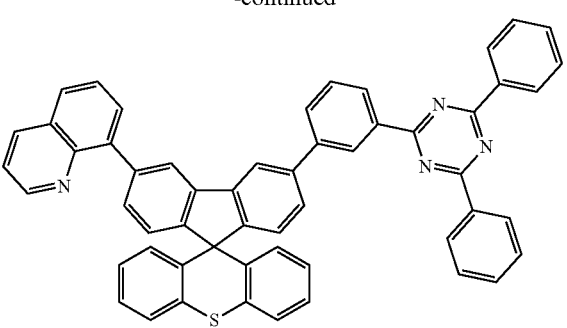
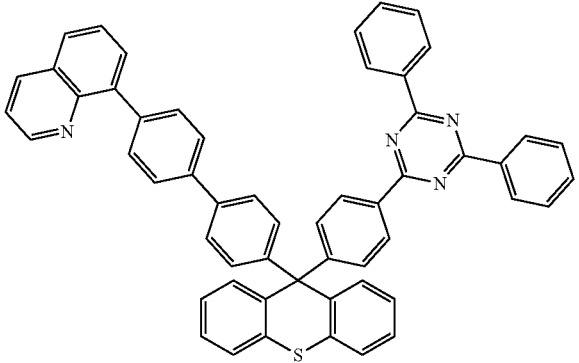
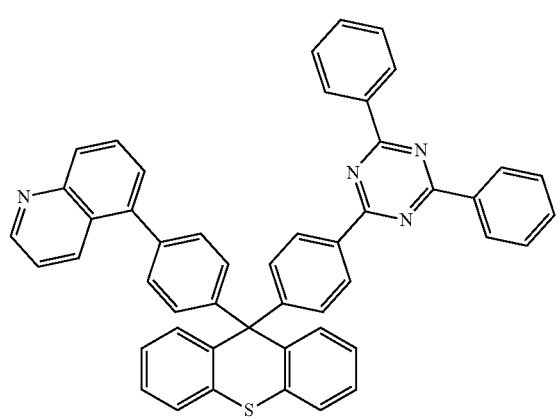
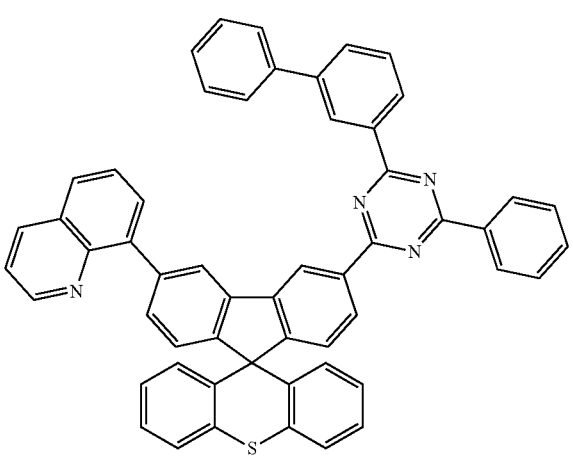

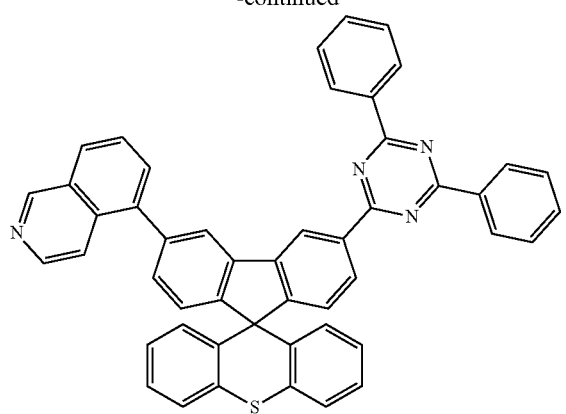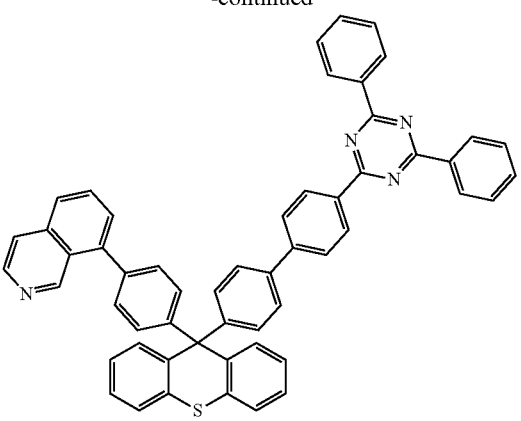

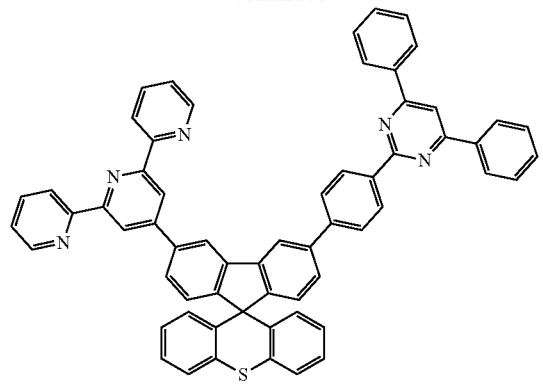
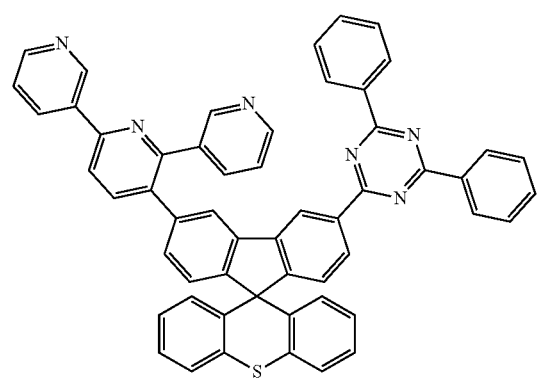
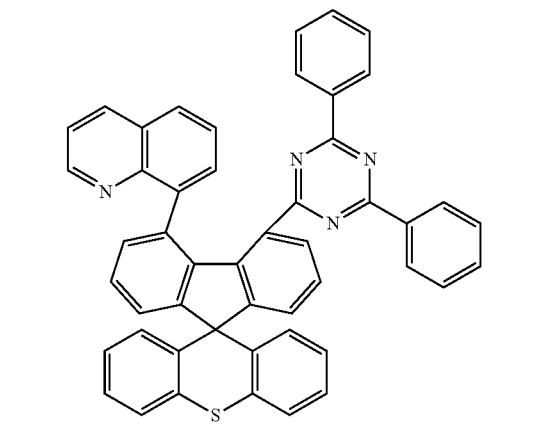
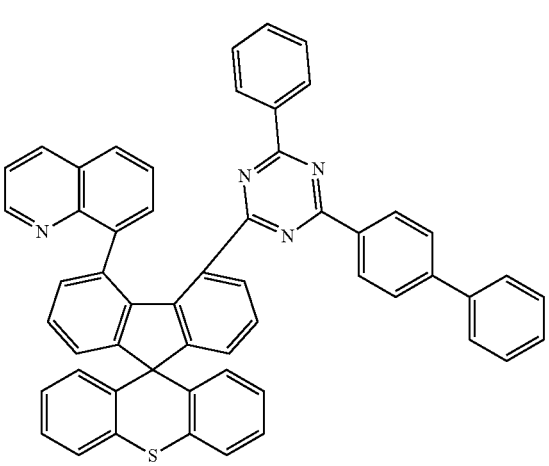
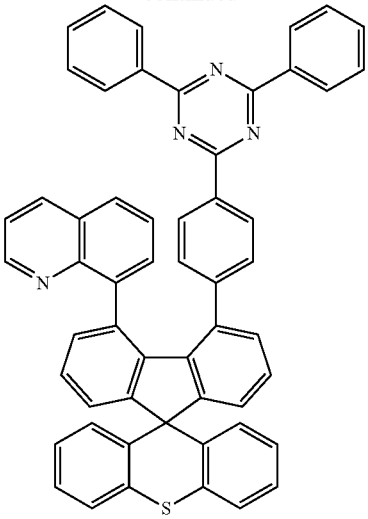
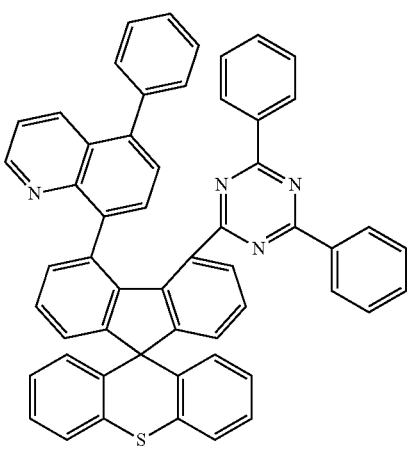
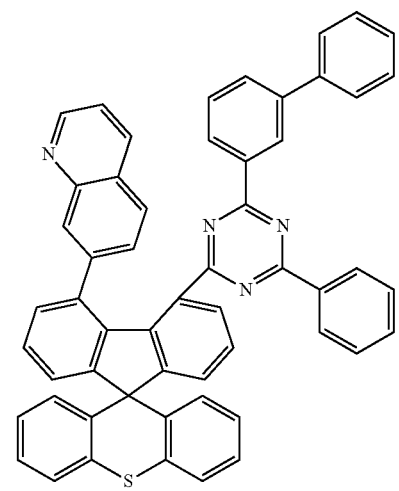

105
-continued
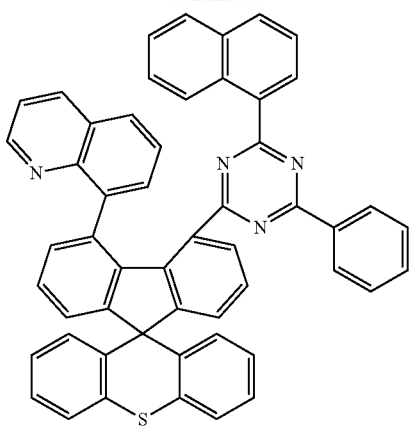
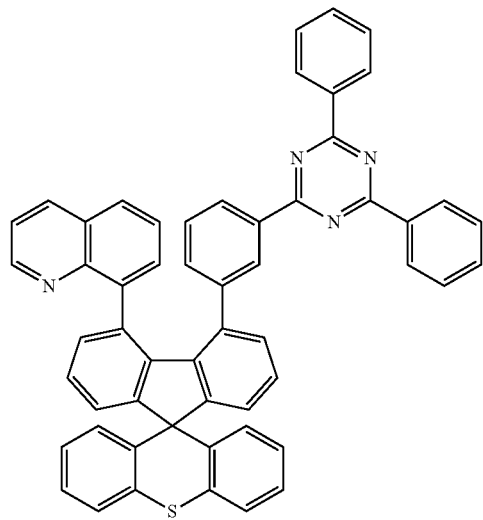
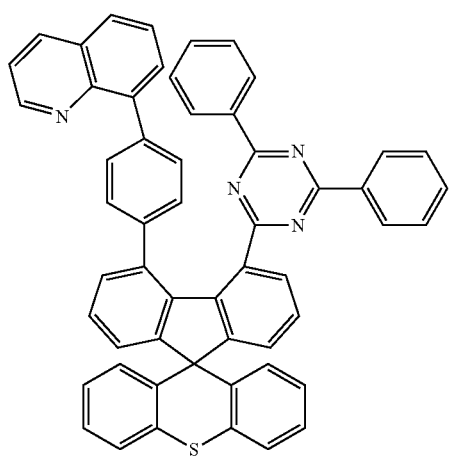
106
-continued
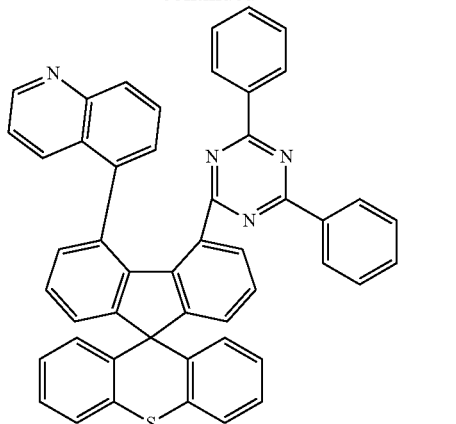
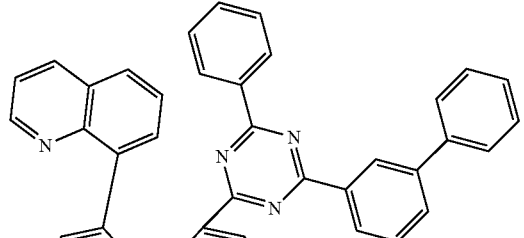
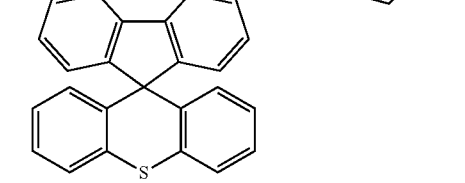
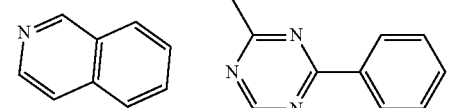
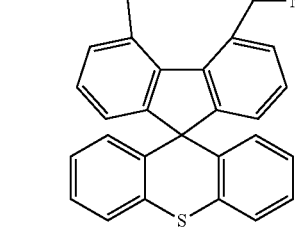
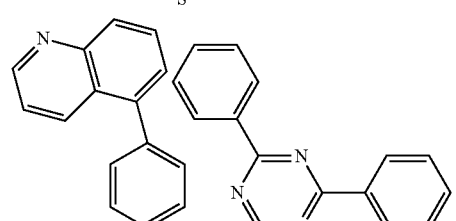

107
-continued
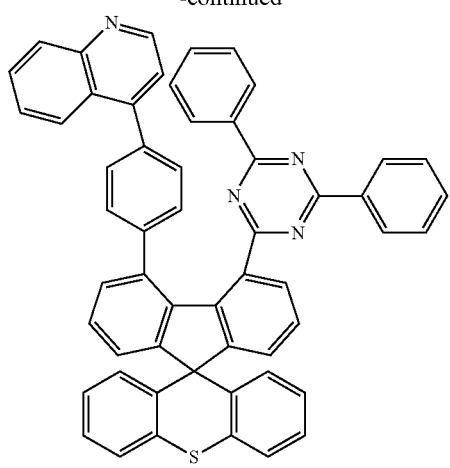
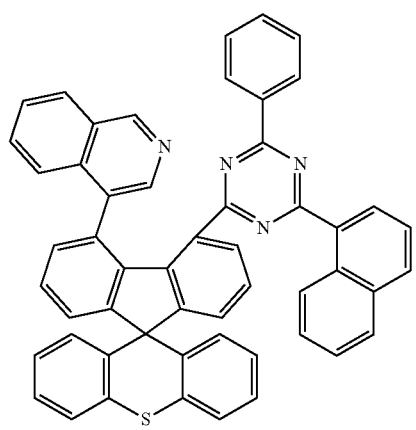
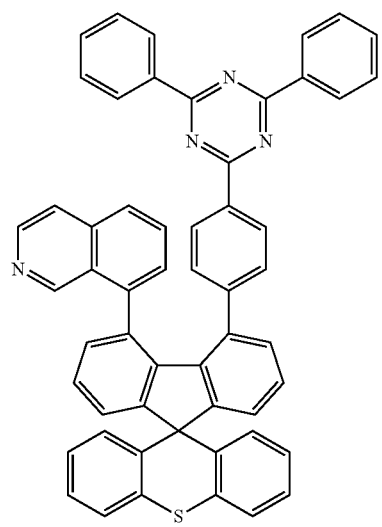
108
-continued
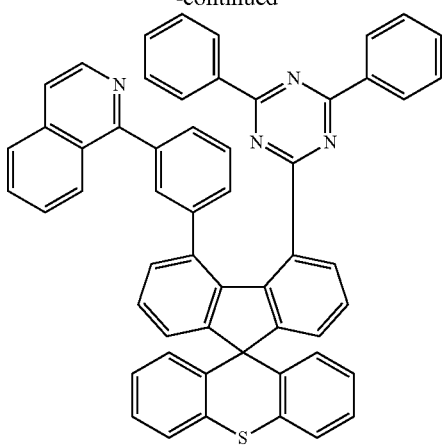
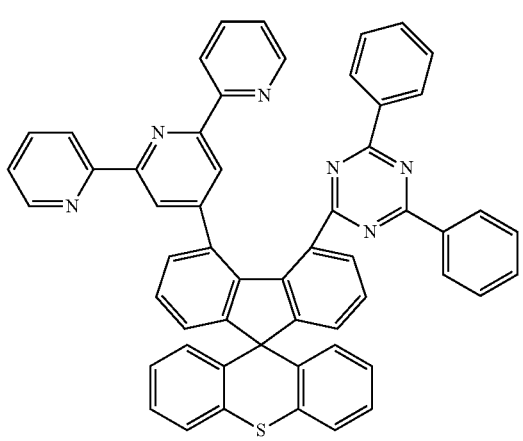
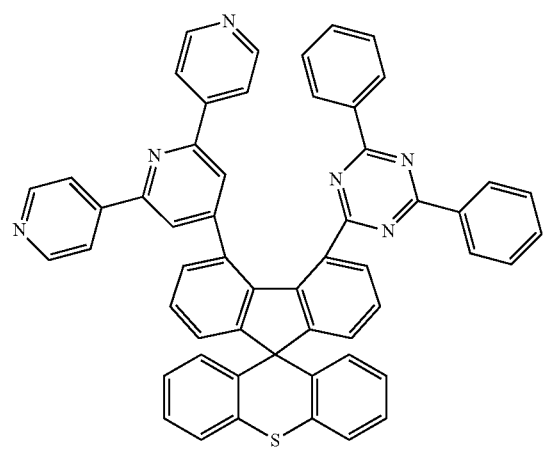

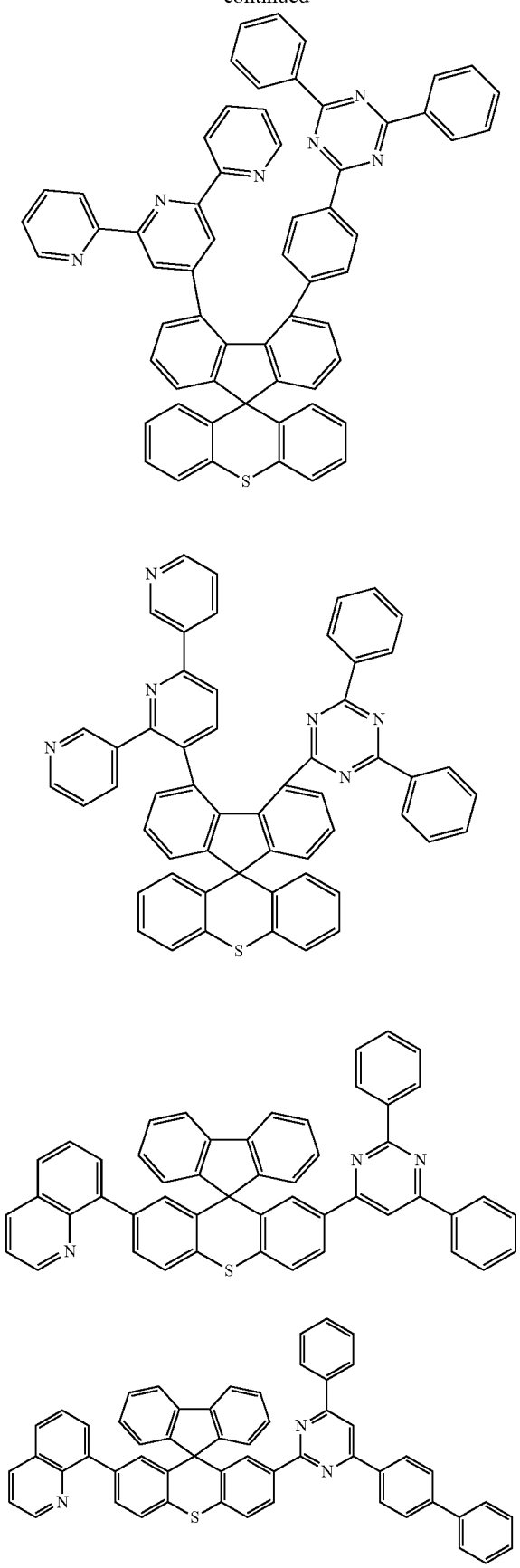
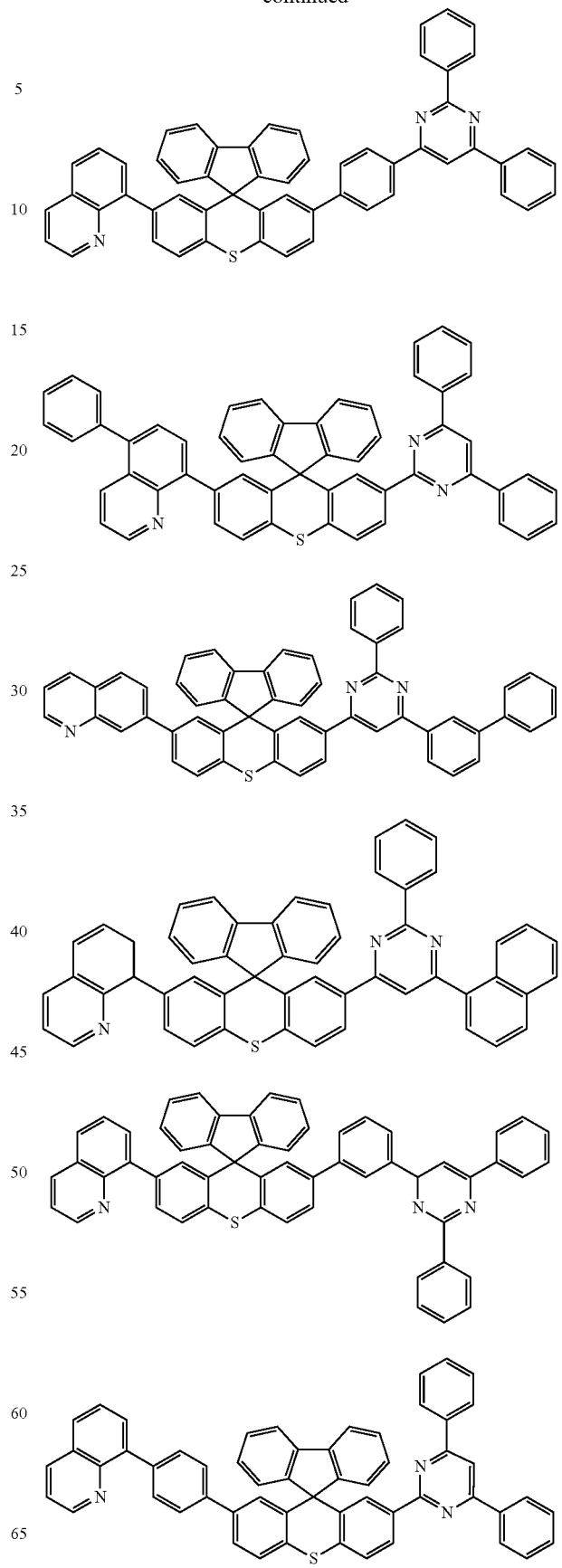

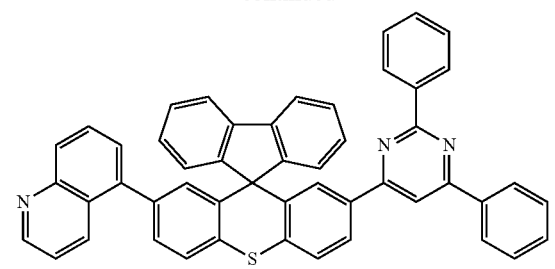
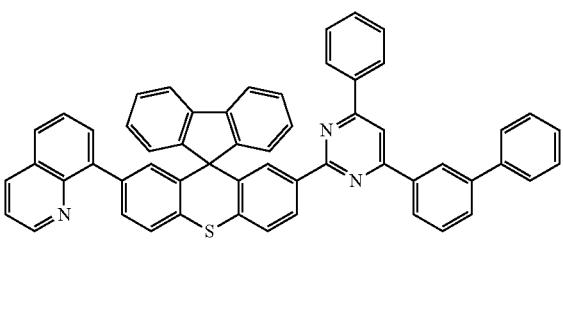
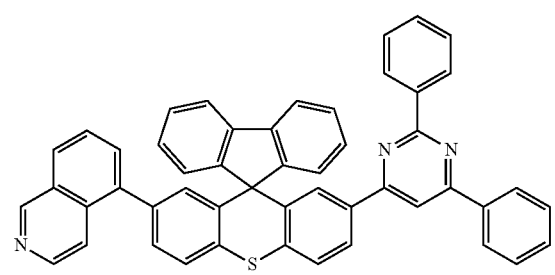
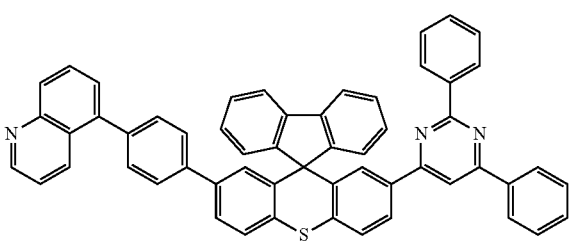
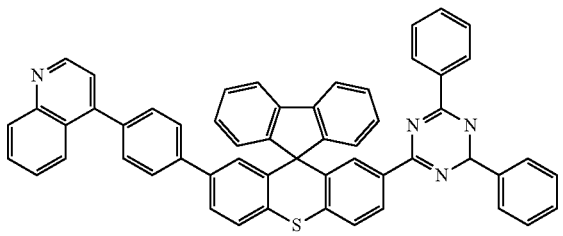
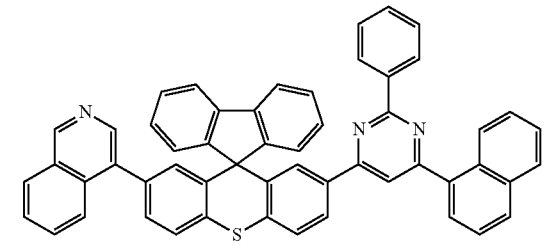
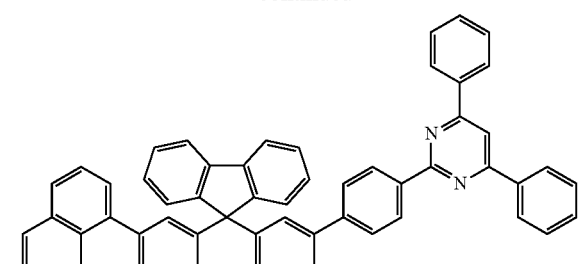
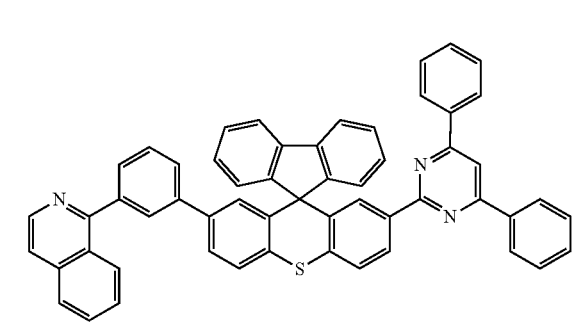
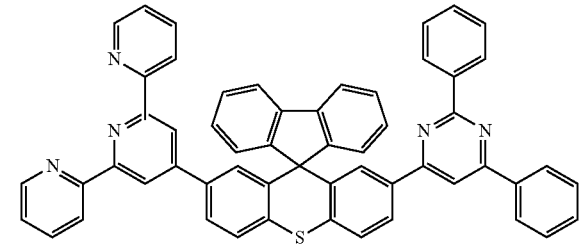
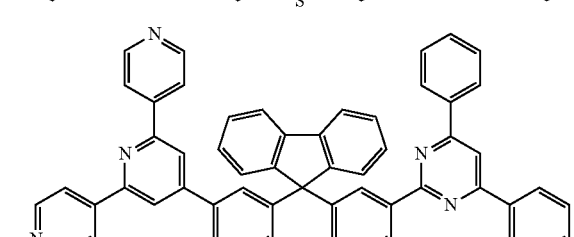
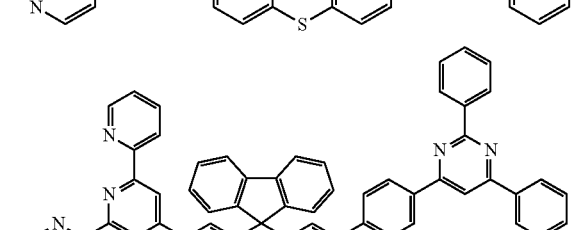
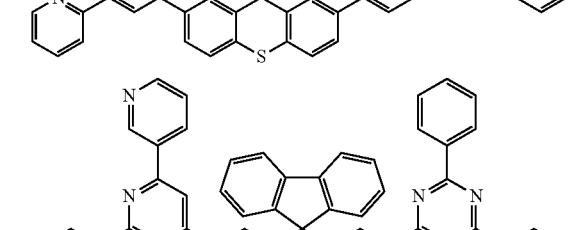
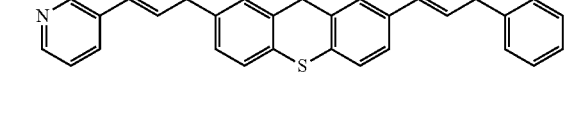

113
-continued
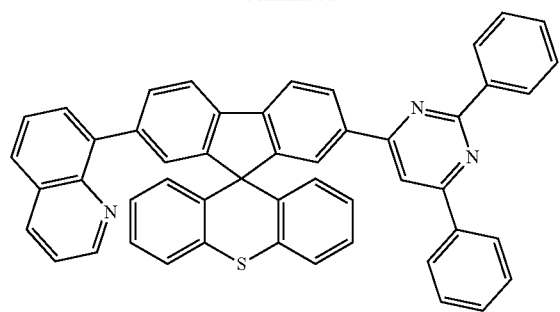
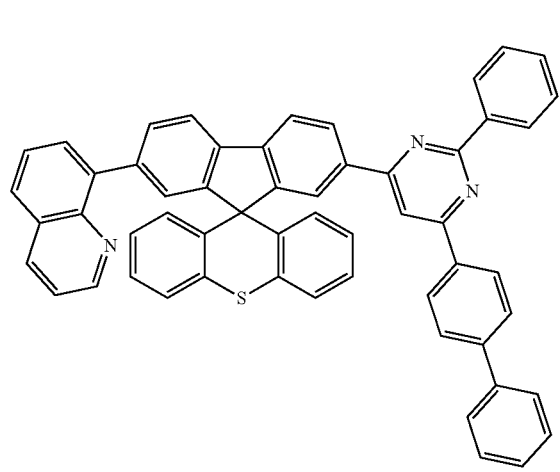
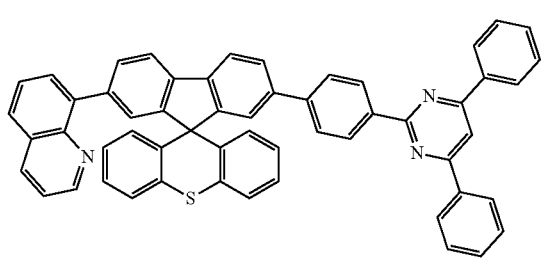
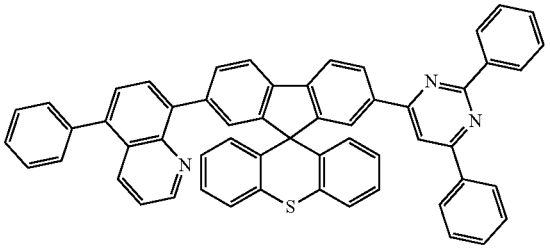
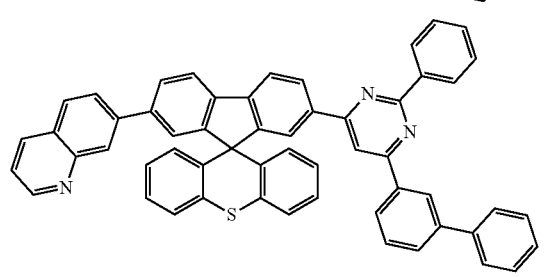
114
-continued
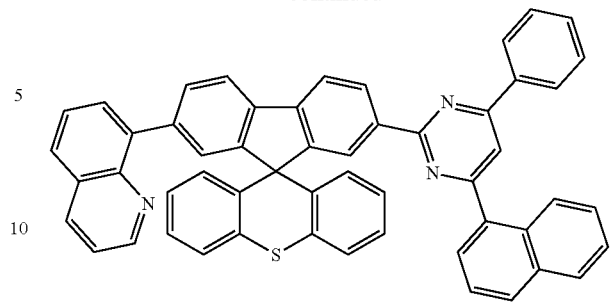
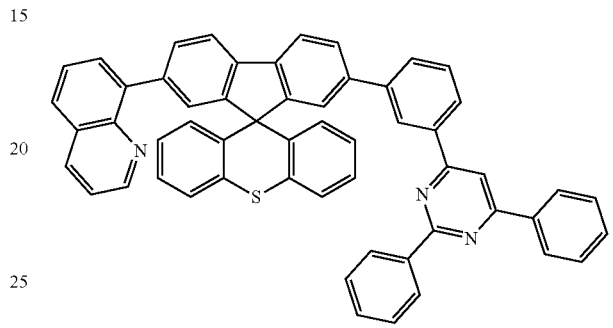
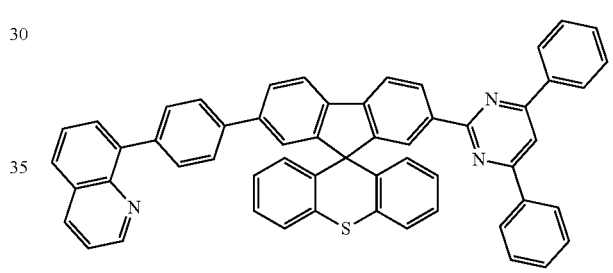
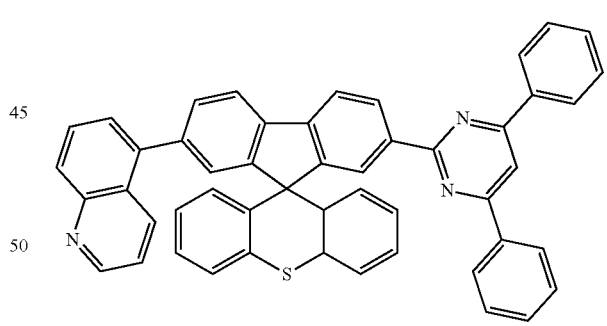
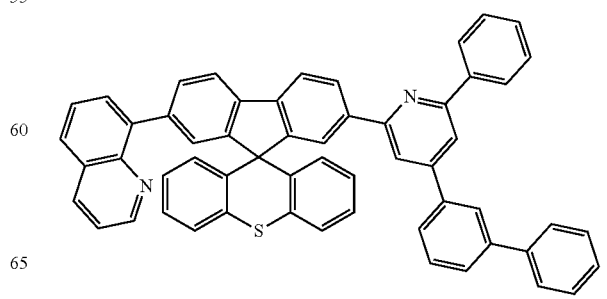

115
-continued
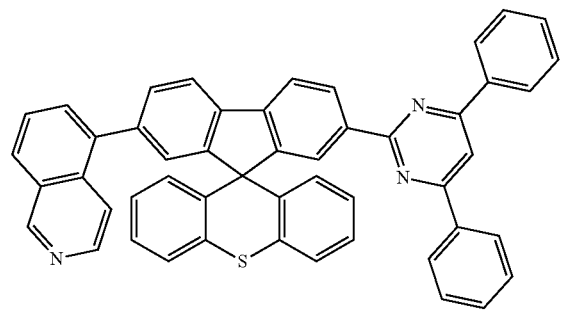
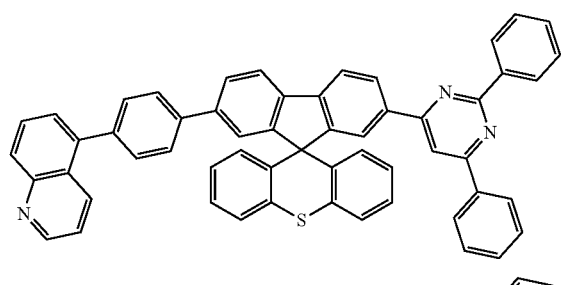
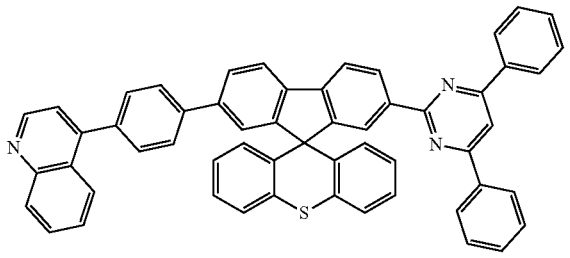
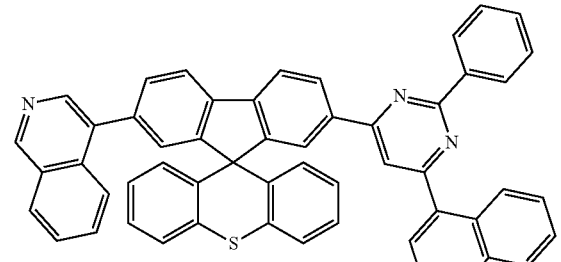
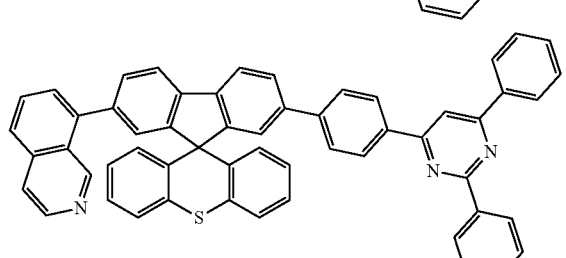
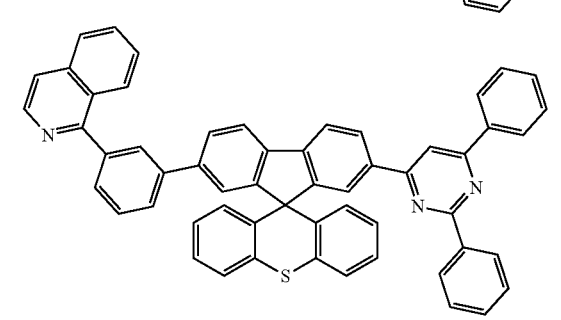
116
-continued
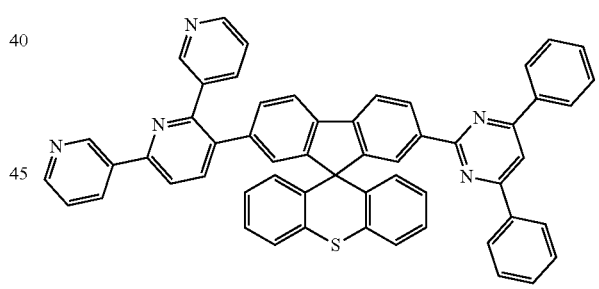
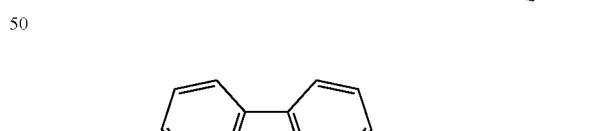
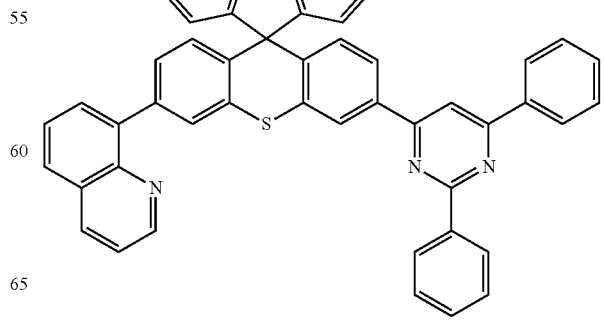
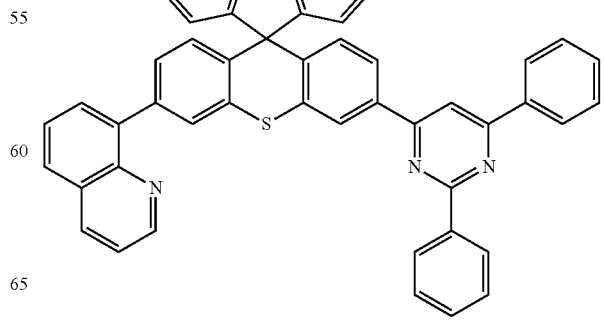
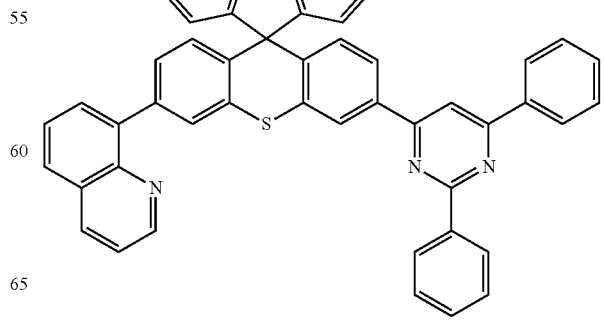
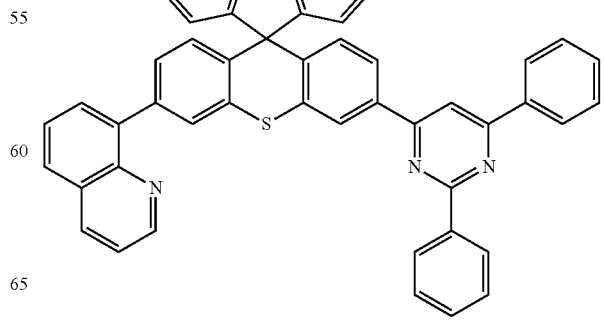
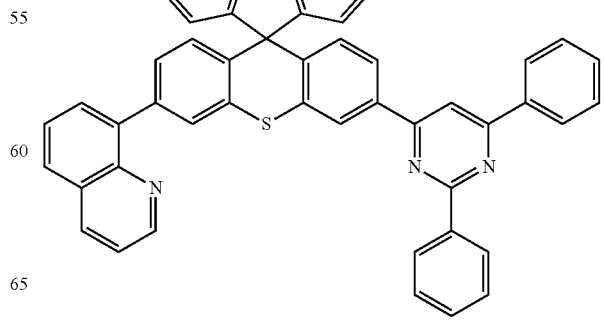

117
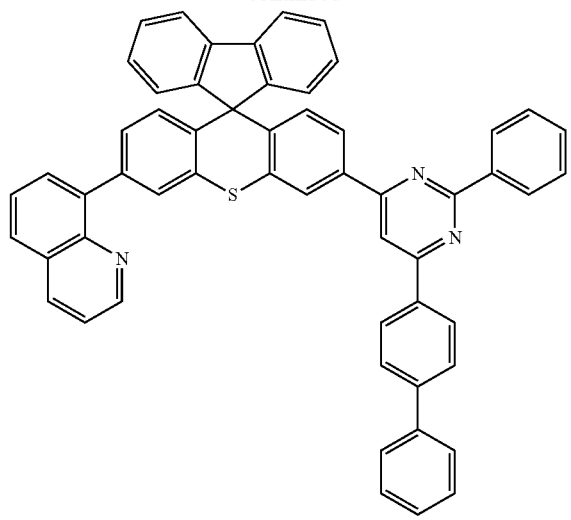
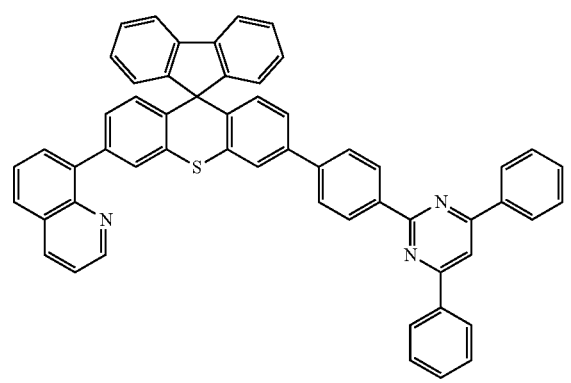
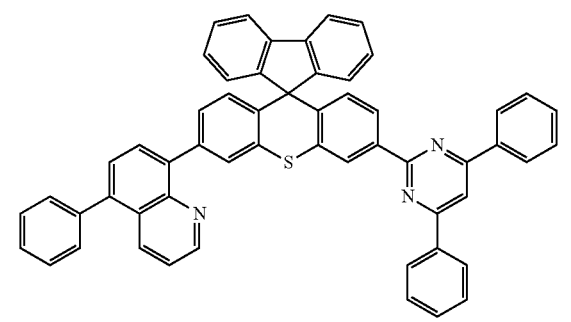
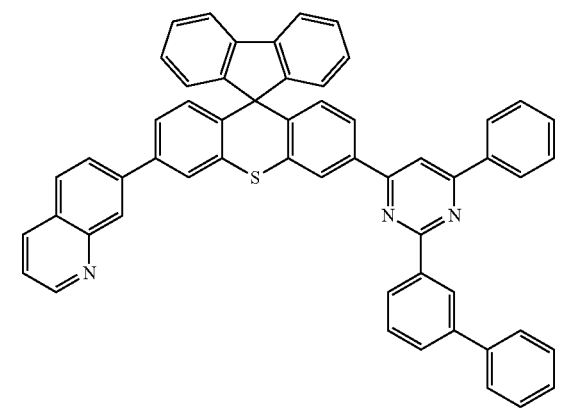
118
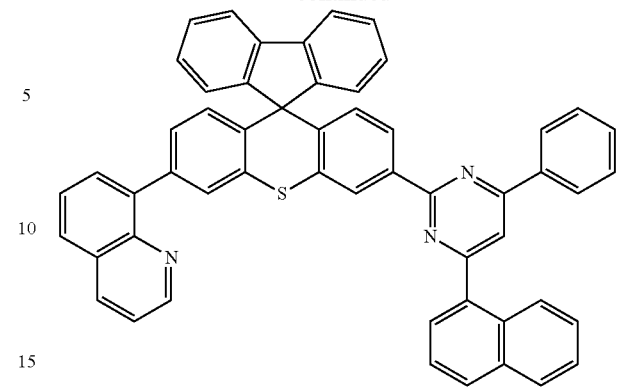
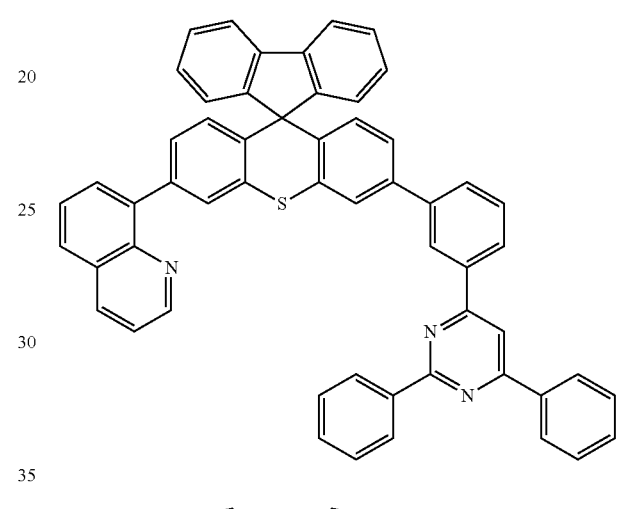
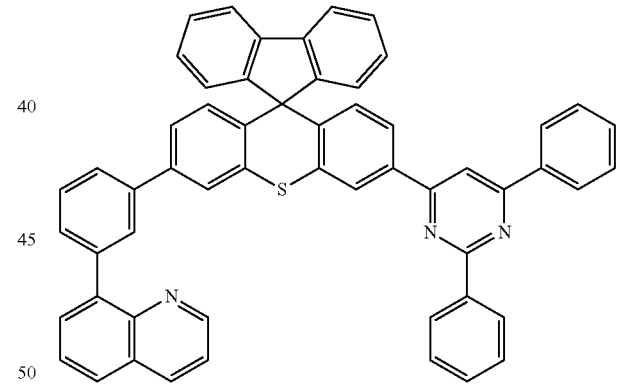
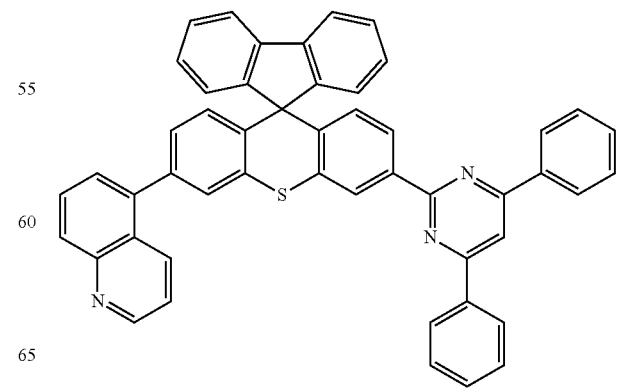

119
-continued
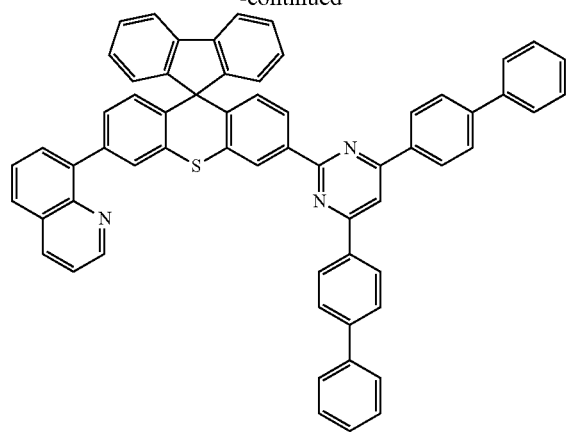
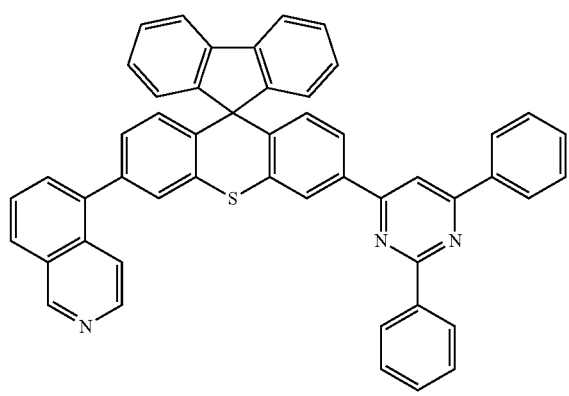
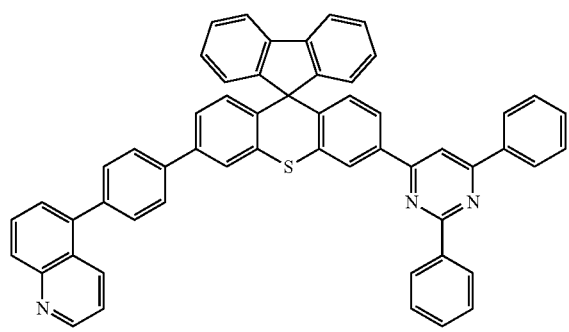
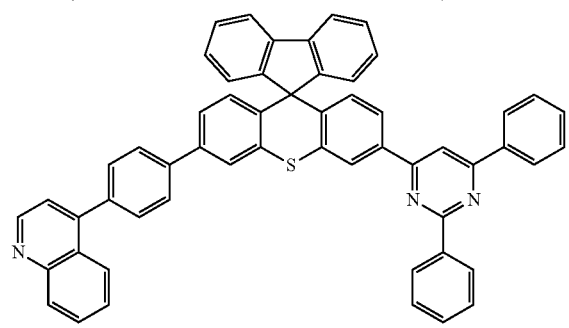
120
-continued
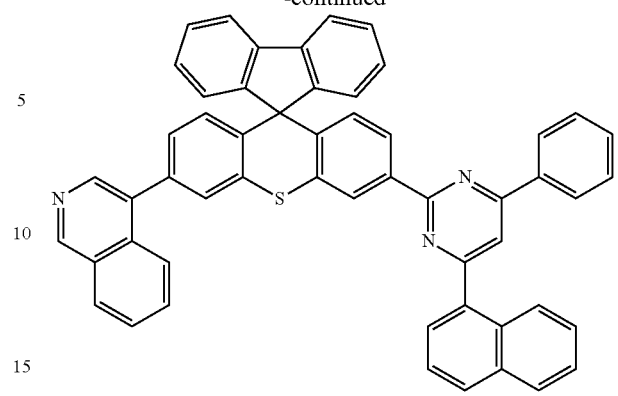
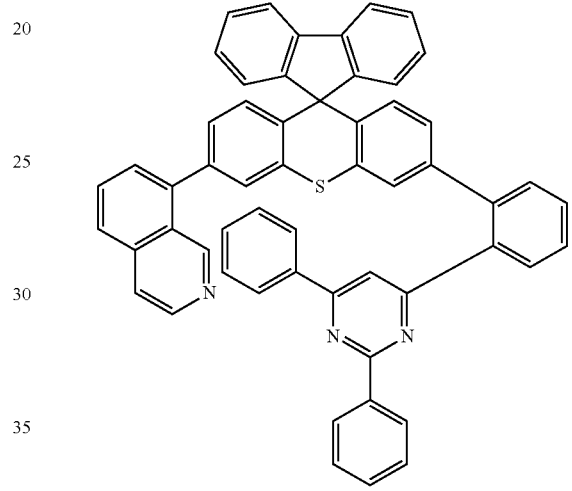
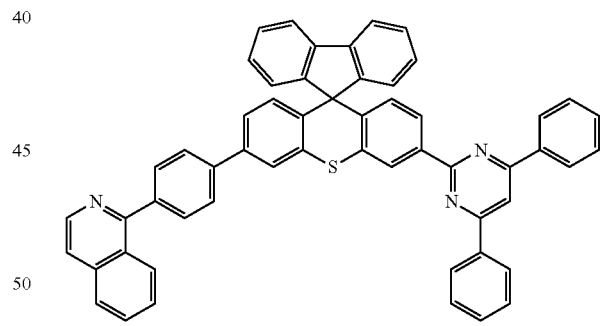
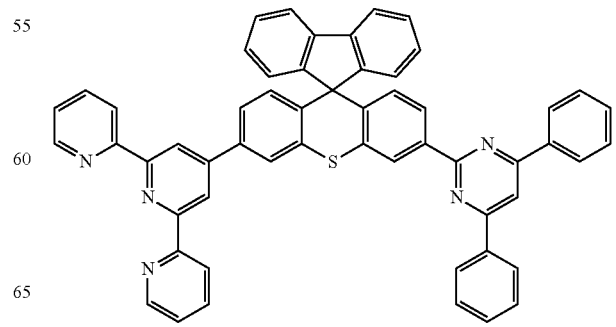

121
-continued
122
-continued
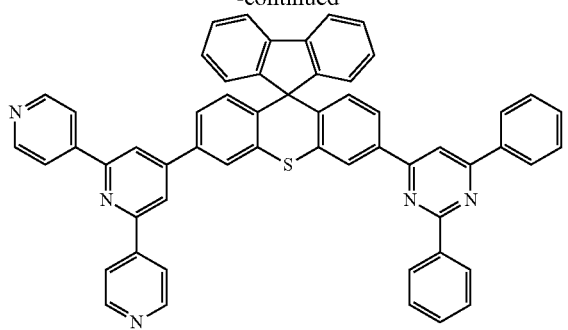
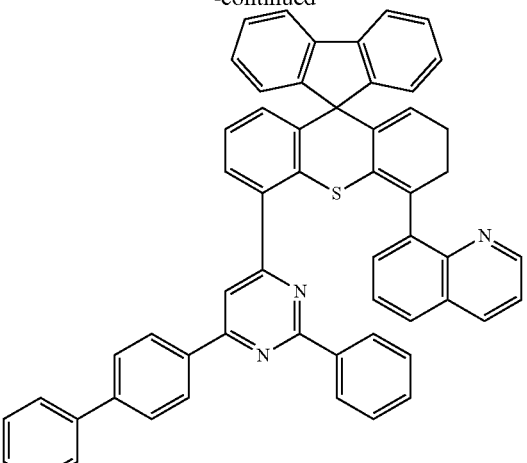
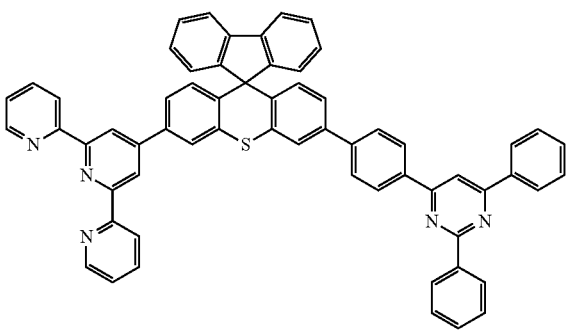
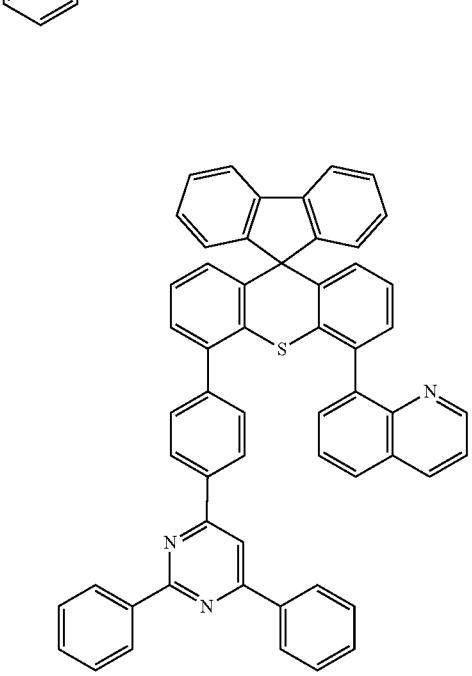
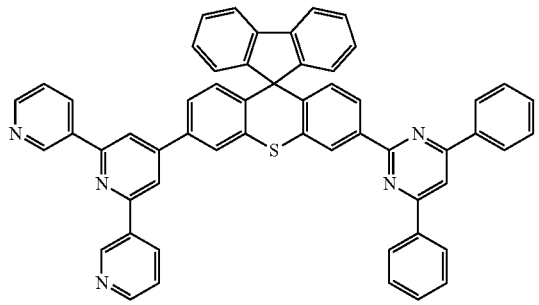
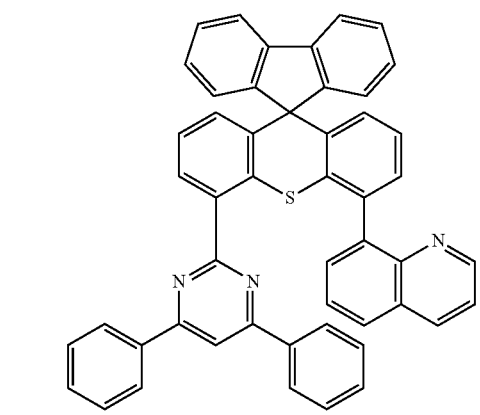
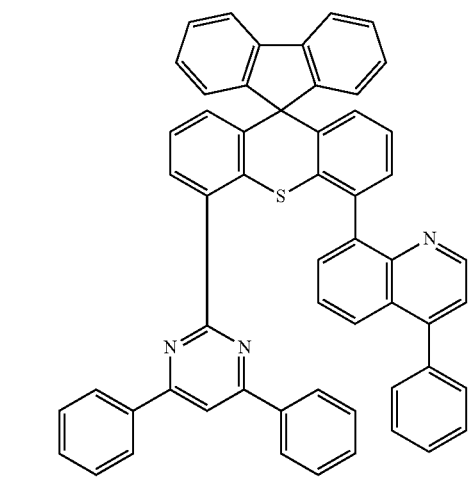

123
-continued
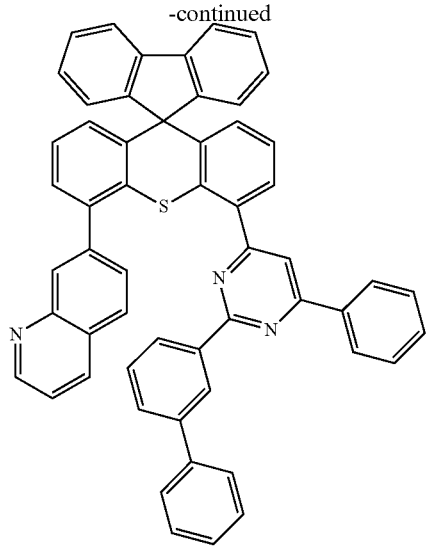
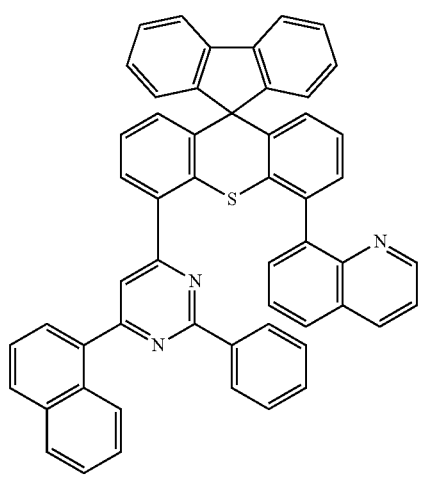
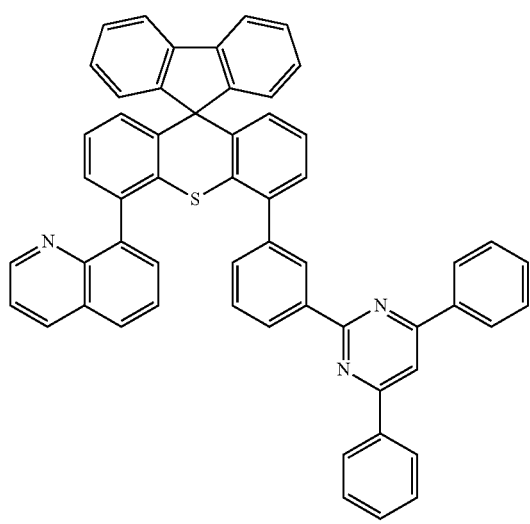
124
-continued
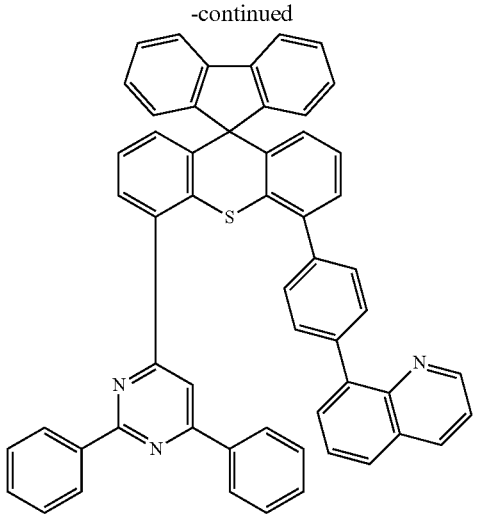
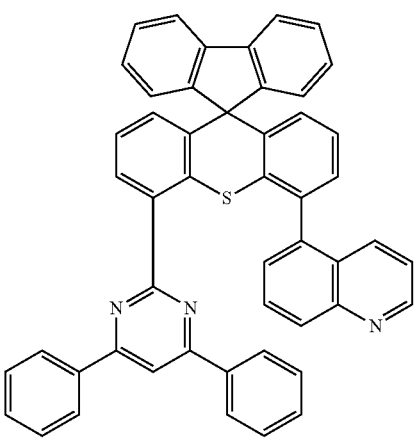
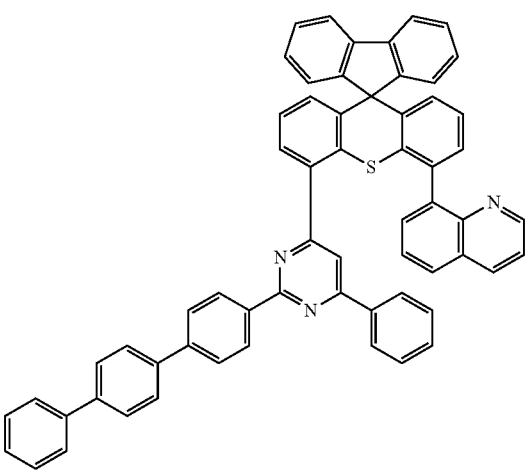

125
-continued
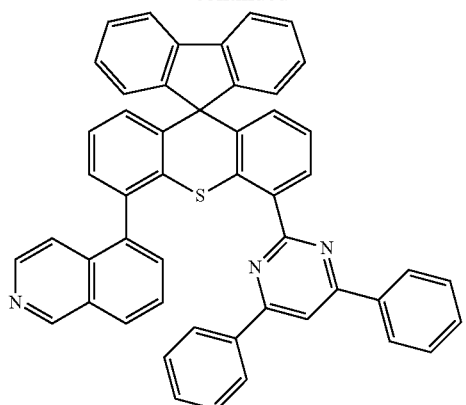
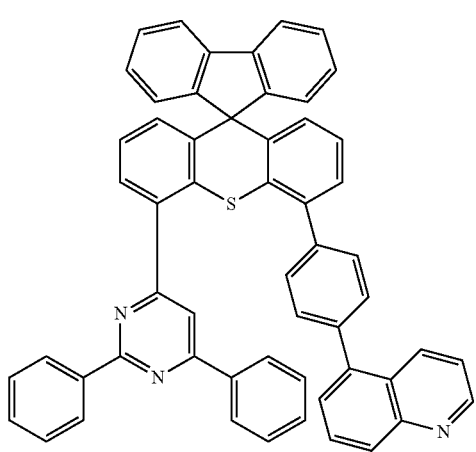
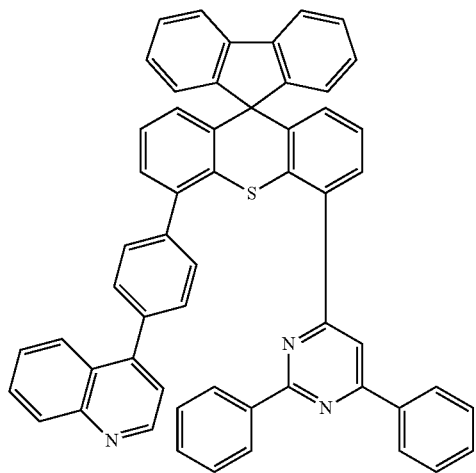
126
-continued
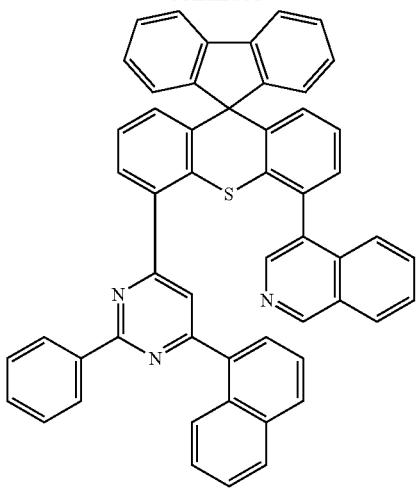
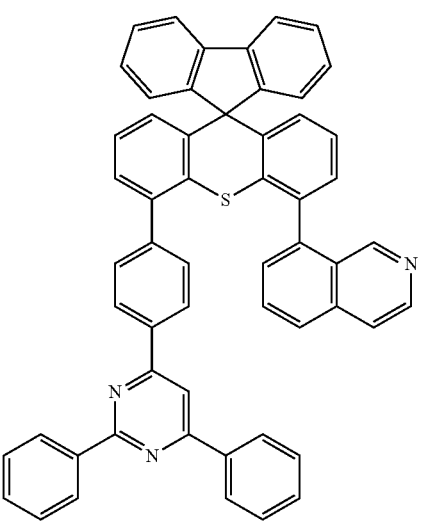
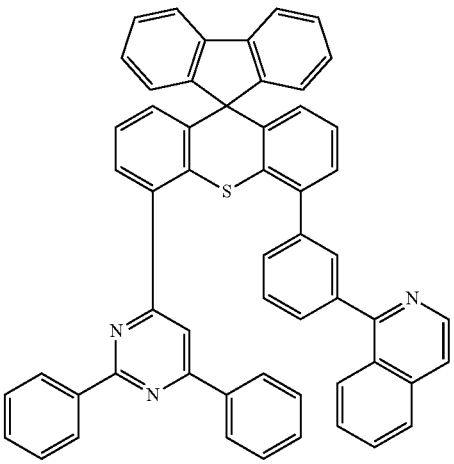

127
-continued
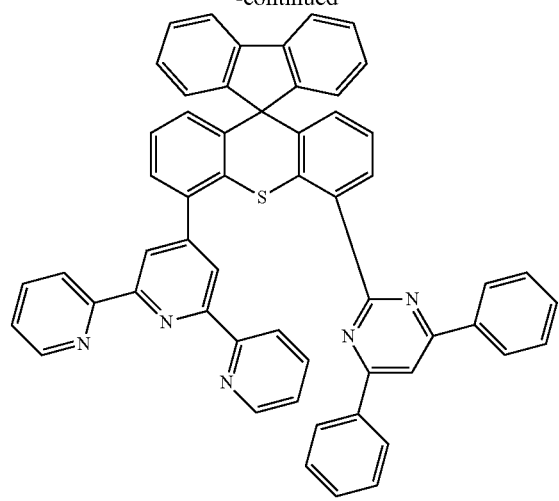
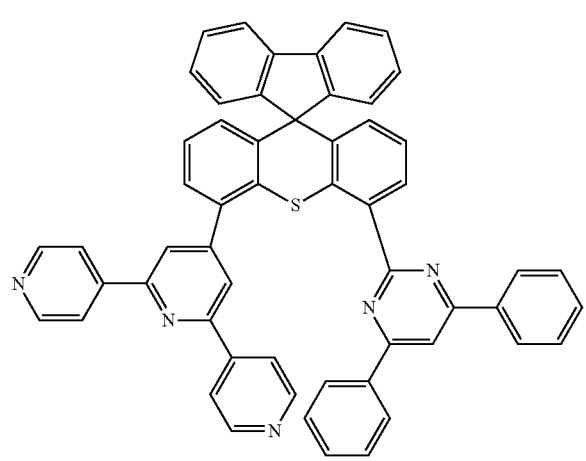
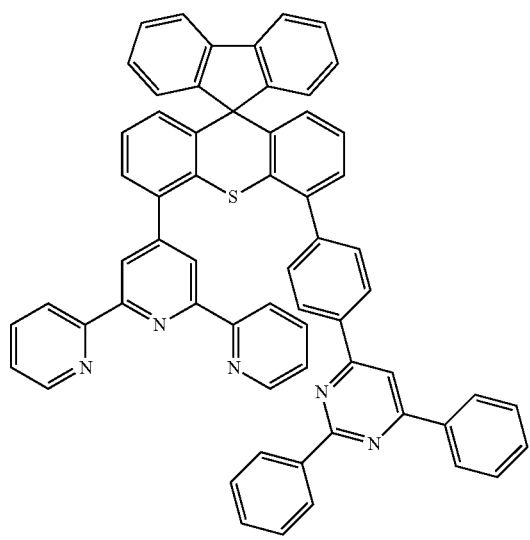
128
-continued
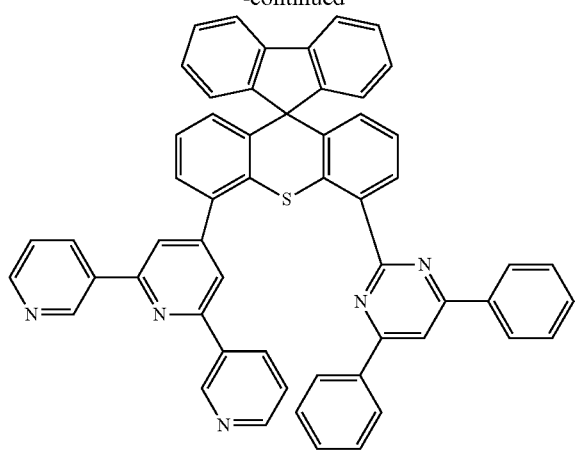
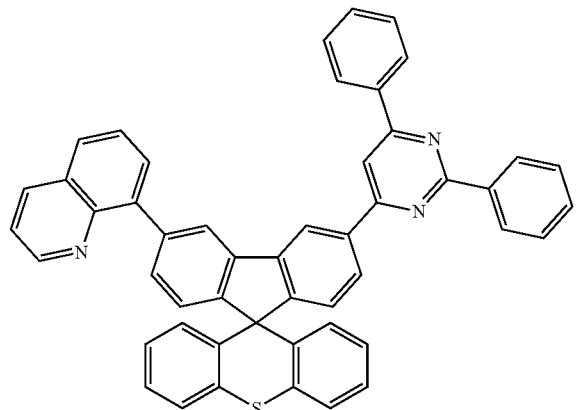
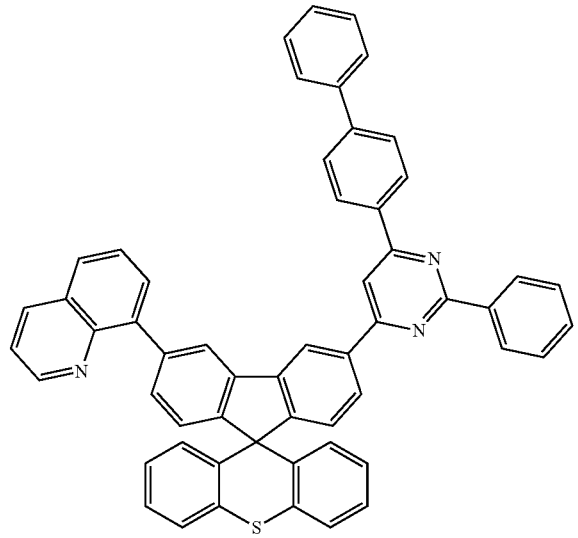

-continued
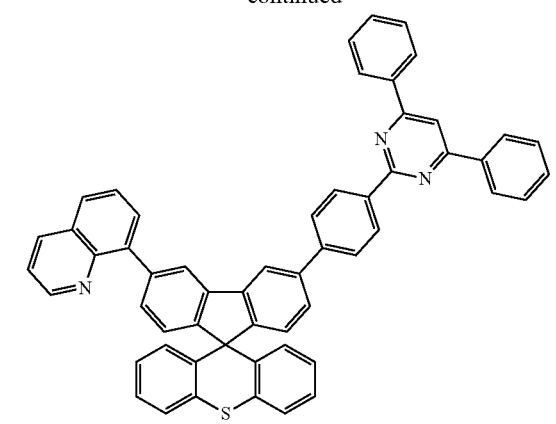
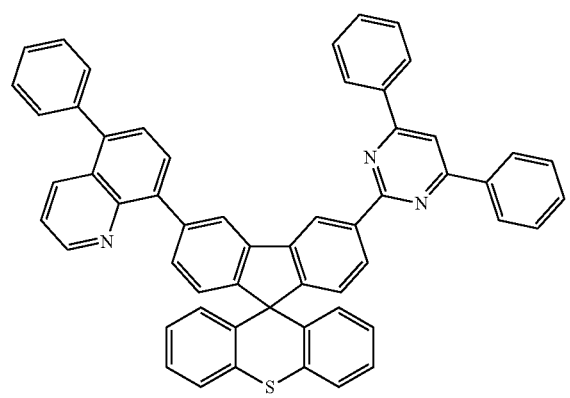
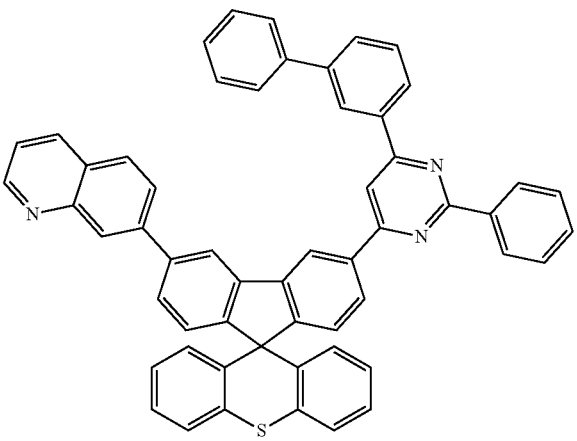
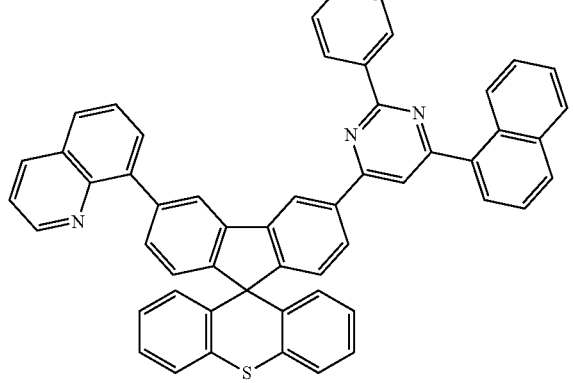
-continued
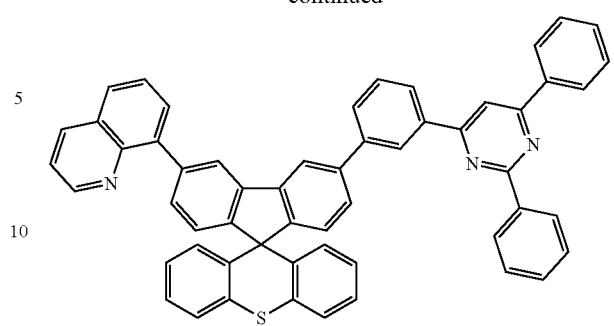
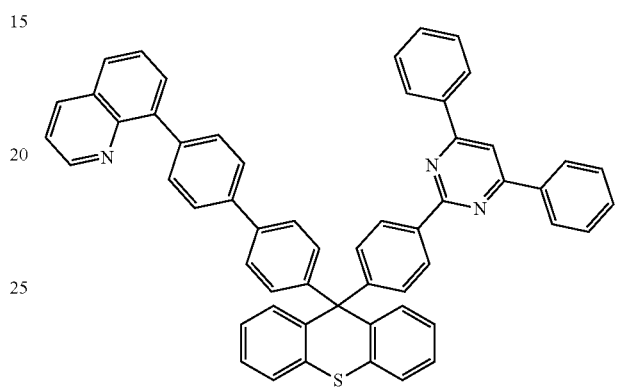
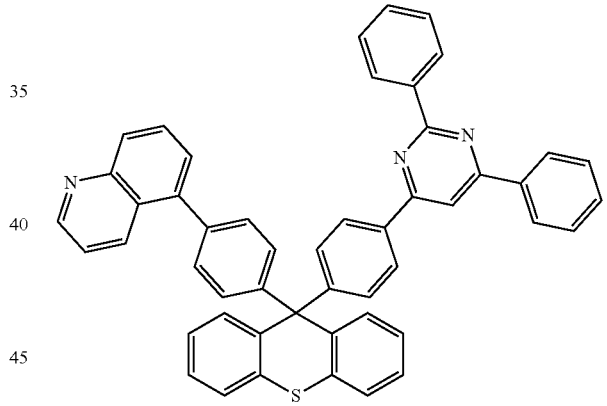
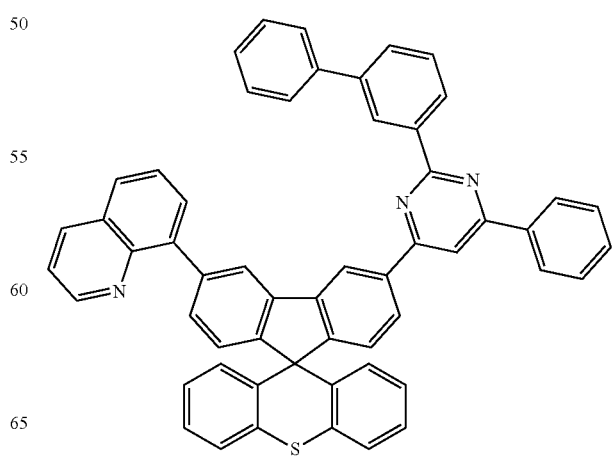

-continued
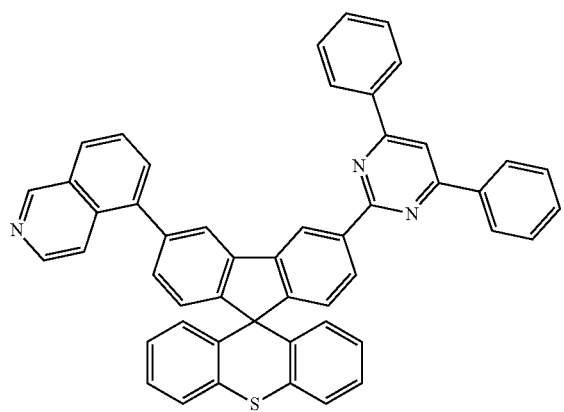
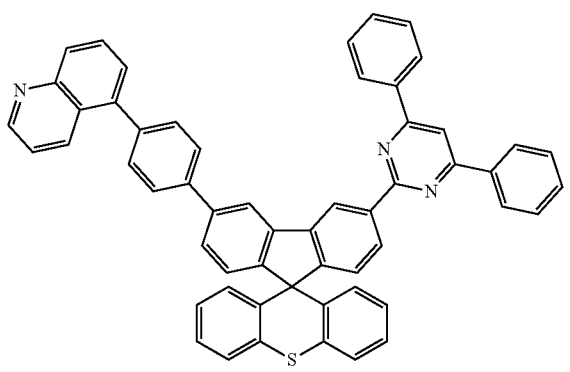
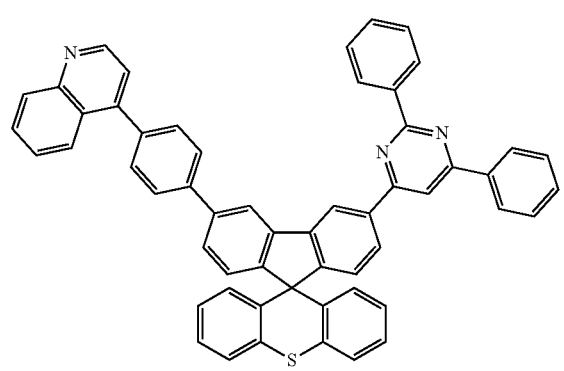
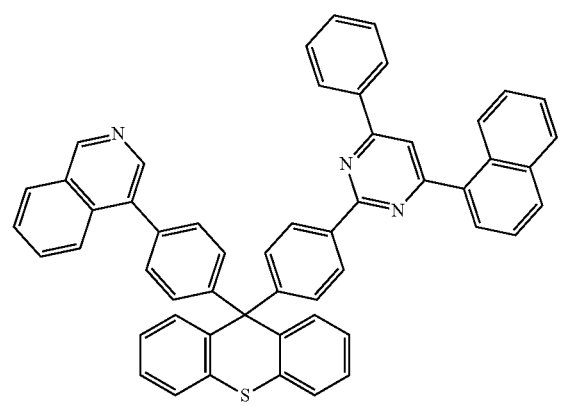
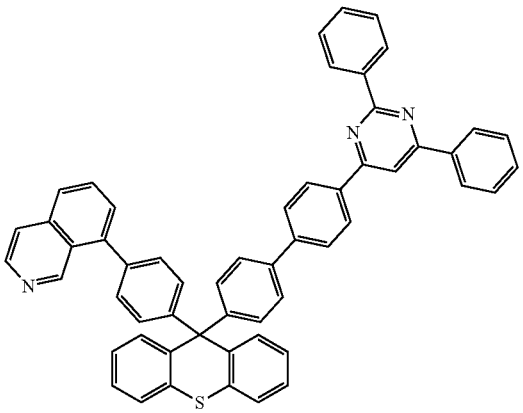
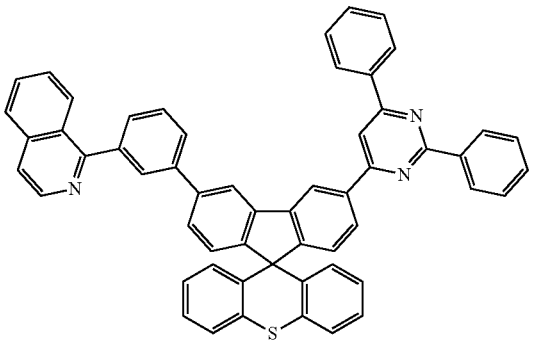
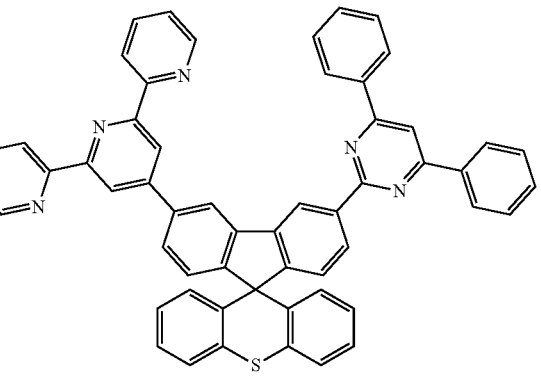
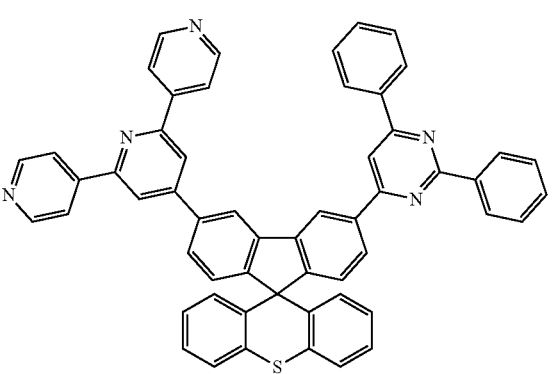

133
-continued
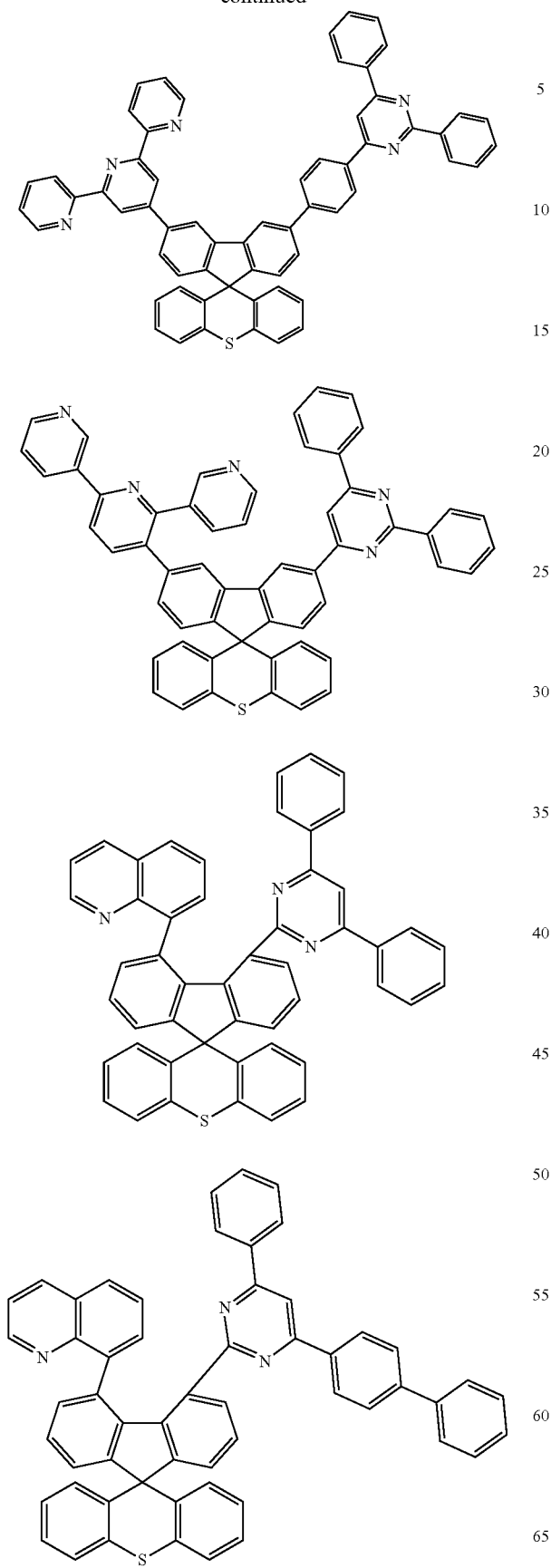
134
-continued
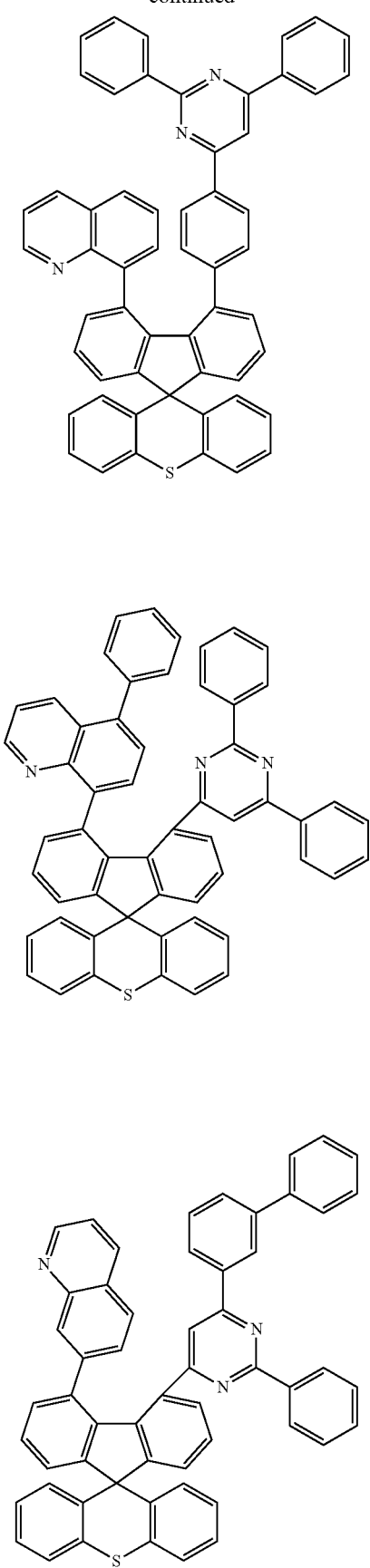

-continued
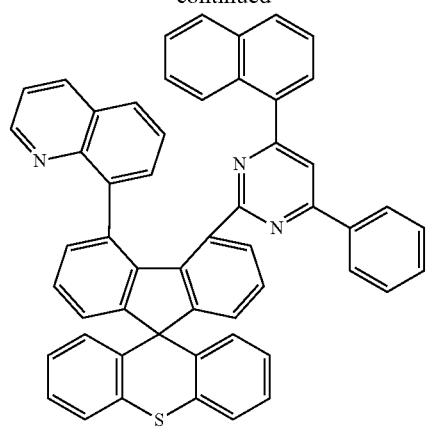
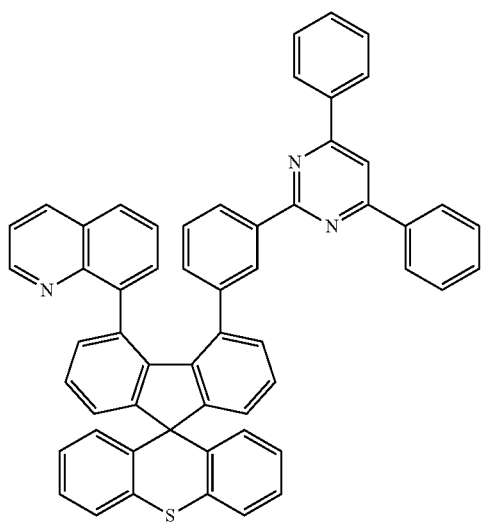
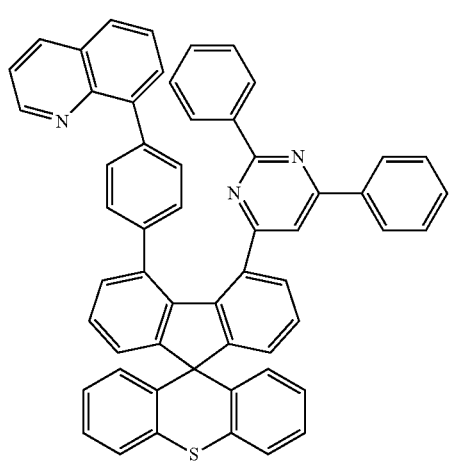
-continued
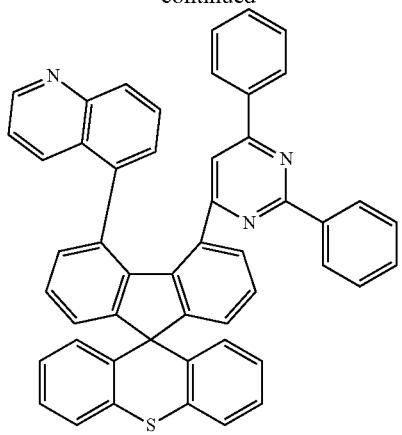
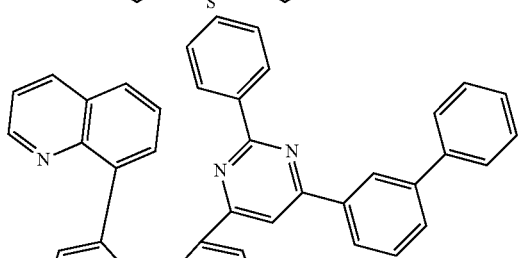
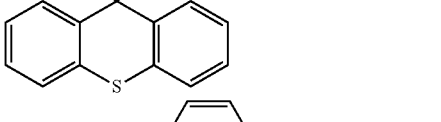
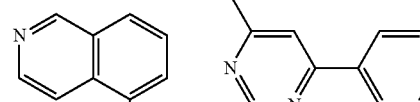
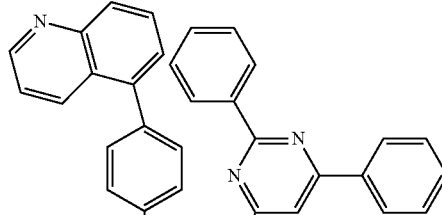
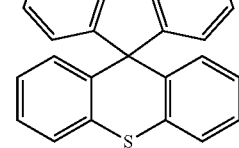

137
-continued
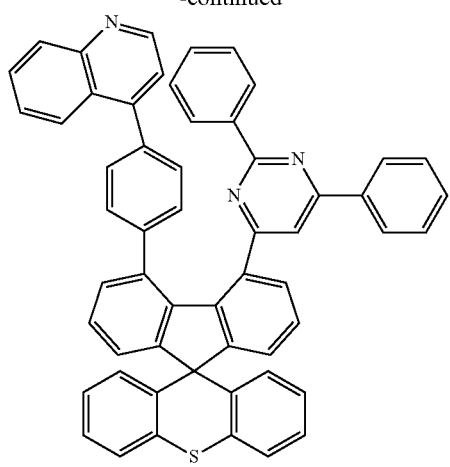
138
-continued
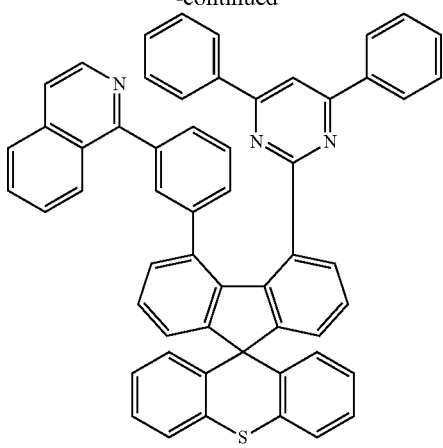
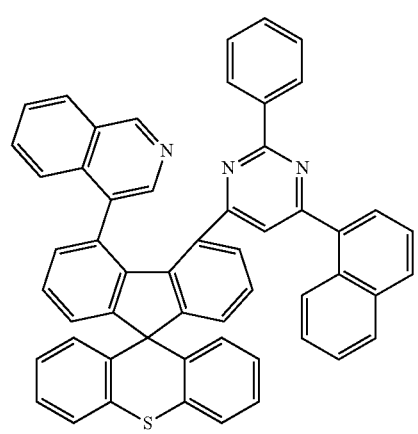
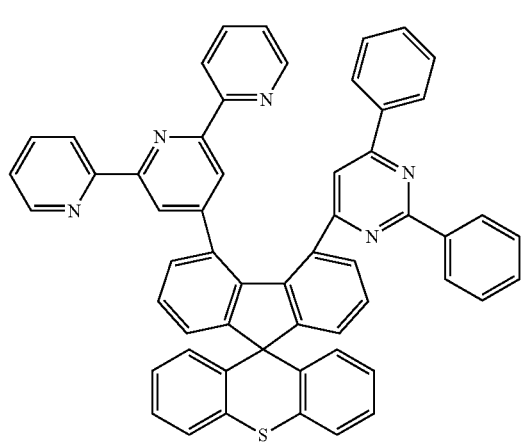
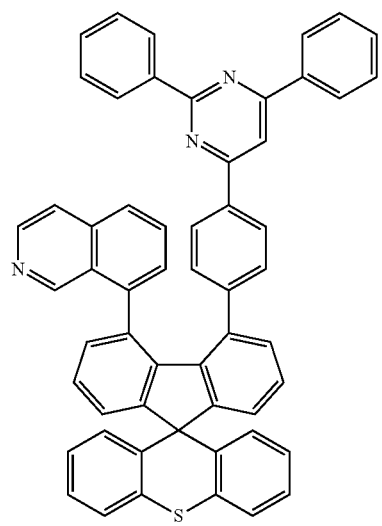
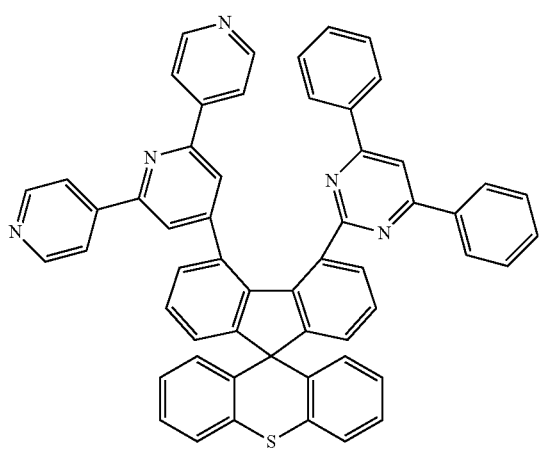

-continued

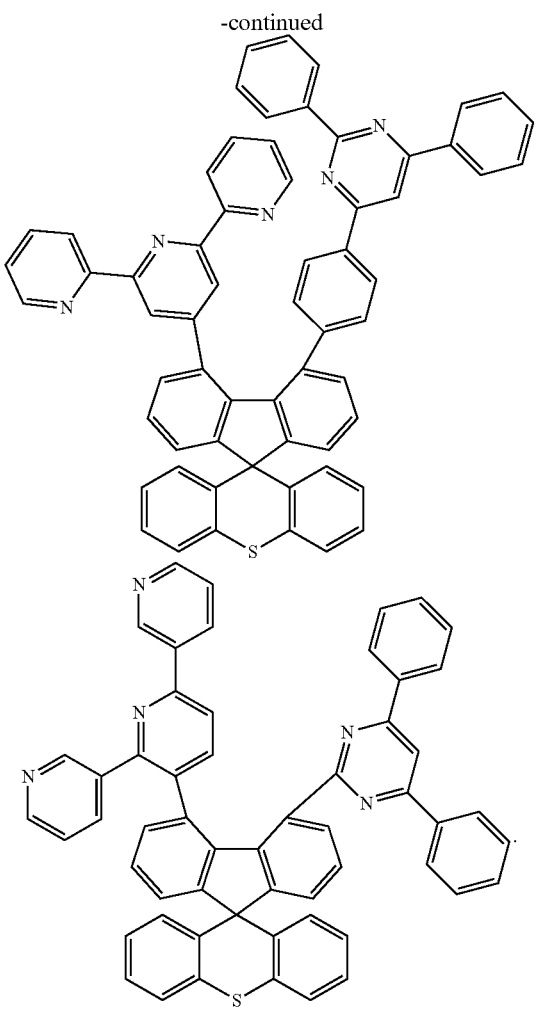

One embodiment of the present specification provides an organic light emitting device including a first electrode; a second electrode provided opposite to the first electrode; and one or more organic material layers provided between the first electrode and the second electrode, wherein one or more layers of the organic material layers include the above-described heterocyclic compound.

According to one embodiment of the present specification, the organic material layer of the organic light emitting device of the present specification can be formed in a single layer structure, but can be formed in a multilayer structure in which two or more organic material layers are laminated. For example, the organic light emitting device of the present disclosure can have a structure including a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and can include less or more numbers of organic material layers.

For example, the organic light emitting device of the present specification can have structures as illustrated in FIG. 1 and FIG. 2, however, the structure is not limited thereto.

FIG. 1 illustrates a structure of the organic light emitting device (10) in which a first electrode (30), a light emitting layer (40) and a second electrode (50) are consecutively laminated on a substrate (20). FIG. 1 is an exemplary structure of the organic light emitting device according to one embodiment of the present specification, and other organic material layers can be further included.

FIG. 2 illustrates a structure of the organic light emitting device (11) in which a first electrode (30), a hole injection layer (60), a hole transfer layer (70), a light emitting layer (40), a layer carrying out electron injection and electron transfer at the same time (80) and a second electrode (50) are consecutively laminated on a substrate (20). FIG. 2 is an exemplary structure of according to an embodiment of the present specification, and other organic material layers can be further included.

According to one embodiment of the present specification, the organic material layer includes an electron injection layer, an electron transfer layer, or a layer carrying out electron injection and electron transfer at the same time, and the electron injection layer, the electron transfer layer, or the layer carrying out electron injection and electron transfer at the same time includes the heterocyclic compound of Chemical Formula 1.

In one embodiment of the present specification, when using the heterocyclic compound of Chemical Formula 1 in the organic material layer capable of carrying out electron injection and electron transfer at the same time, an n-type dopant used in the art can be mixed thereto and used.

In one embodiment of the present specification, when the electron transfer layer, the electron injection layer, or the layer carrying out electron injection and electron transfer at the same time further includes an n-type dopant in addition to the compound of Chemical Formula 1, the compound of Chemical Formula 1 and the n-type dopant can have a weight ratio of 1:100 to 100:1. Specifically, the weight ratio can be from 1:10 to 10:1. More specifically, the weight ratio can be 1:1.

In one embodiment of the present specification, the n-type dopant can be a metal complex and the like, and an alkali metal such as Li, Na, K, Rb, Cs or Fr; an alkaline-earth metal such as Be, Mg, Ca, Sr, Ba or Ra; a rare-earth metal such as La, Ce, Pr, Nd, Sm, Eu, Tb, Th, Dy, Ho, Er, Em, Gd, Yb, Lu, Y or Mn; or a metal compound including one or more metals of the above-mentioned metals can be used, however, the n-type dopant is not limited thereto, and those known in the art can be used. According to one embodiment, the electron transfer layer, the electron injection layer, or the layer carrying out electron injection and electron transfer at the same time including the compound of Chemical Formula 1 can further include LiQ.

According to one embodiment of the present specification, the organic material layer includes a hole blocking layer, and the hole blocking layer includes the heterocyclic compound of Chemical Formula 1.

According to one embodiment of the present specification, the organic material layer includes an electron control layer, and the electron control layer includes the heterocyclic compound of Chemical Formula 1.

According to one embodiment of the present specification, the organic material layer can further include one or more layers selected from the group consisting of a hole injection layer, a hole transfer layer, a light emitting layer, an electron transfer layer and an electron injection layer.

The organic light emitting device of the present specification can be manufactured using materials and methods known in the art, except that one or more layers of the organic material layers include the heterocyclic compound of the present specification, that is, the heterocyclic compound of Chemical Formula 1.

When the organic light emitting device includes a plurality of organic material layers, the organic material layers can be formed with materials the same as or different from each other.

For example, the organic light emitting device of the present specification can be manufactured by consecutively laminating a first electrode, an organic material layer and a second electrode on a substrate. Herein, the organic light emitting device can be manufactured by forming a first electrode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a second electrode thereon. In addition to such a method, the organic light emitting device can also be manufactured by consecutively depositing a second electrode material, an organic material layer and a first electrode material on a substrate. In addition, the heterocyclic compound of Chemical Formula 1 can be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferred so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al, $LiO_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition thereto, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer receiving holes from a hole injection layer and transferring the holes to a light emitting layer, and as the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

The light emitting material of the light emitting layer is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxy-quinoline aluminum complexes ($Alq_3$); carbazole series compounds; dimerized styryl compounds; BAlq; 10-hydroxybenzoquinoline-metal compounds; benzoxazole, benzothiazole and benzimidazole series compounds; poly(p-phenylenevinylene) (PPV) series polymers; spiro compounds; polyfluorene; rubrene, and the like, but are not limited thereto.

The light emitting layer can include a host material and a dopant material. The host material can include fused aromatic ring derivatives, heteroring-containing compounds or the like. Specifically, as the fused aromatic ring derivative, anthracene derivatives, pyrene derivatives, naphthalene derivatives, pentacene derivatives, phenanthrene compounds, fluoranthene compounds and the like can be included, and as the heteroring-containing compound, carbazole derivatives, dibenzofuran derivatives, ladder-type furan compounds, pyrimidine derivatives and the like can be included, however, the host material is not limited thereto.

The dopant material can include aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group, and arylamino group-including pyrene, anthracene, chrysene, peryflanthene and the like can be included. The styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group can be substituted or unsubstituted. Specifically, styrylamine, styryldiamine, styryltriamine, styryltetramine and the like can be included, however, the styrylamine compound is not limited thereto. As the metal complex, iridium complexes, platinum complexes and the like can be used, however, the metal complex is not limited thereto.

The electron transfer layer is a layer receiving electrons from an electron injection layer and transferring the electrons to a light emitting layer, and as the electron transfer material, materials capable of favorably receiving electrons from a cathode, moving the electrons to a light emitting layer, and having high mobility for the electrons are suited. Specific examples thereof include Al complexes of 8-hydroxyquinoline; complexes including Alq₃; organic radical compounds; hydroxyflavon-metal complexes, and the like, but are not limited thereto. The electron transfer layer can be used together with any desired cathode material as used in the art. Particularly, examples of the suitable cathode material can include common materials having low work function and having an aluminum layer or a silver layer following. Specifically, cesium, barium, calcium, ytterbium and samarium are included, and in each case, an aluminum layer or a silver layer follows.

The electron injection layer is a layer injecting electrons from an electrode, and compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The hole blocking layer is layer blocking holes from reaching a cathode, and can be generally formed under the same condition as the hole injection layer. Specific examples thereof can include oxadiazole derivatives, triazole derivatives, phenanthroline derivatives, BCP, aluminum complexes and the like, but are not limited thereto.

The metal complex compound includes 8-hydroxyquinolinato lithium, bis(8-hydroxyquinolinato)zinc, bis(8-hydroxy-quinolinato)copper, bis(8-hydroxyquinolinato)manganese, tris(8-hydroxyquinolinato)aluminum, tris(2-methyl-8-hydroxy-quinolinato) aluminum, tris (8-hydroxyquinolinato) gallium, bis (10-hydroxybenzo[h] quinolinato)berylium, bis (10-hydroxybenzo[h]-quinolinato)zinc, bis(2-methyl-8-quinolinato)chlorogallium, bis(2-methyl-8-quinolinato) (o-cresolato)gallium, bis(2-methyl-8-quinolinato) (1-naphtholato)aluminum, bis(2-methyl-8-quinolinato)-(2-naphtholato)gallium and the like, but is not limited thereto.

The organic light emitting device according to the present specification can be a top-emission type, a bottom-emission type or a dual-emission type depending on the materials used.

According to one embodiment of the present specification, the heterocyclic compound of Chemical Formula 1 can be included in an organic solar cell or an organic transistor in addition to the organic light emitting device.

Preparation of the compound of Chemical Formula 1, and manufacturing of an organic electroluminescent device including the same will be specifically described in the following examples. However, the following examples are for illustrative purposes only, and the scope of the present specification is not limited thereby.

PREPARATION EXAMPLE

Example 1 (E1)

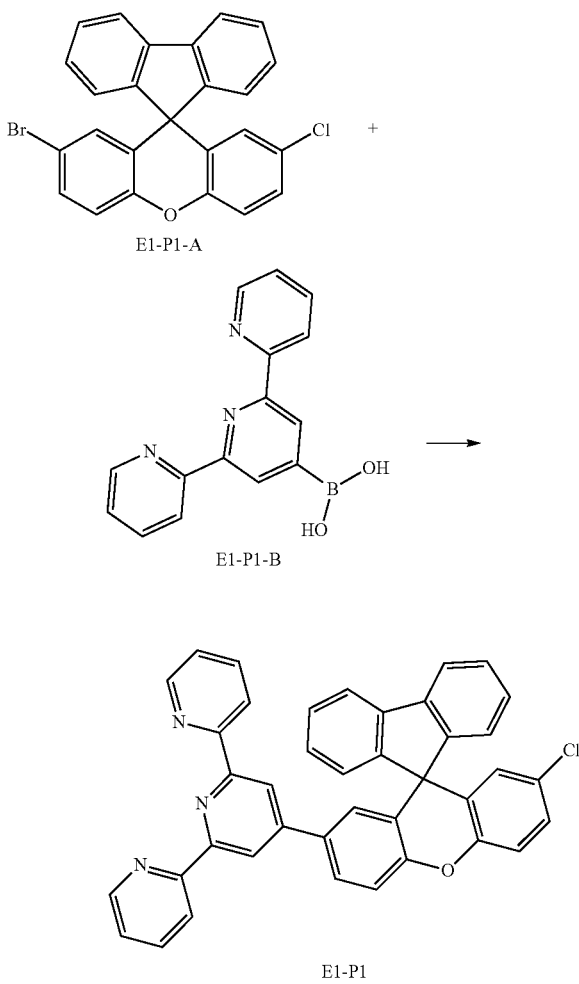

After completely dissolving a compound of Chemical Formula E1-P1-A (10 g, 22.4 mmol) and a compound of Chemical Formula E1-P1-B (6.2 g, 22.4 mmol) in tetrahydrofuran (THF) (100 mL), potassium carbonate (9.3 g, 67.2 mmol) dissolved in water (40 mL) was added thereto. After introducing tetrakistriphenyl-phosphinopalladium (0.8 g, 0.673 mmol) thereto, the result was stirred for 8 hours with heating. After lowering the temperature to room temperature, the reaction was terminated, and then the potassium carbonate solution was removed to filter white solids. The filtered white solids were washed twice each with tetrahydrofuran (THF) and ethyl acetate to prepare a compound of Chemical Formula E1-P1 (9.3 g, yield 69%).

MS [M+H]⁺=598

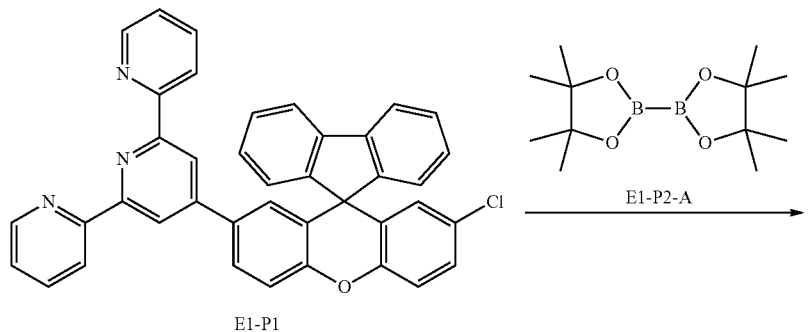

E1-P1

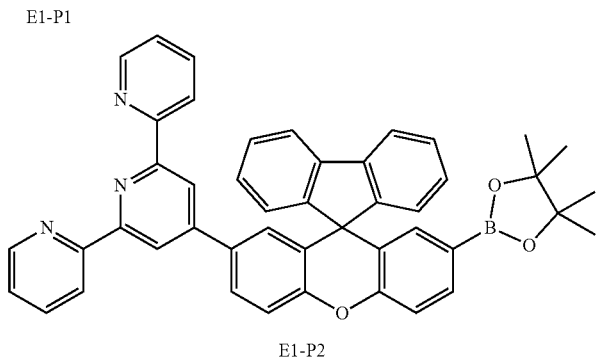

E1-P2

After completely dissolving a compound of Chemical Formula E1-P1 (9.3 g, 15.5 mmol) and a compound of Chemical Formula E1-P2-A (4.3 g, 17.2 mmol) in dioxane (90 mL), potassium acetate (4.6 g, 46.6 mmol) was added thereto, and the result was stirred with heating. After lowering the temperature to room temperature, the reaction was terminated, and then the potassium carbonate was removed and filtered to remove potassium acetate. The filtered solution was solidified with ethanol and then filtered. White solids were washed twice with ethanol to prepare a compound of Chemical Formula E1-P2 (8.6 g, yield 80%).

MS [M+H]$^+$=690

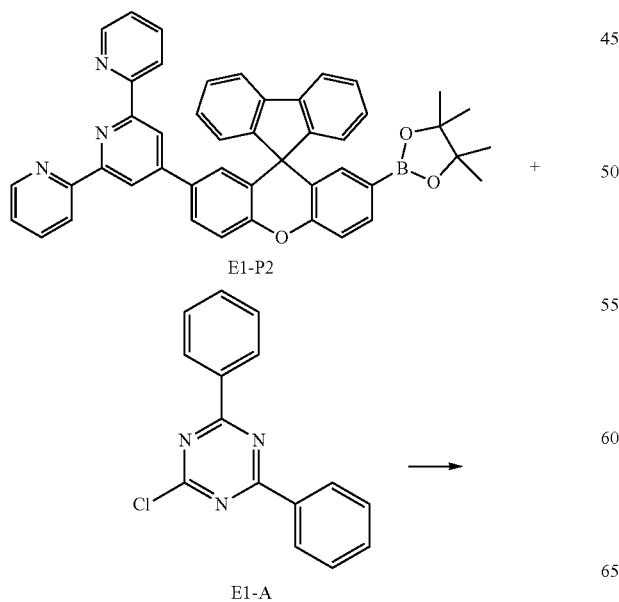

-continued

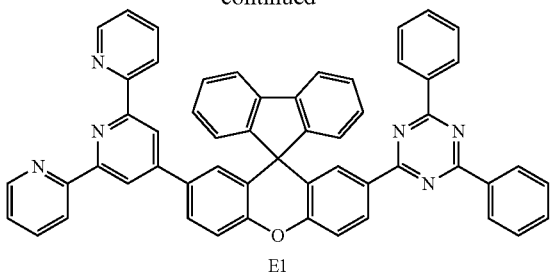

E1

After completely dissolving a compound of Chemical Formula E1-P2 (8.6 g, 12.5 mmol) and a compound of Chemical Formula E1-A (3.3 g, 12.5 mmol) in tetrahydrofuran (THF) (90 mL), potassium carbonate (5.2 g, 37.4 mmol) dissolved in water (40 mL) was added thereto. After introducing tetrakistriphenyl-phosphinopalladium (0.4 g, 0.374 mmol) thereto, the result was stirred for 8 hours with heating. After lowering the temperature to room temperature, the reaction was terminated, and then the potassium carbonate solution was removed to filter white solids. The filtered white solids were washed twice each with tetrahydrofuran (THF) and ethyl acetate to prepare a compound of Chemical Formula E1 (6.4 g, yield 65%).

MS [M+H]$^+$=795

Example 2 (E2)
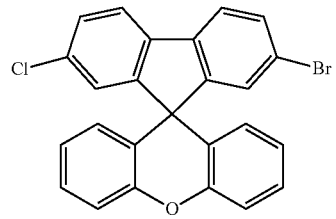
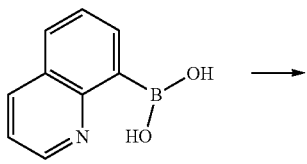
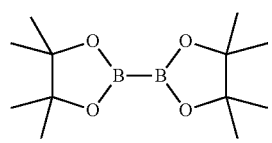
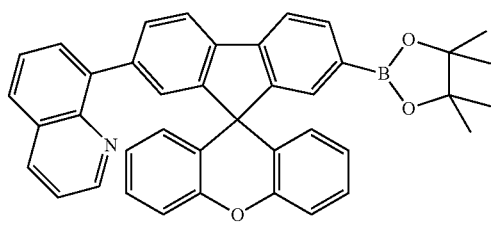
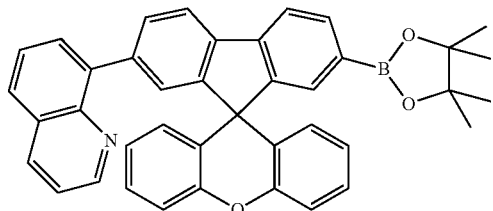
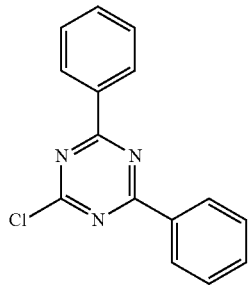
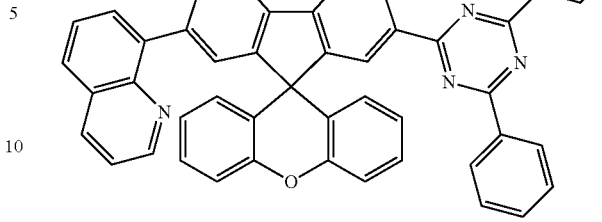
E2
A compound of Chemical Formula E2 was prepared in the same manner as in the preparation method of E1 of Example 1 except that each starting material was as in the above-described reaction scheme.
MS [M+H]⁺=691
Example 3 (E3)
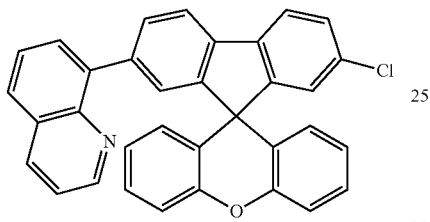

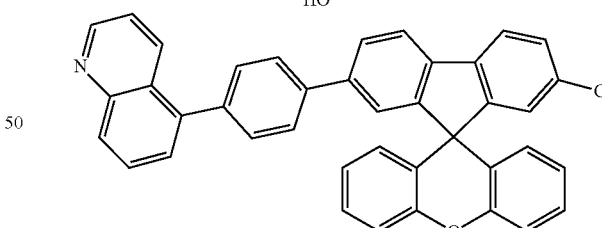
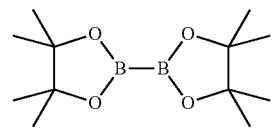
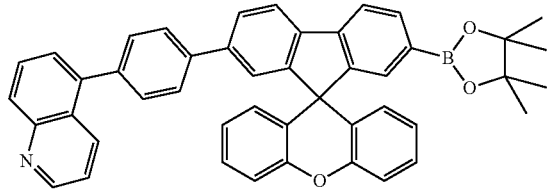

149

-continued

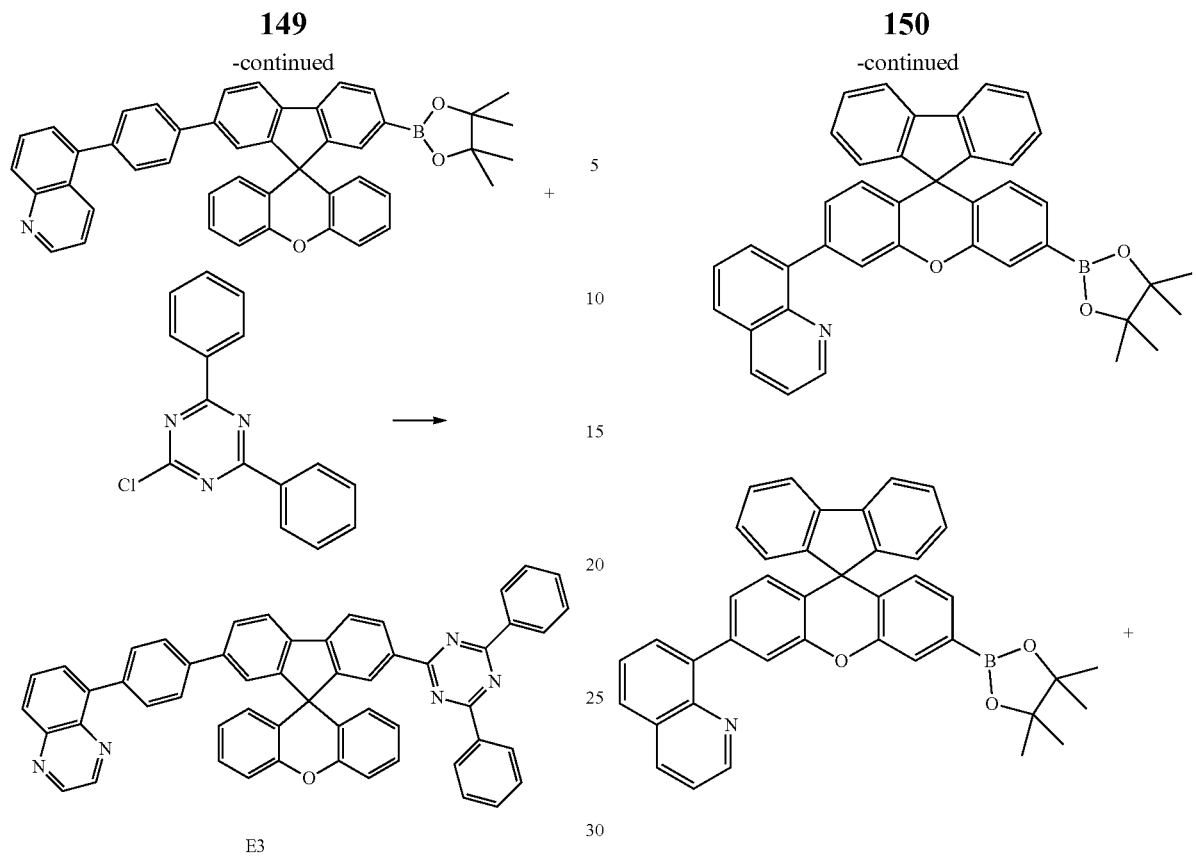

E3

A compound of Chemical Formula E3 was prepared in the same manner as in the preparation method of E1 of Example 1 except that each starting material was as shown in the above-described reaction scheme.

MS [M+H]$^+$=767

Example 4 (E4)

150

-continued

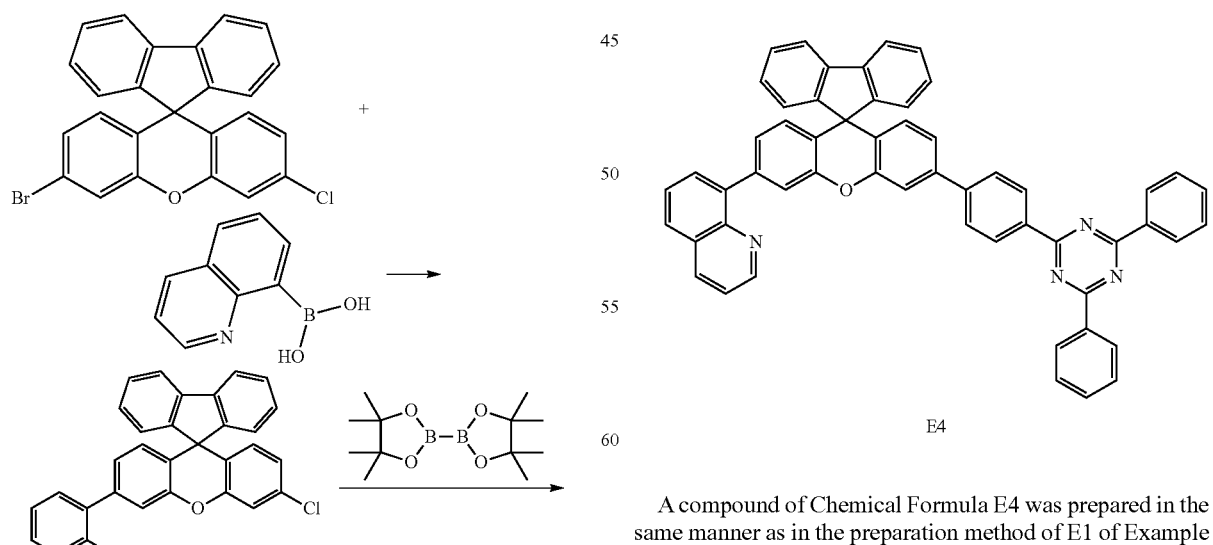

E4

A compound of Chemical Formula E4 was prepared in the same manner as in the preparation method of E1 of Example 1 except that each starting material was as in the above-described reaction scheme.

MS [M+H]$^+$=767

Example 5 (E5)
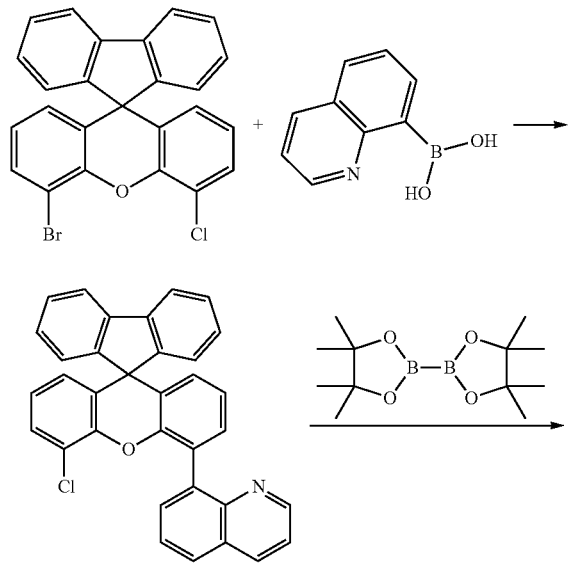
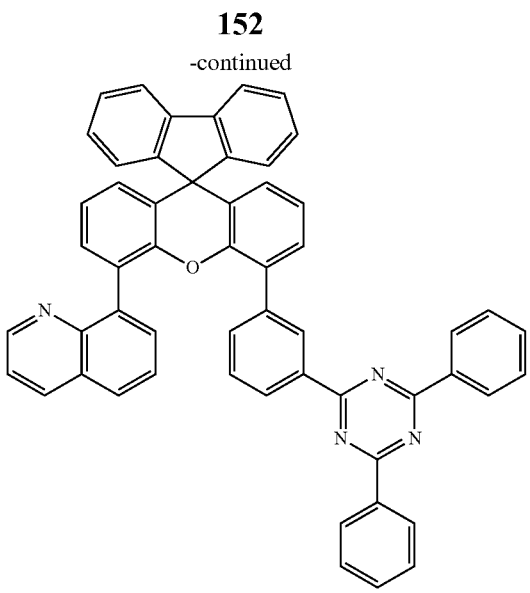
A compound of Chemical Formula E5 was prepared in the same manner as in the preparation method of E1 of Example 1 except that each starting material was as in the above-described reaction scheme.
MS [M+H]$^+$=767
Example 6 (E6)
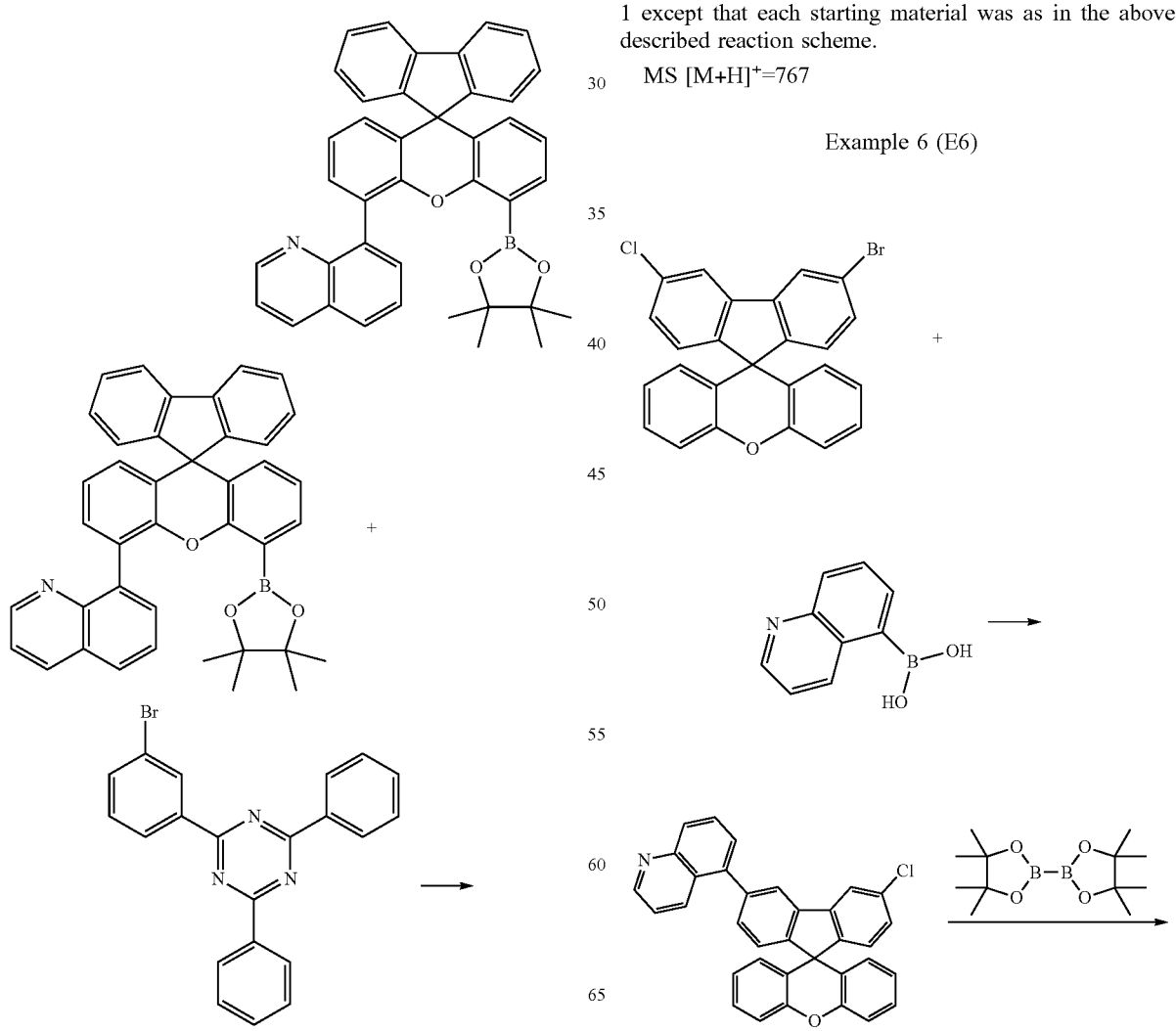

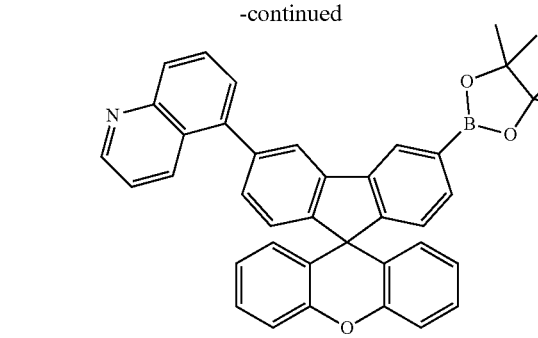
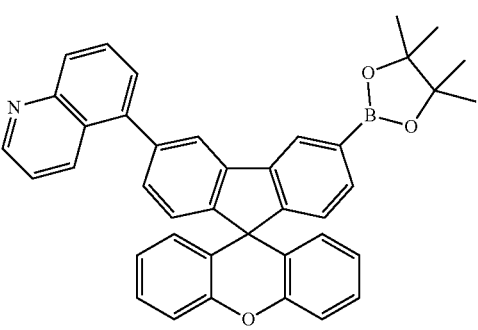
+
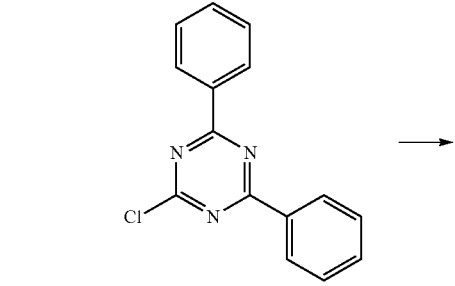
→
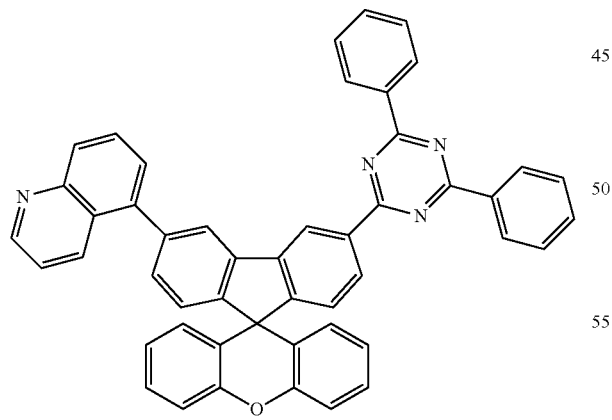
E6
A compound of Chemical Formula E6 was prepared in the same manner as in the preparation method of E1 of Example 1 except that each starting material was as in the above-described reaction scheme.
MS [M+H]$^+$=691
Example 7 (E7)
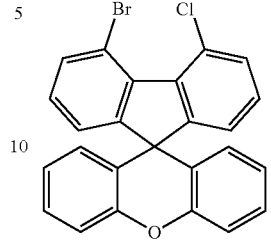 + 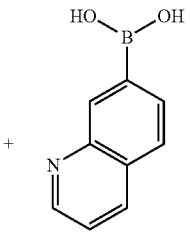 →
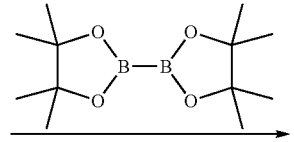
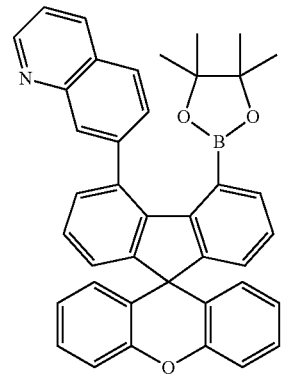
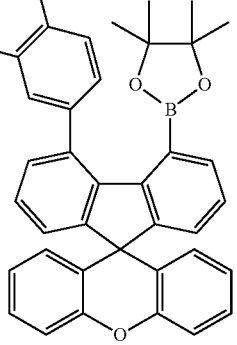
+

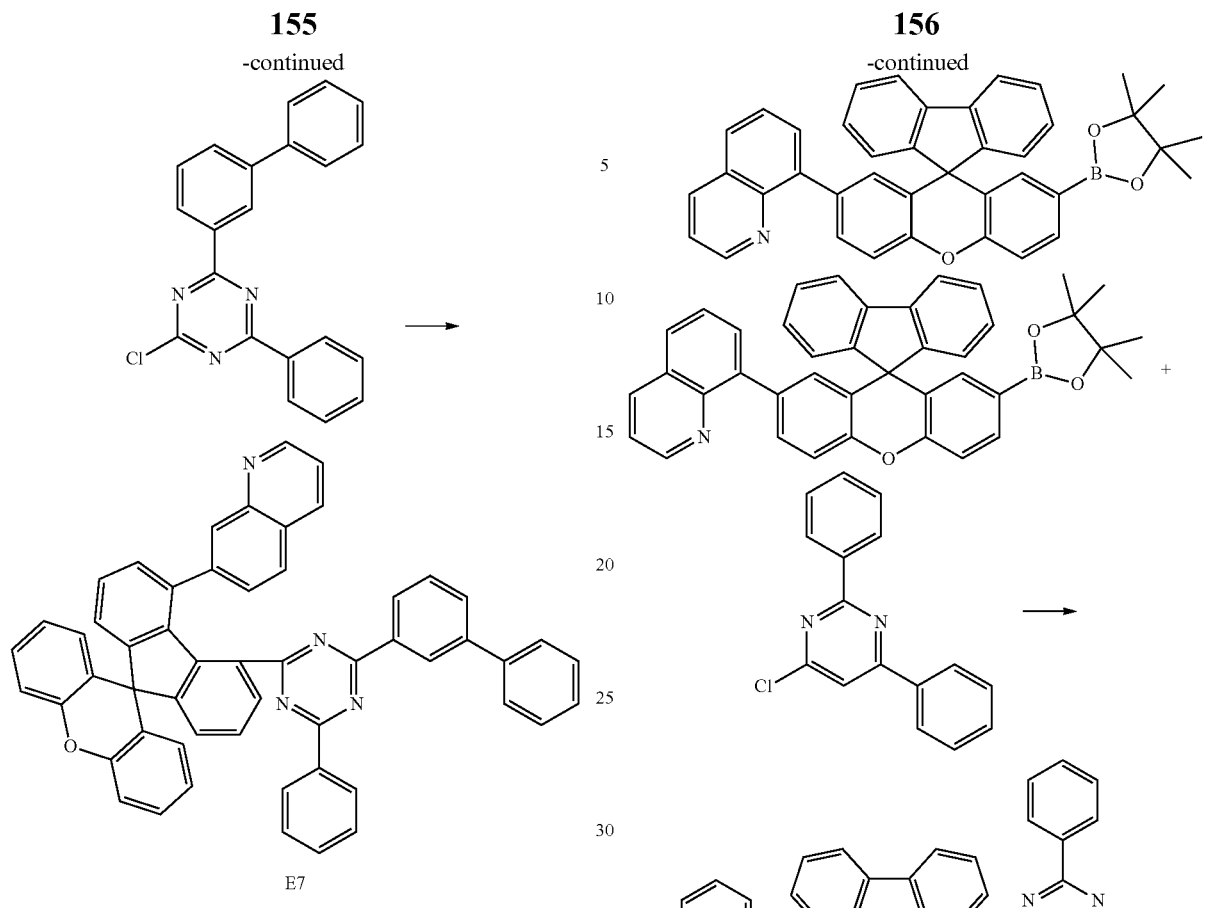

A compound of Chemical Formula E7 was prepared in the same manner as in the preparation method of E1 of Example 1 except that each starting material was as in the above-described reaction scheme.

MS [M+H]$^+$=767

Example 8 (E8)

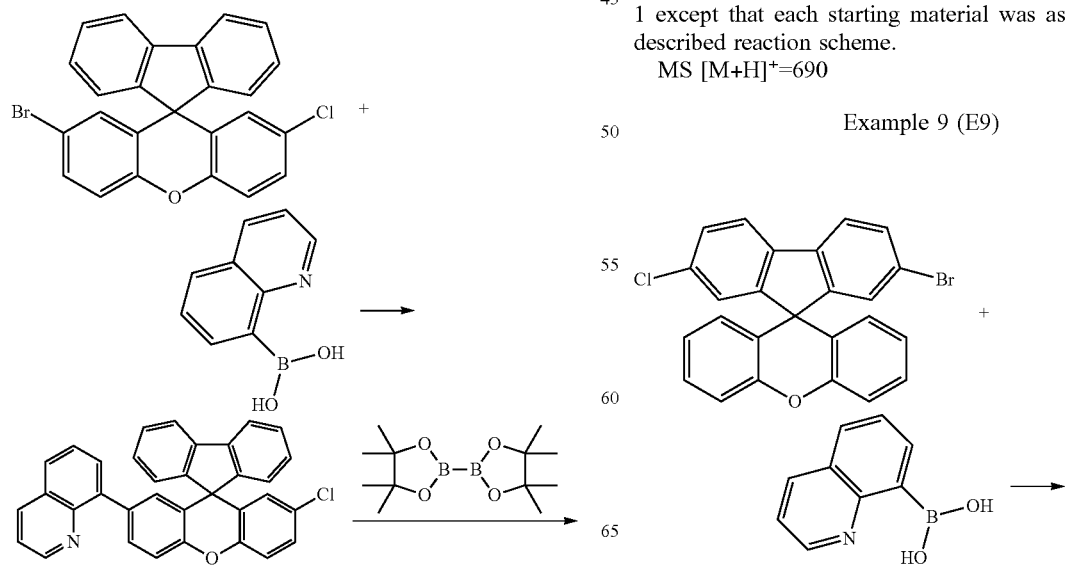

A compound of Chemical Formula E8 was prepared in the same manner as in the preparation method of E1 of Example 1 except that each starting material was as in the above-described reaction scheme.

MS [M+H]$^+$=690

Example 9 (E9)

157
-continued
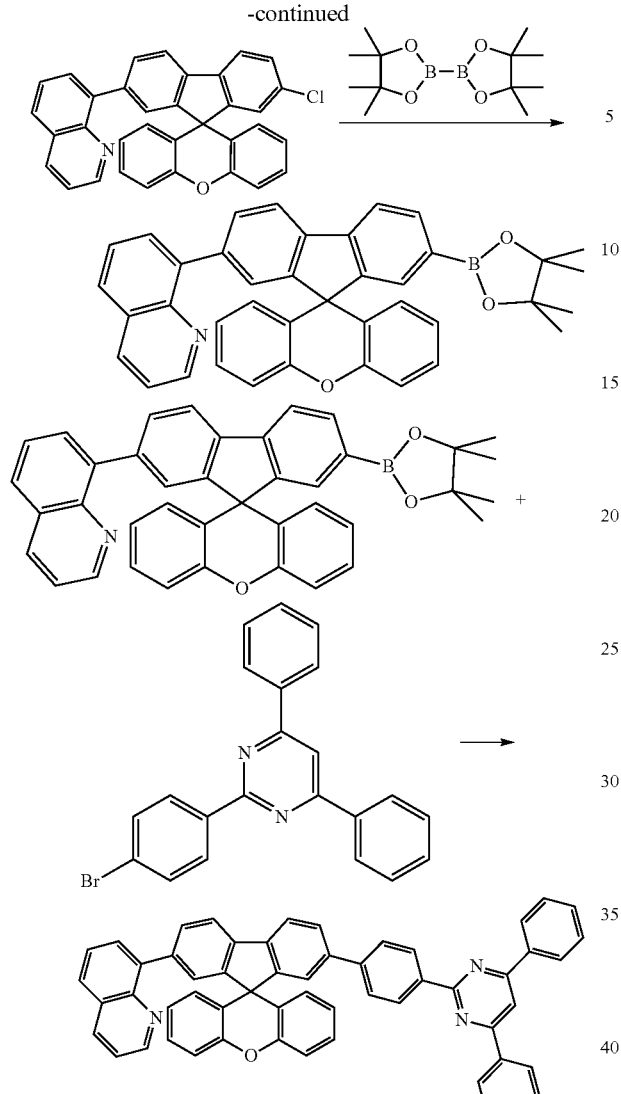
E9
A compound of Chemical Formula E9 was prepared in the same manner as in the preparation method of E1 of Example 1 except that each starting material was as in the above-described reaction scheme.
MS [M+H]$^+$=766
Example 10 (E10)
158
-continued
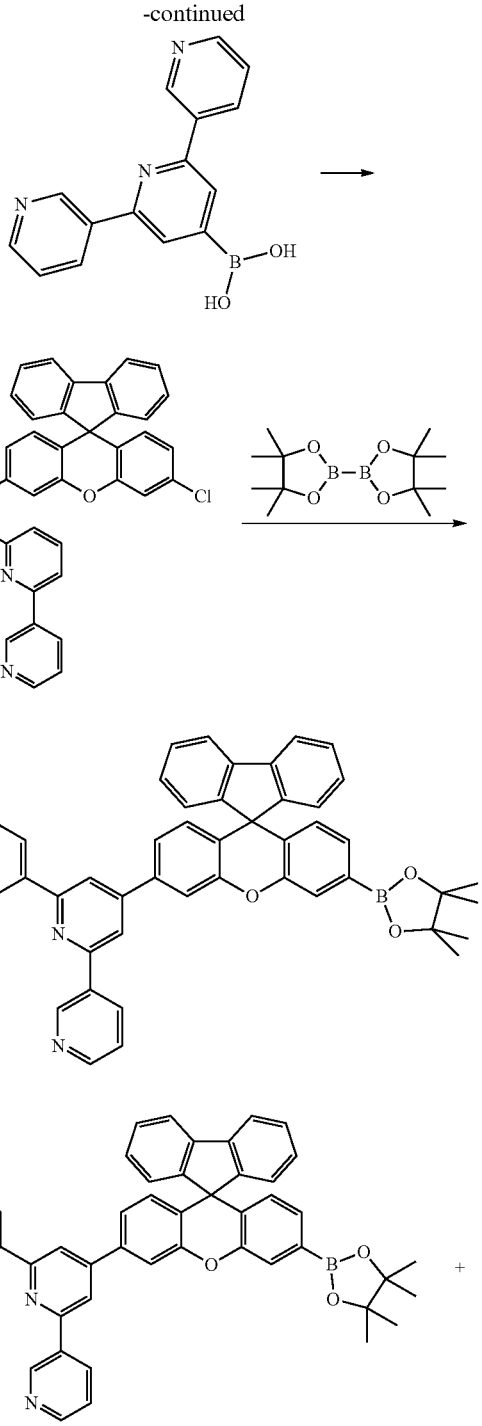
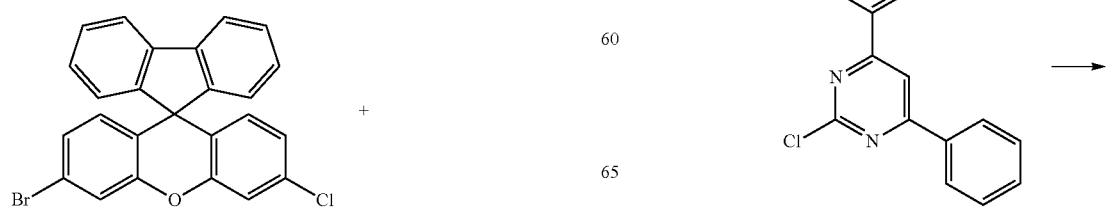

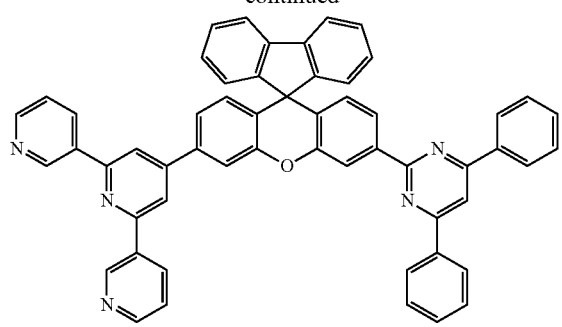
E10
A compound of Chemical Formula E10 was prepared in the same manner as in the preparation method of E1 of Example 1 except that each starting material was as in the above-described reaction scheme.
MS [M+H]⁺=794
Example 11 (E11)
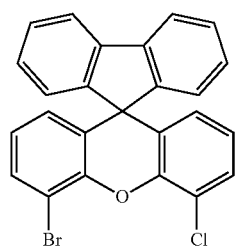
+
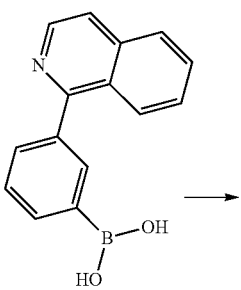
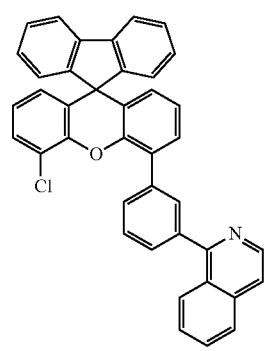 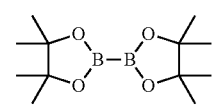
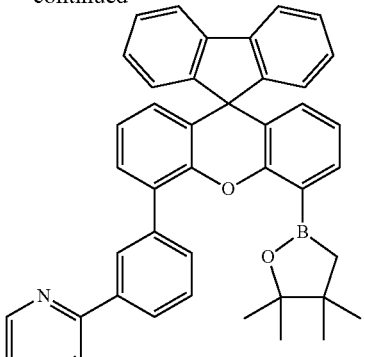
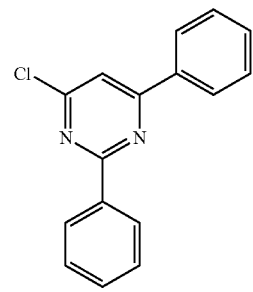
+
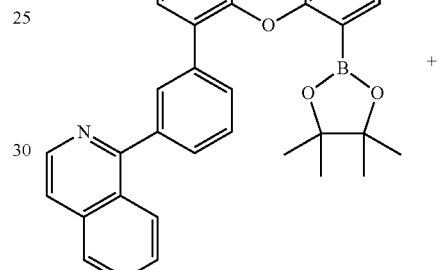
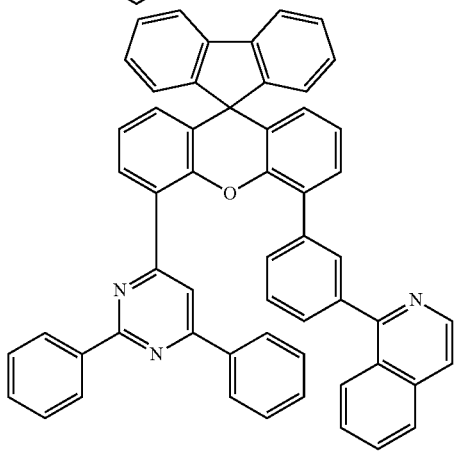
E11
A compound of Chemical Formula E11 was prepared in the same manner as in the preparation method of E1 of Example 1 except that each starting material was as in the above-described reaction scheme.
MS [M+H]⁺=766
Example 12 (E12)
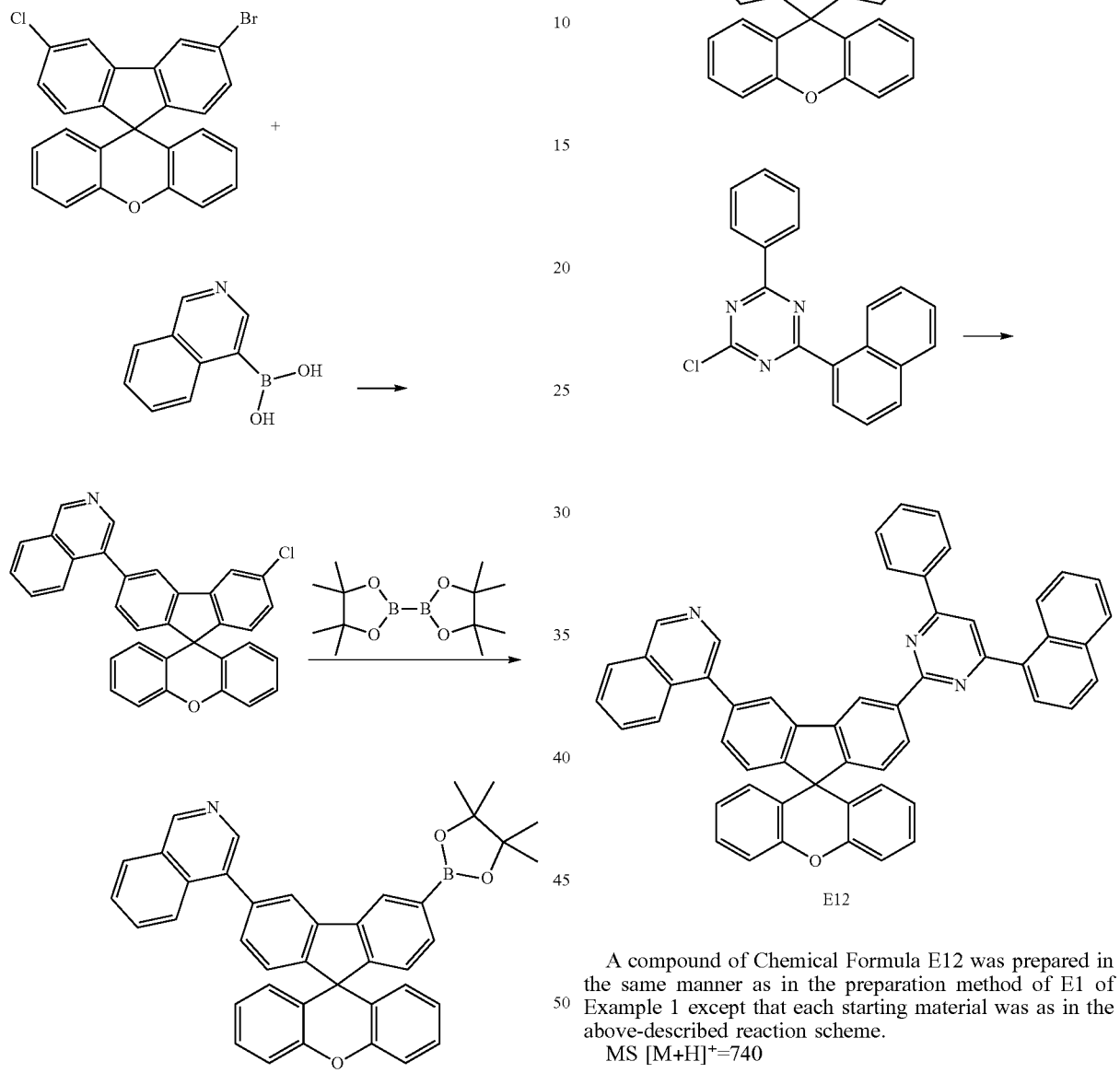
A compound of Chemical Formula E12 was prepared in the same manner as in the preparation method of E1 of Example 1 except that each starting material was as in the above-described reaction scheme.
MS [M+H]⁺=740
Example 13 (E13)
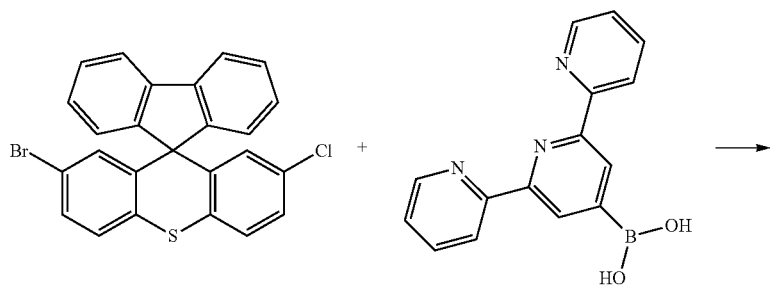

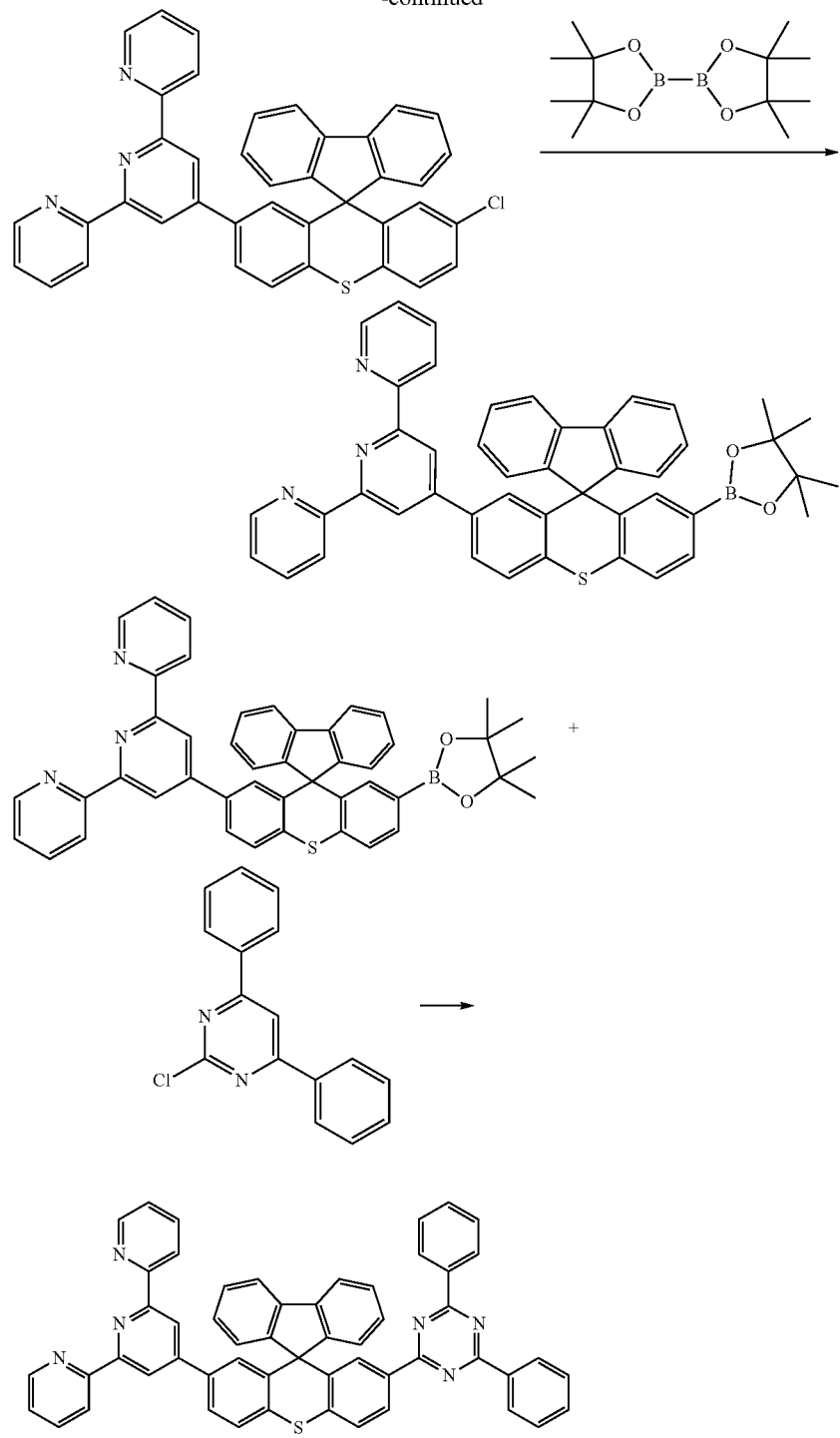
E13
A compound of Chemical Formula E13 was prepared in the same manner as in the preparation method of E1 of Example 1 except that each starting material was as in the above-described reaction scheme.
MS [M+H]$^+$=811

Example 14 (E14)
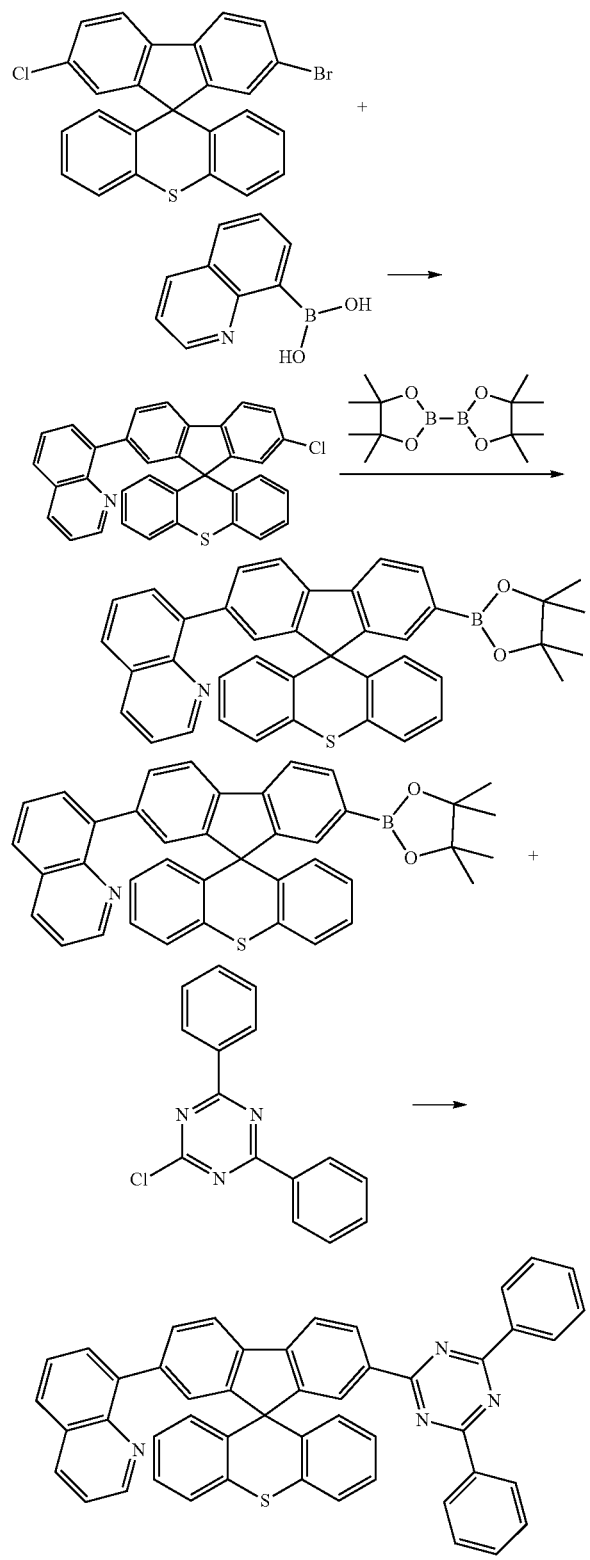
E14
A compound of Chemical Formula E14 was prepared in the same manner as in the preparation method of E1 of Example 1 except that each starting material was as in the above-described reaction scheme.
MS [M+H]$^+$=707
Example 15 (E15)
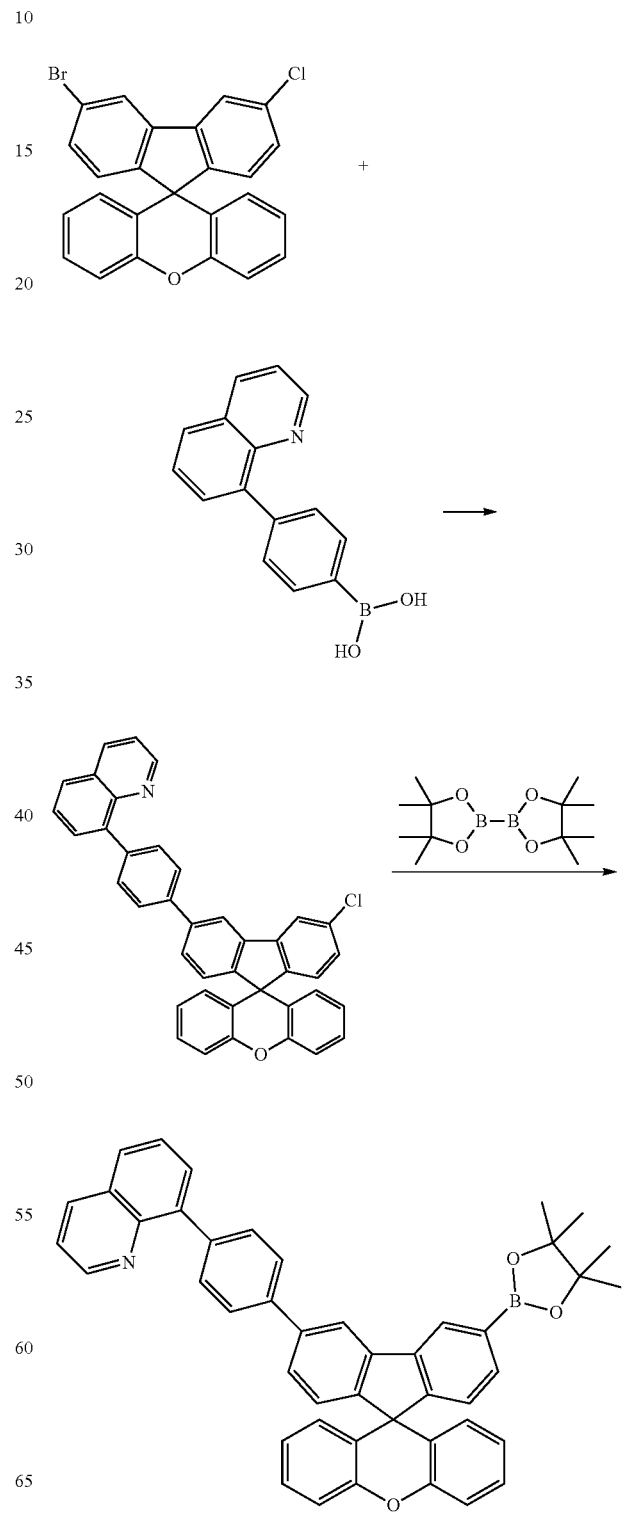

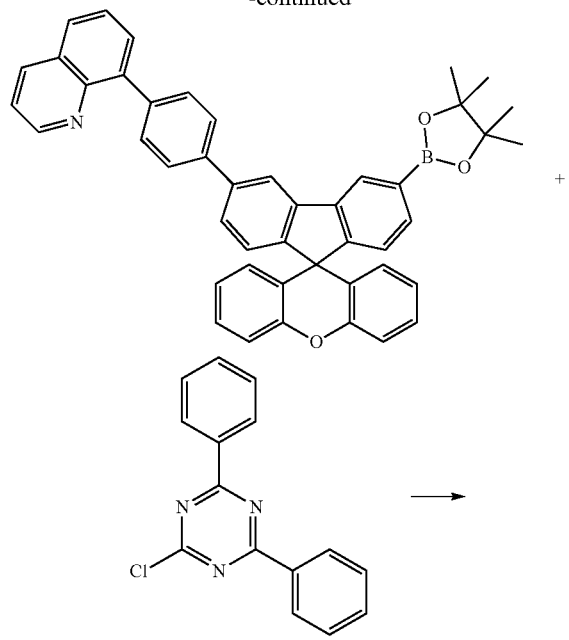

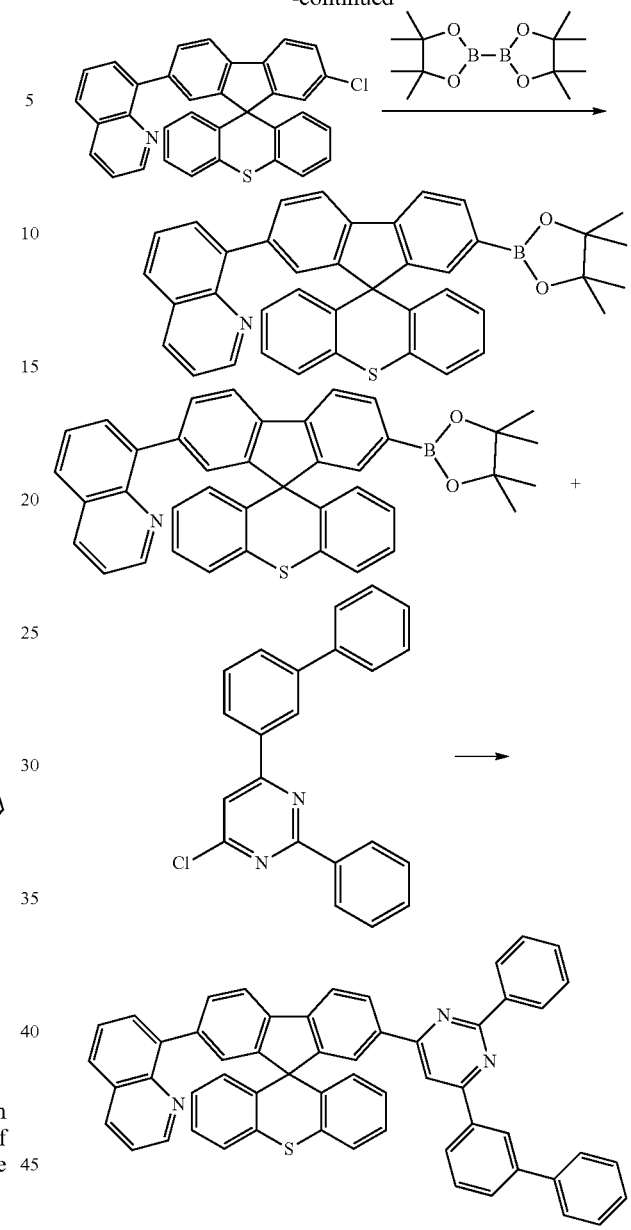

E15

A compound of Chemical Formula E15 was prepared in the same manner as in the preparation method of E1 of Example 1 except that each starting material was as in the above-described reaction scheme.

MS [M+H]$^+$=783

Example 16 (E16)

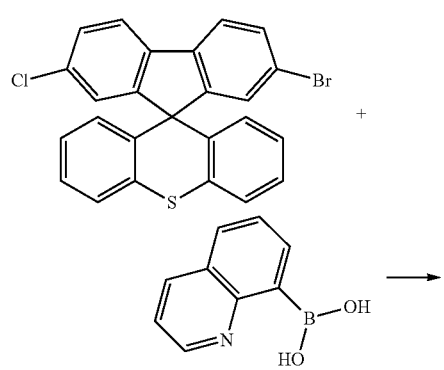

E16

A compound of Chemical Formula E16 was prepared in the same manner as in the preparation method of E1 of Example 1 except that each starting material was as in the above-described reaction scheme.

MS [M+H]$^+$=782

Experimental Example 1-1

A glass substrate on which indium tin oxide (ITO) was coated as a thin film to a thickness of 1,000 Å was placed in detergent-containing distilled water and ultrasonically cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing the following compound [HI-A] to a thickness of 600 Å. A hole transfer layer was formed on the hole injection layer by vacuum depositing hexaazatriphenylene (HAT) of the following chemical formula to 50 Å and the following compound [HT-A] (600 Å) in consecutive order.

Subsequently, a light emitting layer was formed on the hole transfer layer to a film thickness of 200 Å by vacuum depositing the following compounds [BH] and [BD] in a weight ratio of 25:1.

A layer carrying out electron injection and electron transfer at the same time was formed on the light emitting layer to a thickness of 350 Å by vacuum depositing the compound of [Chemical Formula E1] and the lithium quinolate [LiQ] compound in a weight ratio of 1:1. A cathode was formed on the electron injection and transfer layer by depositing lithium fluoride (LiF) to a thickness of 10 Å and aluminum to a thickness of 1,000 Å in consecutive order.

An organic light emitting device was manufactured by maintaining, in the above-mentioned processes, the deposition rates of the organic materials at 0.4 Å/sec to 0.9 Å/sec, the deposition rates of the lithium fluoride and the aluminum of the cathode at 0.3 Å/sec and 2 Å/sec, respectively, and the degree of vacuum during the deposition at $1 \times 10^{-7}$ torr to $5 \times 10^{-8}$ torr.

[HAT]

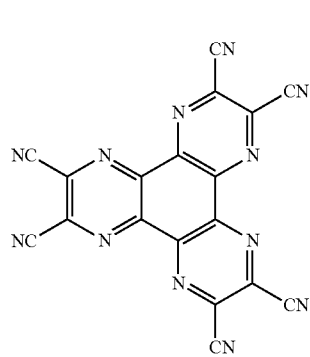

[HI-A]

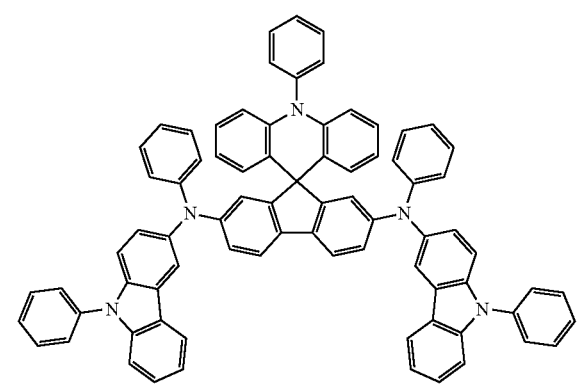

[HT-A]

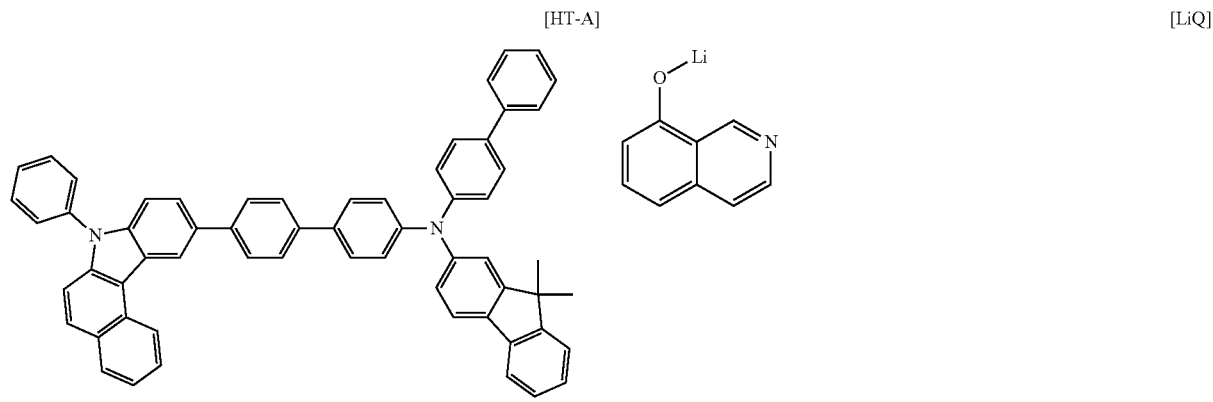

[LiQ]

-continued
| 171 | 172 |
|---|---|
| [BH] 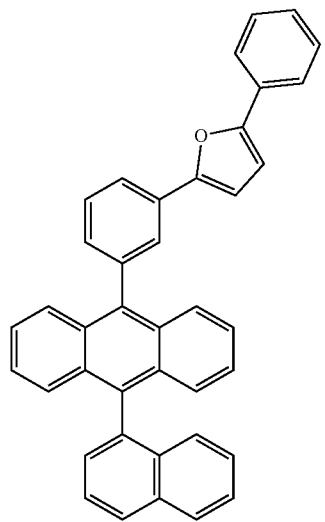 | [BD] 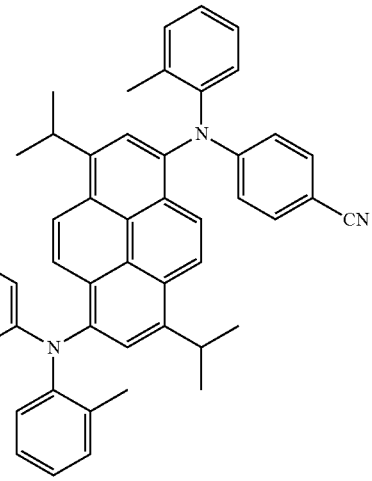 |
| [ET-A] 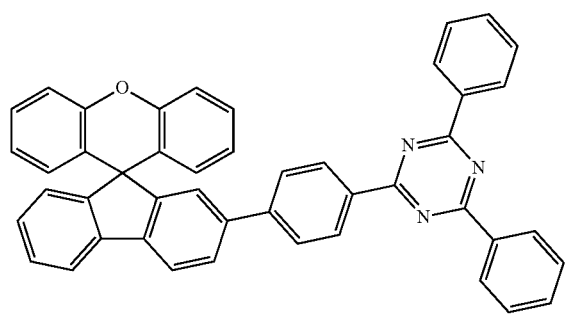 | [ET-B] 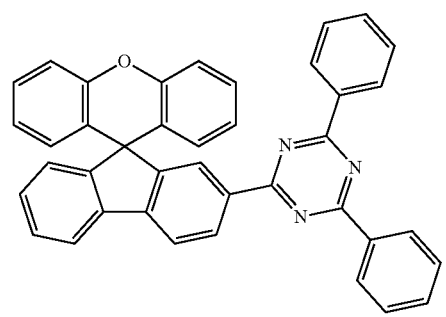 |
| [ET-C] 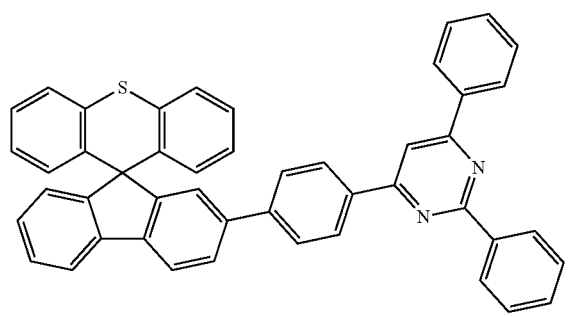 | [ET-D] 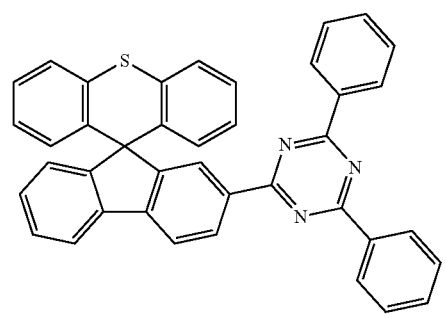 |
| [ET-E] 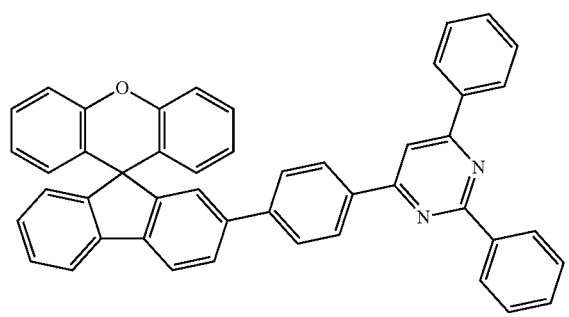 | [ET-F] 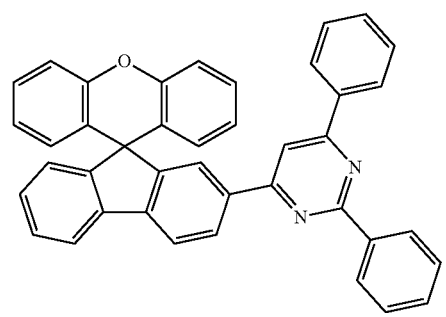 |

[ET-G]
[ET-H]
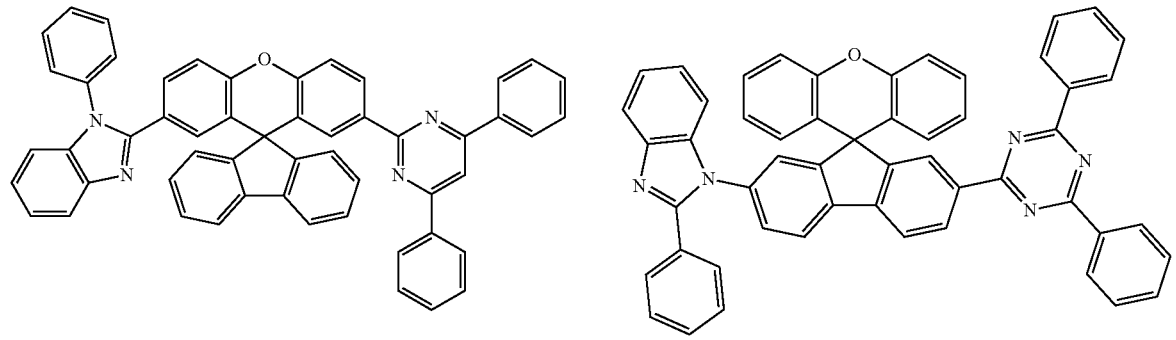
[ET-I]
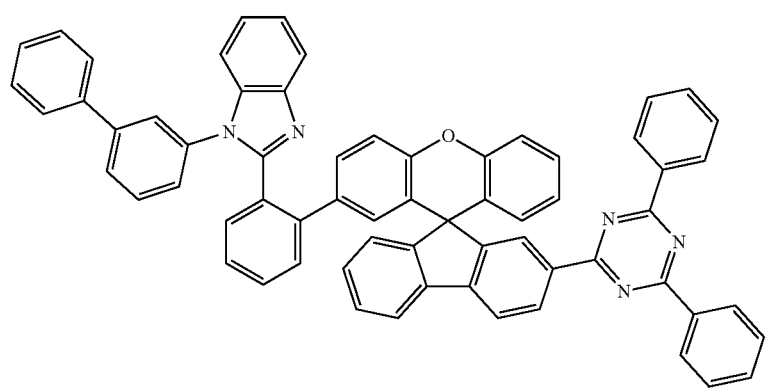
[ET-J]
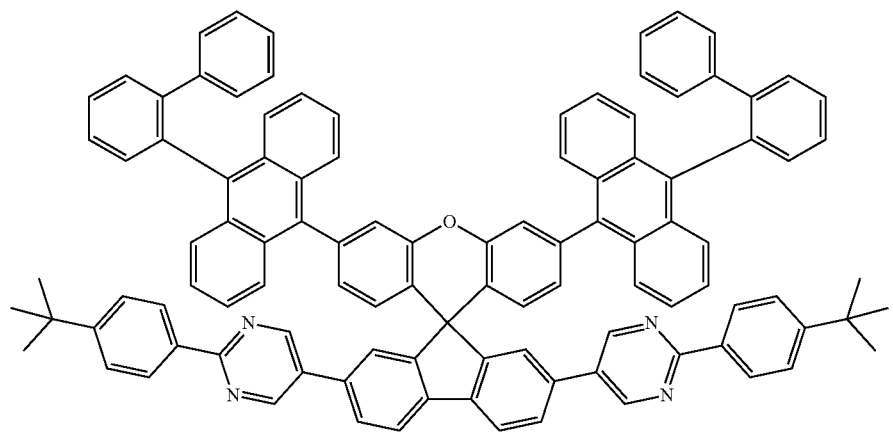
[ET-K]
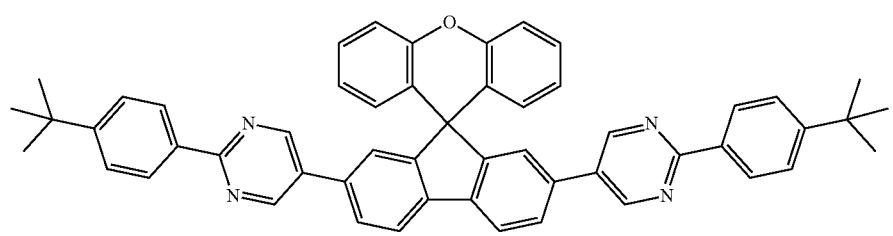

-continued

[ET-L]

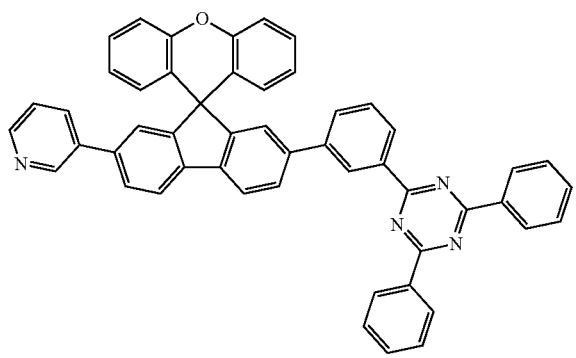

[ET-M]

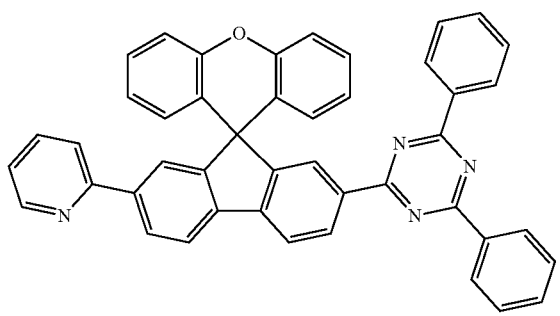

[ET-N]

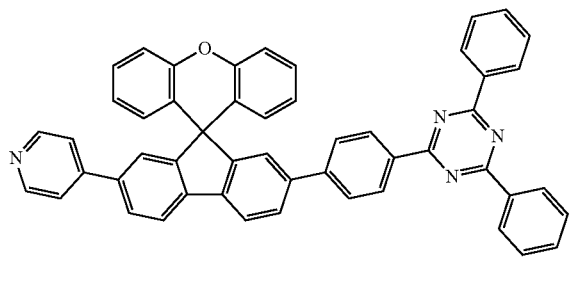

[ET-O]

Experimental Example 1-2

An organic light emitting device was manufactured in the same manner as in Experimental Example 1-1 except that the compound of Chemical Formula E2 was used instead of the compound of Chemical Formula E1.

Experimental Example 1-3

An organic light emitting device was manufactured in the same manner as in Experimental Example 1-1 except that the compound of Chemical Formula E3 was used instead of the compound of Chemical Formula E1.

Experimental Example 1-4

An organic light emitting device was manufactured in the same manner as in Experimental Example 1-1 except that the compound of Chemical Formula E4 was used instead of the compound of Chemical Formula E1.

Experimental Example 1-5

An organic light emitting device was manufactured in the same manner as in Experimental Example 1-1 except that the compound of Chemical Formula E5 was used instead of the compound of Chemical Formula E1.

Experimental Example 1-6

An organic light emitting device was manufactured in the same manner as in Experimental Example 1-1 except that the compound of Chemical Formula E6 was used instead of the compound of Chemical Formula E1.

Experimental Example 1-7

An organic light emitting device was manufactured in the same manner as in Experimental Example 1-1 except that the compound of Chemical Formula E7 was used instead of the compound of Chemical Formula E1.

Experimental Example 1-8

An organic light emitting device was manufactured in the same manner as in Experimental Example 1-1 except that the compound of Chemical Formula E8 was used instead of the compound of Chemical Formula E1.

Experimental Example 1-9

An organic light emitting device was manufactured in the same manner as in Experimental Example 1-1 except that the compound of Chemical Formula E9 was used instead of the compound of Chemical Formula E1.

Experimental Example 1-10

An organic light emitting device was manufactured in the same manner as in Experimental Example 1-1 except that the compound of Chemical Formula E10 was used instead of the compound of Chemical Formula E1.

Experimental Example 1-11

An organic light emitting device was manufactured in the same manner as in Experimental Example 1-1 except that the compound of Chemical Formula E11 was used instead of the compound of Chemical Formula E1.

Experimental Example 1-12

An organic light emitting device was manufactured in the same manner as in Experimental Example 1-1 except that the compound of Chemical Formula E12 was used instead of the compound of Chemical Formula E1.

Experimental Example 1-13

An organic light emitting device was manufactured in the same manner as in Experimental Example 1-1 except that the compound of Chemical Formula E13 was used instead of the compound of Chemical Formula E1.

Experimental Example 1-14

An organic light emitting device was manufactured in the same manner as in Experimental Example 1-1 except that the compound of Chemical Formula E14 was used instead of the compound of Chemical Formula E1.

Experimental Example 1-15

An organic light emitting device was manufactured in the same manner as in Experimental Example 1-1 except that the compound of Chemical Formula E15 was used instead of the compound of Chemical Formula E1.

Experimental Example 1-16

An organic light emitting device was manufactured in the same manner as in Experimental Example 1-1 except that the compound of Chemical Formula E16 was used instead of the compound of Chemical Formula E1.

Comparative Example 1-1

An organic light emitting device was manufactured in the same manner as in Experimental Example 1-1 except that the compound of Chemical Formula ET-A was used instead of the compound of Chemical Formula E1.

Comparative Example 1-2

An organic light emitting device was manufactured in the same manner as in Experimental Example 1-1 except that the compound of Chemical Formula ET-B was used instead of the compound of Chemical Formula E1.

Comparative Example 1-3

An organic light emitting device was manufactured in the same manner as in Experimental Example 1-1 except that the compound of Chemical Formula ET-C was used instead of the compound of Chemical Formula E1.

Comparative Example 1-4

An organic light emitting device was manufactured in the same manner as in Experimental Example 1-1 except that the compound of Chemical Formula ET-D was used instead of the compound of Chemical Formula E1.

Comparative Example 1-5

An organic light emitting device was manufactured in the same manner as in Experimental Example 1-1 except that the compound of Chemical Formula ET-E was used instead of the compound of Chemical Formula E1.

Comparative Example 1-6

An organic light emitting device was manufactured in the same manner as in Experimental Example 1-1 except that the compound of Chemical Formula ET-F was used instead of the compound of Chemical Formula E1.

Comparative Example 1-7

An organic light emitting device was manufactured in the same manner as in Experimental Example 1-1 except that the compound of Chemical Formula ET-G was used instead of the compound of Chemical Formula E1.

Comparative Example 1-8

An organic light emitting device was manufactured in the same manner as in Experimental Example 1-1 except that the compound of Chemical Formula ET-H was used instead of the compound of Chemical Formula E1.

Comparative Example 1-9

An organic light emitting device was manufactured in the same manner as in Experimental Example 1-1 except that the compound of Chemical Formula ET-I was used instead of the compound of Chemical Formula E1.

Comparative Example 1-10

An organic light emitting device was manufactured in the same manner as in Experimental Example 1-1 except that the compound of Chemical Formula ET-J was used instead of the compound of Chemical Formula E1.

Comparative Example 1-11

An organic light emitting device was manufactured in the same manner as in Experimental Example 1-1 except that the compound of Chemical Formula ET-K was used instead of the compound of Chemical Formula E1.

Comparative Example 1-12

An organic light emitting device was manufactured in the same manner as in Experimental Example 1-1 except that the compound of Chemical Formula ET-L was used instead of the compound of Chemical Formula E1.

Comparative Example 1-13

An organic light emitting device was manufactured in the same manner as in Experimental Example 1-1 except that the compound of Chemical Formula ET-M was used instead of the compound of Chemical Formula E1.

Comparative Example 1-14

An organic light emitting device was manufactured in the same manner as in Experimental Example 1-1 except that the compound of Chemical Formula ET-N was used instead of the compound of Chemical Formula E1.

Comparative Example 1-15

An organic light emitting device was manufactured in the same manner as in Experimental Example 1-1 except that the compound of Chemical Formula ET-O was used instead of the compound of Chemical Formula E1.

For the organic light emitting devices manufactured using the methods of Experimental Examples 1-1 to 1-16 and Comparative Examples 1-1 to 1-15 described above, a driving voltage and light emission efficiency were measured at a current density of 10 mA/cm$^2$, and time taken for the luminance decreasing to 90% compared to its initial luminance ($T_{90}$) was measured at a current density of 20 mA/cm$^2$. The results are shown in the following Table 1.

TABLE 1

|  | Chemical Formula | Voltage (V@10 mA/cm$^2$) | Efficiency (cd/A@10 mA/cm$^2$) | Color Coordinate (x, y) | Lifetime (h) $T_{90}$ at 20 mA/Cm$^2$ |
|---|---|---|---|---|---|
| Experimental Example 1-1 | E1 | 4.27 | 5.46 | (0.142, 0.097) | 145 |
| Experimental Example 1-2 | E2 | 4.23 | 5.52 | (0.142, 0.096) | 146 |
| Experimental Example 1-3 | E3 | 4.11 | 5.54 | (0.142, 0.096) | 124 |
| Experimental Example 1-4 | E4 | 4.20 | 5.39 | (0.142, 0.096) | 158 |
| Experimental Example 1-5 | E5 | 4.10 | 5.59 | (0.142, 0.096) | 121 |
| Experimental Example 1-6 | E6 | 4.17 | 5.56 | (0.142, 0.097) | 118 |
| Experimental Example 1-7 | E7 | 4.20 | 5.58 | (0.142, 0.096) | 123 |
| Experimental Example 1-8 | E8 | 4.11 | 5.40 | (0.142, 0.099) | 124 |
| Experimental Example 1-9 | E9 | 4.10 | 5.47 | (0.142, 0.096) | 112 |
| Experimental Example 1-10 | E10 | 4.12 | 5.45 | (0.142, 0.098) | 119 |
| Experimental Example 1-11 | E11 | 4.14 | 5.47 | (0.142, 0.096) | 107 |
| Experimental Example 1-12 | E12 | 4.30 | 5.32 | (0.142, 0.097) | 110 |
| Experimental Example 1-13 | E13 | 4.14 | 5.34 | (0.142, 0.096) | 115 |
| Experimental Example 1-14 | E14 | 4.29 | 5.31 | (0.142, 0.097) | 169 |
| Experimental Example 1-15 | E15 | 4.23 | 5.42 | (0.142, 0.097) | 152 |
| Experimental Example 1-16 | E16 | 4.17 | 5.50 | (0.142, 0.097) | 140 |
| Comparative Example 1-1 | ET-A | 4.32 | 4.91 | (0.142, 0.098) | 22 |
| Comparative Example 1-2 | ET-B | 4.24 | 5.01 | (0.142, 0.102) | 11 |
| Comparative Example 1-3 | ET-C | 4.23 | 4.99 | (0.142, 0.096) | 11 |
| Comparative Example 1-4 | ET-D | 4.37 | 4.80 | (0.142, 0.096) | 20 |
| Comparative Example 1-5 | ET-E | 4.41 | 4.61 | (0.142, 0.096) | 16 |
| Comparative Example 1-6 | ET-F | 4.30 | 4.52 | (0.142, 0.096) | 18 |
| Comparative Example 1-7 | ET-G | 5.23 | 3.20 | (0.142, 0.096) | 42 |
| Comparative Example 1-8 | ET-H | 5.35 | 3.19 | (0.142, 0.096) | 46 |
| Comparative Example 1-9 | ET-I | 5.15 | 3.38 | (0.142, 0.096) | 30 |
| Comparative Example 1-10 | ET-J | 5.89 | 2.33 | (0.142, 0.096) | 80 |
| Comparative Example 1-11 | ET-K | 5.90 | 2.60 | (0.142, 0.097) | 70 |
| Comparative Example 1-12 | ET-L | 4.30 | 4.71 | (0.142, 0.096) | 64 |
| Comparative Example 1-13 | ET-M | 4.23 | 4.81 | (0.142, 0.096) | 62 |
| Comparative Example 1-14 | ET-N | 4.55 | 4.79 | (0.142, 0.096) | 61 |

TABLE 1-continued

|  | Chemical Formula | Voltage (V@10 mA/cm$^2$) | Efficiency (cd/A@10 mA/cm$^2$) | Color Coordinate (x, y) | Lifetime (h) $T_{90}$ at 20 mA/Cm$^2$ |
|---|---|---|---|---|---|
| Comparative Example 1-15 | ET-O | 4.50 | 4.60 | (0.142, 0.097) | 60 |

From the results of Table 1, it was identified that the heterocyclic compound of Chemical Formula 1 according to one embodiment of the present specification was able to be used in an organic material layer capable of electron injection and electron transfer at the same time of an organic light emitting device.

When specifically comparing Experimental Examples 1-1 to 1-16 with Comparative Examples 1-1 to 1-6, it was identified that the compound having a spirofluorenexanthene or thioxanthene skeleton substituted with a triazine group or a pyrimidine group on a symmetric position of a quinoline group or a terpyridine group as in Chemical Formula 1 exhibited excellent properties in terms of driving voltage, efficiency and, particularly, lifetime in the organic light emitting device compared to the compound having a spirofluorenexanthene or thioxanthene skeleton unsubstituted with a quinoline group or a terpyridine group.

When specifically comparing Experimental Examples 1-1 to 1-16 with Comparative Examples 1-7 to 1-11, it was identified that the compound having a spirofluorenexanthene or thioxanthene skeleton substituted with a triazine group or a pyrimidine group on a symmetric position of a quinoline group or a terpyridine group as in Chemical Formula 1 exhibited excellent properties in terms of driving voltage, efficiency and lifetime in the organic light emitting device compared to the compound having a spirofluorenexanthene or thioxanthene skeleton substituted with other heteroaryl groups instead of a quinoline group or a terpyridine group.

When specifically comparing Experimental Examples 1-1 to 1-16 with Comparative Examples 1-12 to 1-15, it was identified that the compound having a spirofluorenexanthene or thioxanthene skeleton substituted with a triazine group or a pyrimidine group on a symmetric position of a quinoline group or a terpyridine group as in Chemical Formula 1 exhibited excellent properties in terms of driving voltage, efficiency and lifetime in the organic light emitting device compared to the compound having a spirofluorenexanthene, thioxanthene or spirofluorene skeleton substituted with a pyridine group.

Accordingly, the heterocyclic compound of Chemical Formula 1 according to one embodiment of the present specification has low driving voltage and high efficiency, and can enhance device stability by hole stability of the compound.

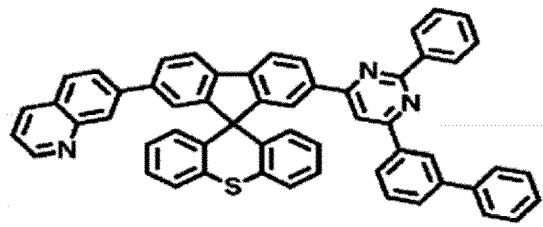

In Claim 12, at Column 307, please replace the 3rd Structure:
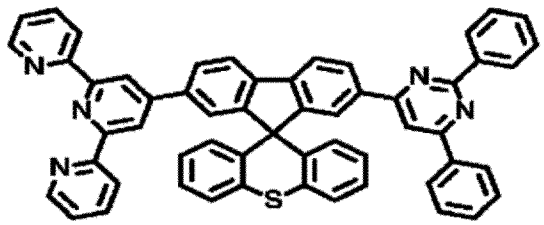
In Claim 12, at Column 313, please replace the 1st Structure:
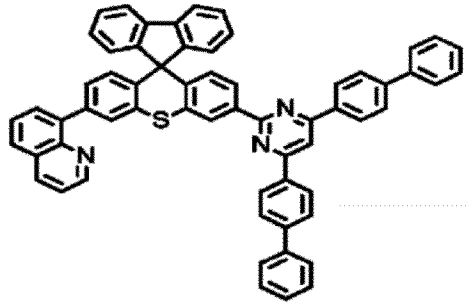
In Claim 12, at Column 315, please replace the 4th Structure:
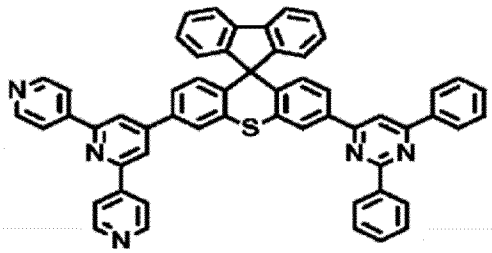
In Claim 12, at Column 317, please replace the 1st Structure:
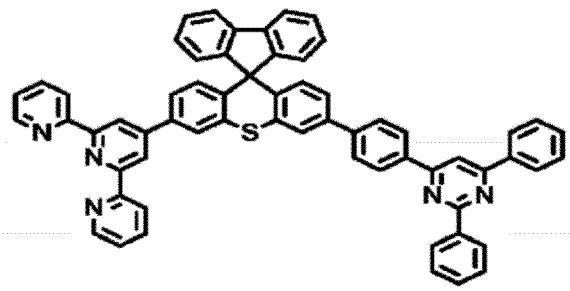

The invention claimed is:
1. A heterocyclic compound of Chemical Formula 1:

[Chemical Formula 1]

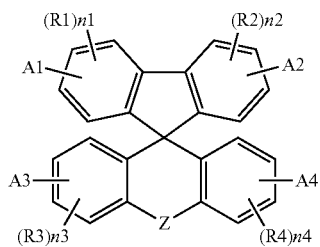

wherein, in Chemical Formula 1:

Z is O or S;

R1 to R4 are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group;

n1 to n4 are the same as or different from each other and each independently is an integer of 0 to 3, and when n1 to n4 are an integer of 2 or greater, substituents in the parentheses are the same as or different from each other;

A1 is hydrogen or -L1-Ar1, A2 is hydrogen or -L2-Ar2, A3 is hydrogen or -L3-Ar3, and A4 is hydrogen or -L4-Ar4;

L1 to L4 are the same as or different from each other, and each independently is a direct bond, a substituted or unsubstituted arylene group, or a substituted or unsubstituted heteroarylene group;

at least two of A1 to A4 are not hydrogen;

A1 and A2 bond to a symmetric position of a core structure;

A3 and A4 bond to a symmetric position of a core structure; and

Ar1 and Ar3 are the same as or different from each other and each independently is the following Chemical Formula A, and Ar2 and Ar4 are the same as or different from each other and each independently is one selected from among the following Chemical Formulae C and D;

[Chemical Formula A]

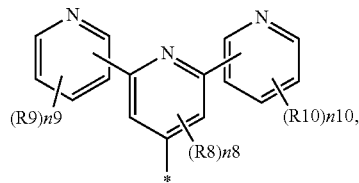

[Chemical Formula C]

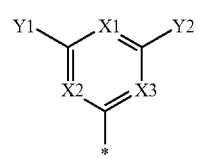

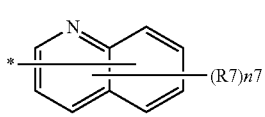

[Chemical Formula D]

wherein in Chemical Formulae A, C and D:

* is a bonding site;

X1 to X3 are the same as or different from each other and each independently is N or CR5, and at least two of X1 to X3 are N;

R5, R7 to R10, Y1 and Y2 are the same as or different from each other, and each independently is hydrogen, deuterium, a nitrile group, a nitro group, a hydroxyl group, a carbonyl group, an ester group, an imide group, an amide group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted amine group, a substituted or unsubstituted arylphosphine group, a substituted or unsubstituted phosphine oxide group, a substituted or unsubstituted aryl group, or a substituted or unsubstituted heteroaryl group; and n9 and n10 are each an integer of 0 to 4, n7 is an integer of 0 to 6, n8 is an integer of 0 to 2, and when n6 to n10 are an integer of 2 or greater, substituents in the parentheses are the same as or different from each other.

2. The heterocyclic compound of claim 1, wherein R1 to R5 and R7 to R10 are hydrogen.

3. The heterocyclic compound of claim 1, wherein Chemical Formula 1 is Chemical Formula 2 or Chemical Formula 3:

[Chemical Formula 2]

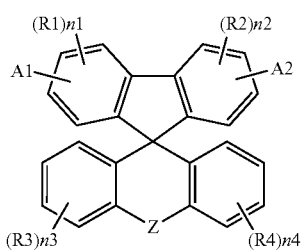

[Chemical Formula 3]

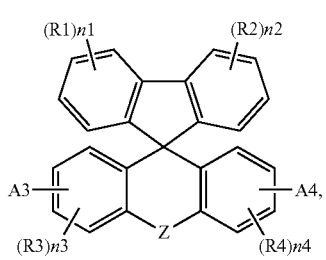

wherein in Chemical Formulae 2 and 3:

A1 is -L1-Ar1, A2 is -L2-Ar2, A3 is -L3-Ar3, and A4 is -L4-Ar4; and the substituents have the same definitions as in Chemical Formula 1.

4. The heterocyclic compound of claim 1, wherein Chemical Formula 1 is one selected from among the following Chemical Formulae 1-1 to 1-8:

[Chemical Formula 1-1]

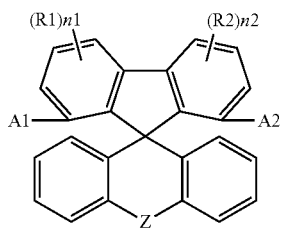

[Chemical Formula 1-2]

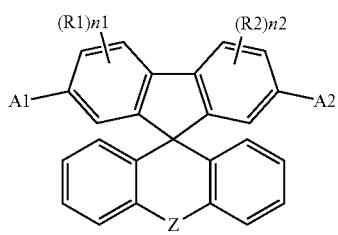

[Chemical Formula 1-3]

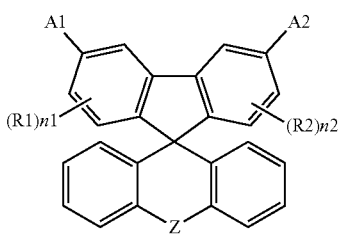

[Chemical Formula 1-4]

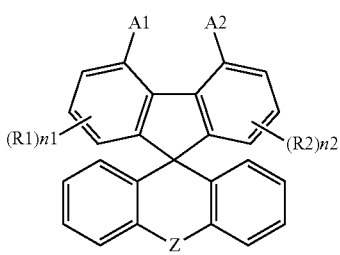

[Chemical Formula 1-5]

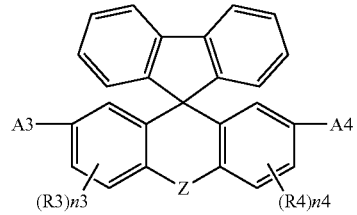

[Chemical Formula 1-6]

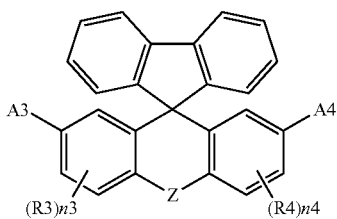

[Chemical Formula 1-7]

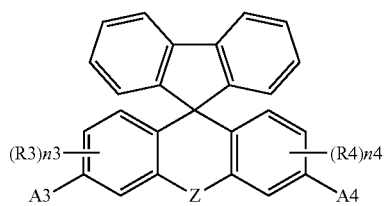

[Chemical Formula 1-8]

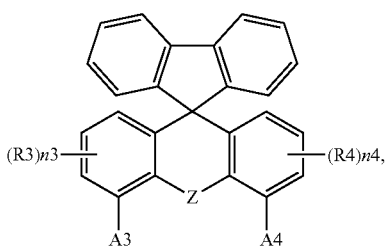

wherein in Chemical Formulae 1-1 to 1-8:

A1 is -L1-Ar1, A2 is -L2-Ar2, A3 is -L3-Ar3, and A4 is -L4-Ar4; and the substituents have the same definitions as in Chemical Formula 1.

5. The heterocyclic compound of claim 1, wherein L1 to L4 are the same as or different from each other, and each independently is a direct bond, a substituted or unsubstituted phenylene group, a substituted or unsubstituted biphenylylene group, a substituted or unsubstituted naphthylene group, a substituted or unsubstituted terphenylene group, a substituted or unsubstituted quaterphenylene group, a substituted or unsubstituted anthracenylene group,] a substituted or unsubstituted phenanthrenylene group, a substituted or unsubstituted triphenylenylene group, a substituted or unsubstituted pyrenylene group, a substituted or unsubstituted fluorenylene group, a substituted or unsubstituted spirocyclopentanefluorenylene group, a substituted or unsubstituted dibenzofuranylene group, a substituted or unsubstituted divalent dibenzothiophene group, a substituted or unsubstituted carbazolene group, a substituted or unsubstituted pyridylene group, a substituted or unsubstituted divalent furan group, or a substituted or unsubstituted divalent thiophene group.

6. The heterocyclic compound of claim 1, wherein Chemical Formula A is one selected from among the following Chemical Formulae A-1 to A-4:

[Chemical Formula A-1]

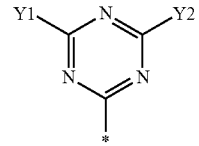

[Chemical Formula A-2]

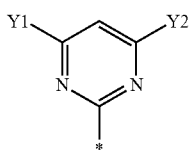

[Chemical Formula A-3]

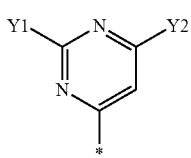

[Chemical Formula A-4]

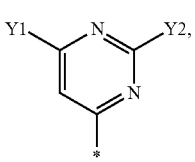

wherein in Chemical Formulae A-1 to A-4, the substituents have the same definitions as in Chemical Formula A.

7. The heterocyclic compound of claim 1, wherein Chemical Formula C is represented by one selected from among the following Chemical Formulae C-1 to C-7:

[Chemical Formula C-1]

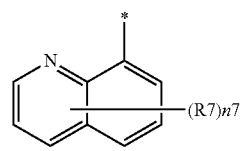

[Chemical Formula C-2]

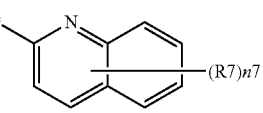

[Chemical Formula C-3]

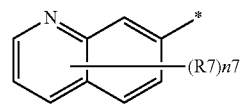

[Chemical Formula C-4]

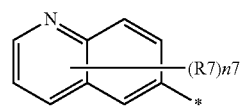

[Chemical Formula C-5]

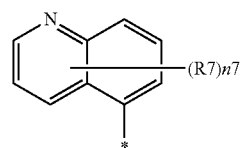

[Chemical Formula C-6]

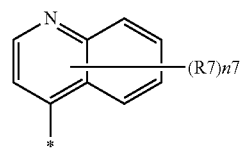

[Chemical Formula C-7]

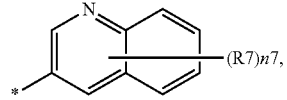

wherein in Chemical Formulae C-1 to C-7, the substituents have the same definitions as in Chemical Formula C.

8. The heterocyclic compound of claim 1, wherein Chemical Formula D is one selected from among the following Chemical Formulae D-1 to D-3:

[Chemical Formula D-1]

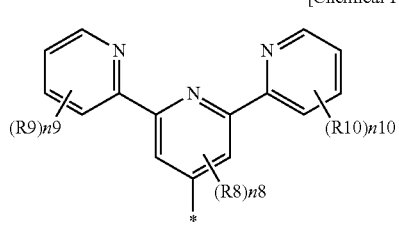

[Chemical Formula D-2]

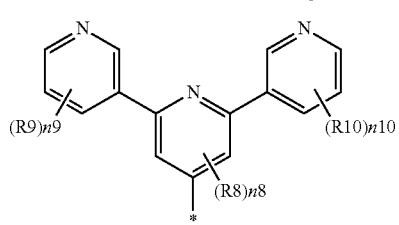

[Chemical Formula D-3]

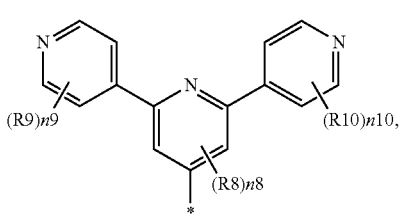

wherein in Chemical Formulae D-1 to D-3, substituents have the same definitions as in Chemical Formula D.

9. The heterocyclic compound of claim 1, wherein:
A1 and A2 are hydrogen, A3 is -L3-Ar3, and A4 is -L4-Ar4; or
A3 and A4 are hydrogen, A1 is -L1-Ar1, and A2 is -L2-Ar2.

10. The heterocyclic compound of claim 1, wherein Y1 and Y2 are the same as or different from each other, and each independently is a substituted or unsubstituted aryl group having 6 to 30 carbon atoms, or a substituted or unsubstituted heteroaryl group having 2 to 30 carbon atoms.

11. The heterocyclic compound of claim 1, wherein Y1 and Y2 are the same as or different from each other, and each independently is a substituted or unsubstituted phenyl group, a substituted or unsubstituted biphenyl group, a substituted or unsubstituted naphthyl group, a substituted or unsubstituted terphenyl group, a substituted or unsubstituted quaterphenyl group, a substituted or unsubstituted anthracenyl group, a substituted or unsubstituted phenanthrenyl group, a substituted or unsubstituted triphenylenyl group, a substituted or unsubstituted pyrenyl group, a substituted or unsubstituted fluorenyl group, a substituted or unsubstituted spirocyclopentanefluorenyl group, a substituted or unsubstituted dibenzofuranyl group, a substituted or unsubstituted dibenzothiophene group, a substituted or unsubstituted carbazole group, a substituted or unsubstituted pyridyl group, a substituted or unsubstituted furan group, or a substituted or unsubstituted thiophene group.

12. The heterocyclic compound of claim 1, wherein Chemical Formula 1 is a compound selected from among the following compounds:

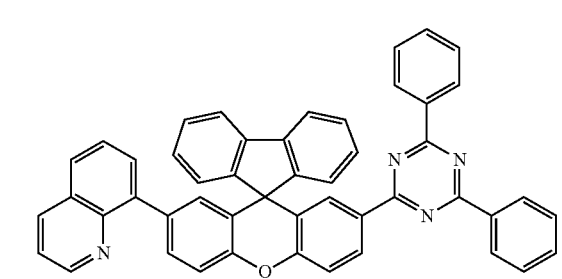

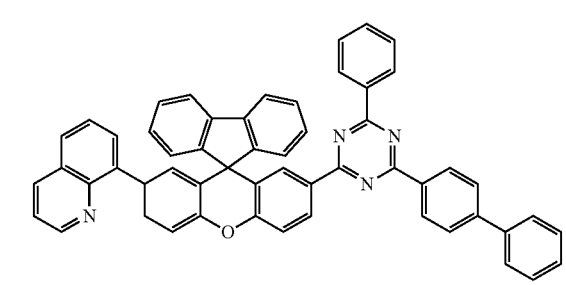

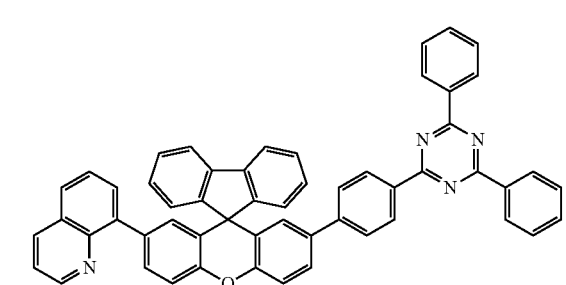

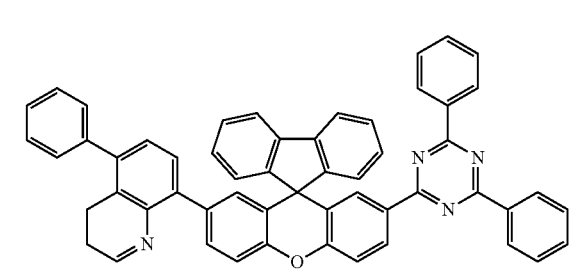

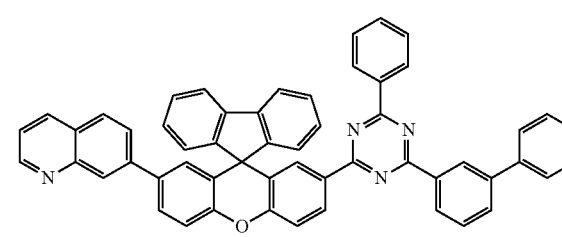

-continued

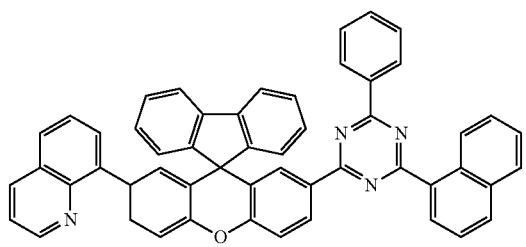

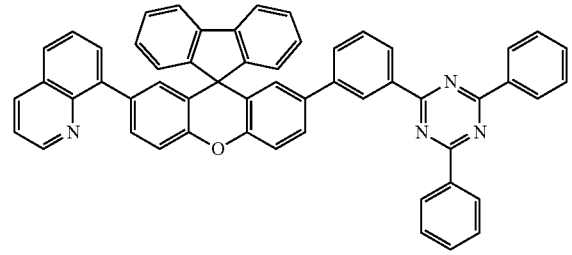

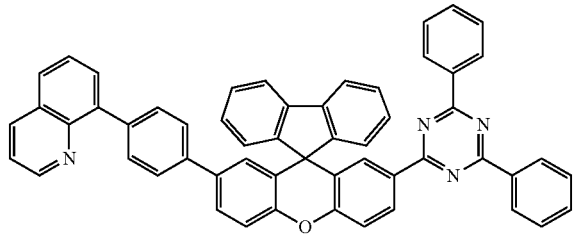

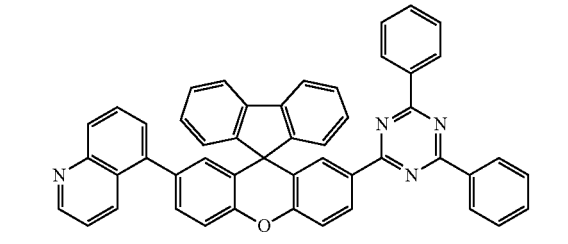

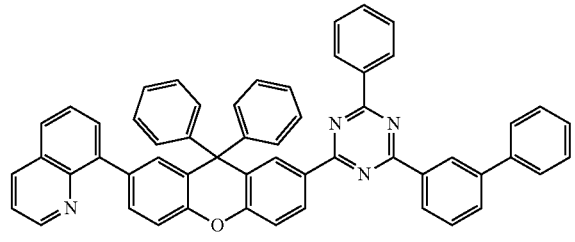

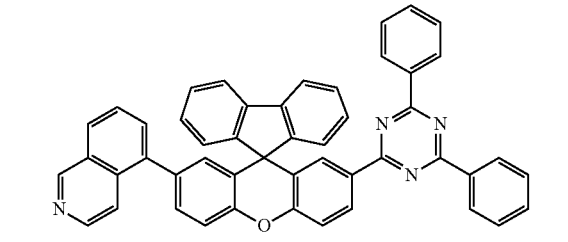

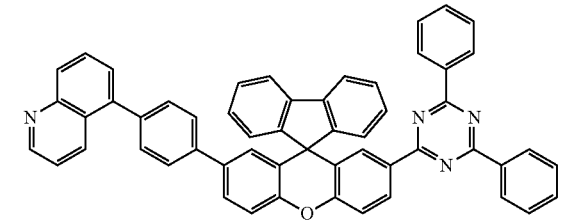

189
-continued
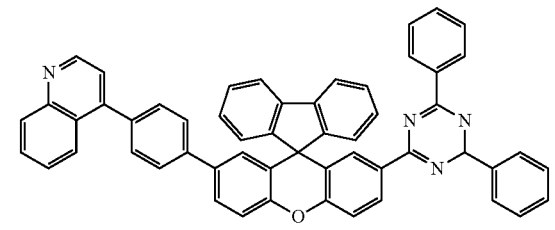
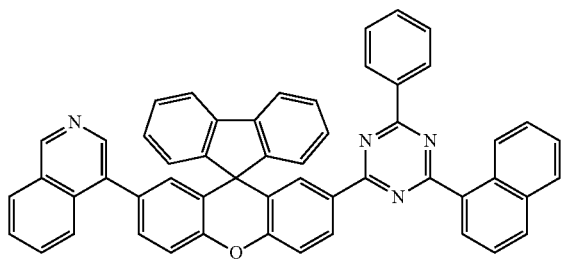
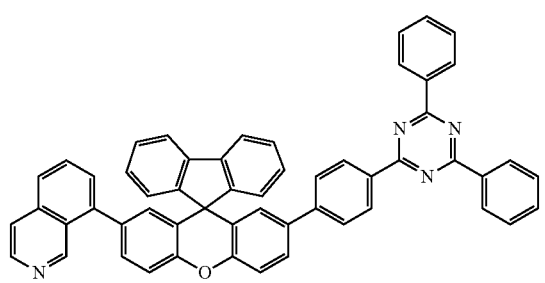
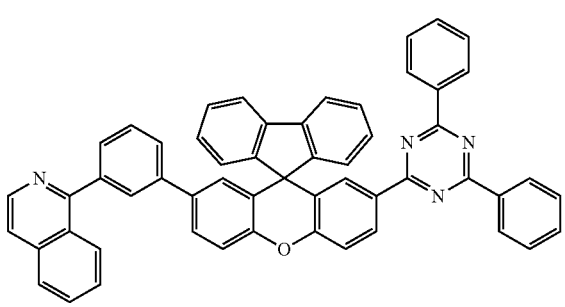
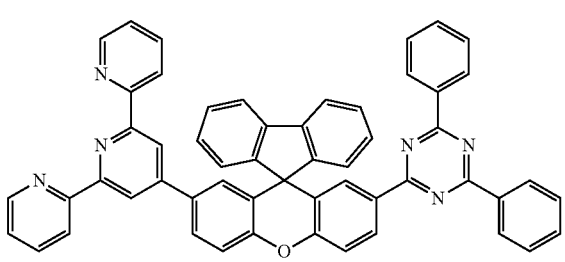
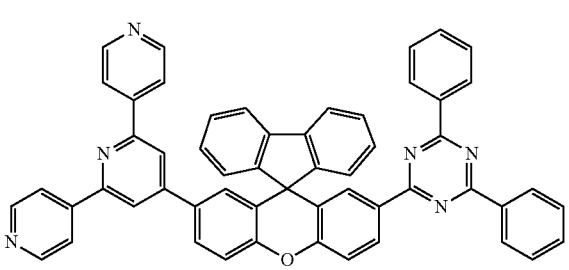
190
-continued
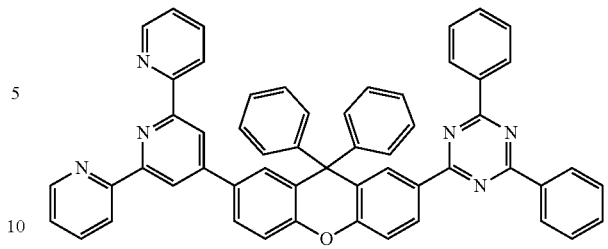
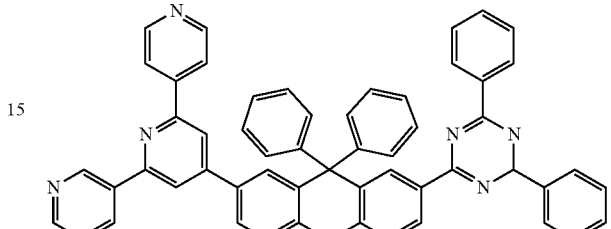
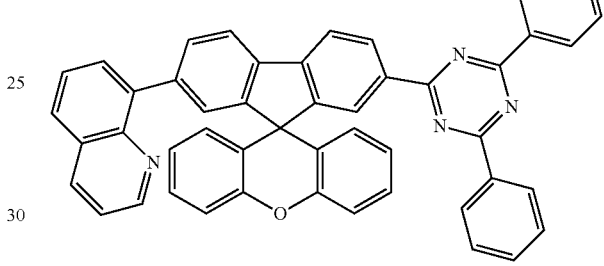
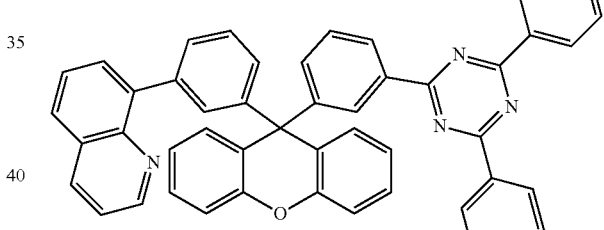
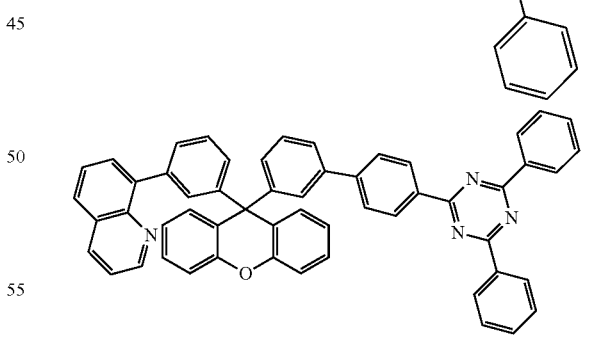
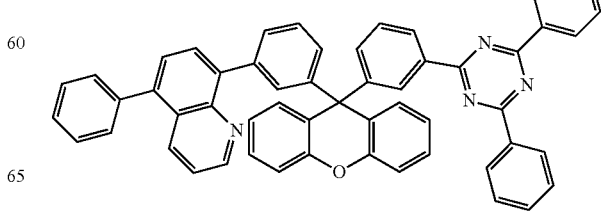

191
-continued
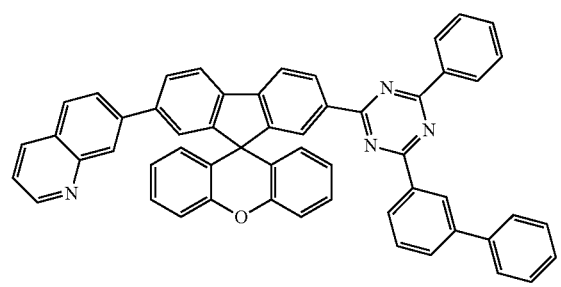
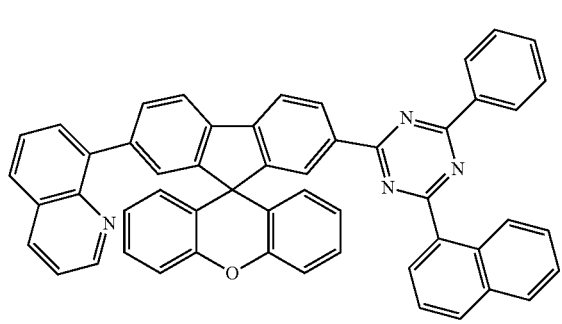
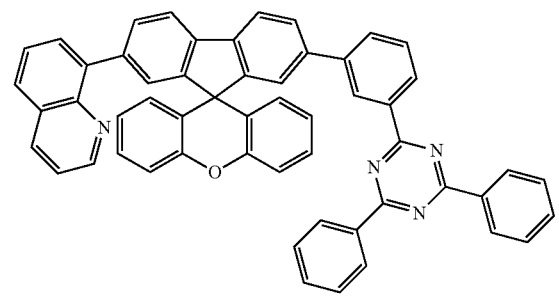
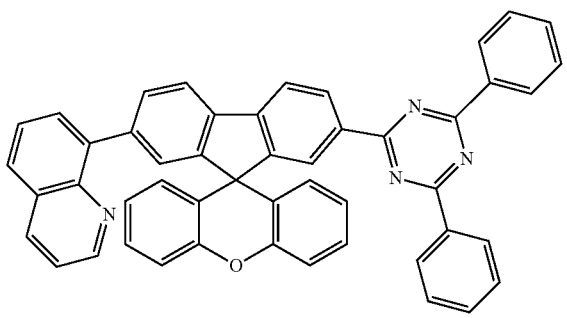
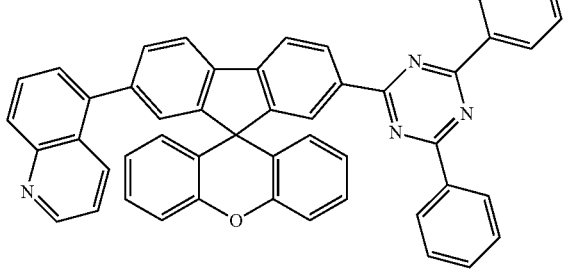
192
-continued
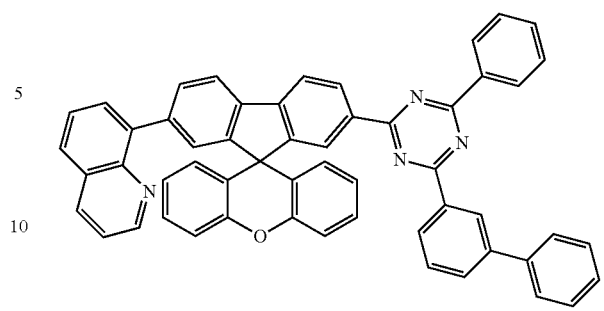
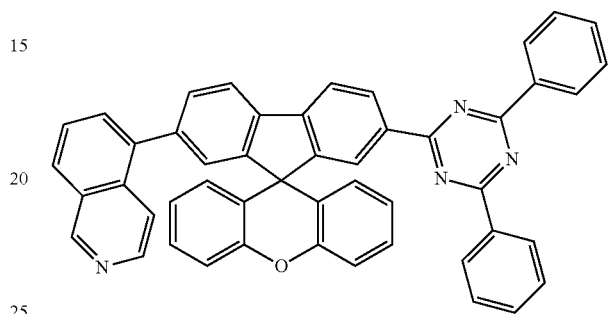
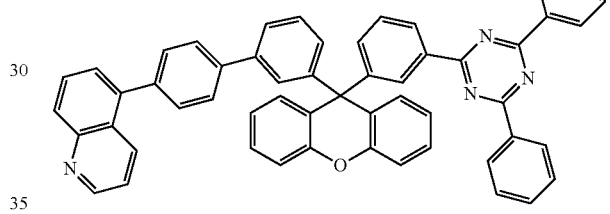
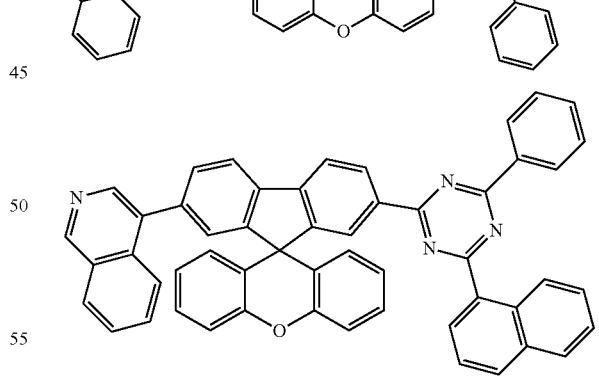
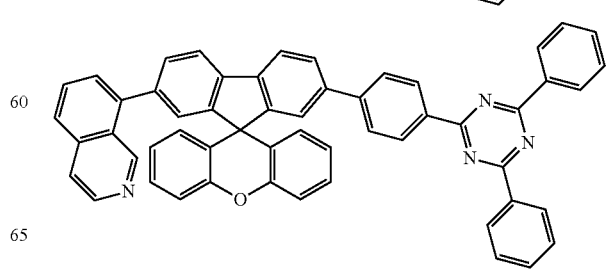

193
-continued
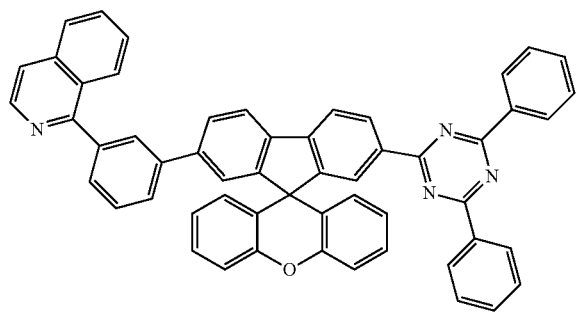
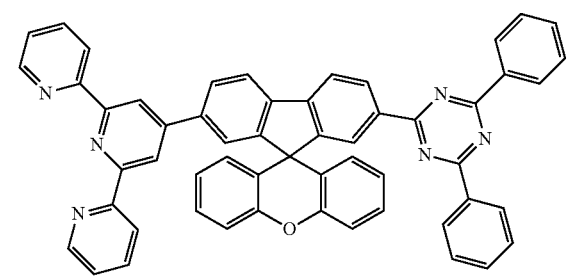
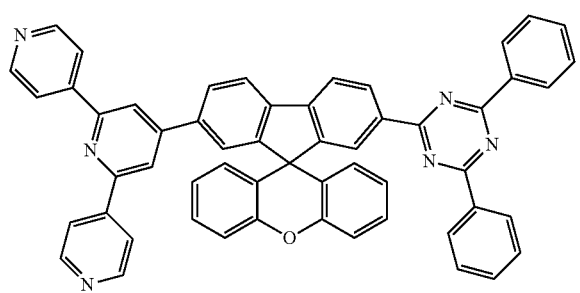
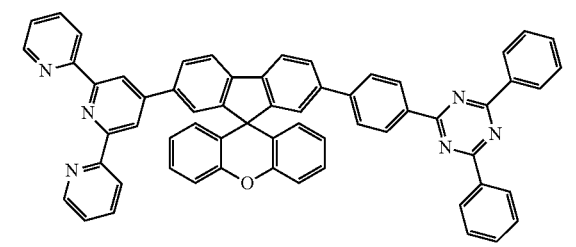
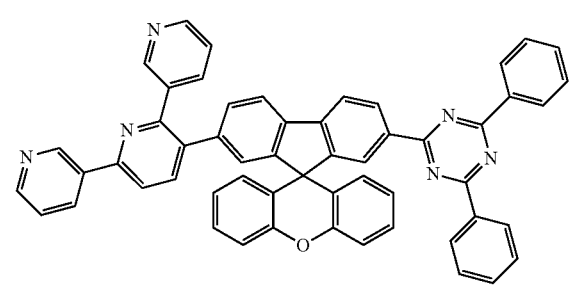
194
-continued
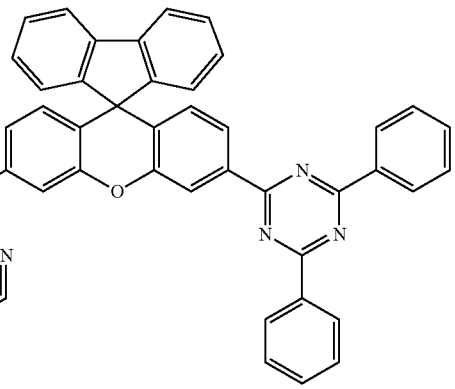
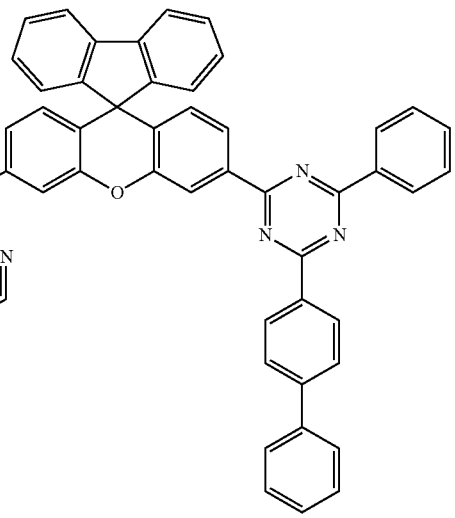
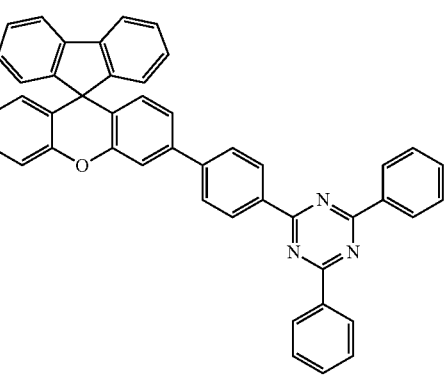
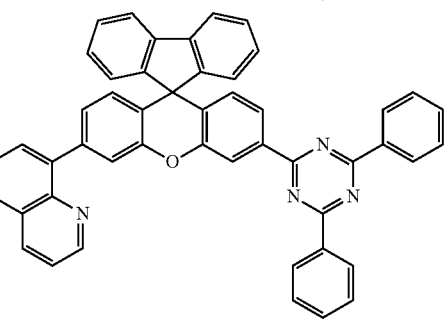

195
-continued
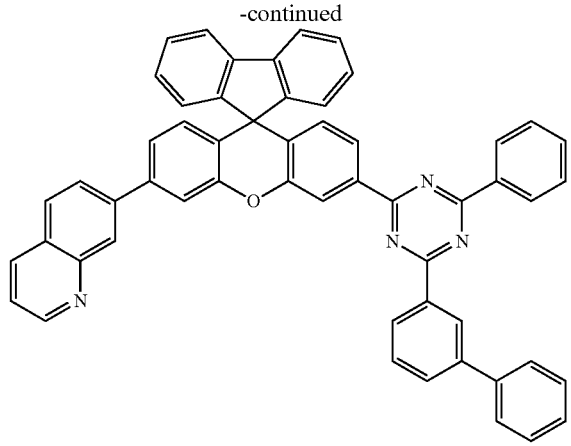
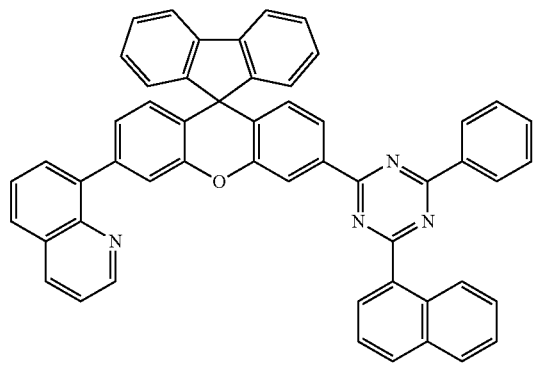
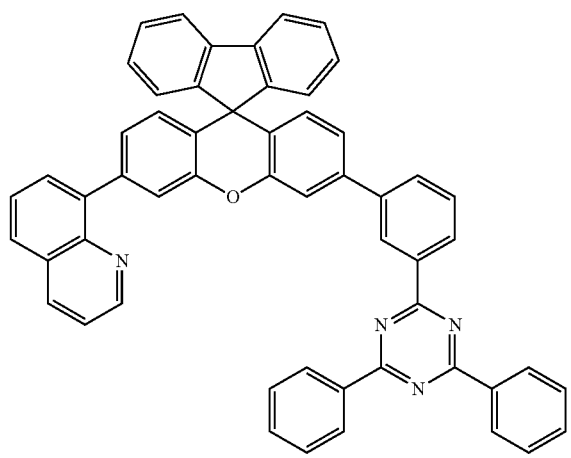
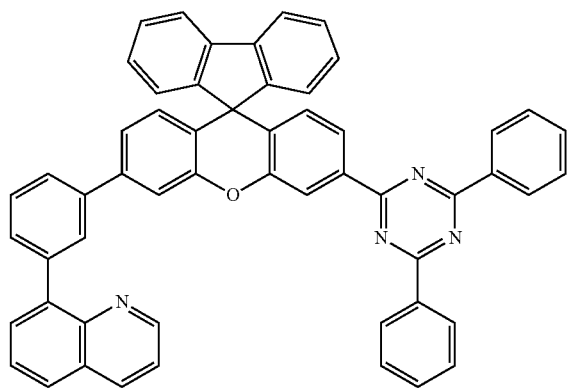
196
-continued
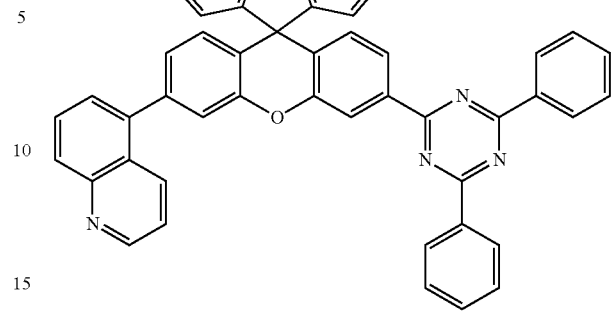
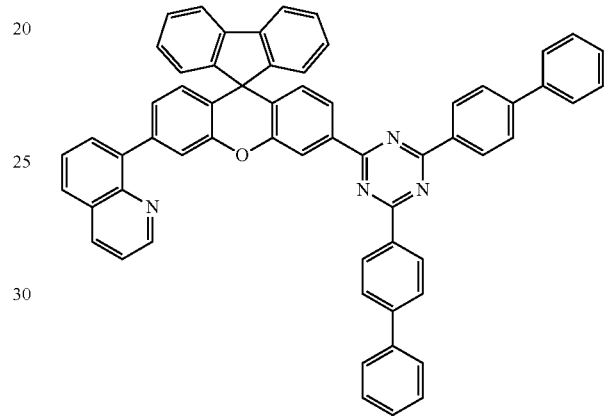
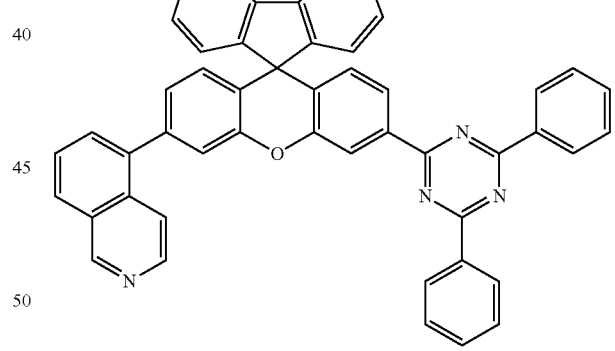
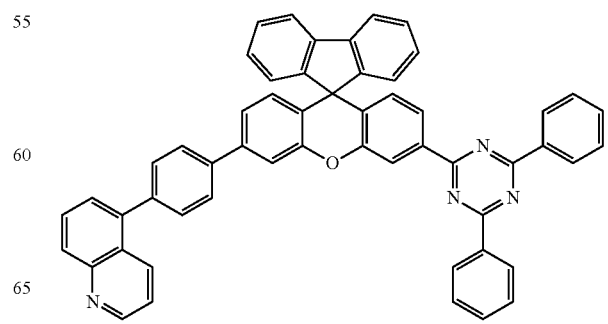

197
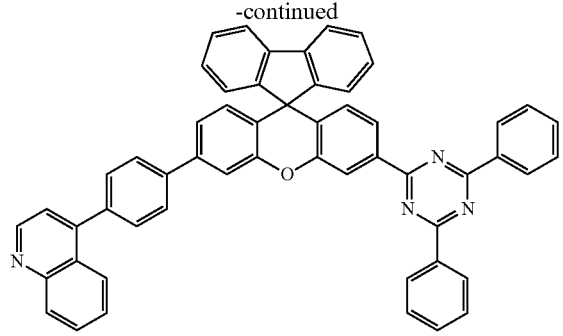
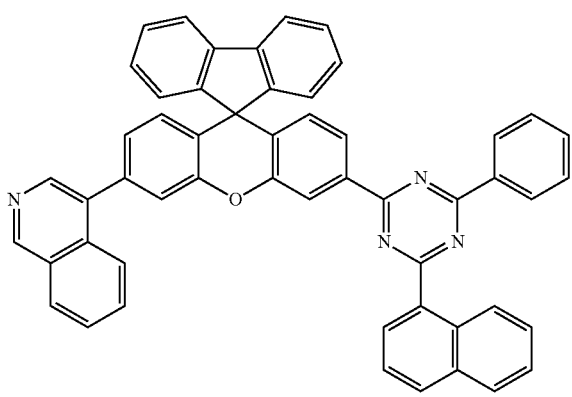
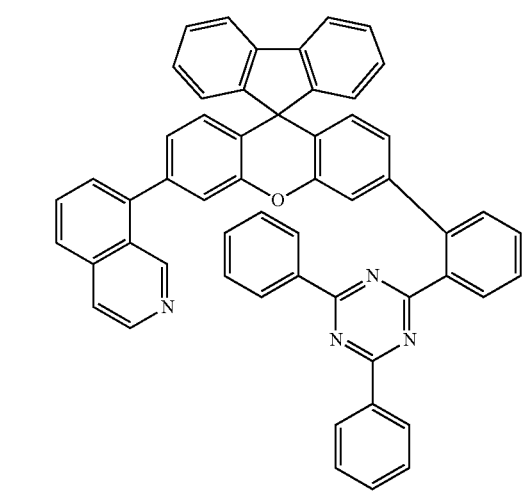
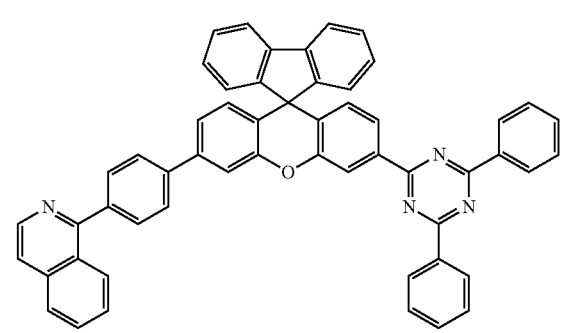
198
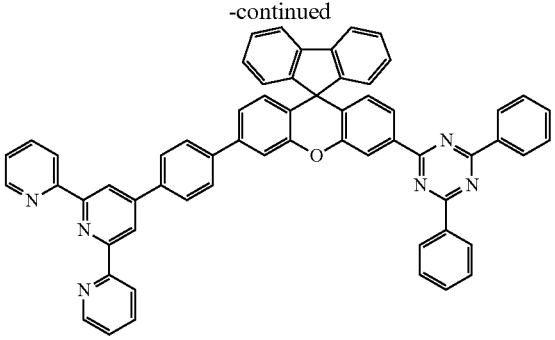
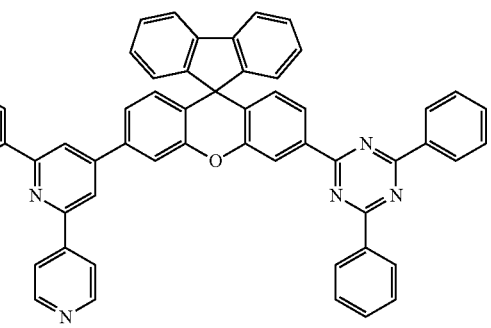
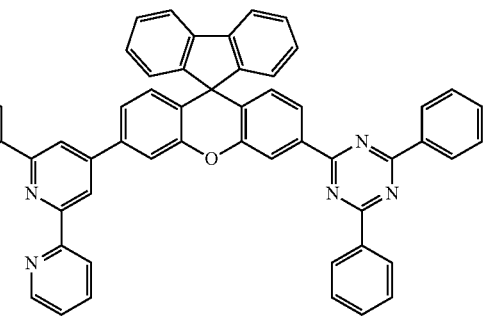
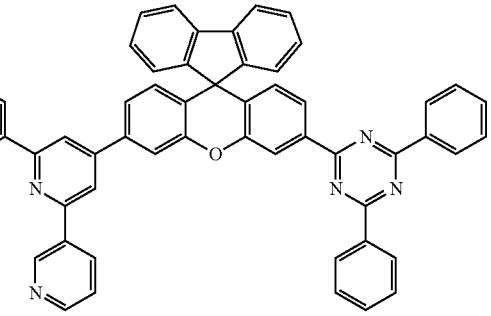
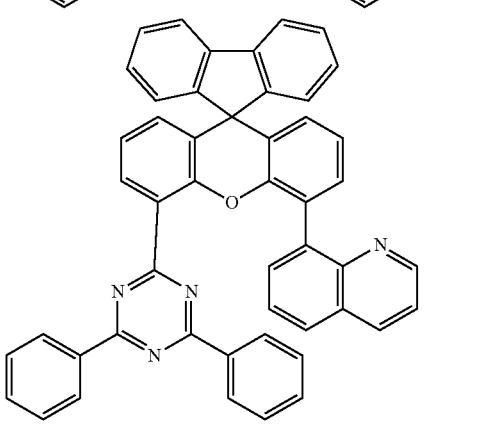

| 199 -continued | 200 -continued |
|---|---|
| 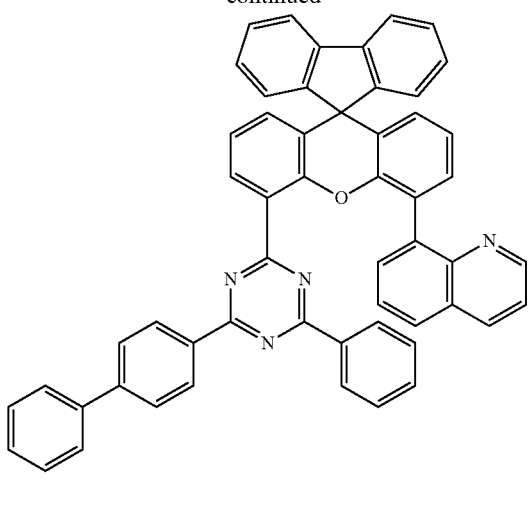 | 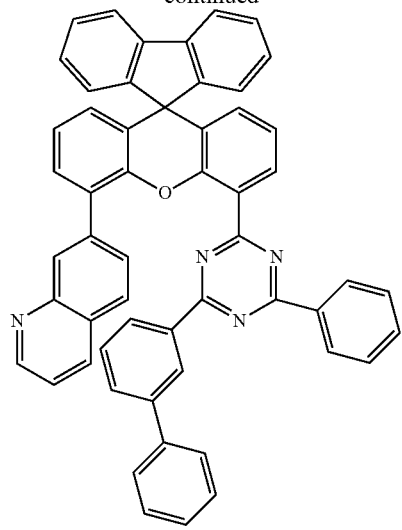 |
| 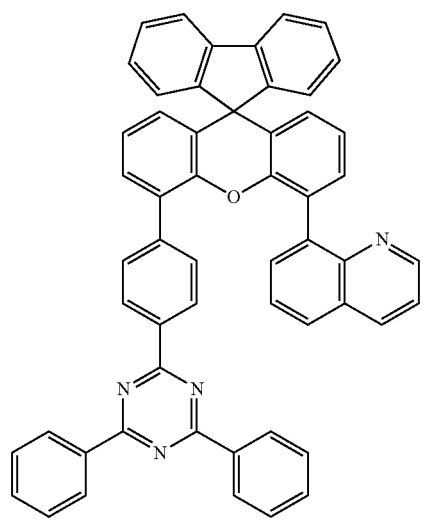 | 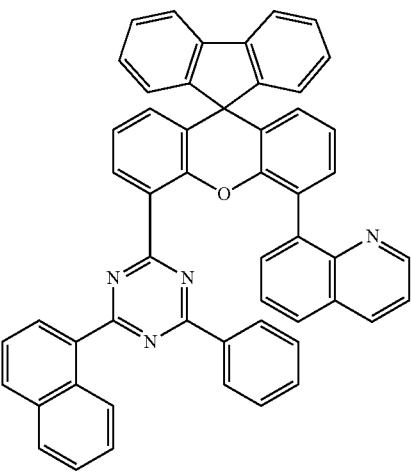 |
| 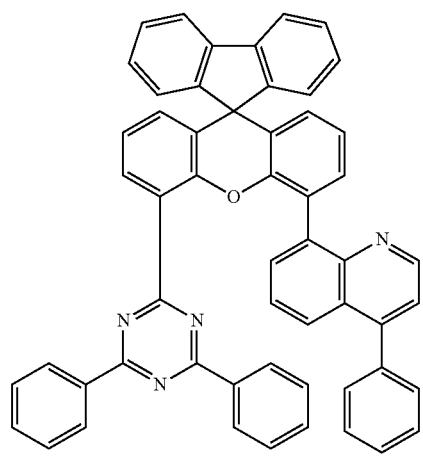 | 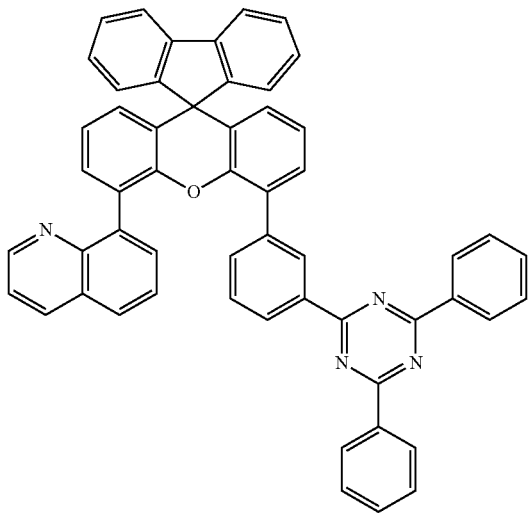 |

201
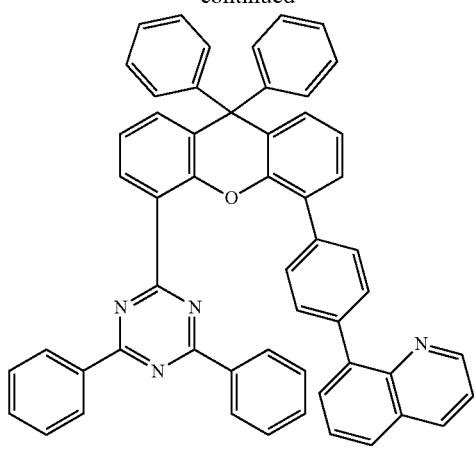
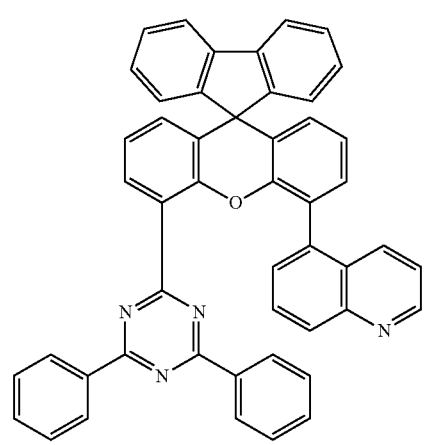
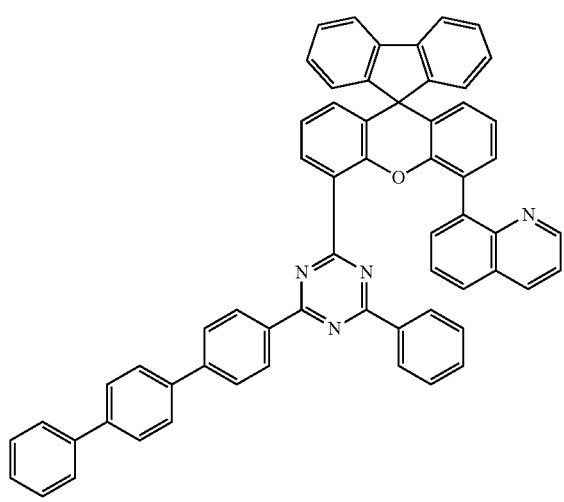
202
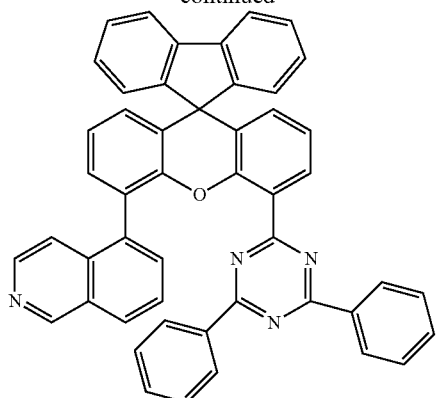
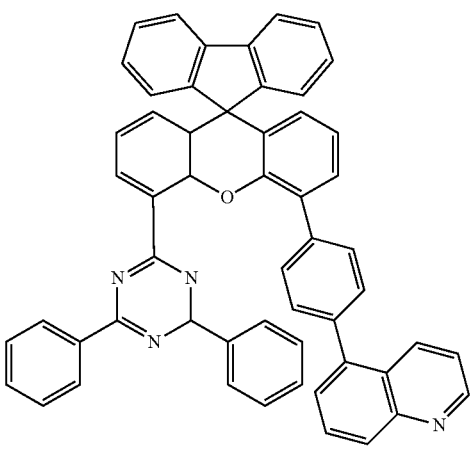
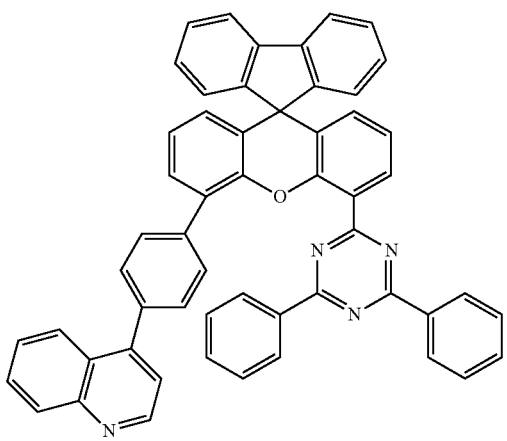

203
-continued
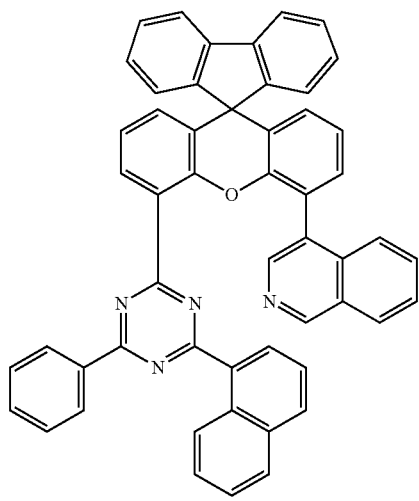
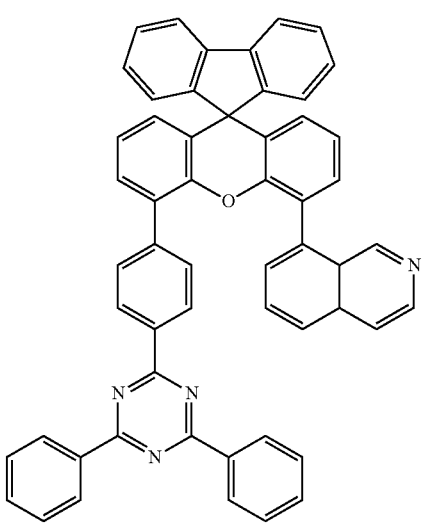
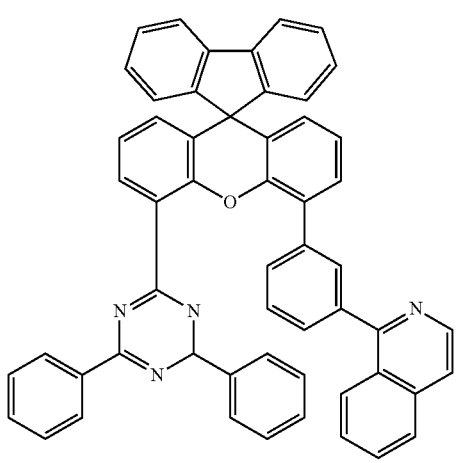
204
-continued
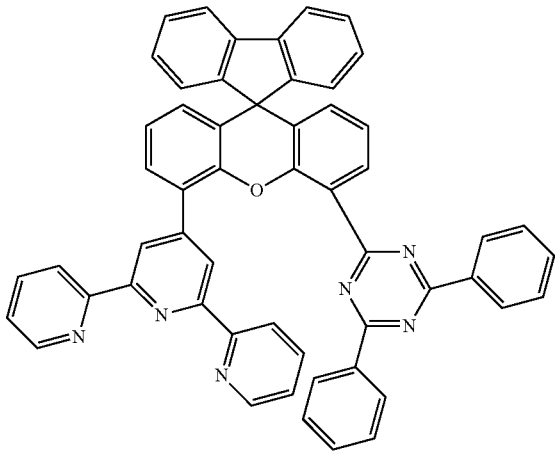
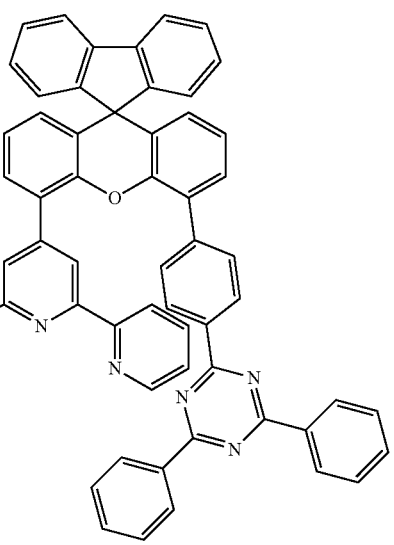

205
-continued
206
-continued
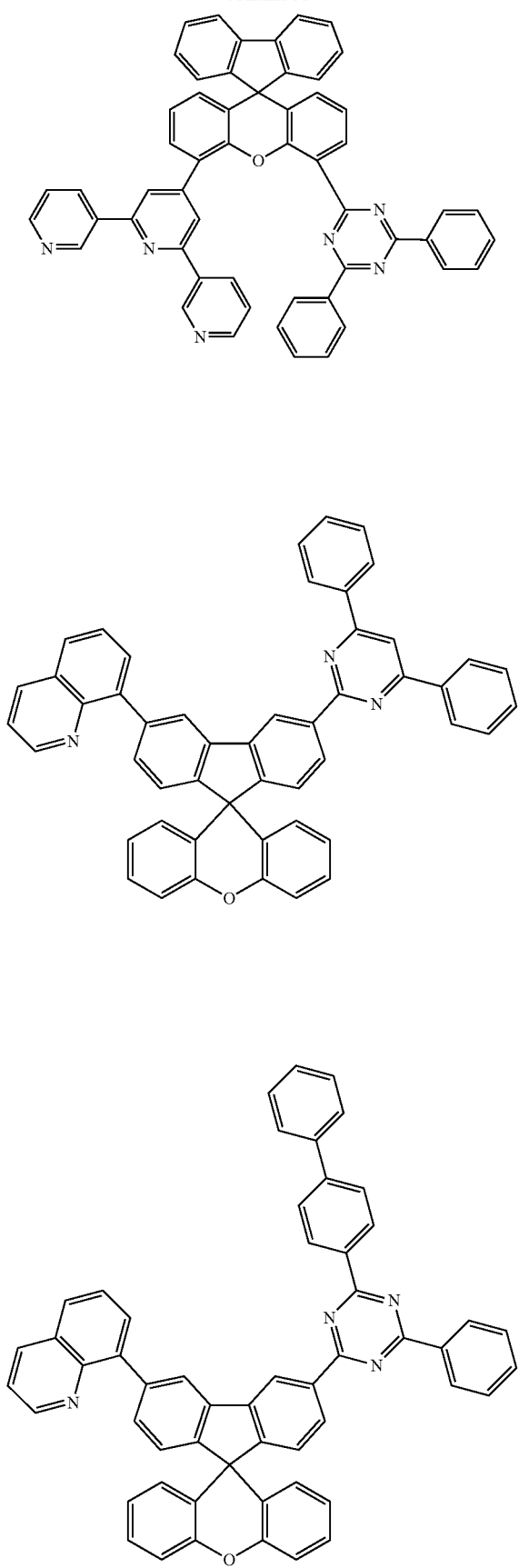
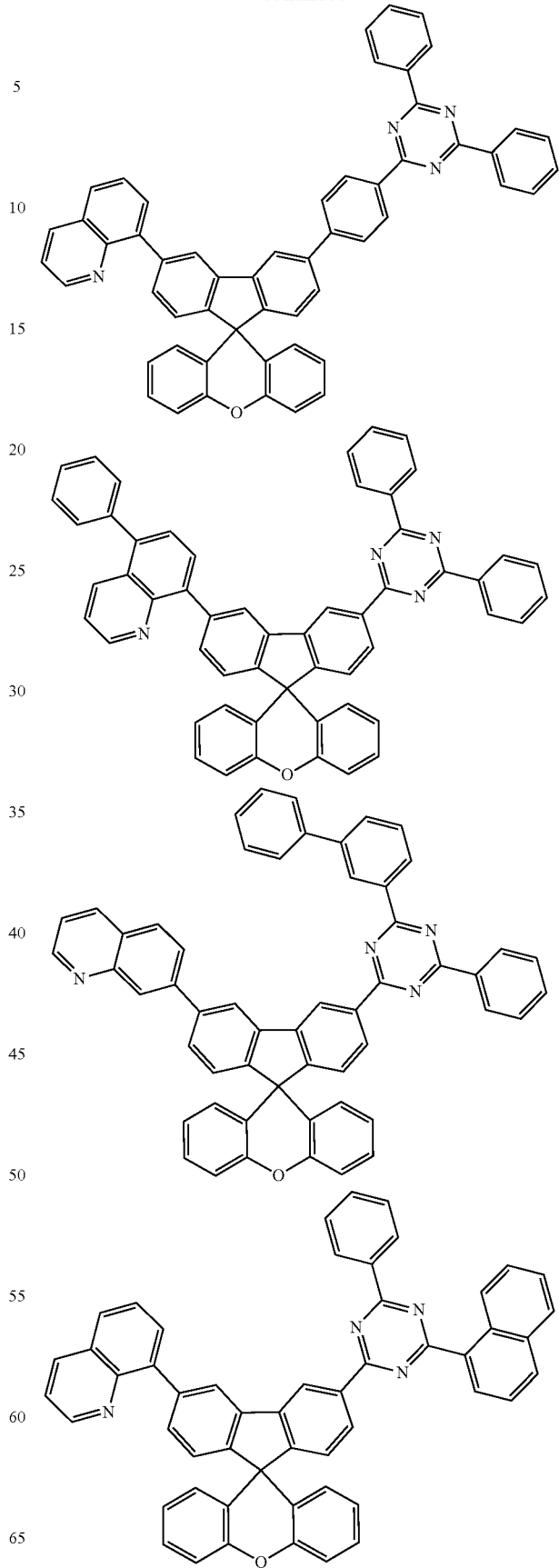

207
-continued
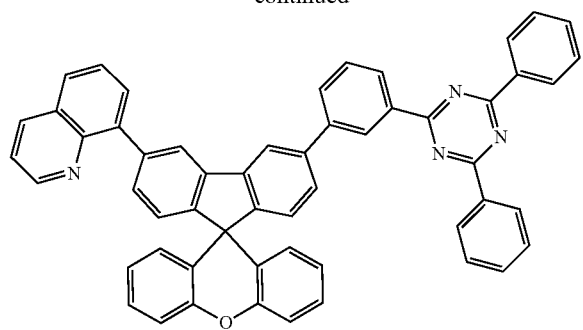
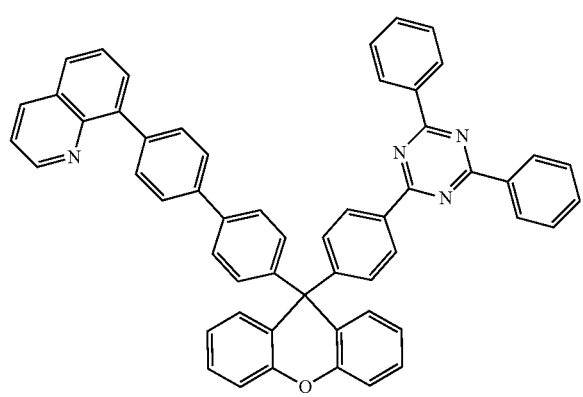
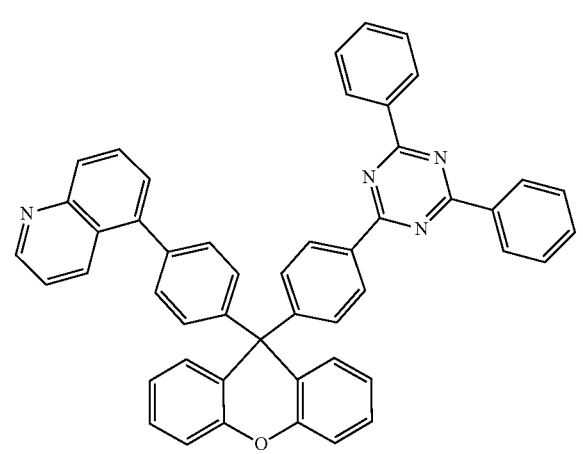
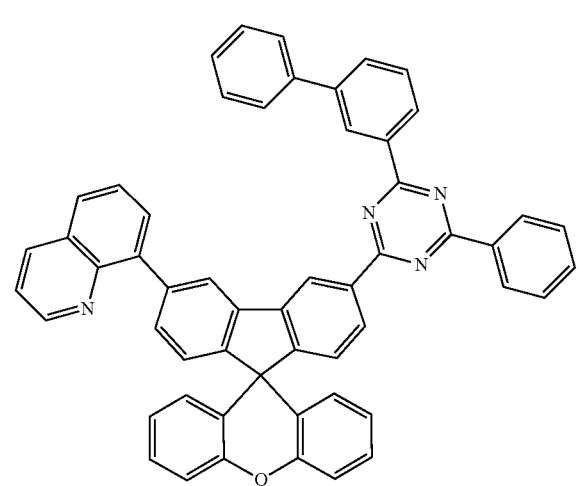
208
-continued
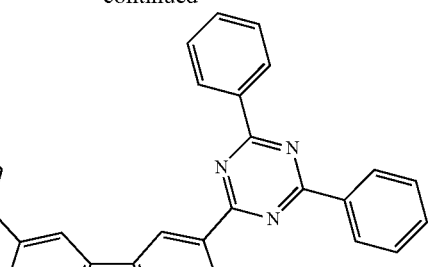
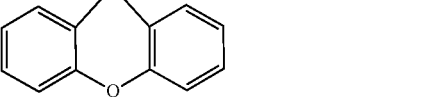
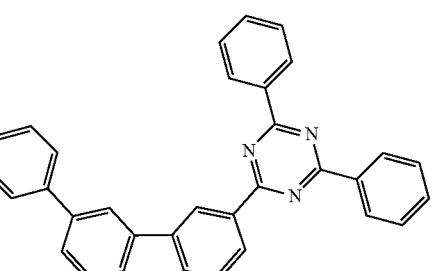
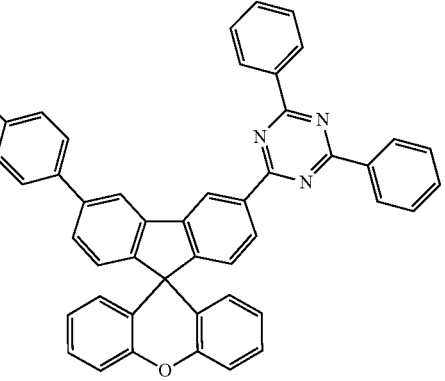
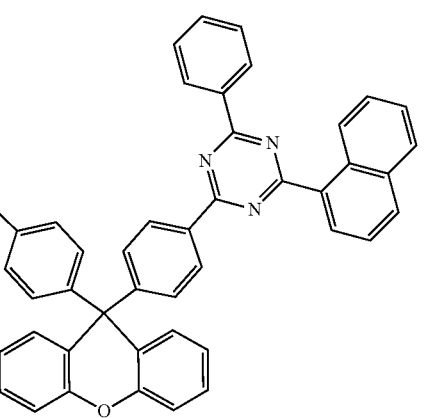

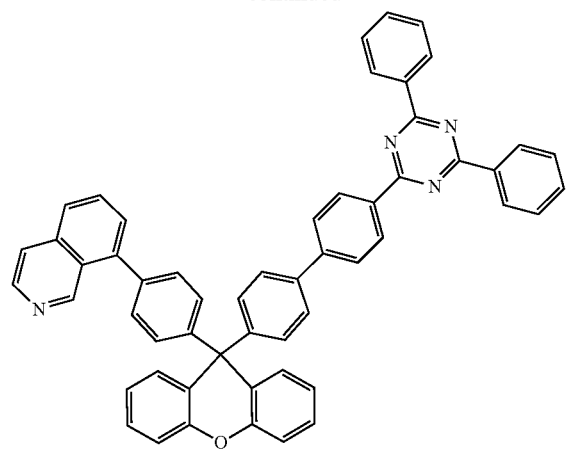
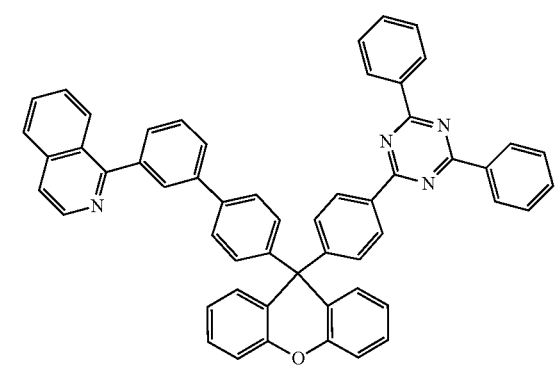
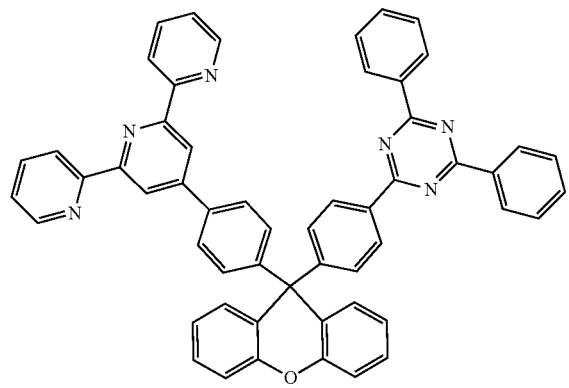
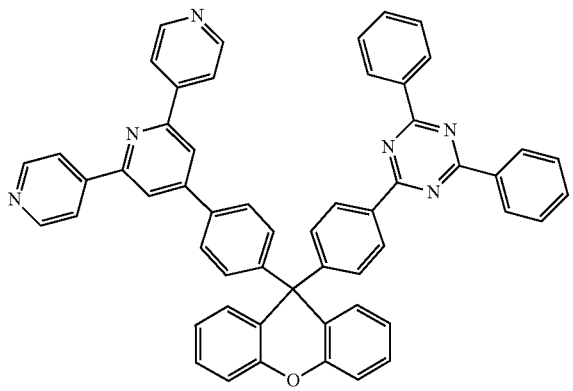
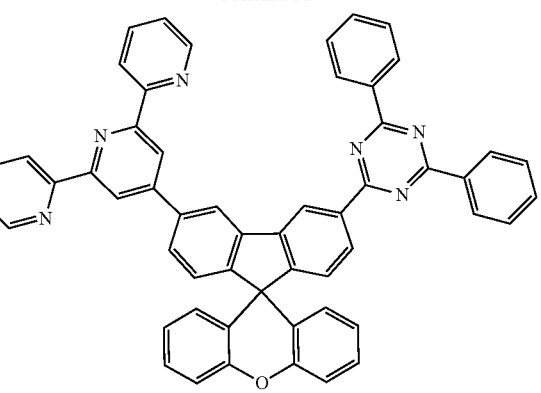
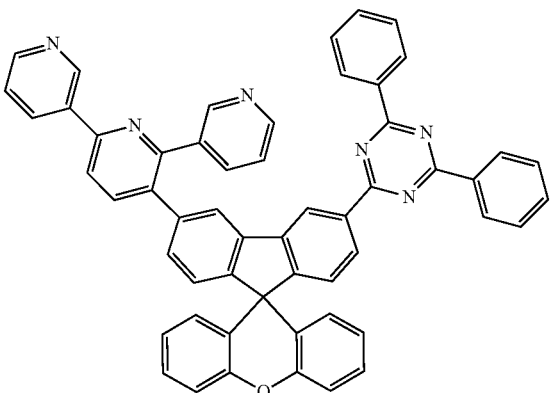
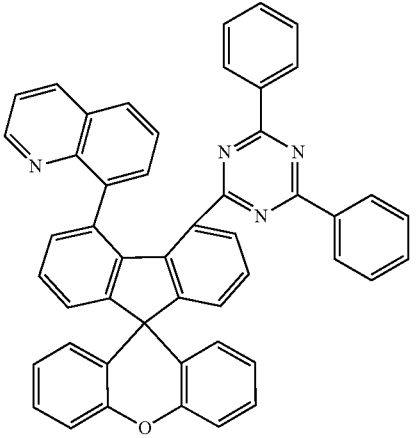
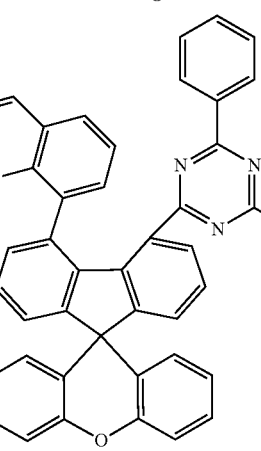

211
-continued
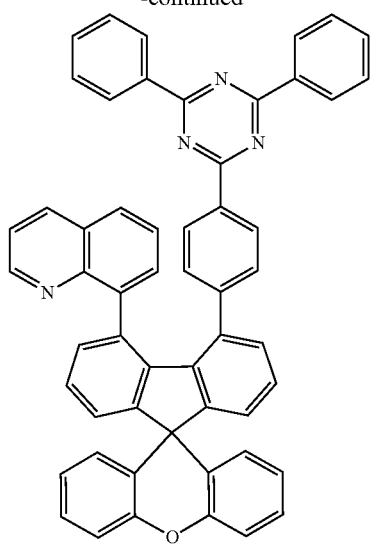
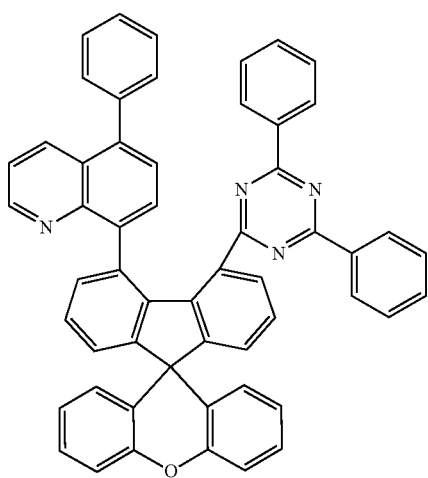
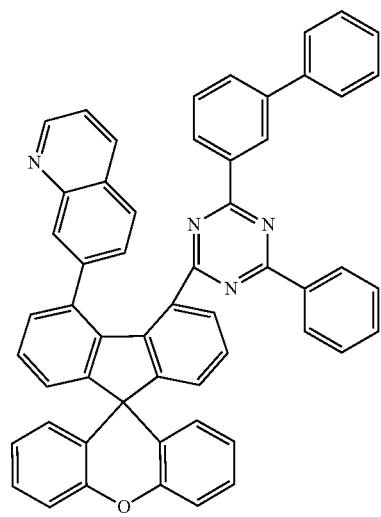
212
-continued
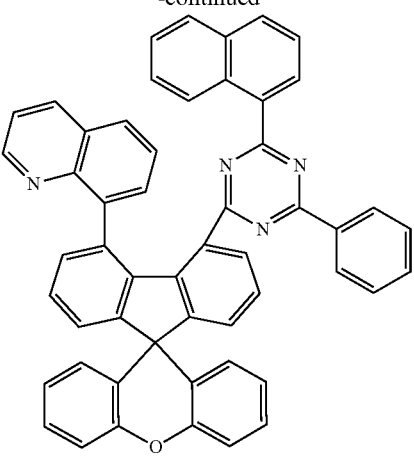
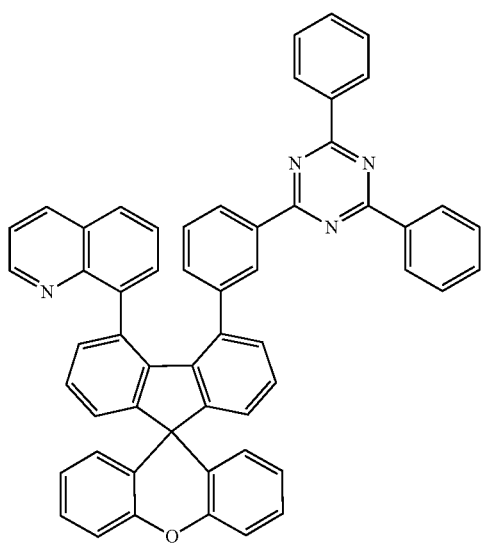
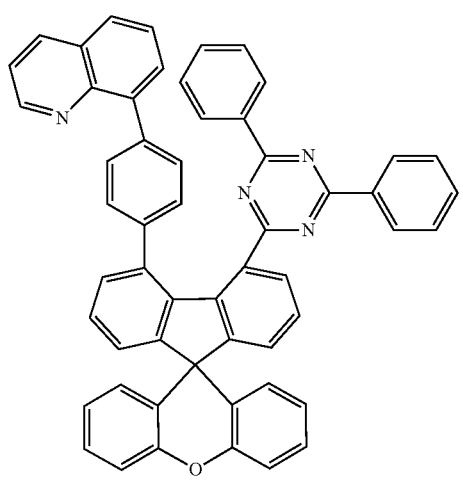

213
-continued
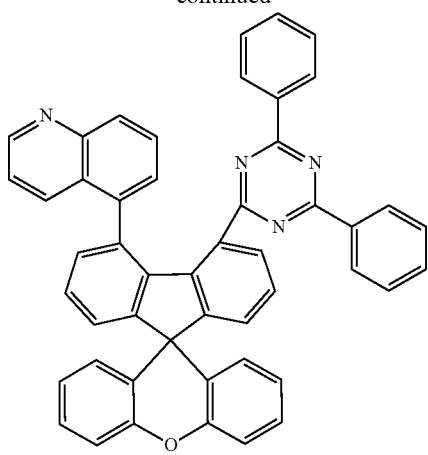
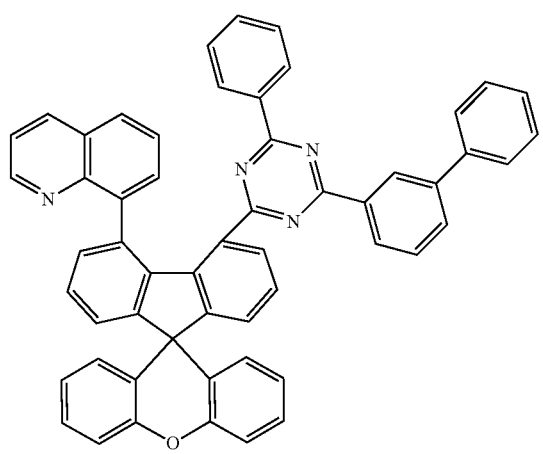
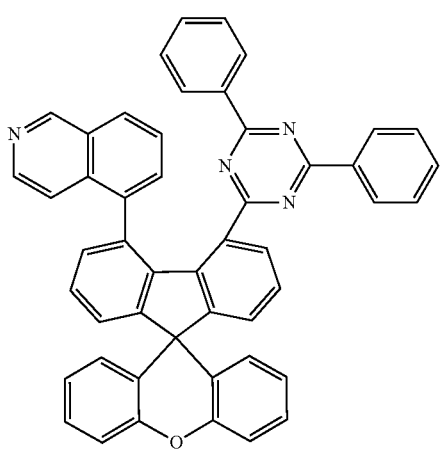
214
-continued
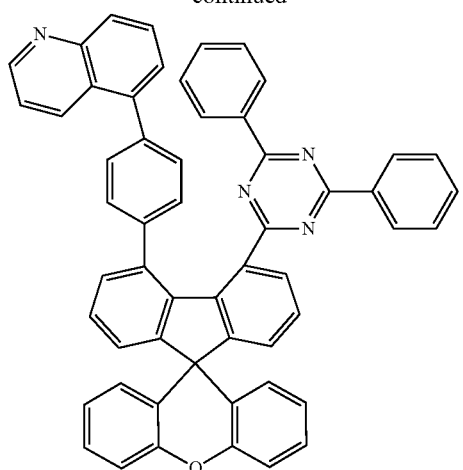
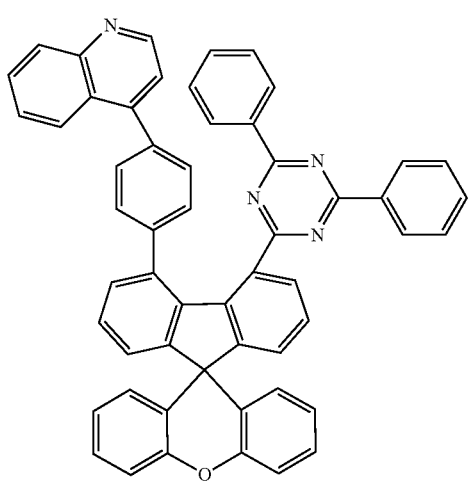
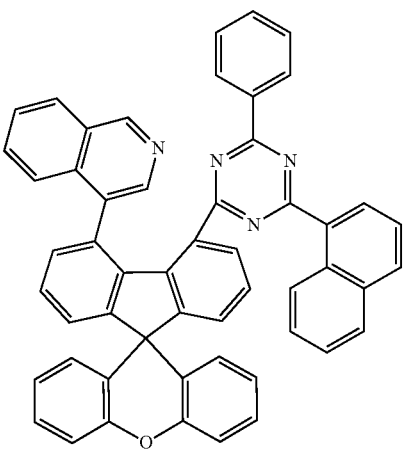

215
-continued
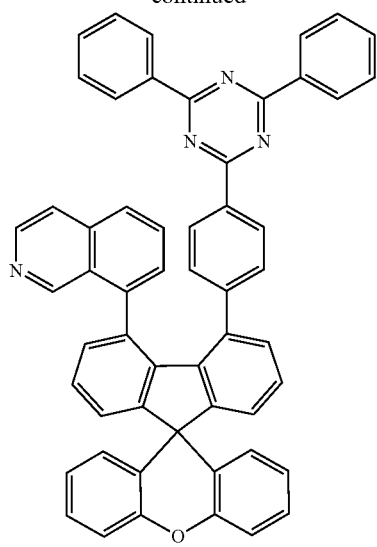
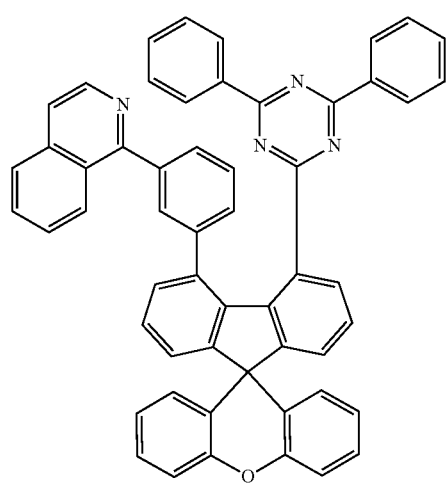
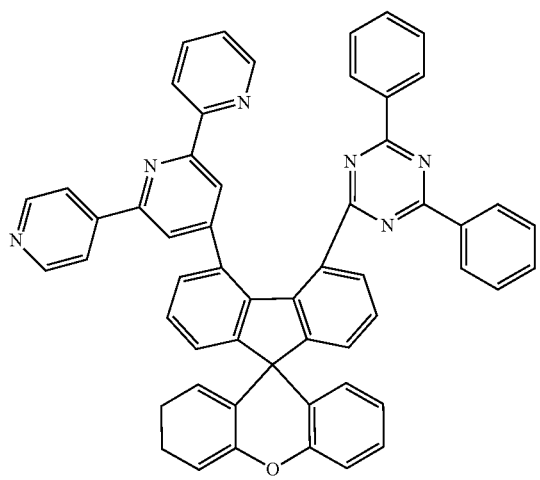
216
-continued
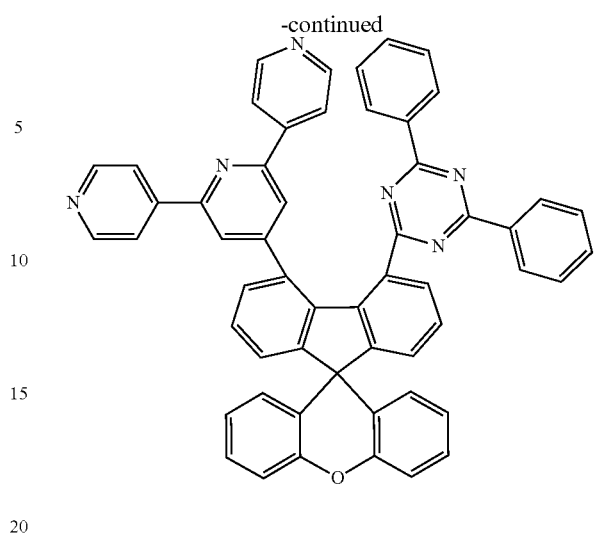
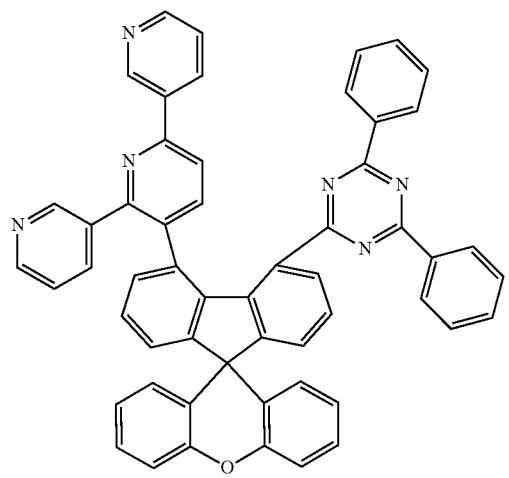
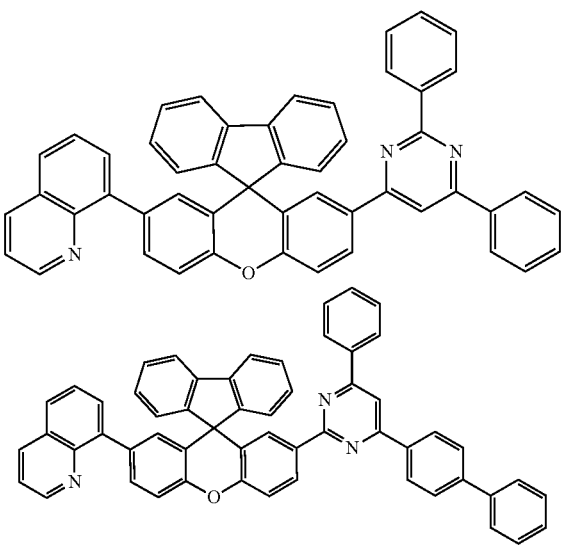

217
-continued
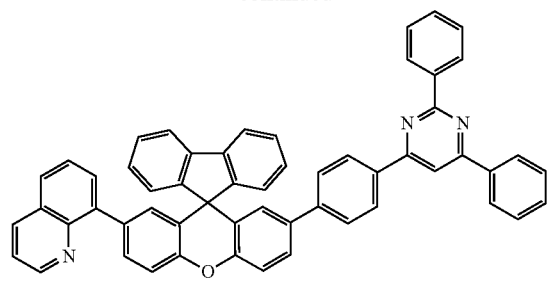
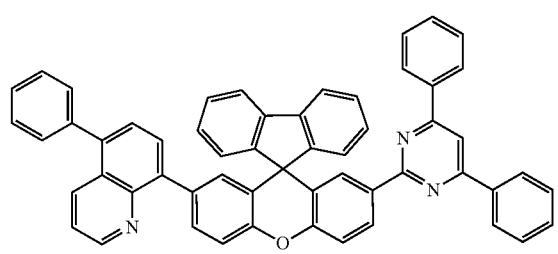
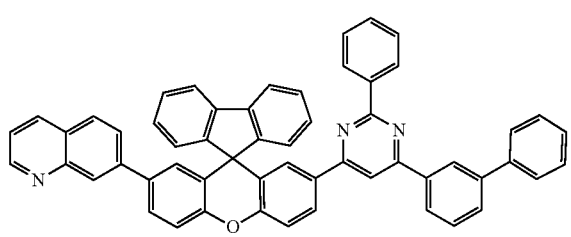
218
-continued
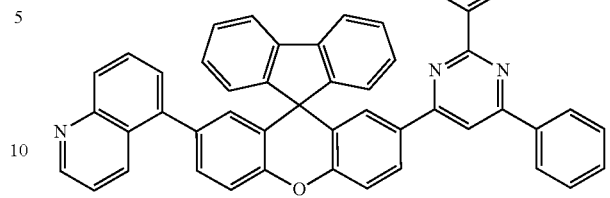
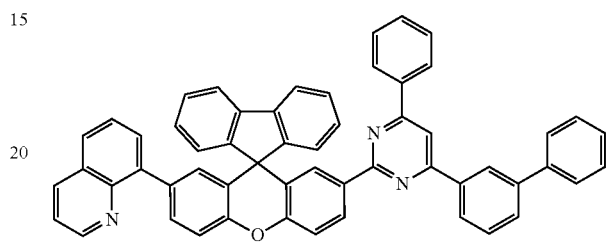
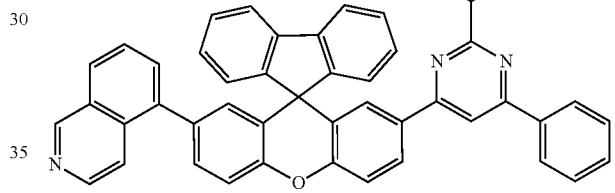
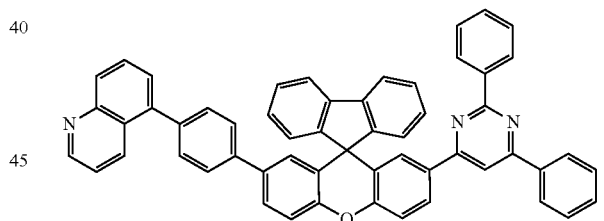
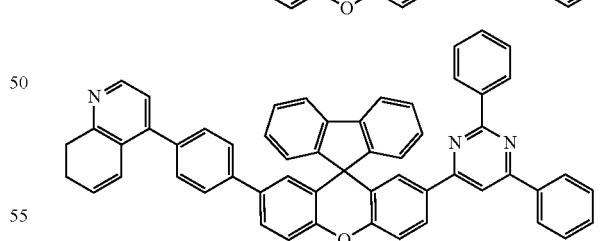
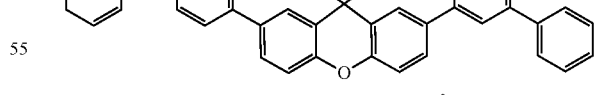
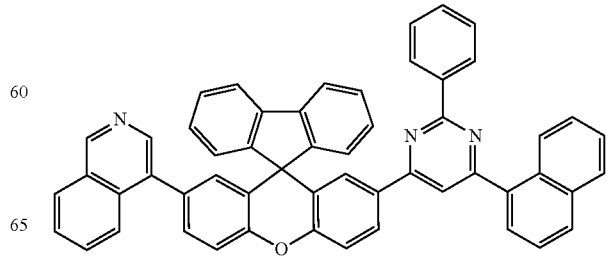
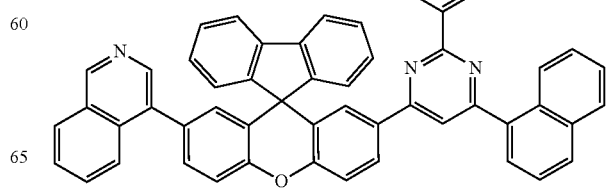
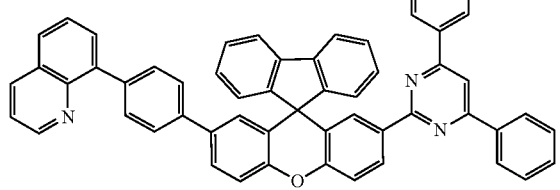

219
-continued
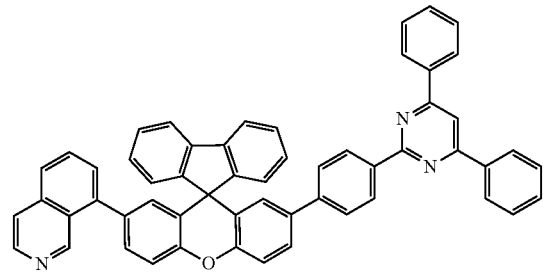
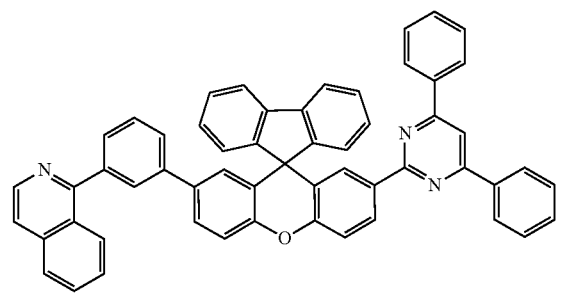
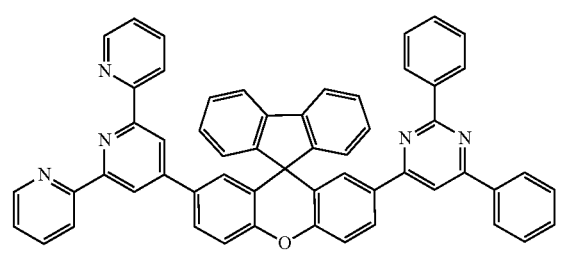
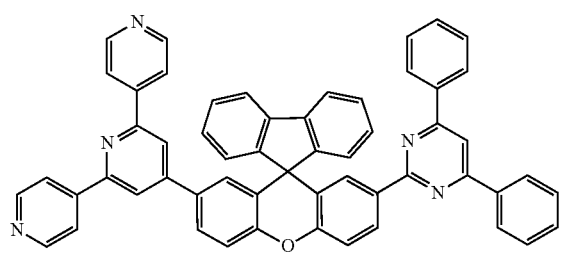
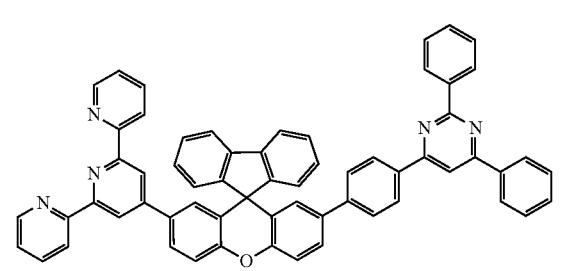
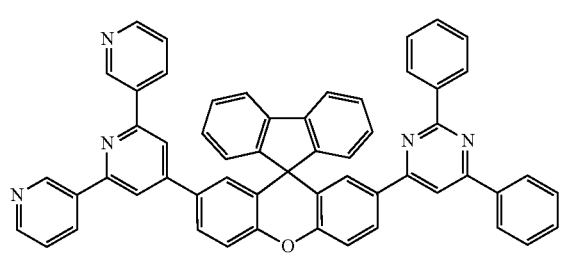
220
-continued
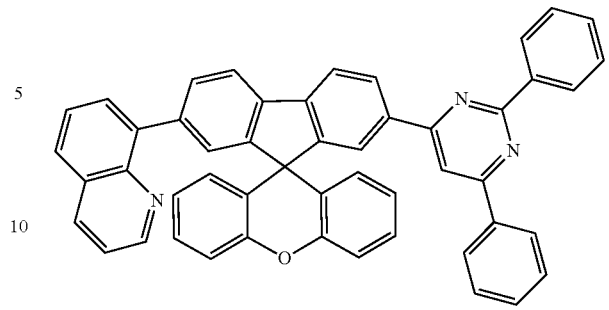
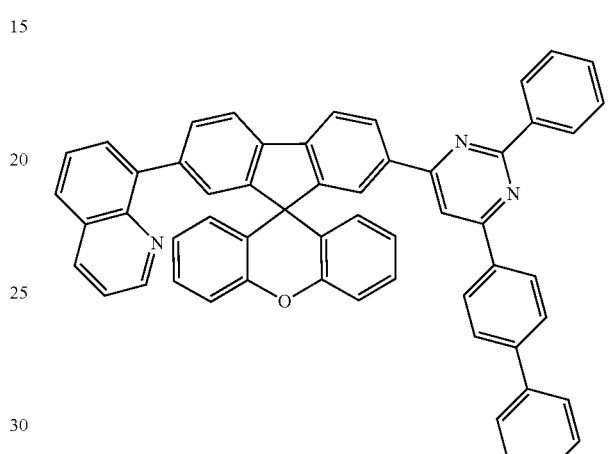
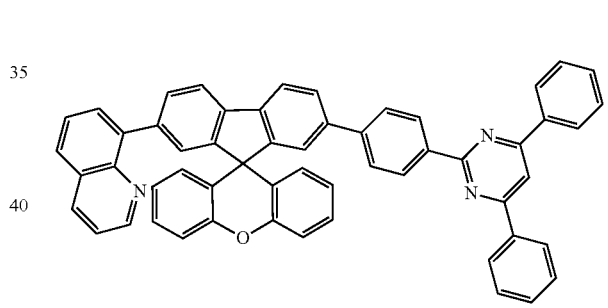
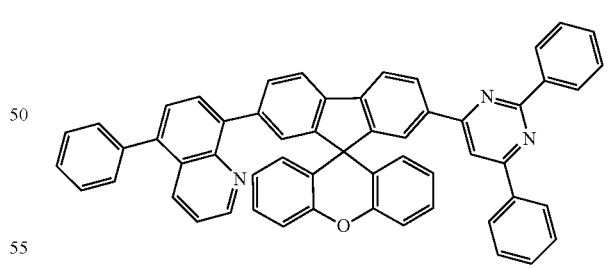
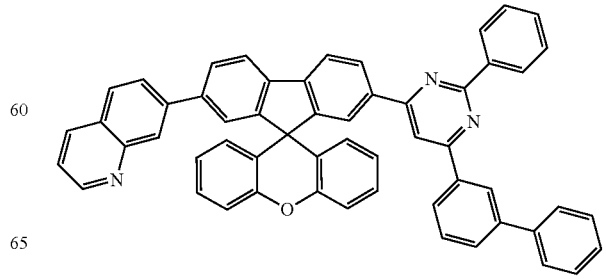

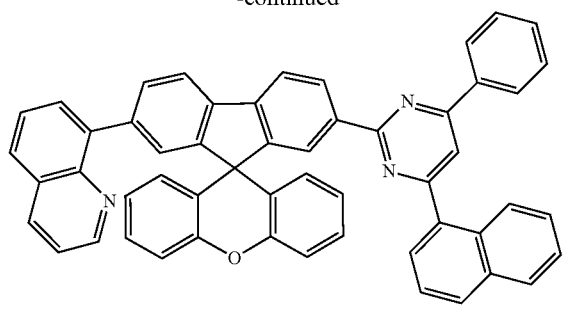
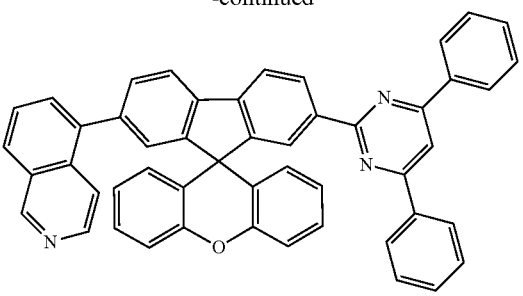

223
-continued
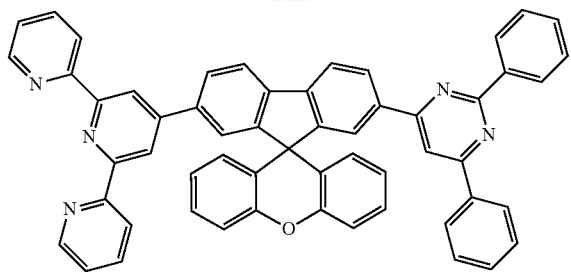
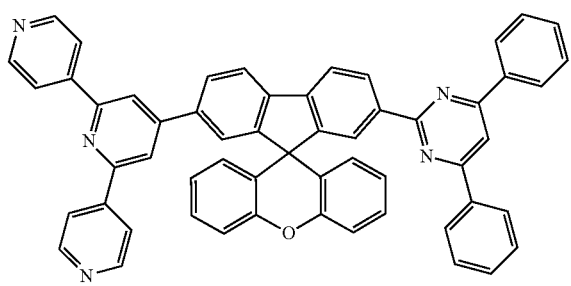
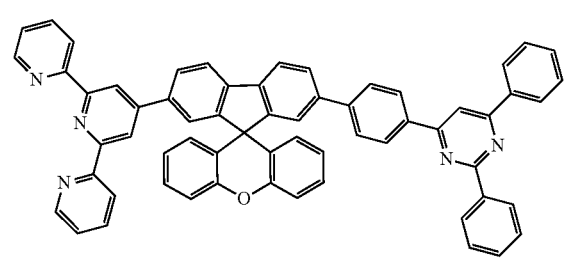
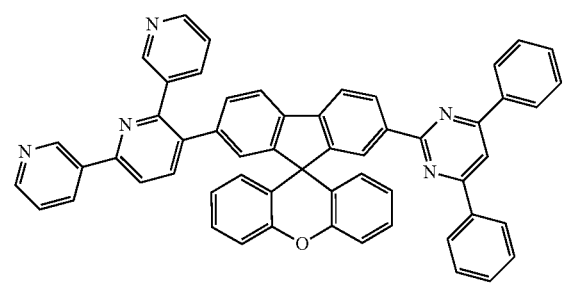
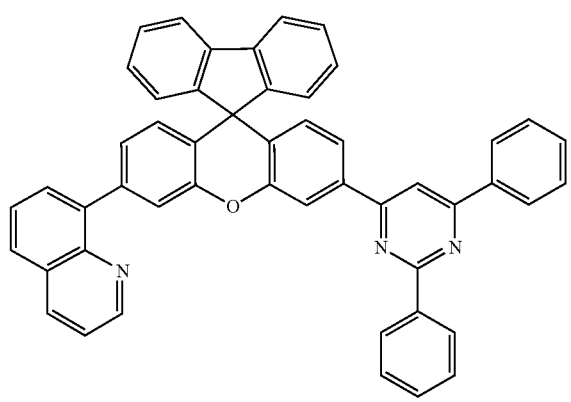
224
-continued
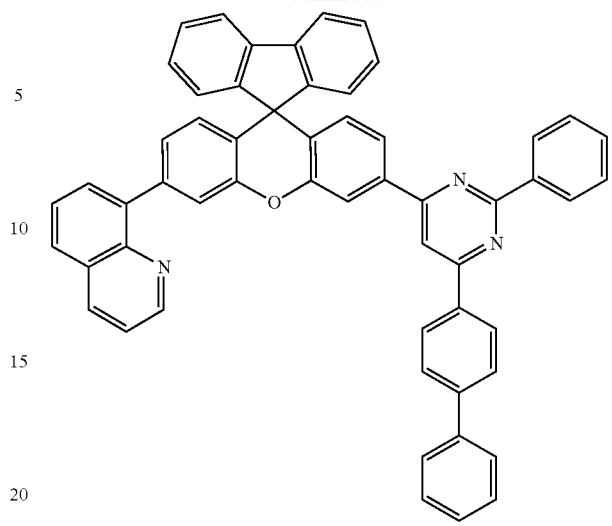
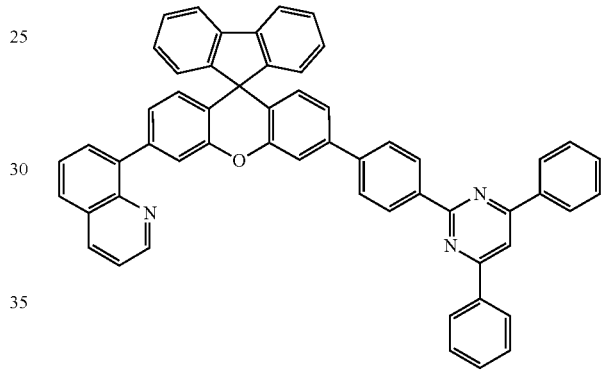
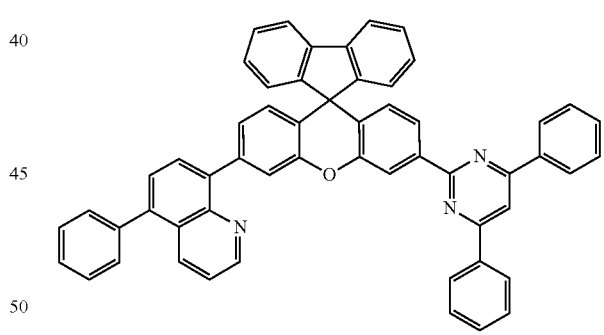
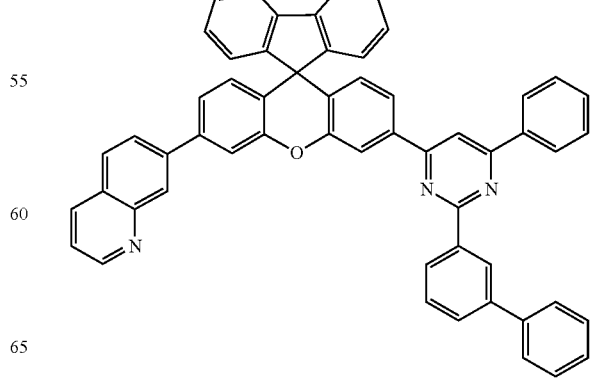

225
-continued
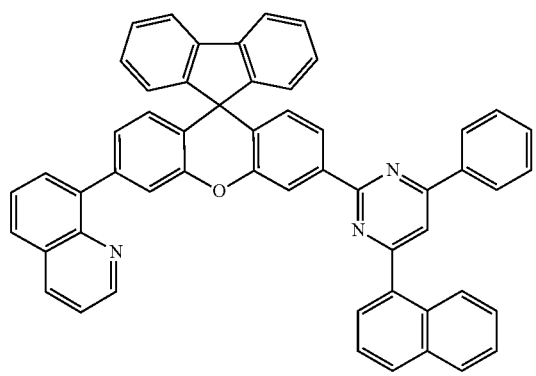
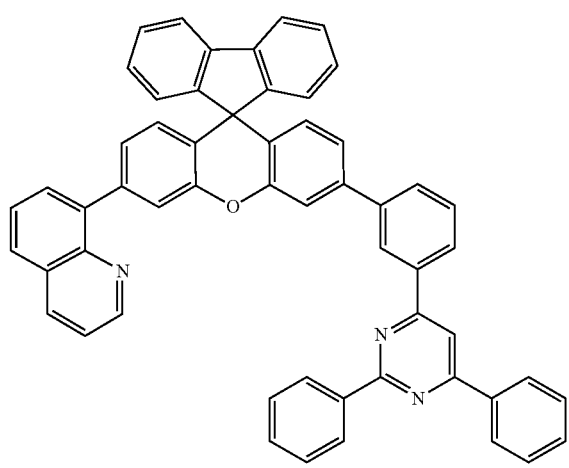
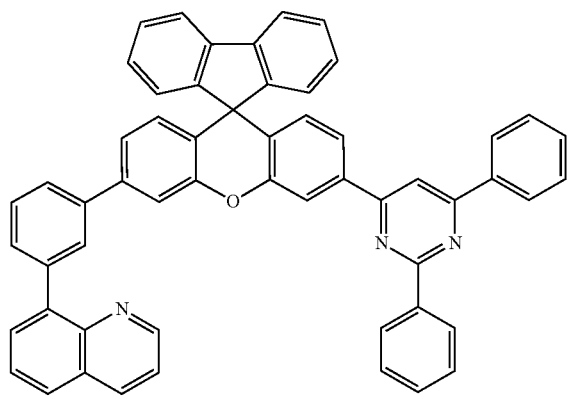
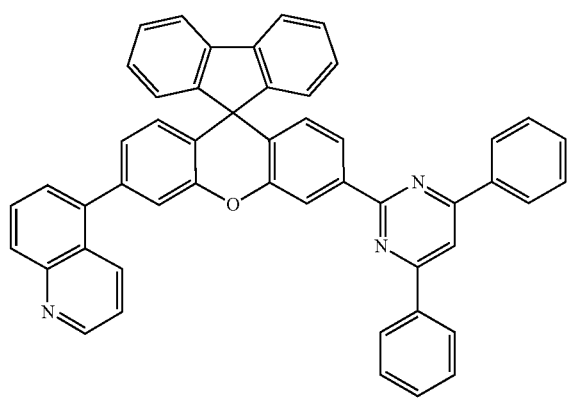
226
-continued
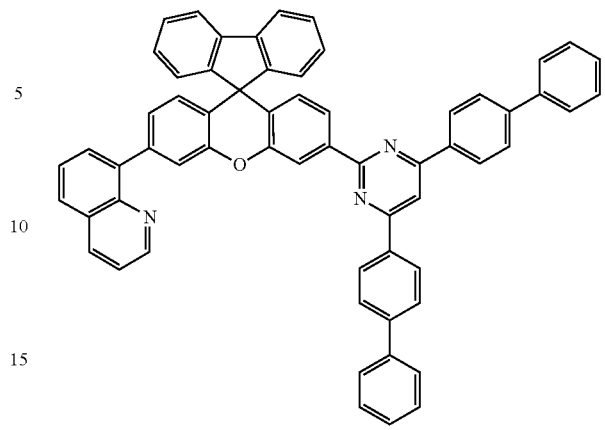
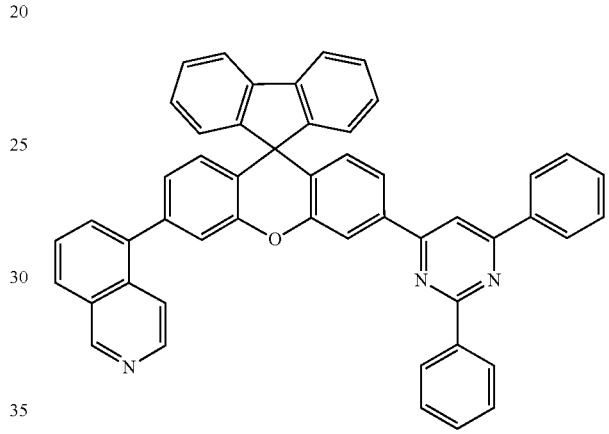
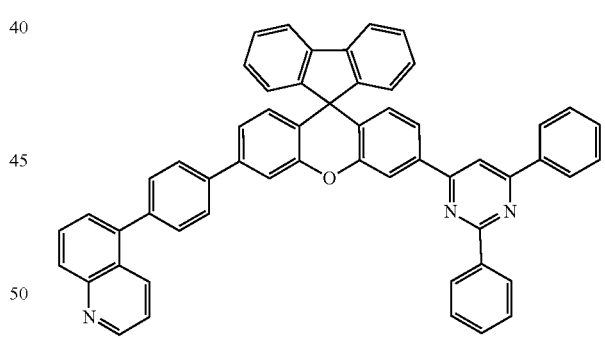
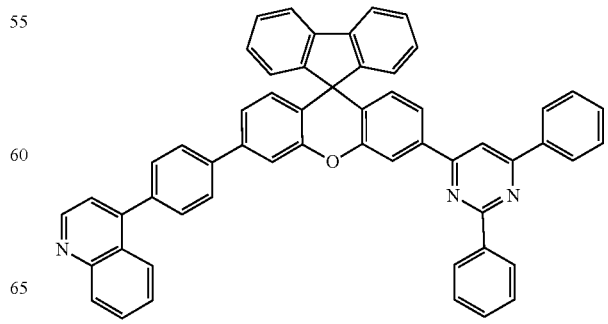

227
-continued
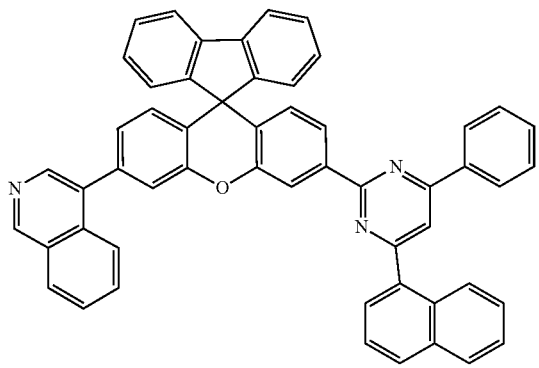
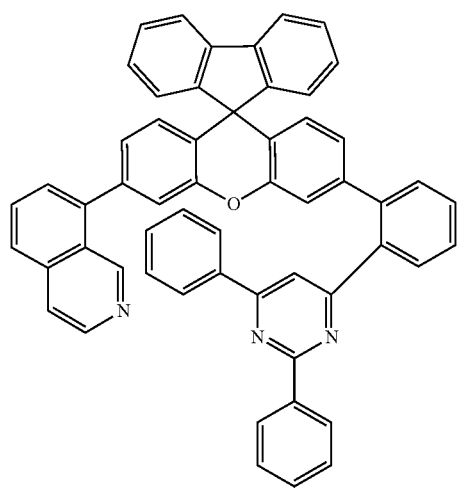
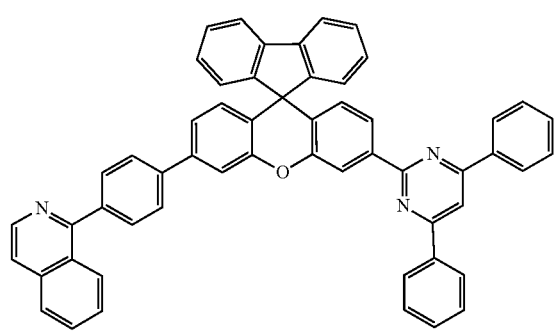
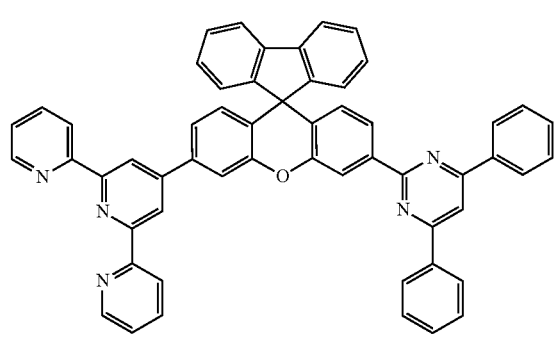
228
-continued
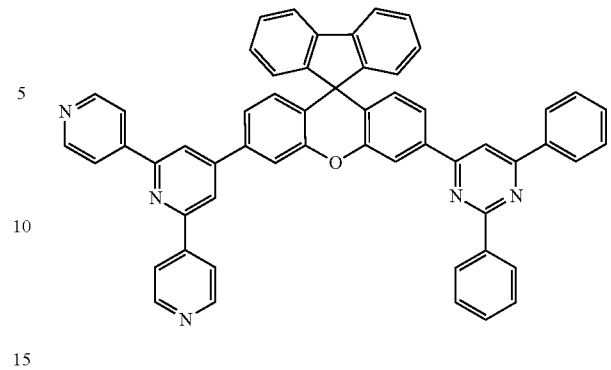
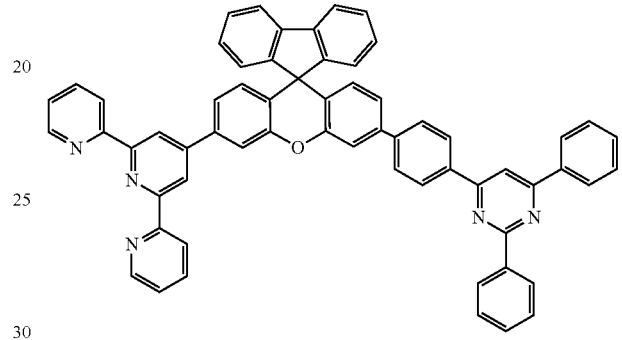
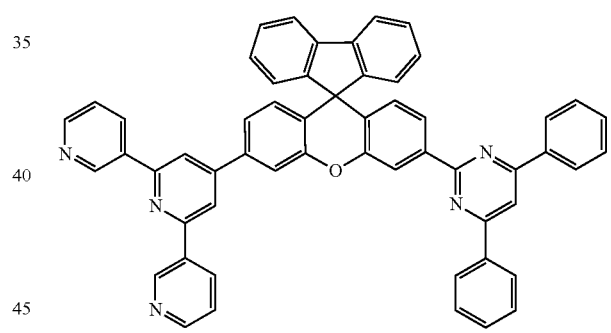
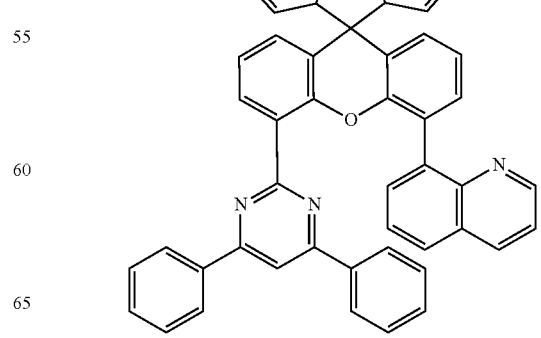

229
-continued
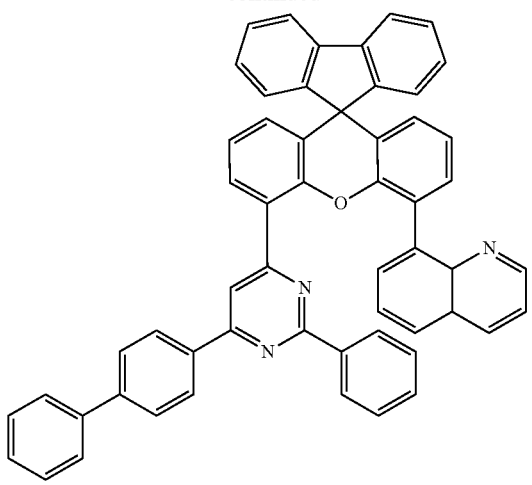
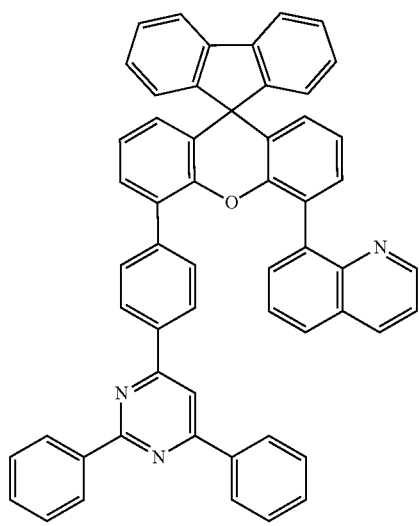
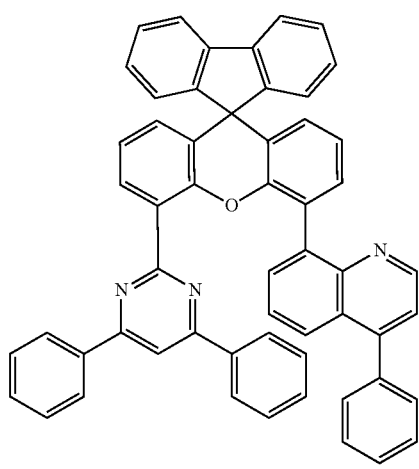
230
-continued
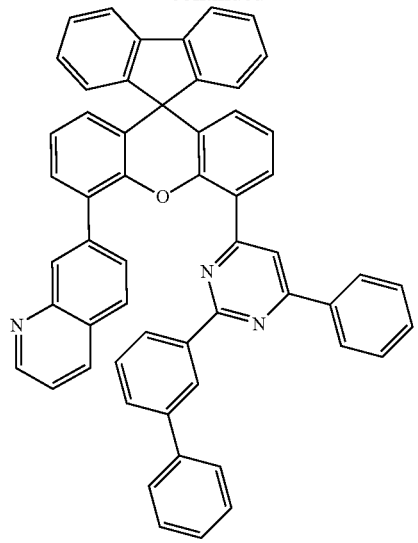
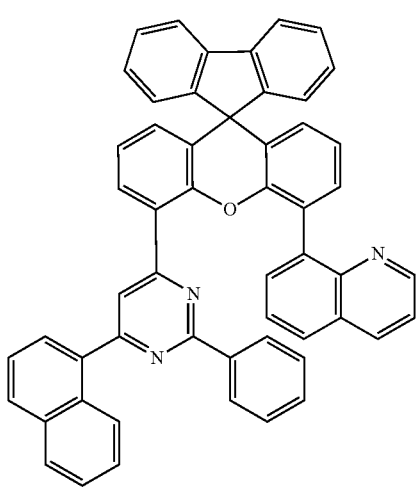
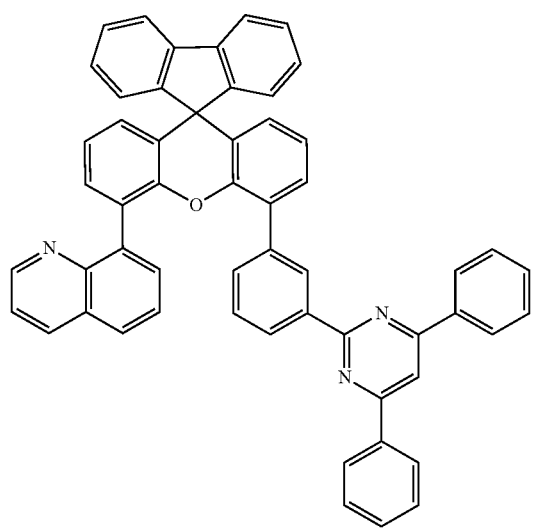

231
-continued
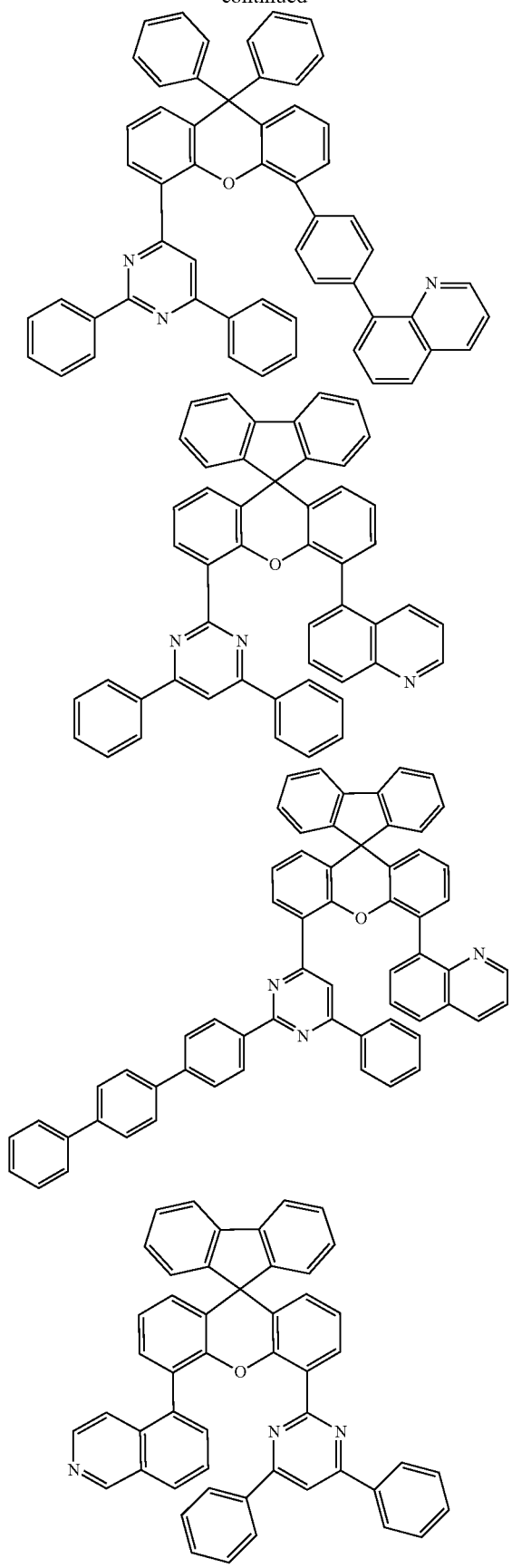
232
-continued
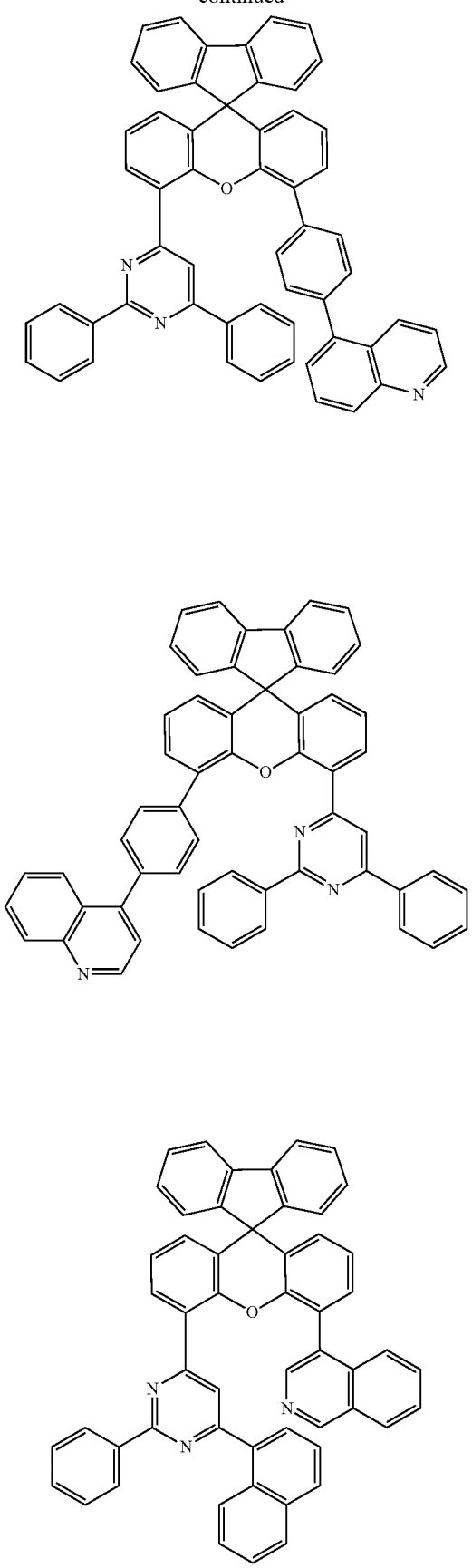

233
-continued
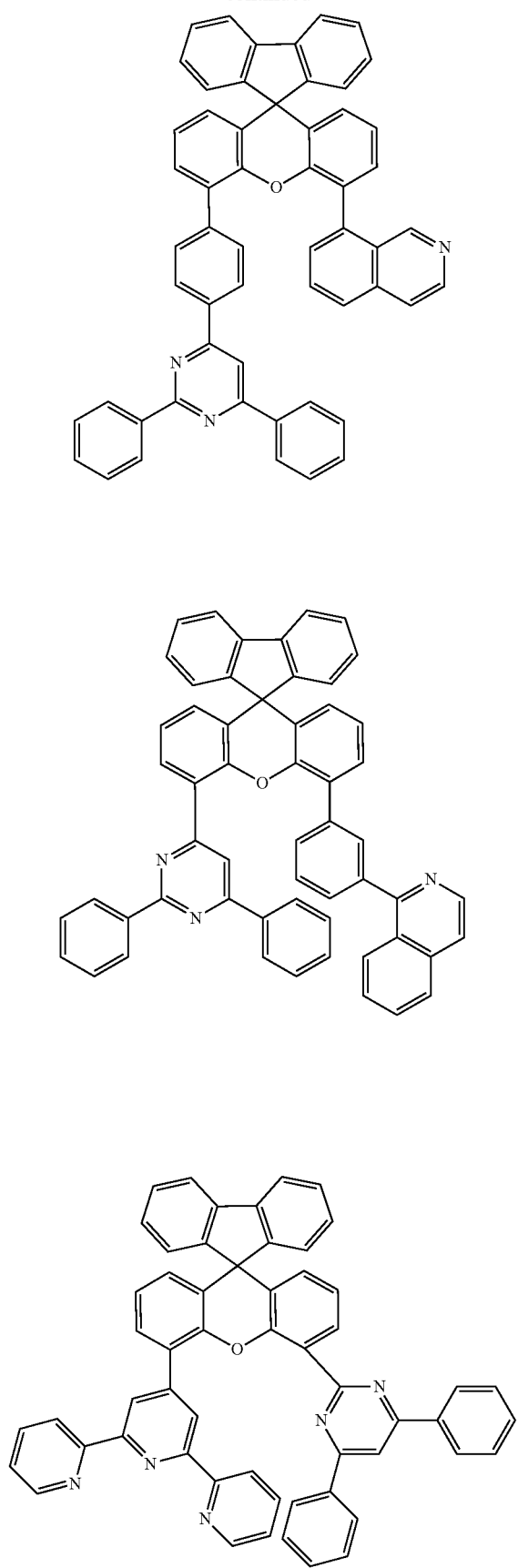
234
-continued
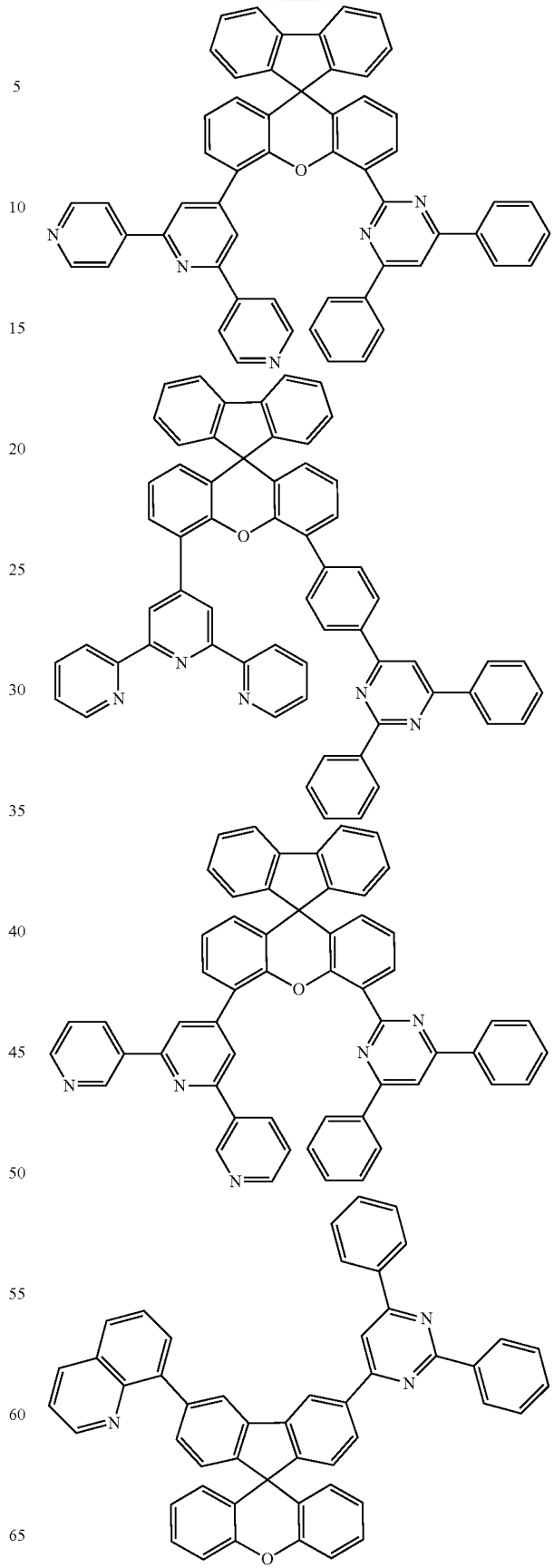

-continued
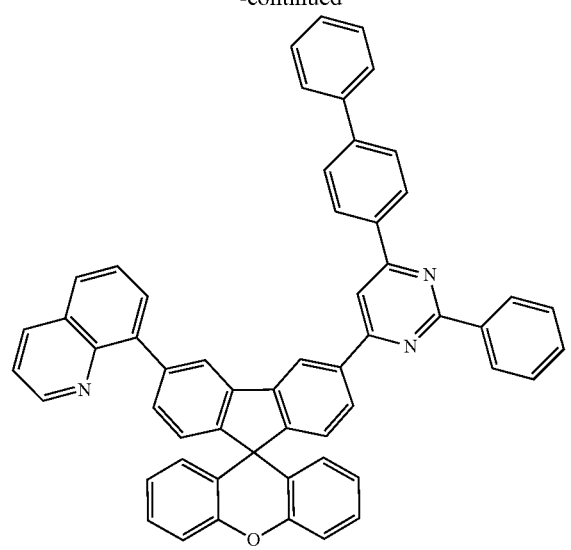
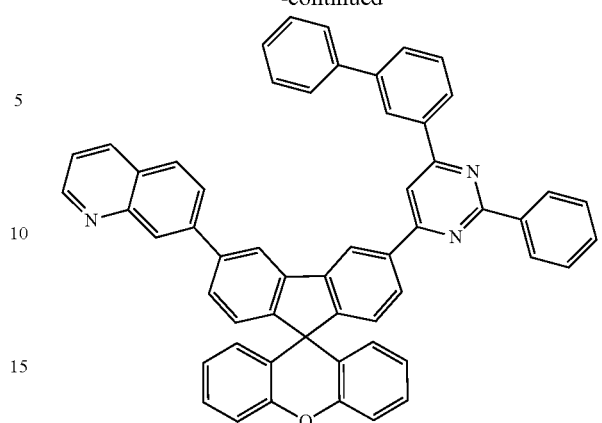
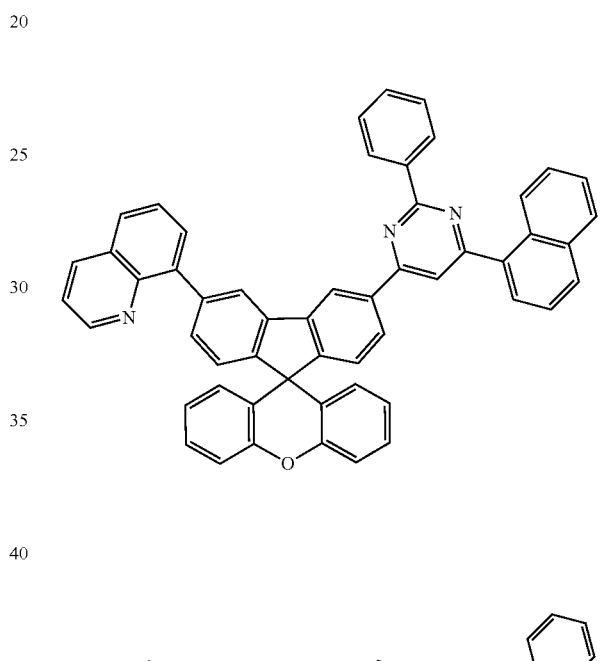
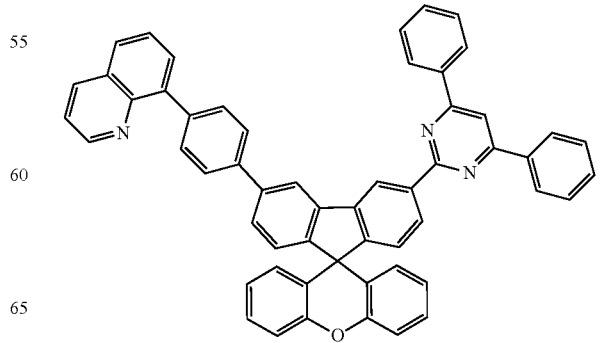

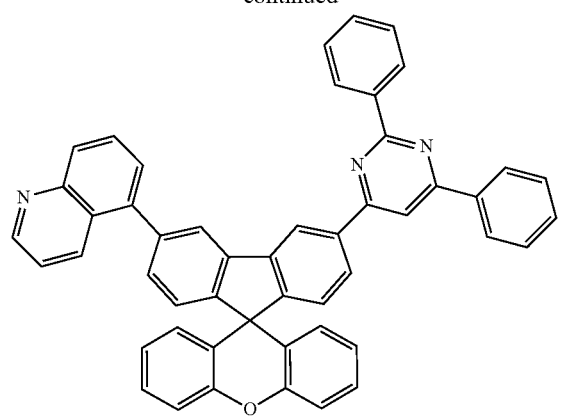
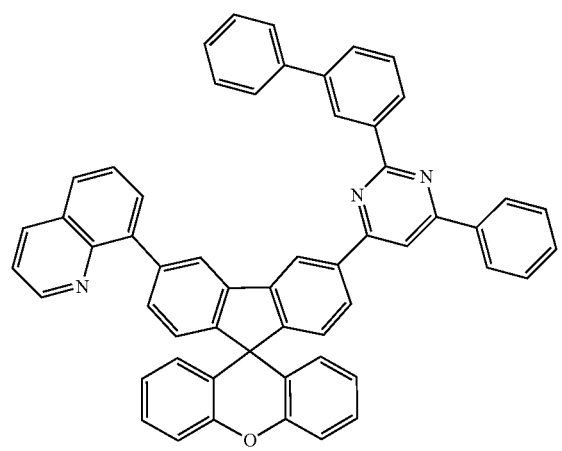
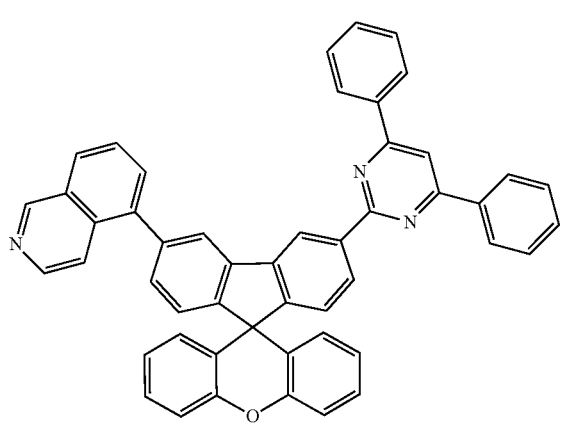
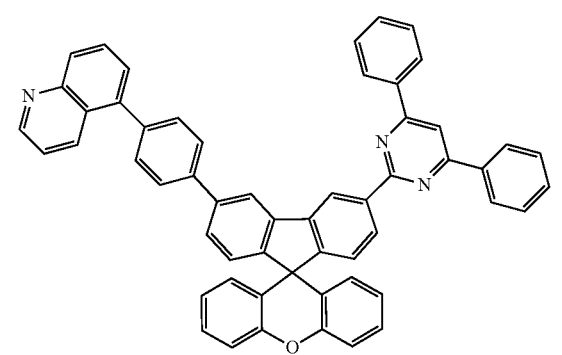
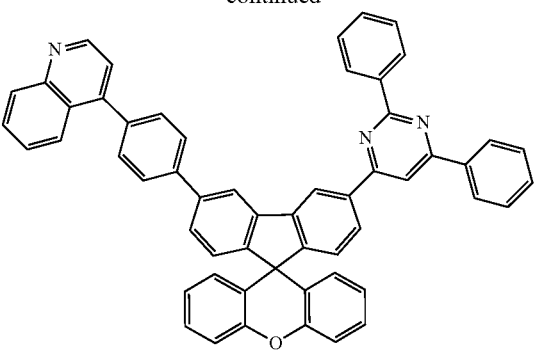
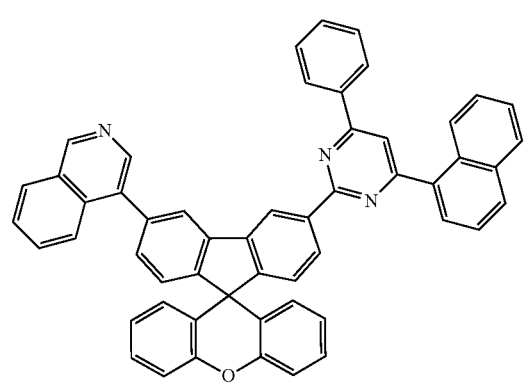
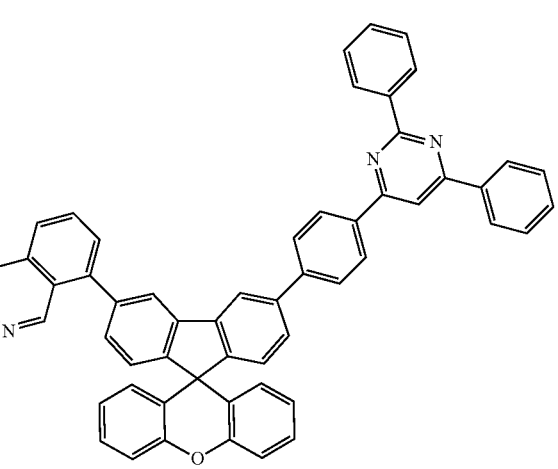
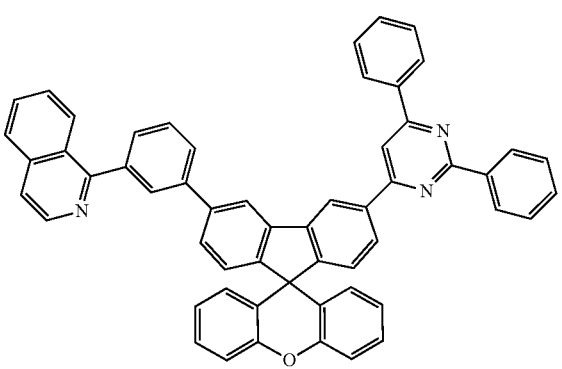

239
-continued
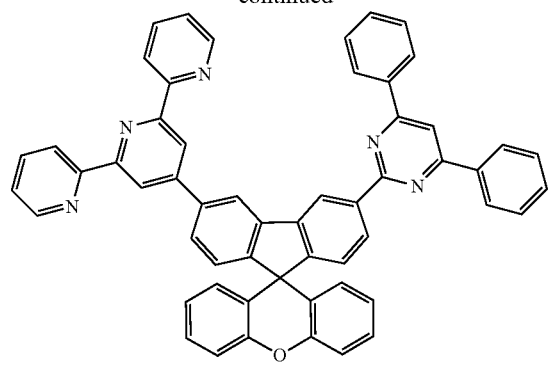
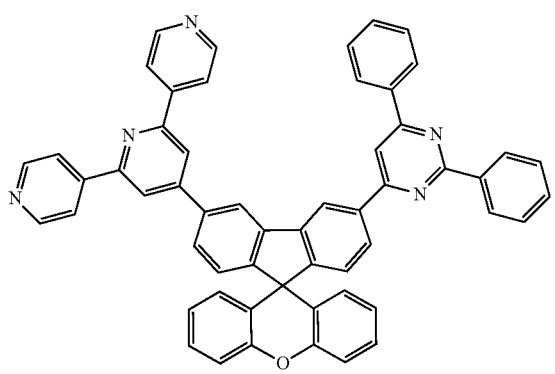
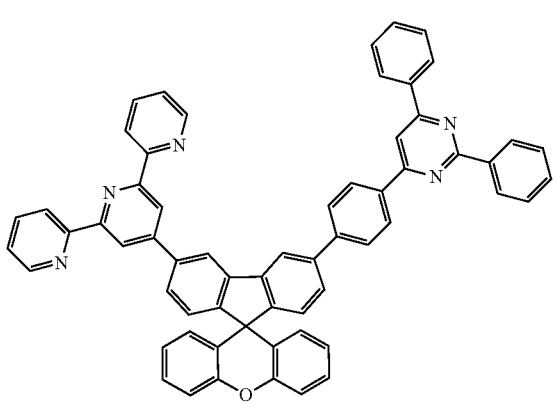
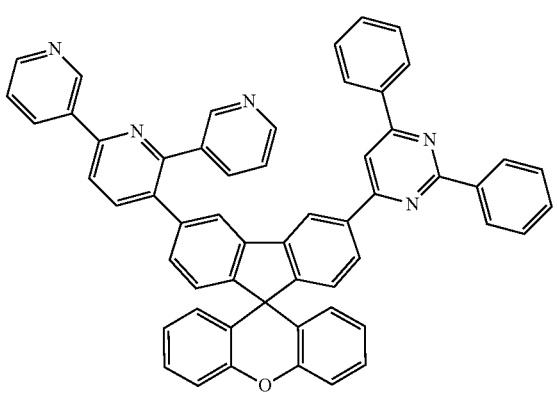
240
-continued
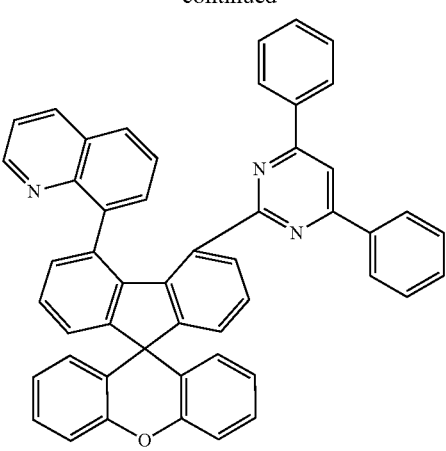
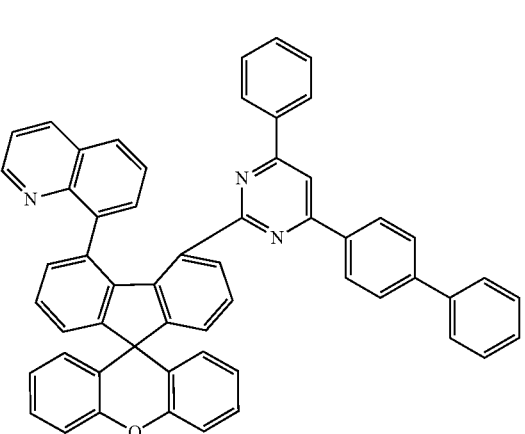
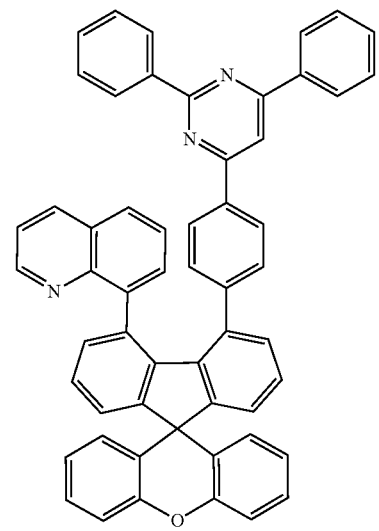

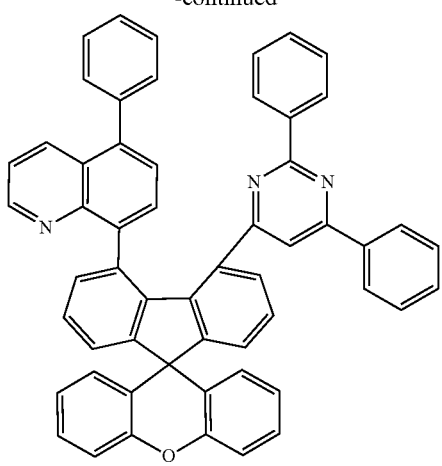
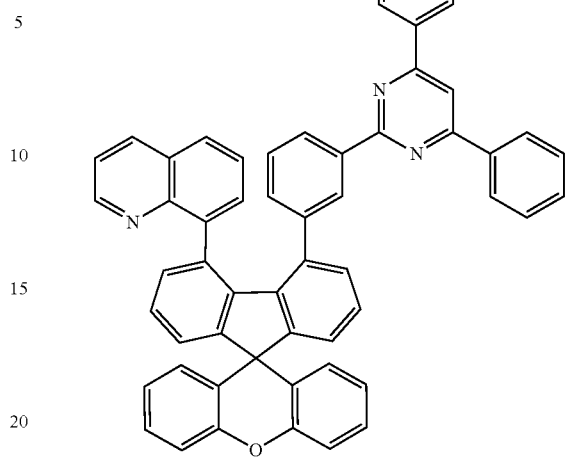
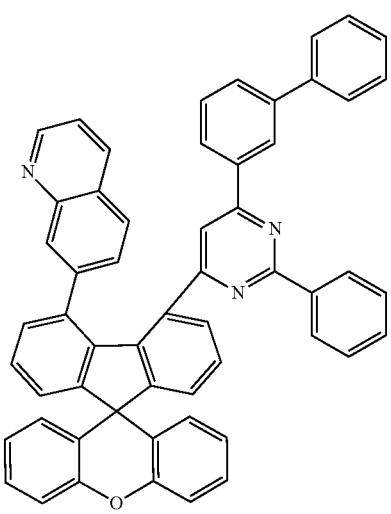
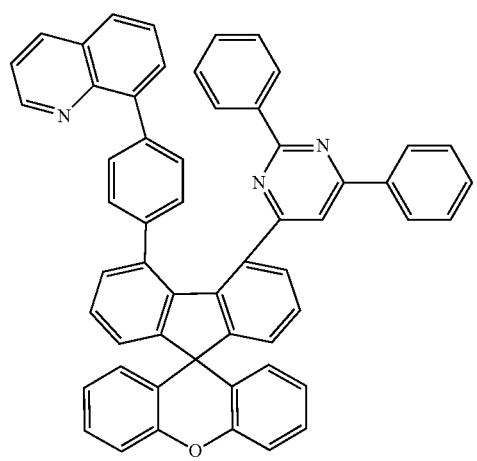
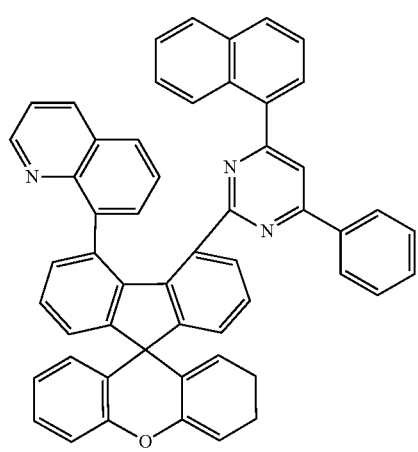
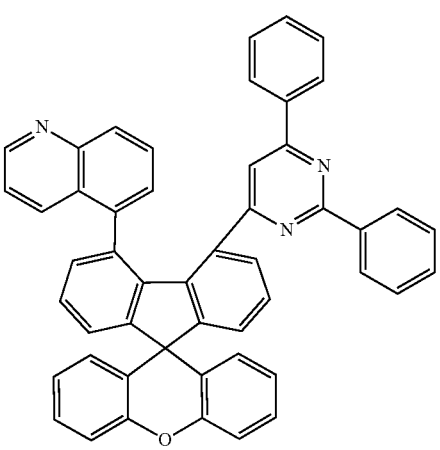

243
-continued
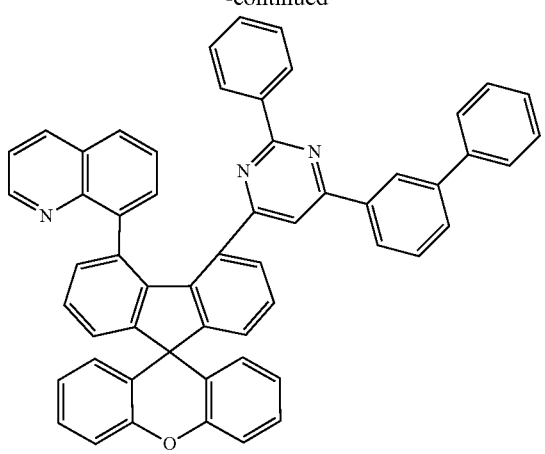
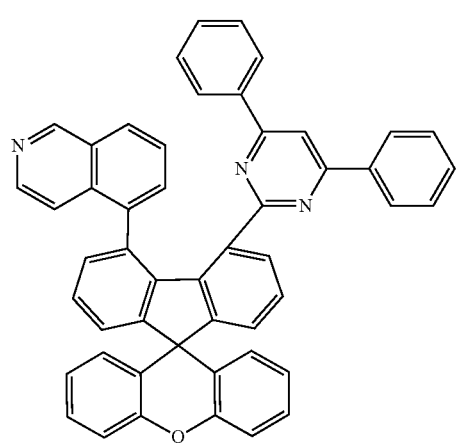
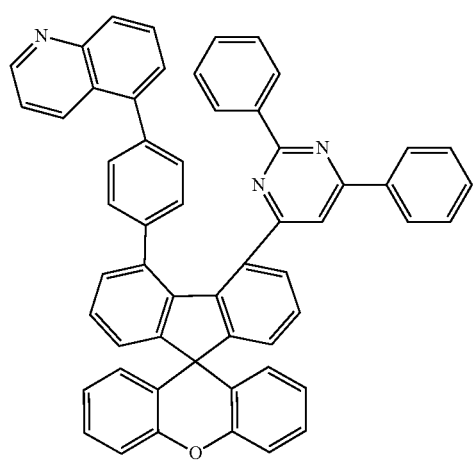
244
-continued
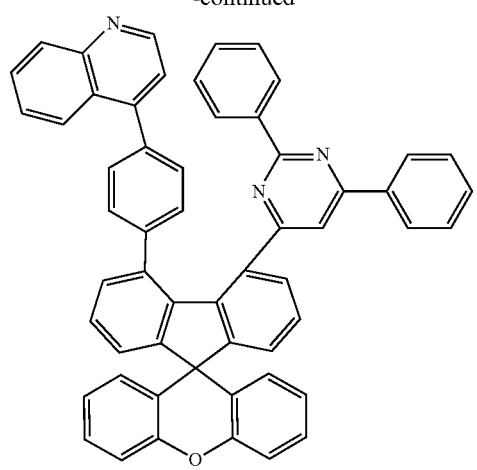
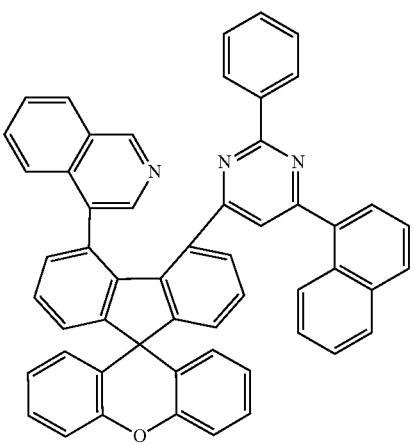
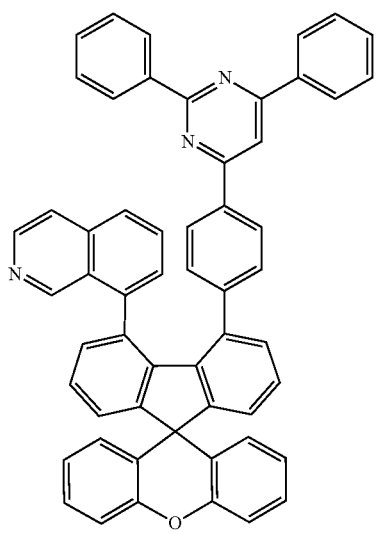

245
-continued
246
-continued
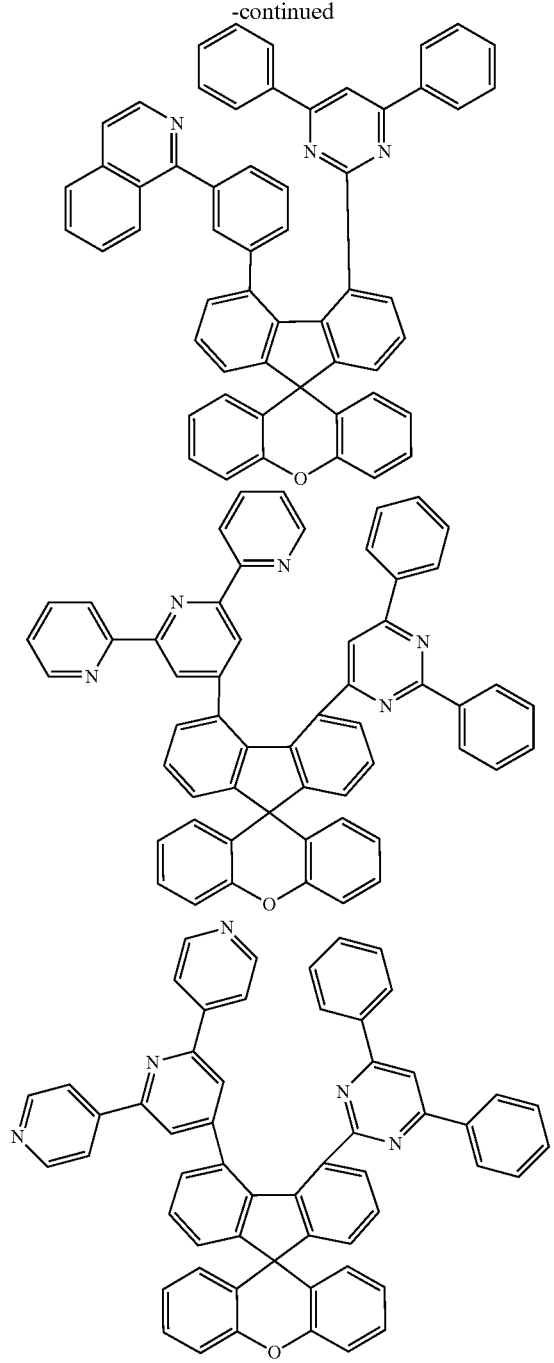
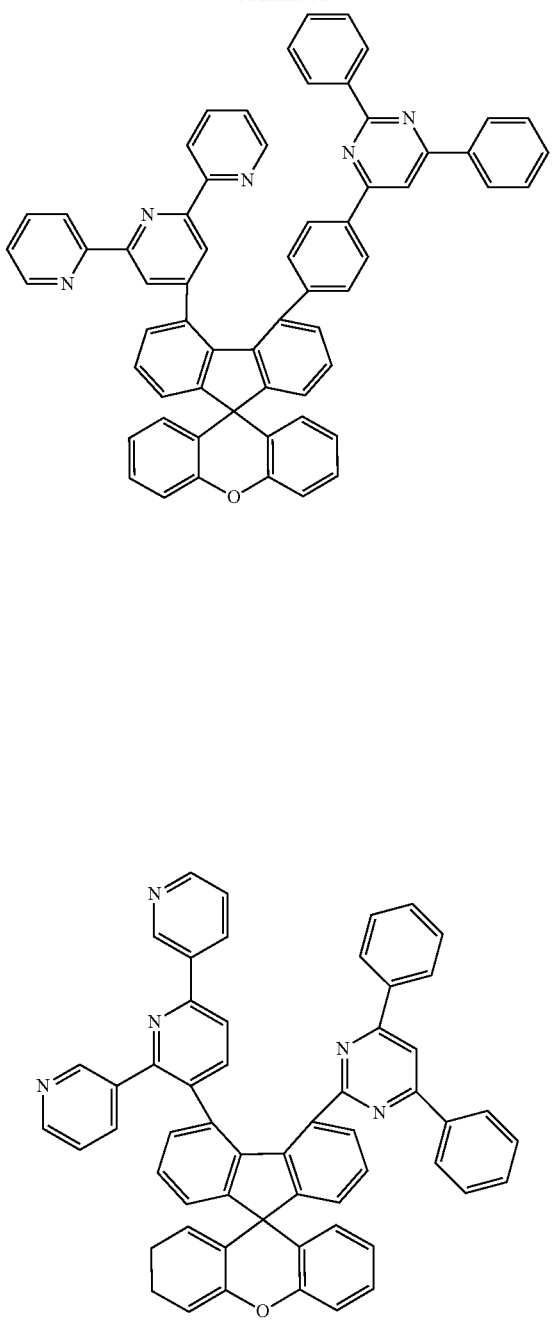
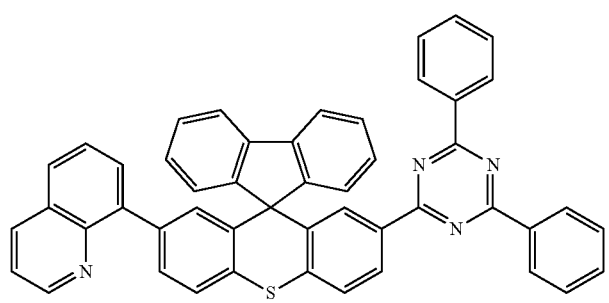

-continued
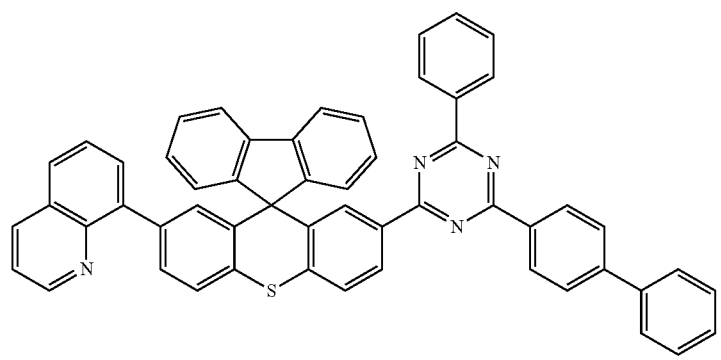
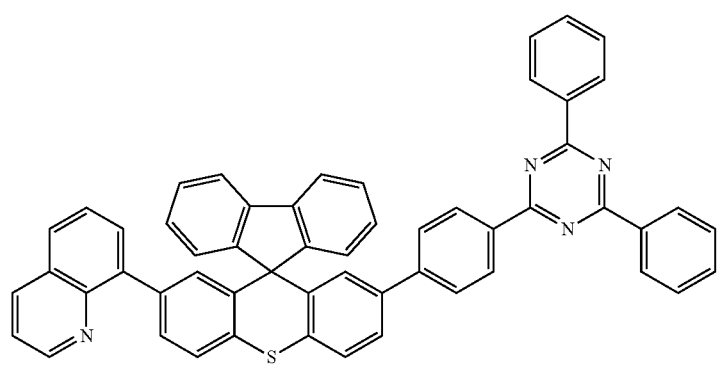
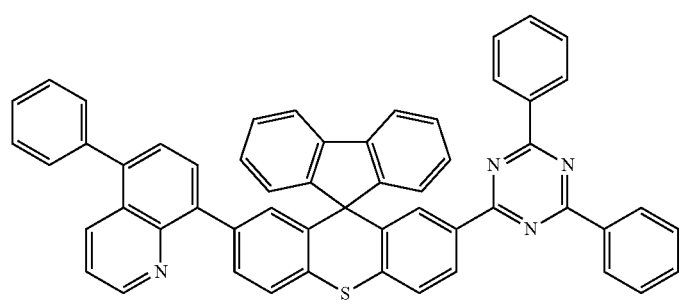
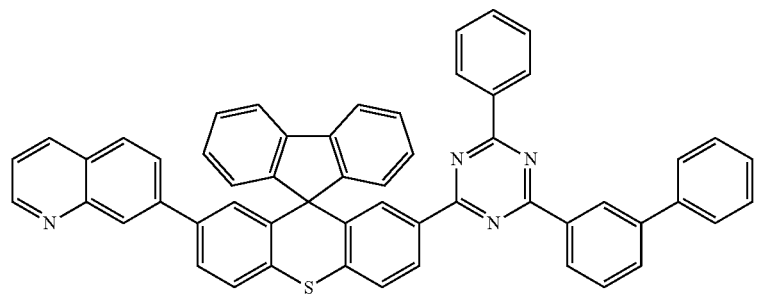
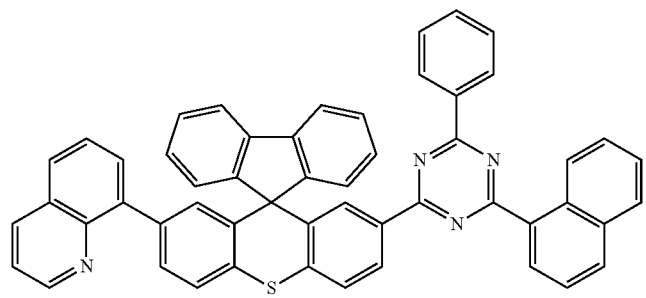

-continued
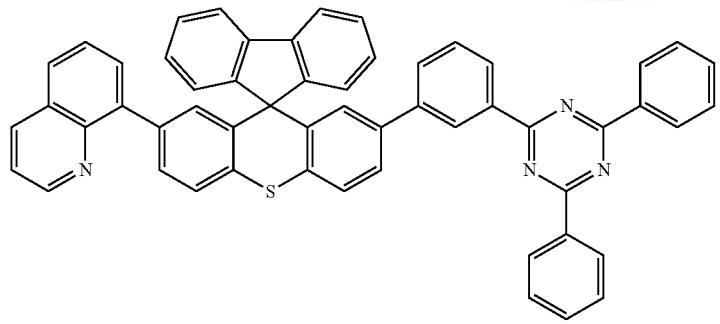
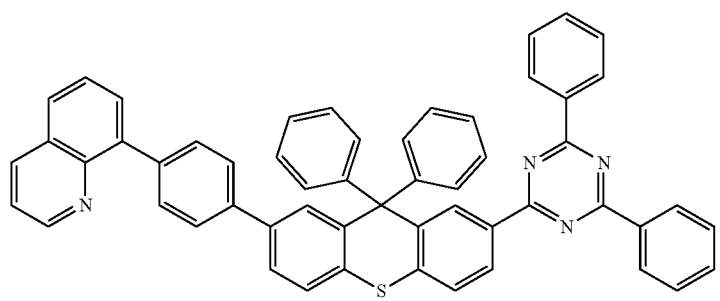
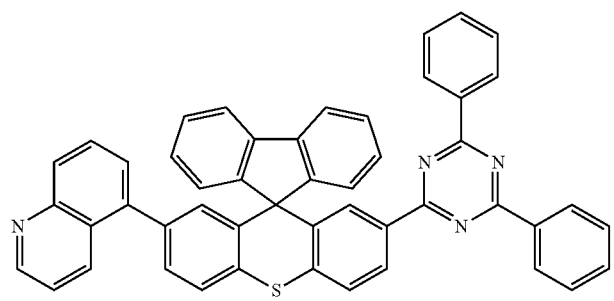
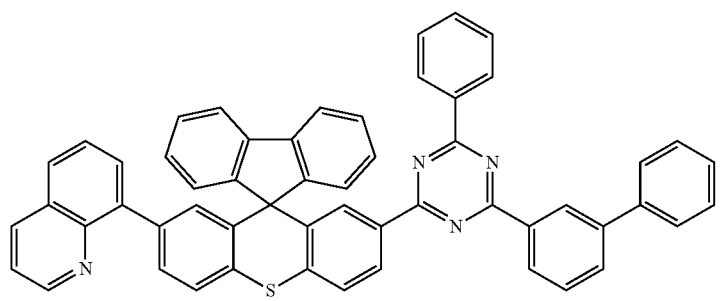
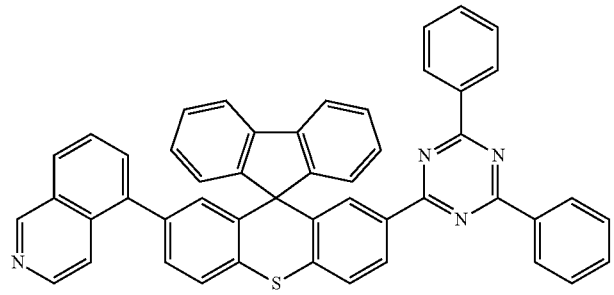

-continued
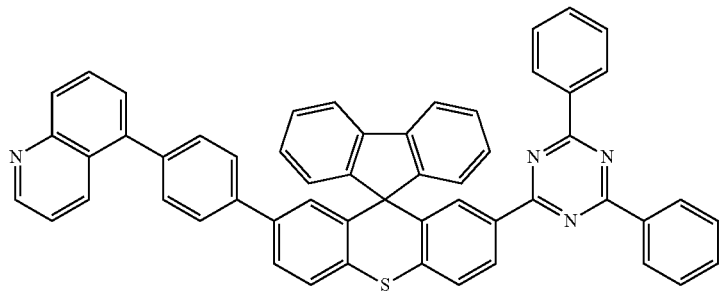
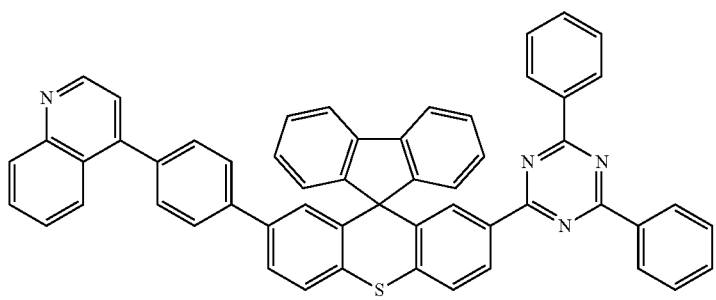
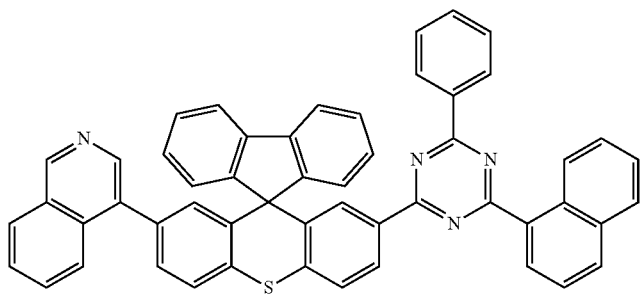
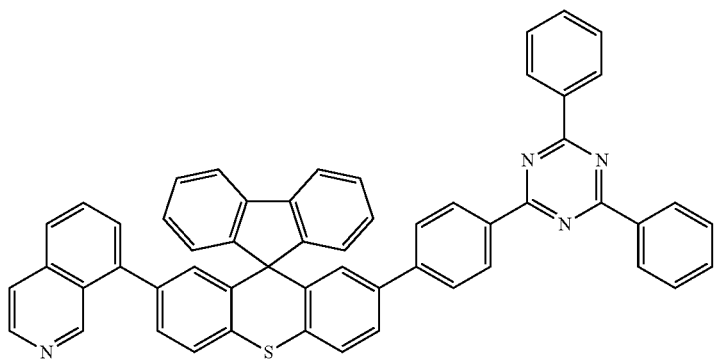
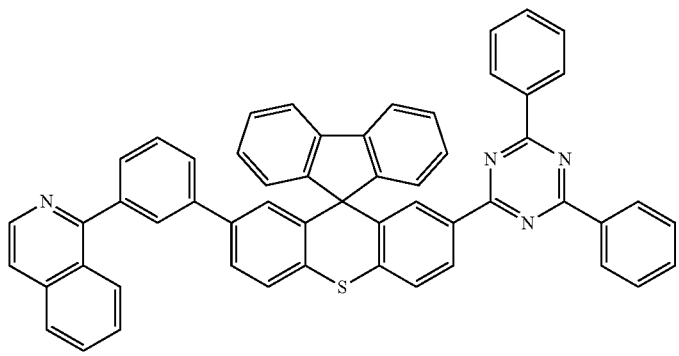

-continued
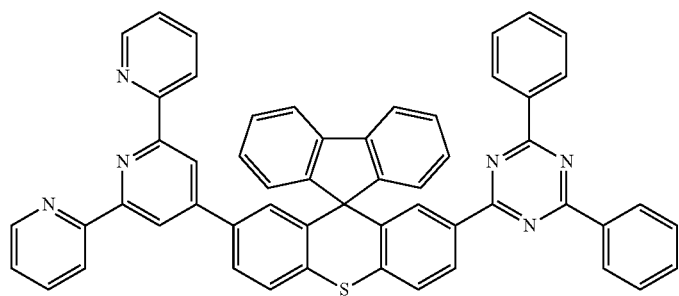
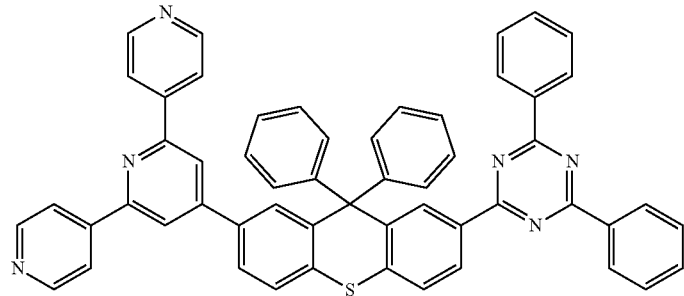
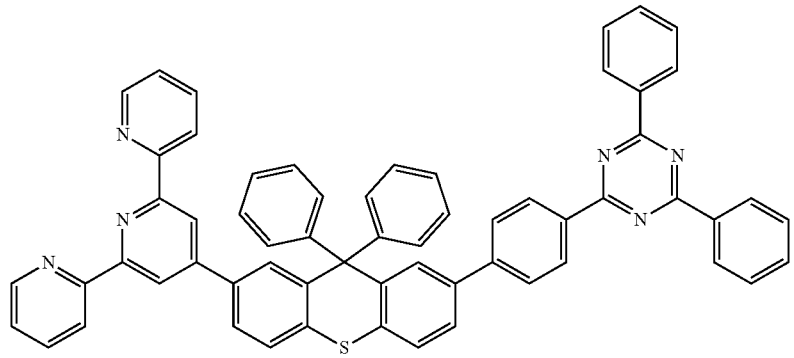
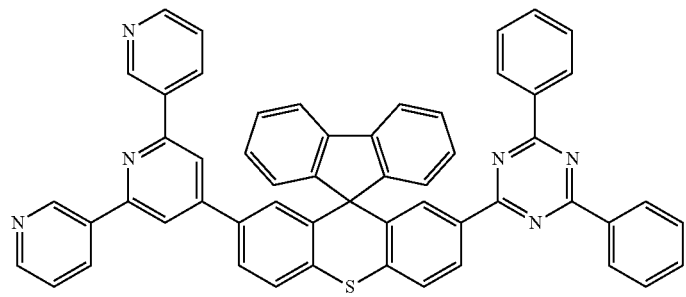
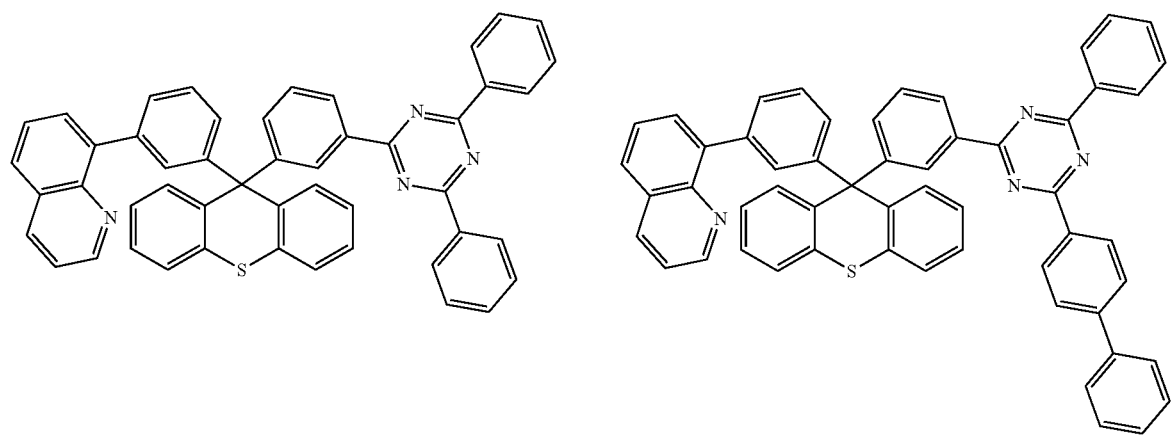

-continued
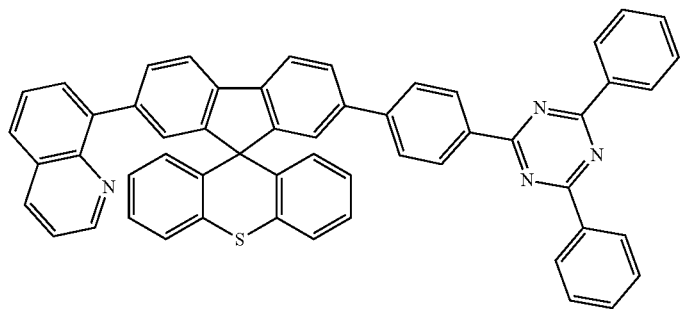
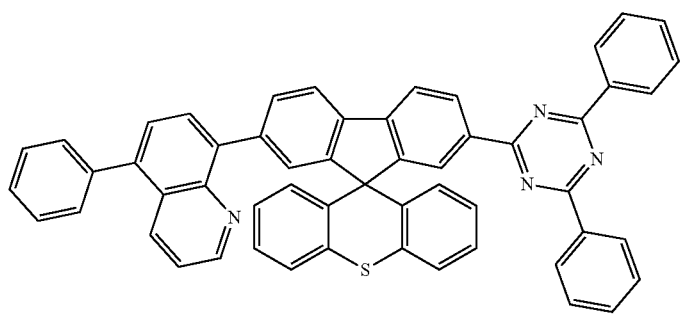
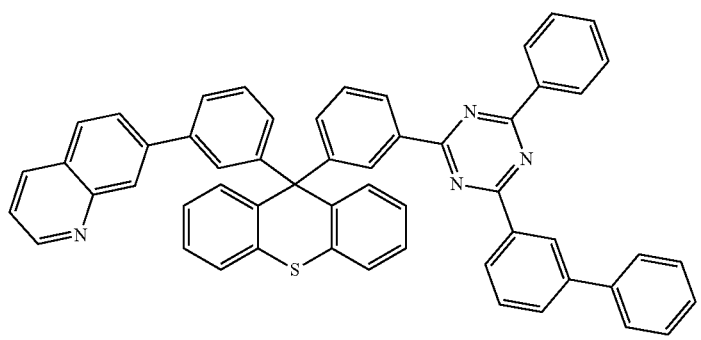
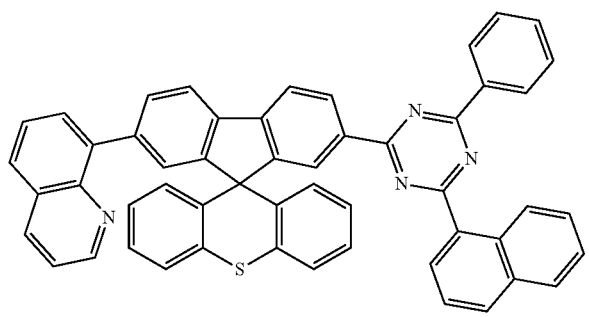
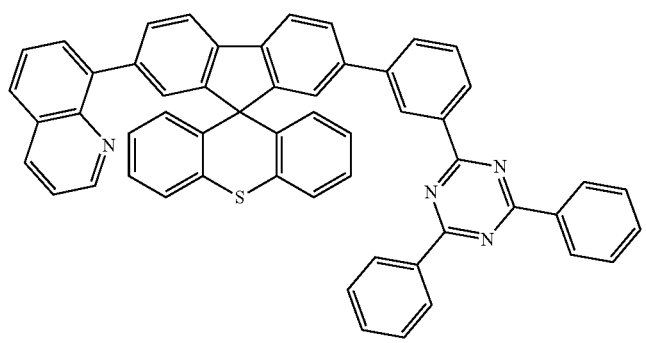

-continued
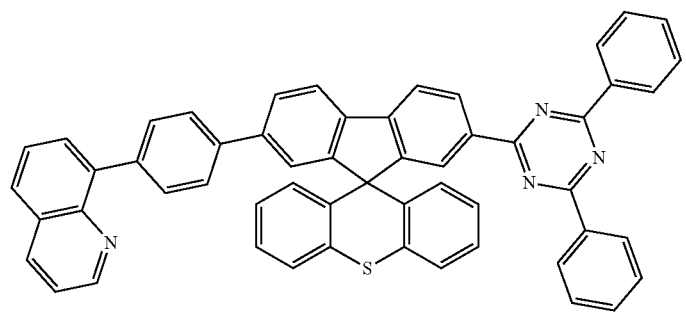
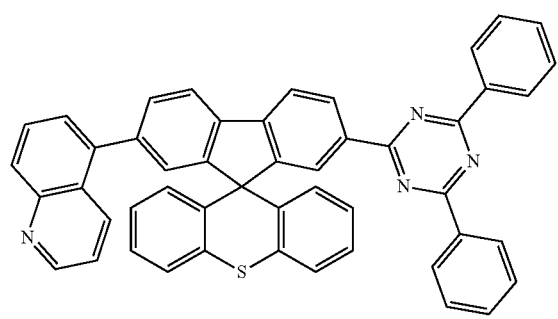
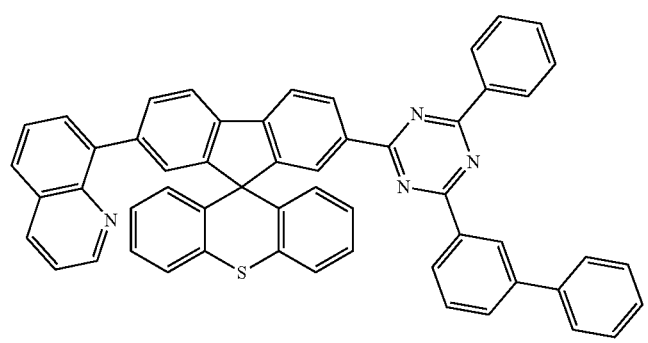
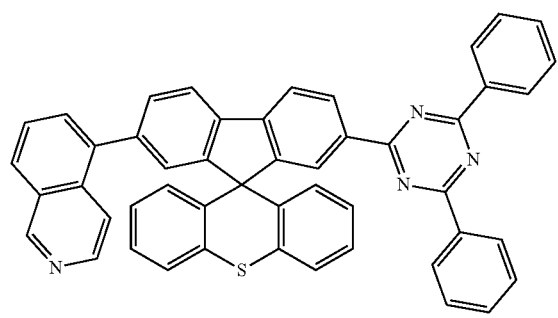
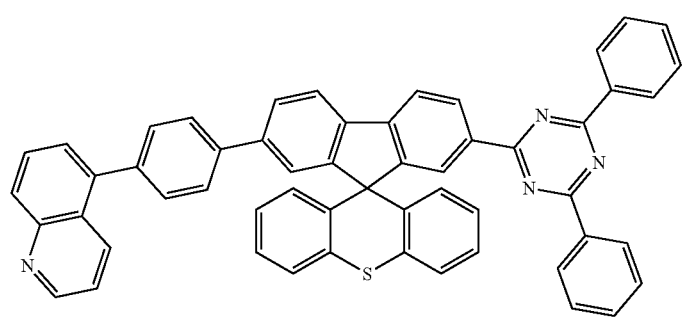

-continued
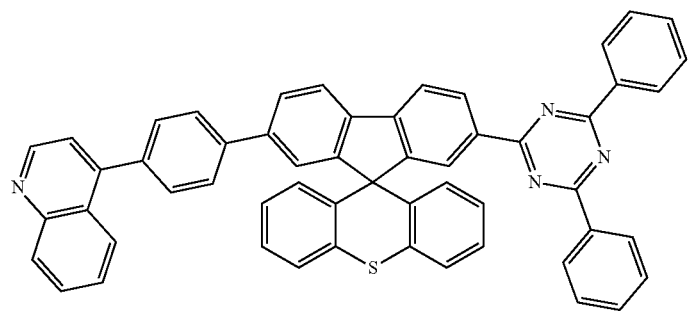
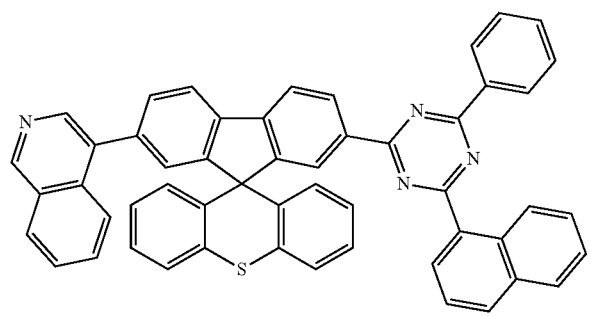
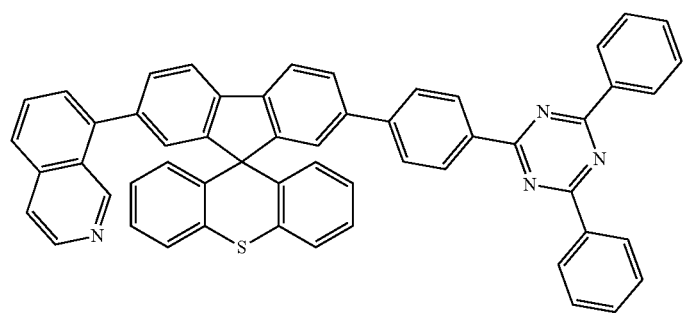
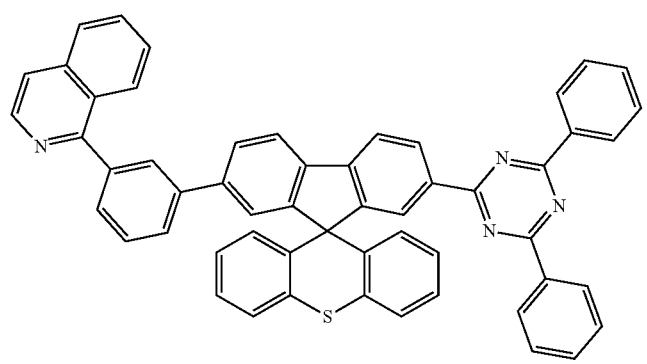
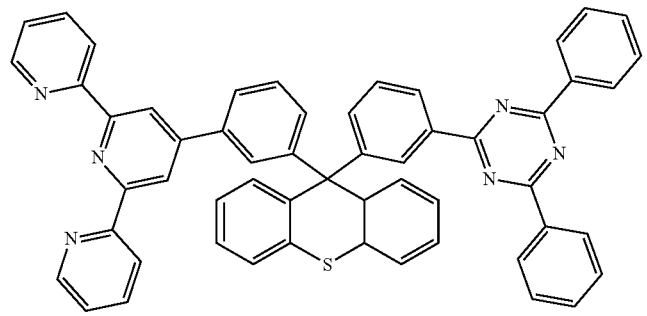

261
-continued
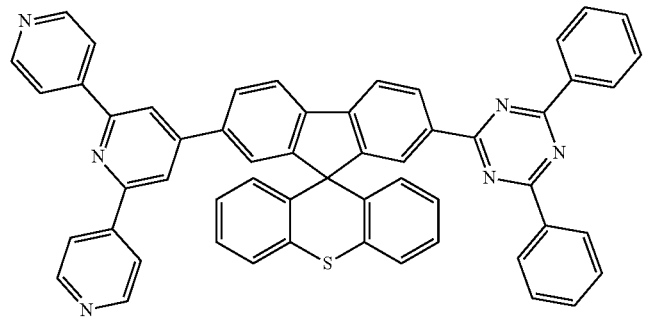
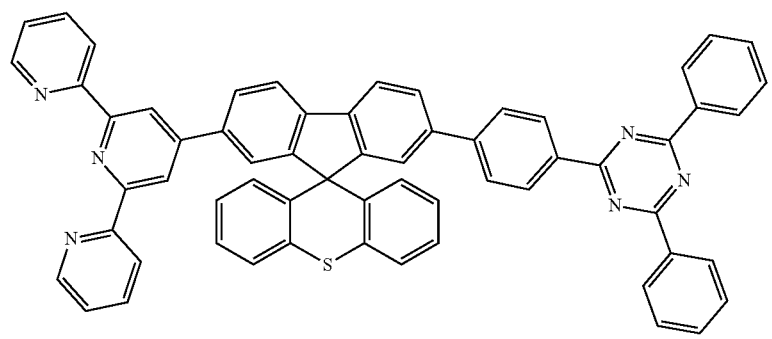
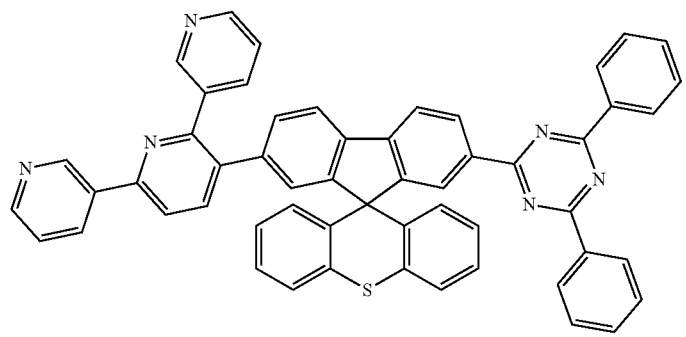
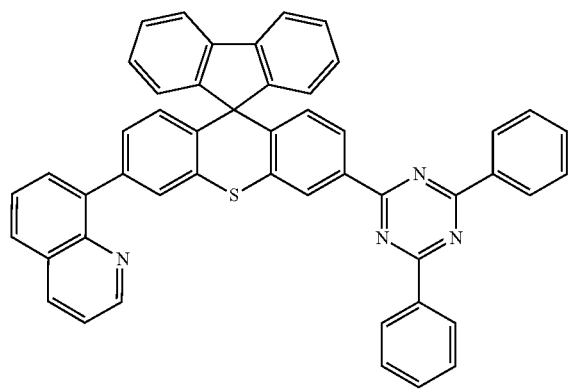
262
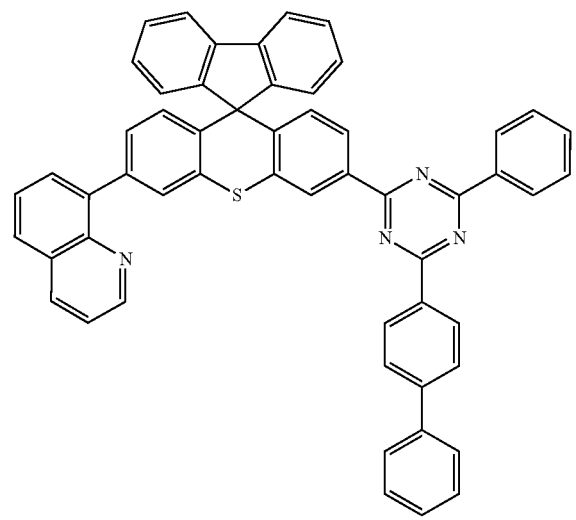

-continued
263
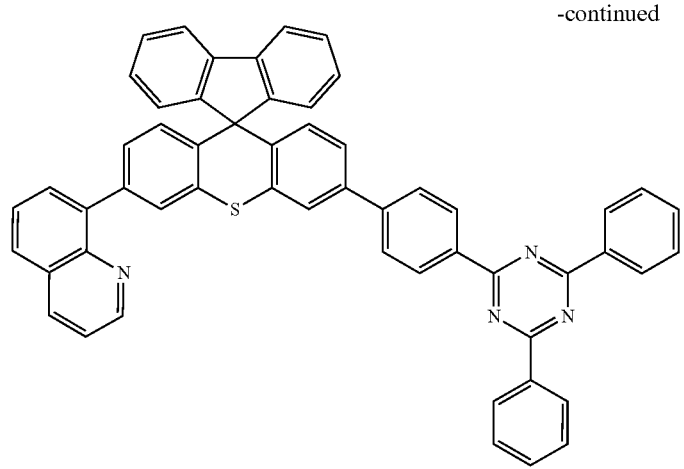
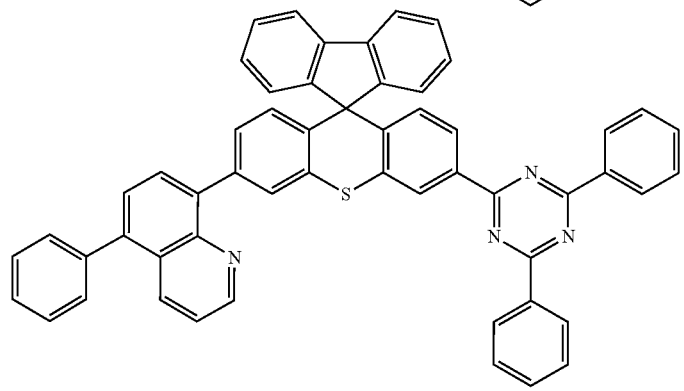
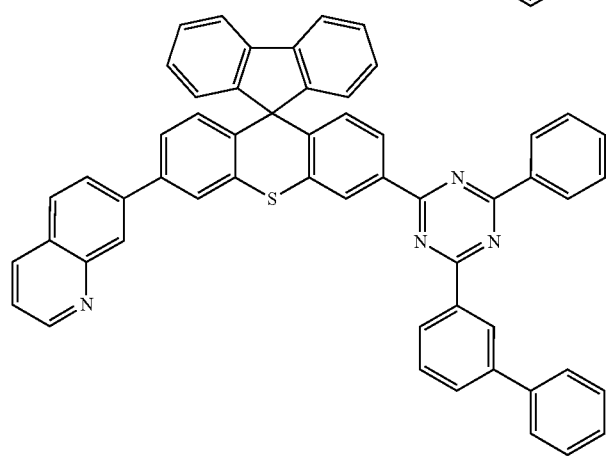
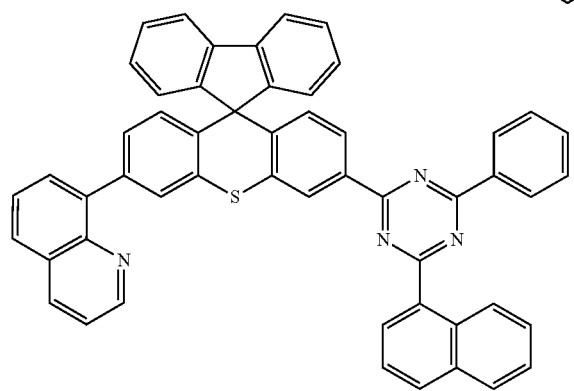
264
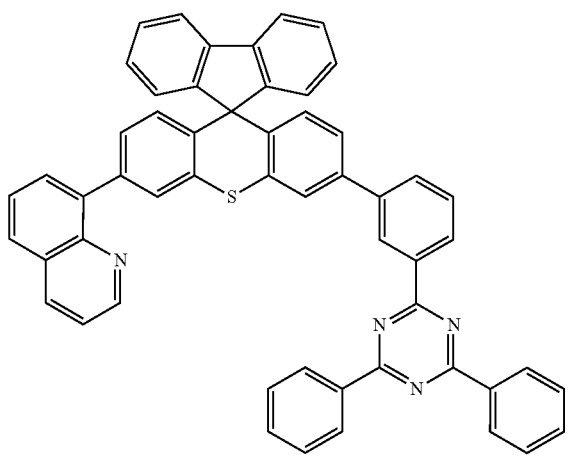

265
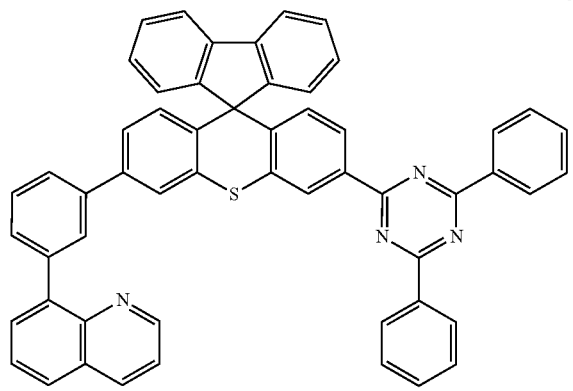
266
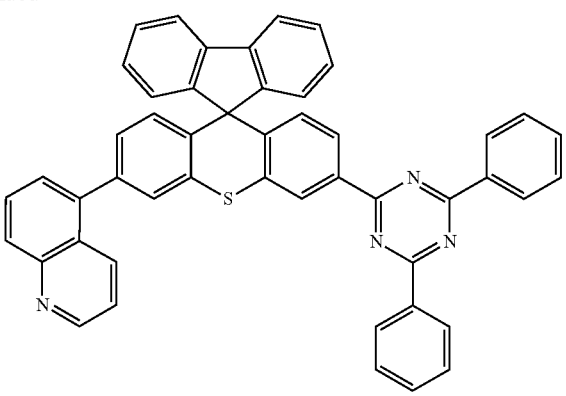
-continued
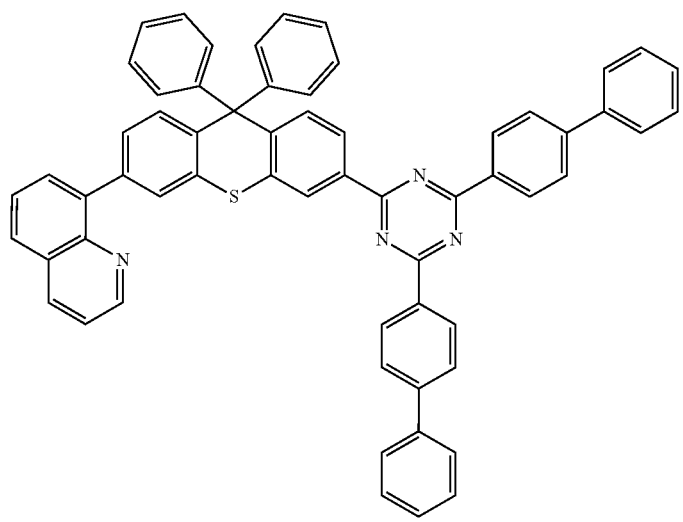
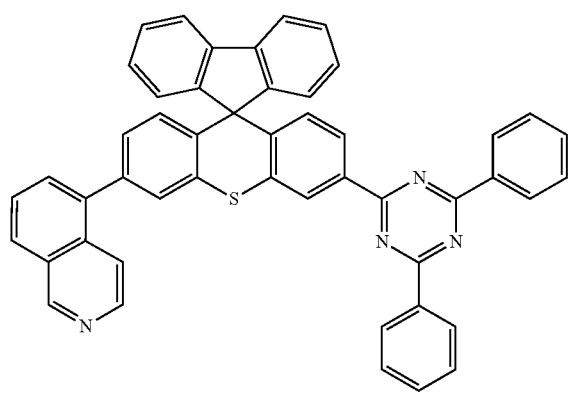
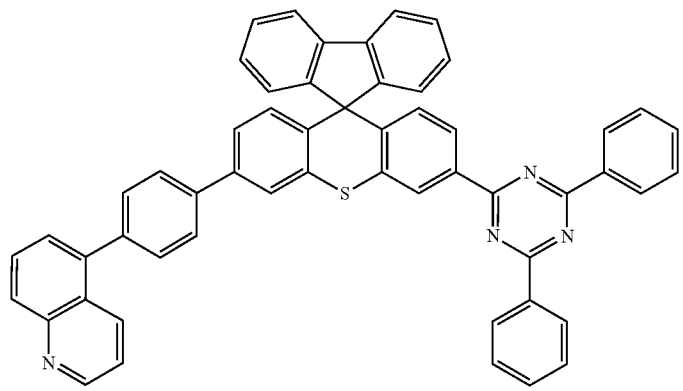

267
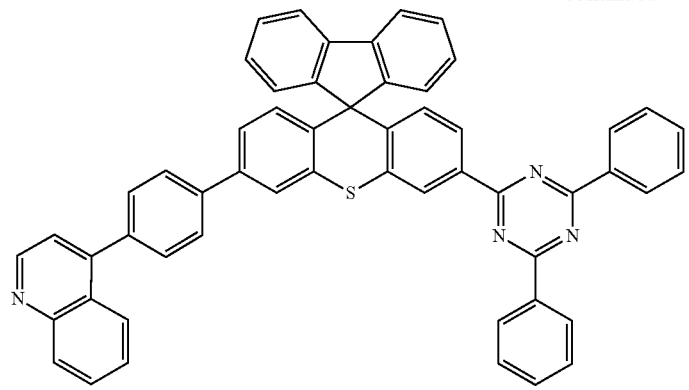
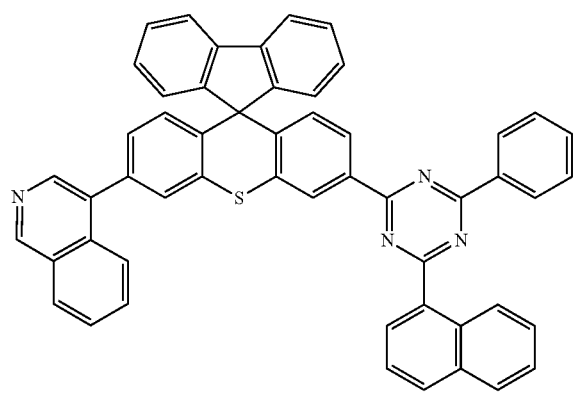
268
-continued
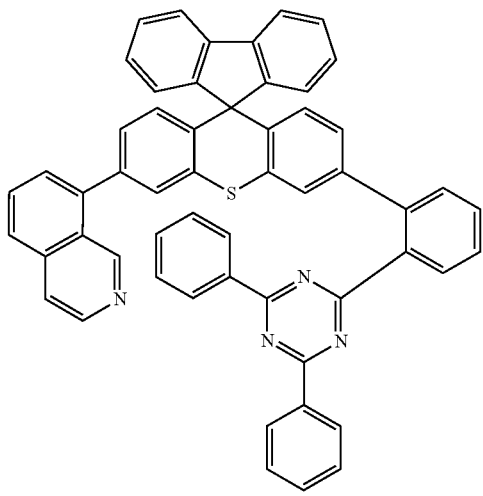
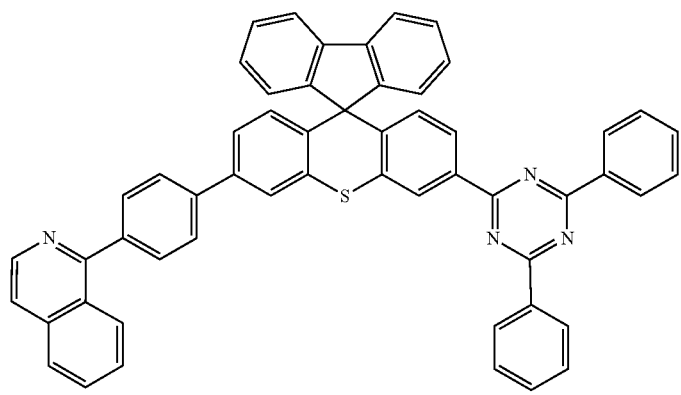
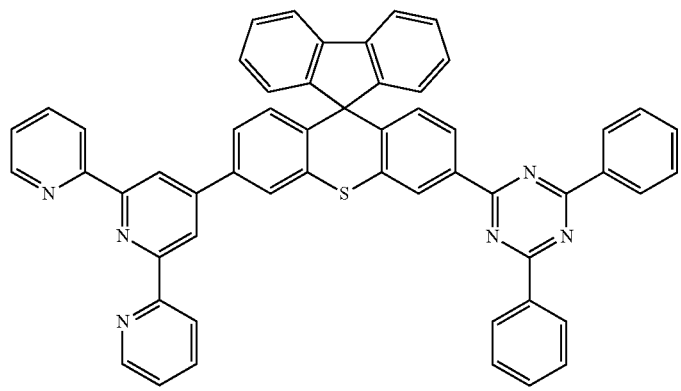

-continued
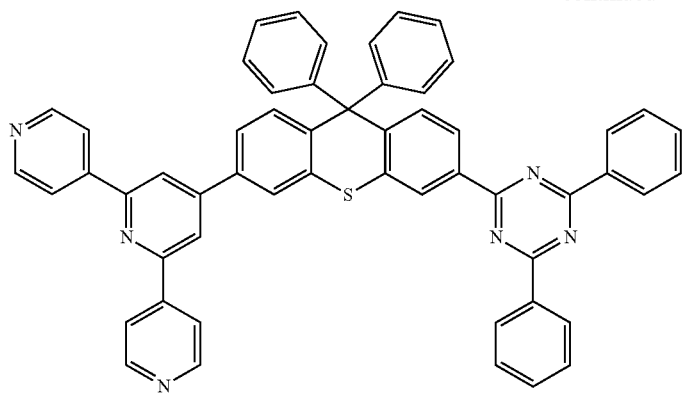
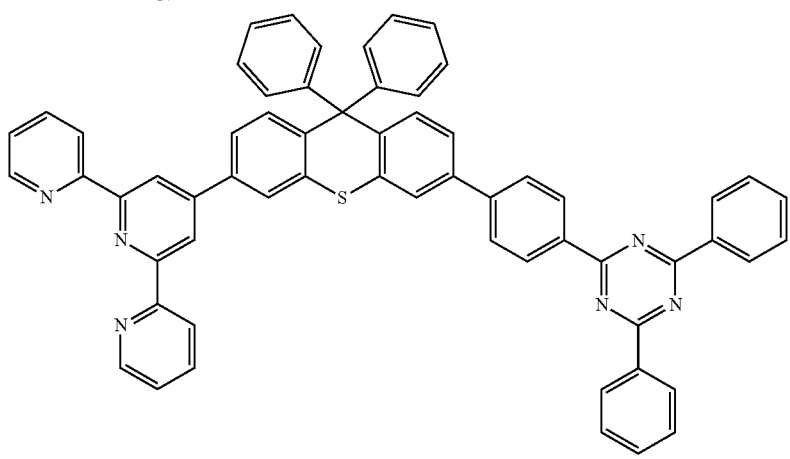
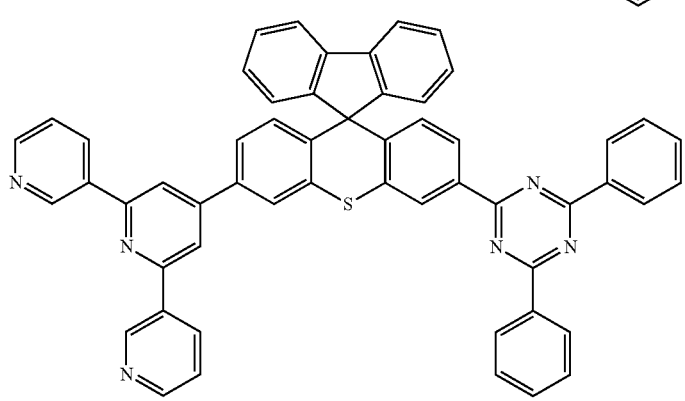
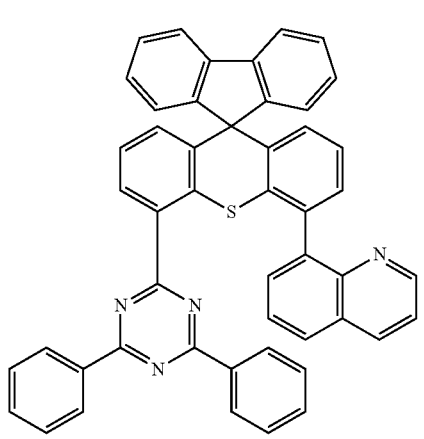
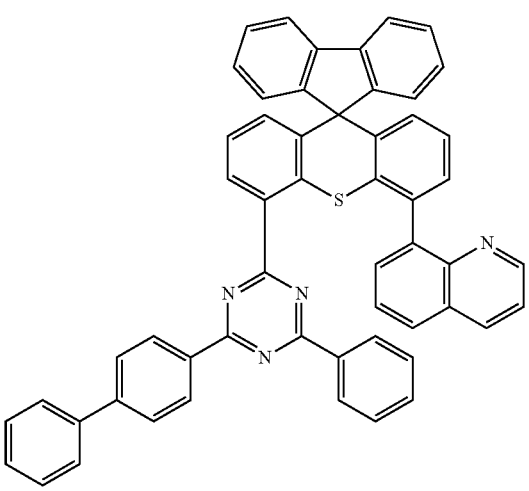

271
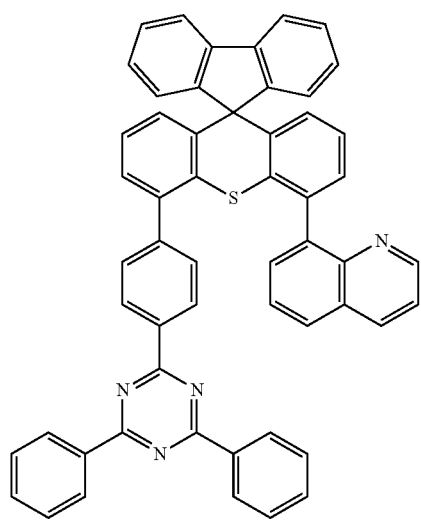
-continued
272
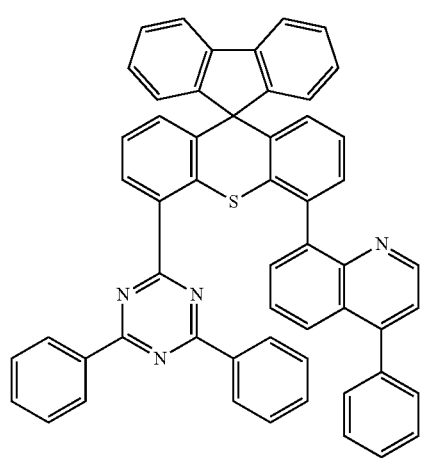
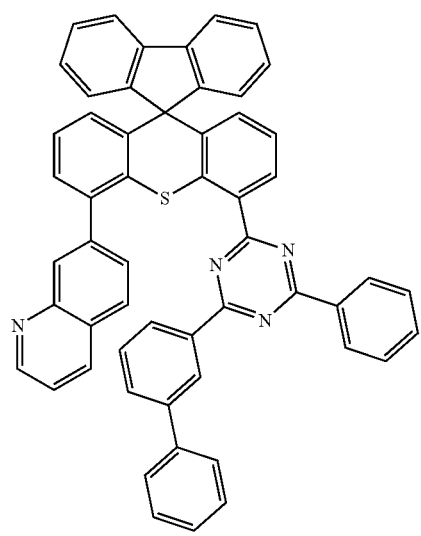
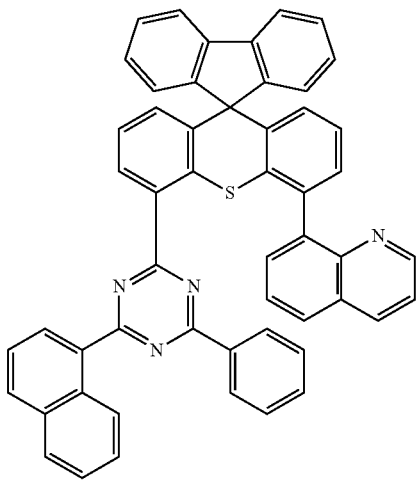
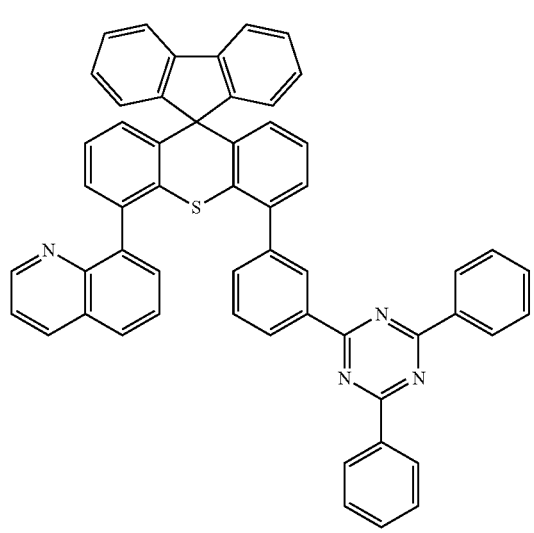
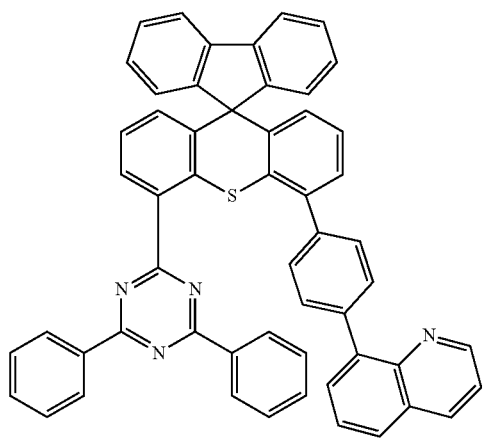

-continued
273
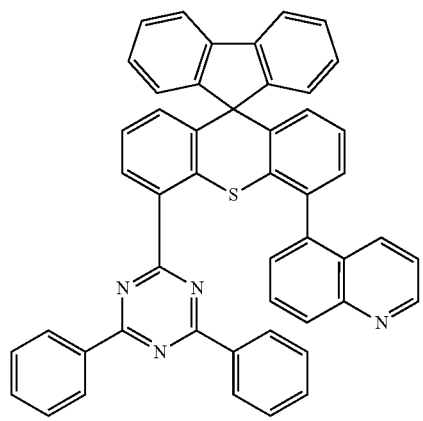
274
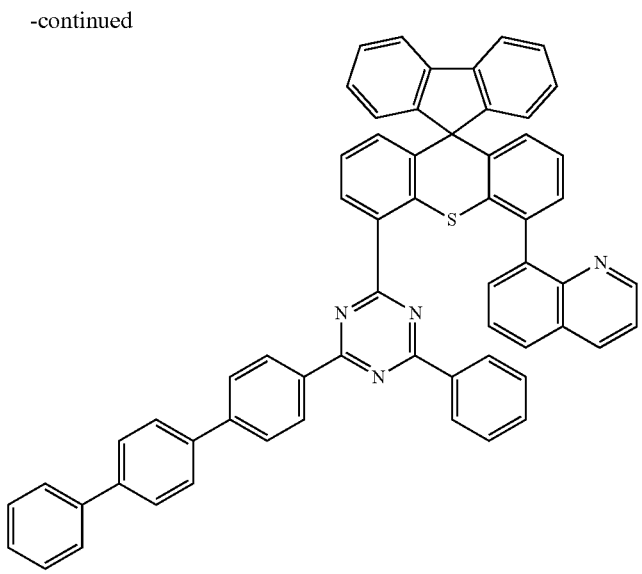
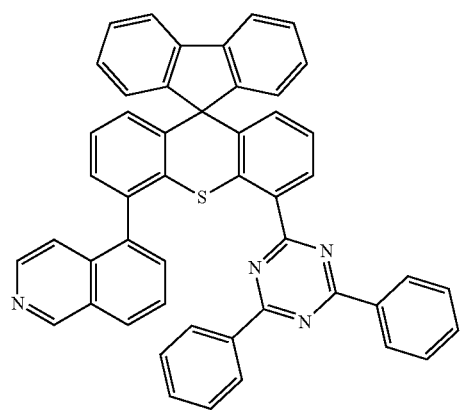
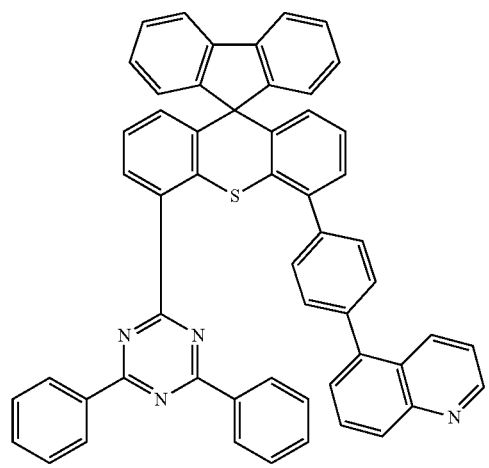
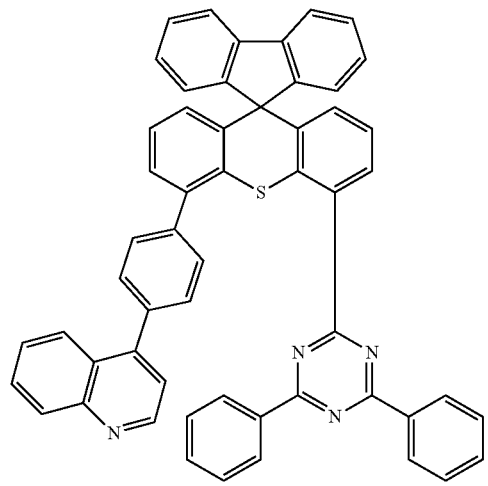
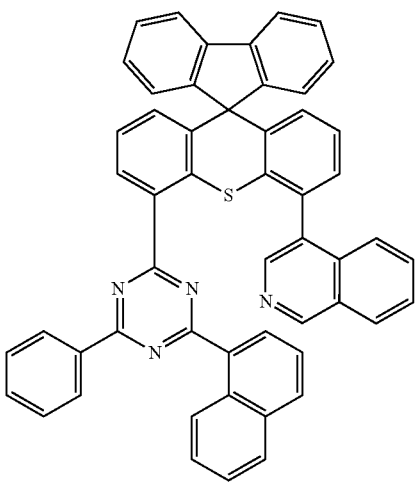

-continued
| 275 | 276 |
|---|---|
| 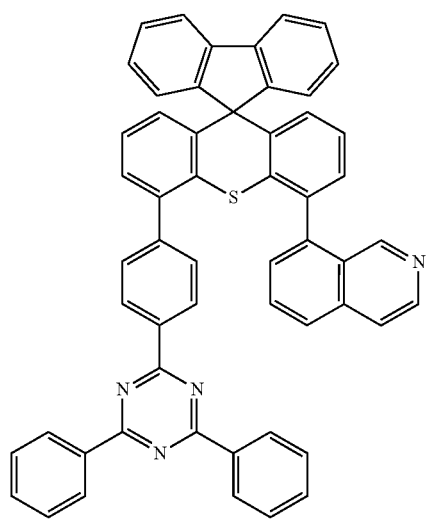 | 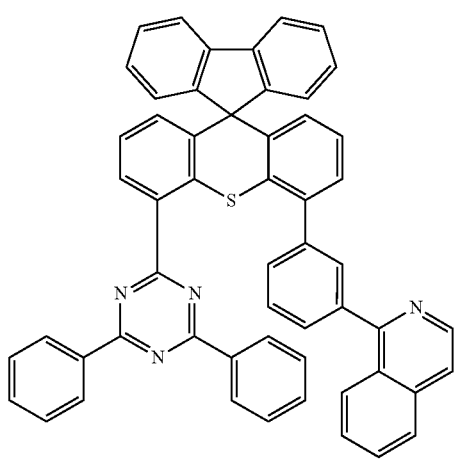 |
| 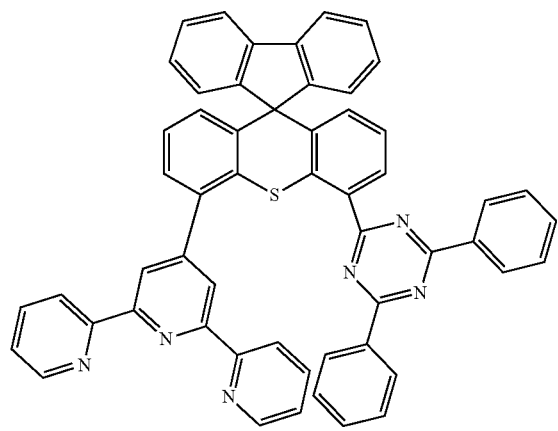 | 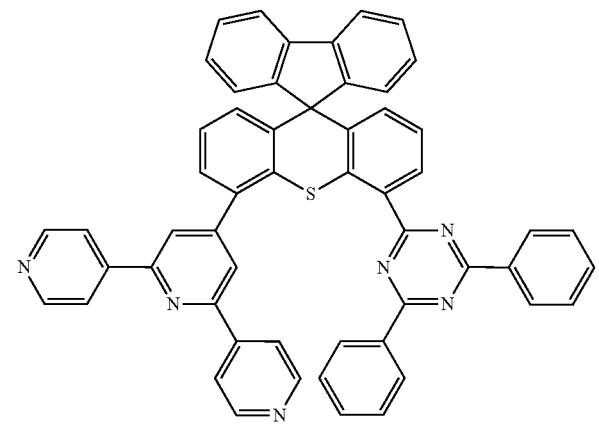 |
| 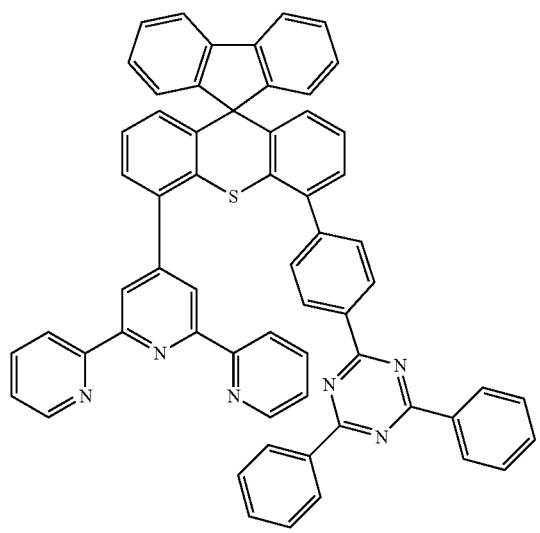 | 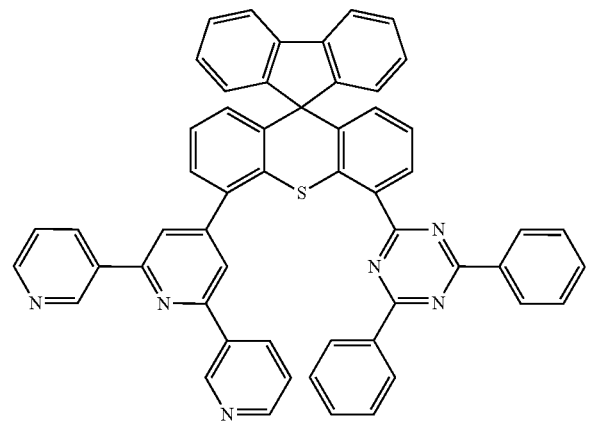 |

-continued
277
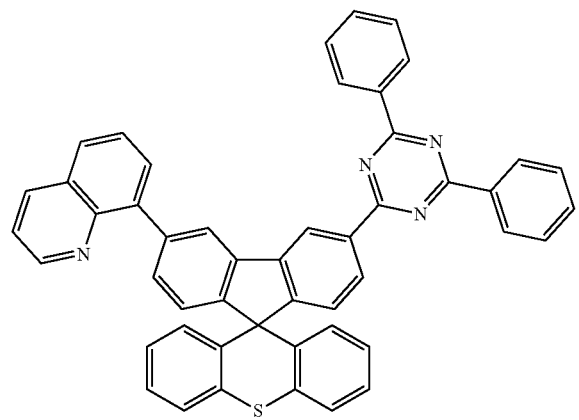
278
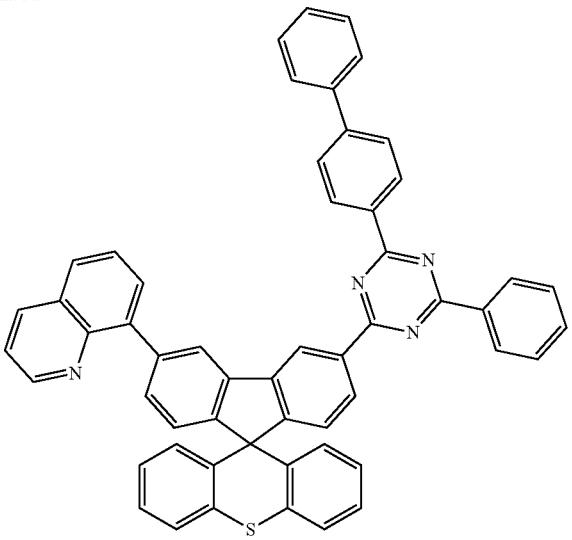
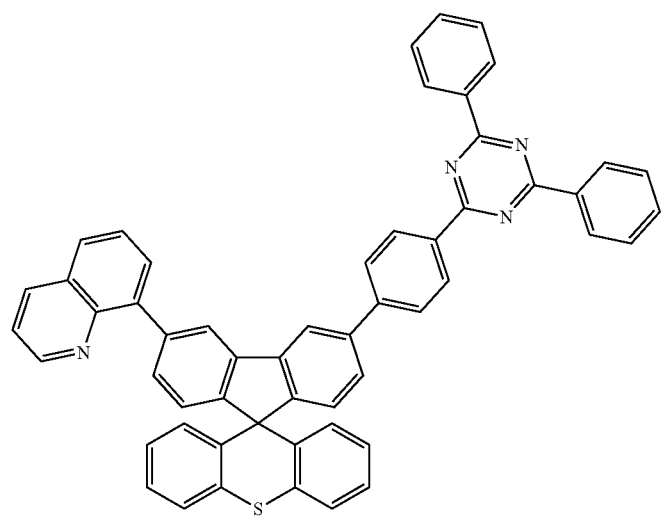
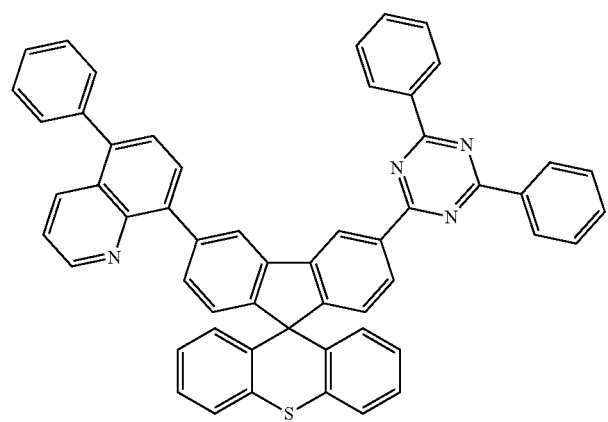

279 280
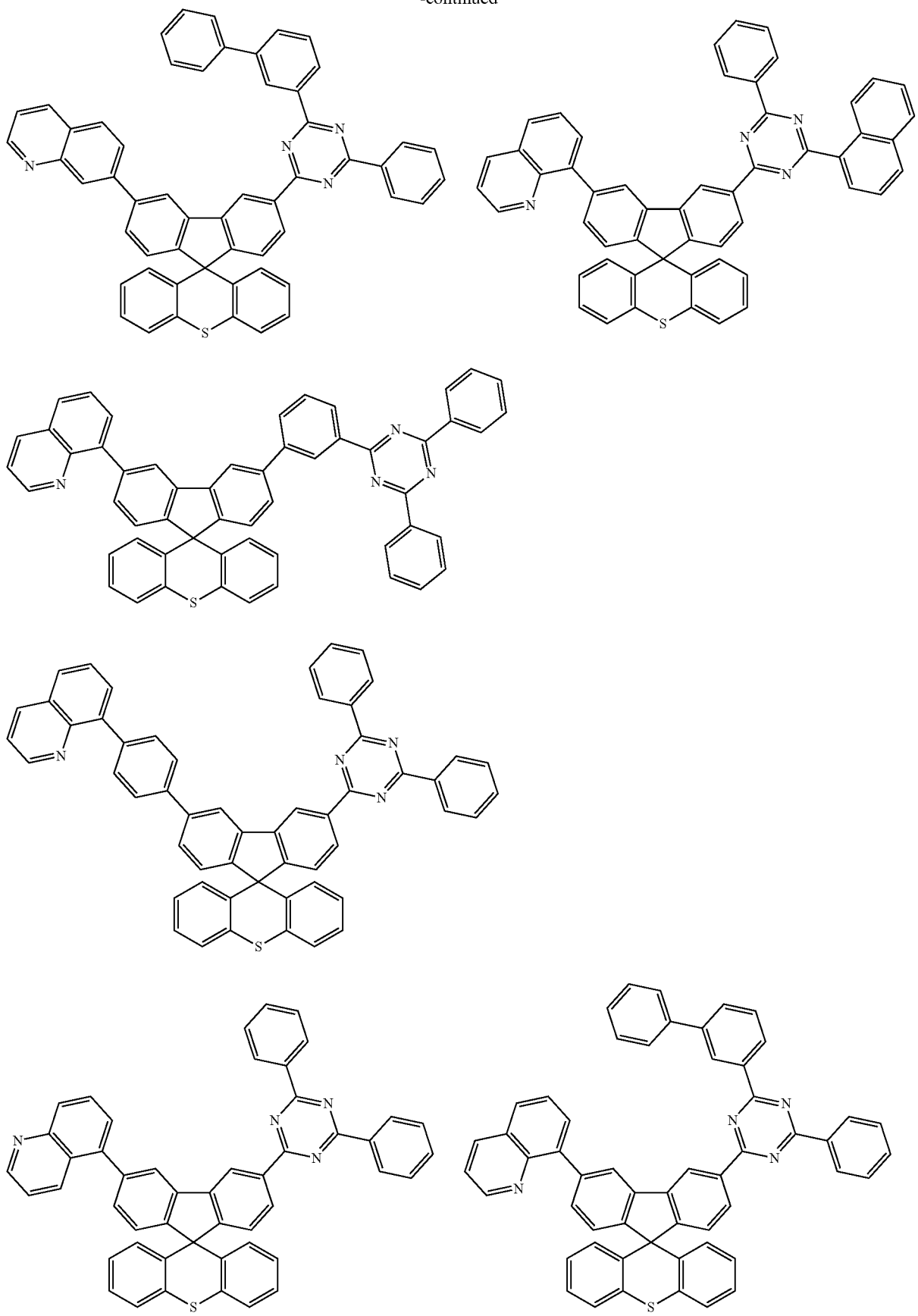

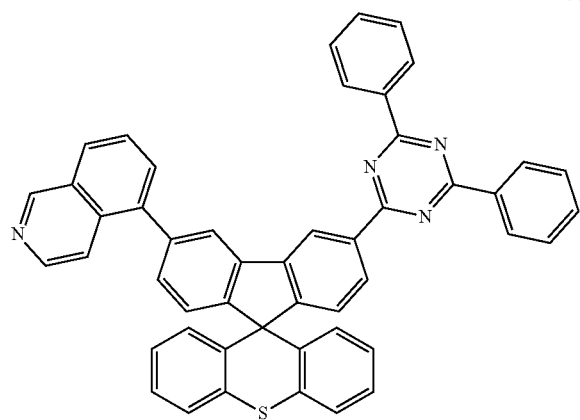
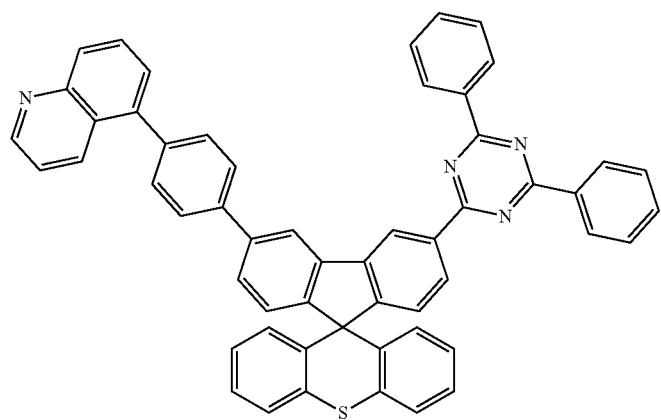
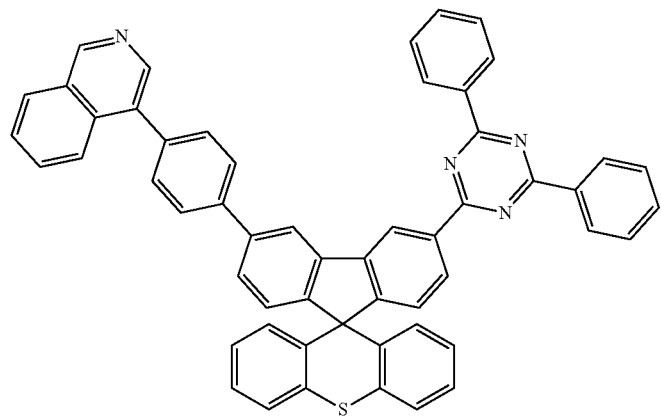
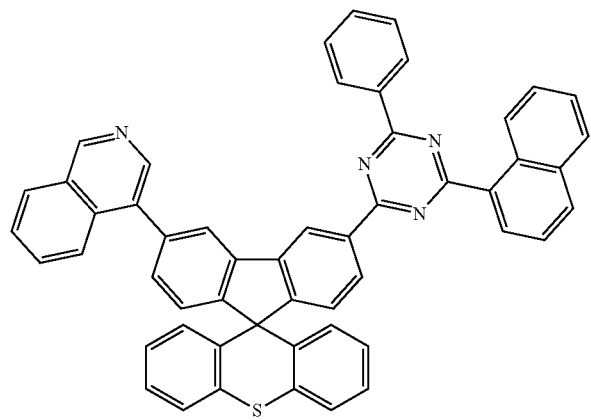

-continued
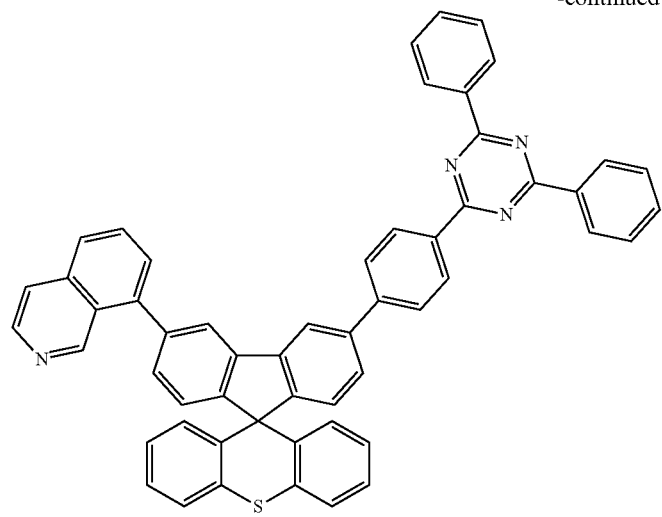
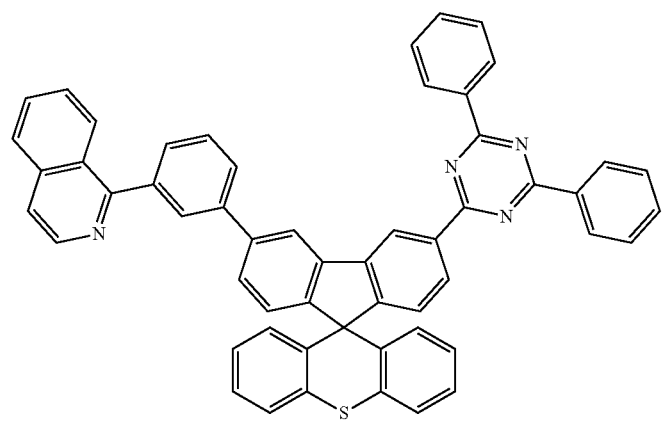
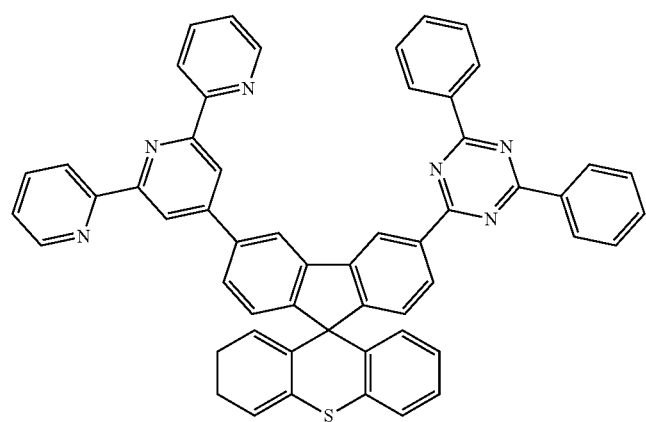

285
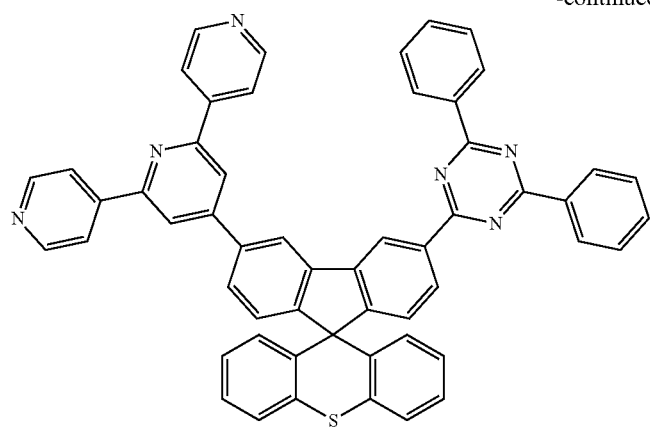
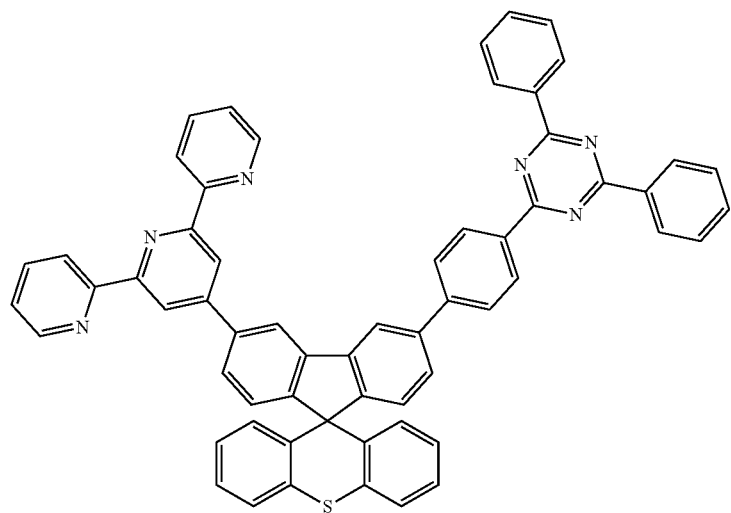
286
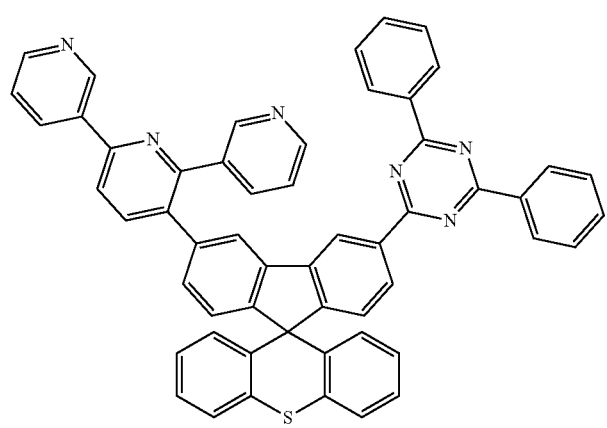
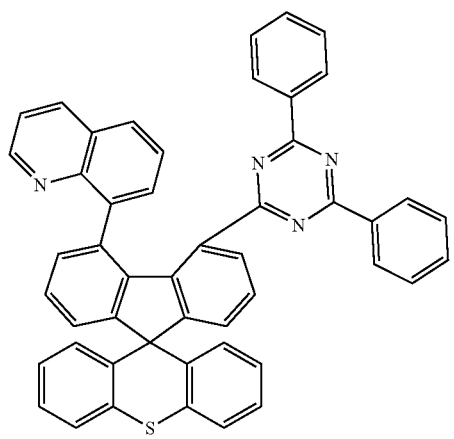

287 288
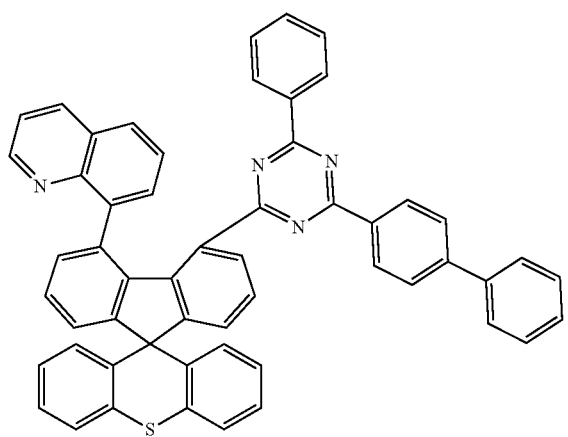
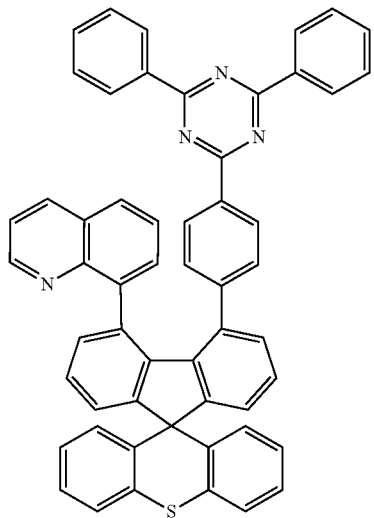
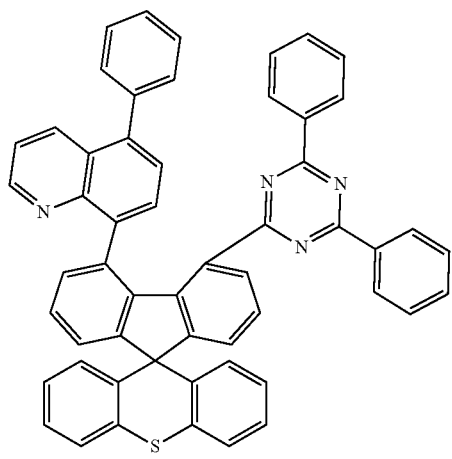
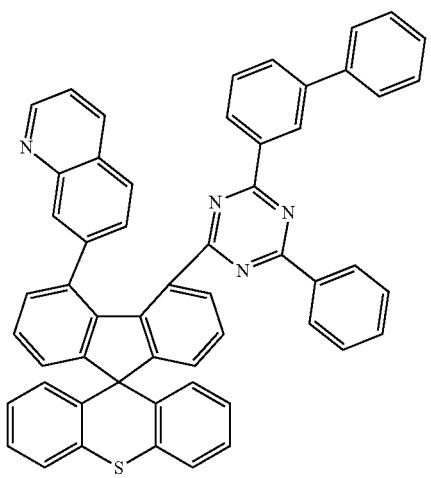
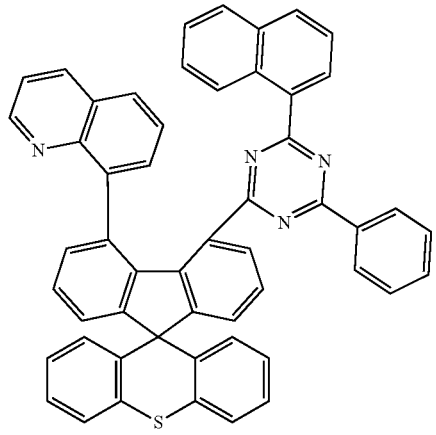
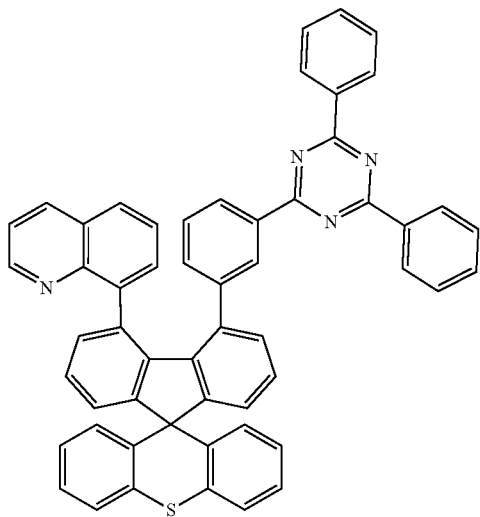

-continued
| 289 | 290 |
|---|---|
| 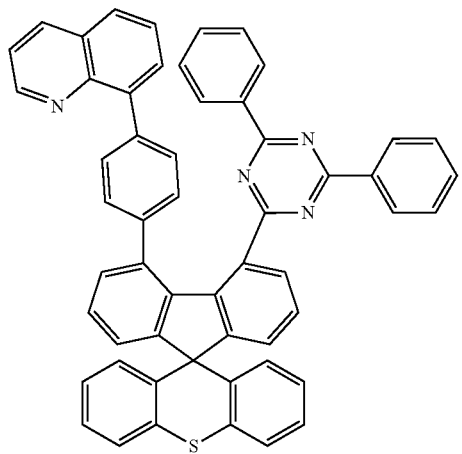 | 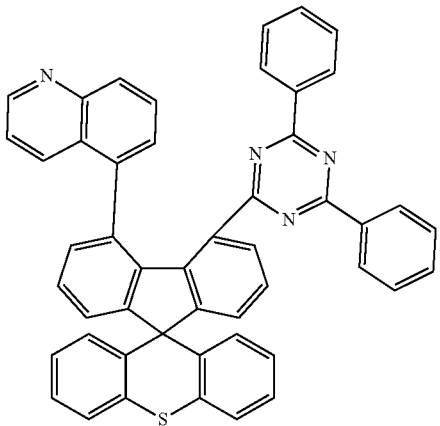 |
| 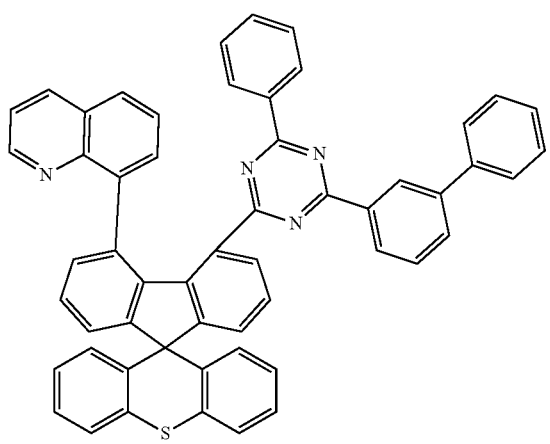 | 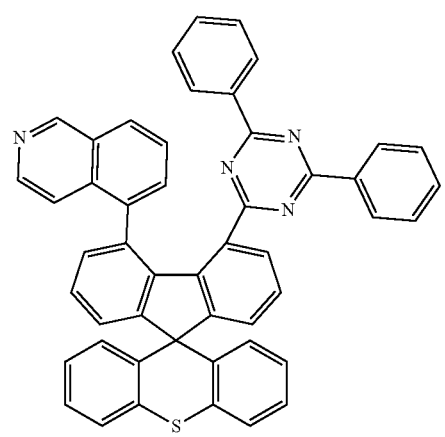 |
| 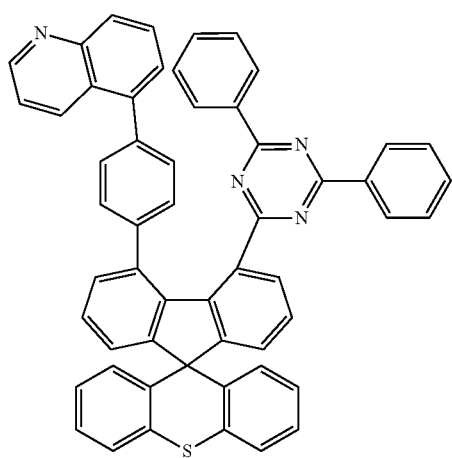 | 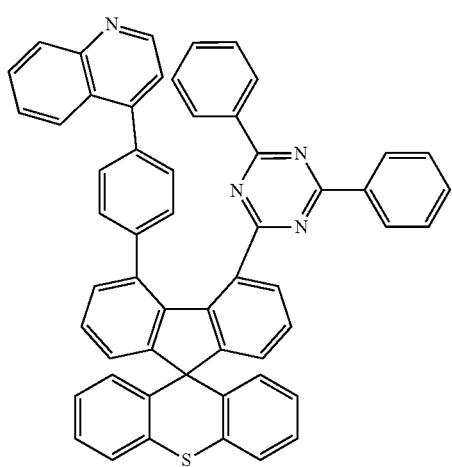 |

291
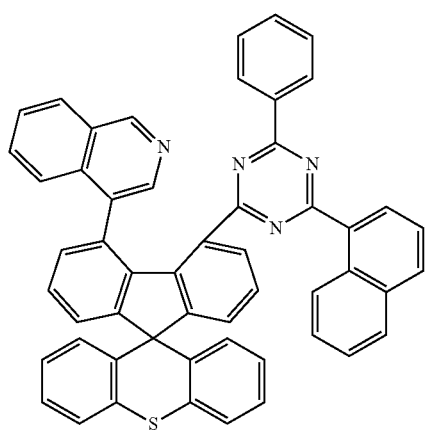
292
-continued
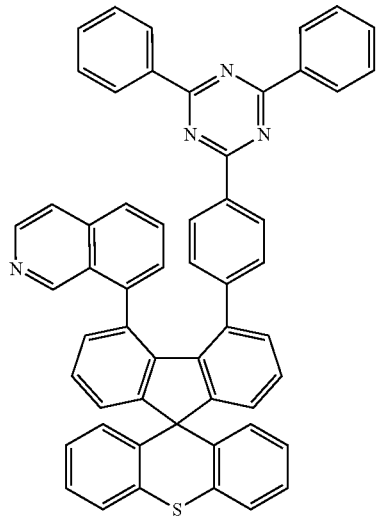
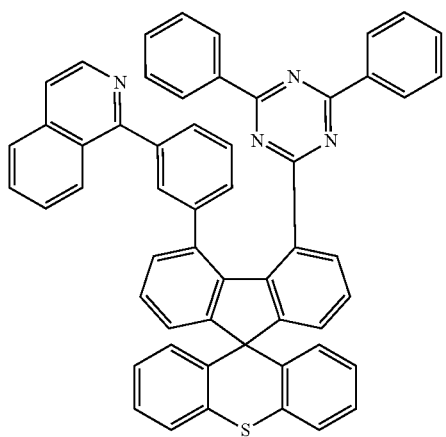
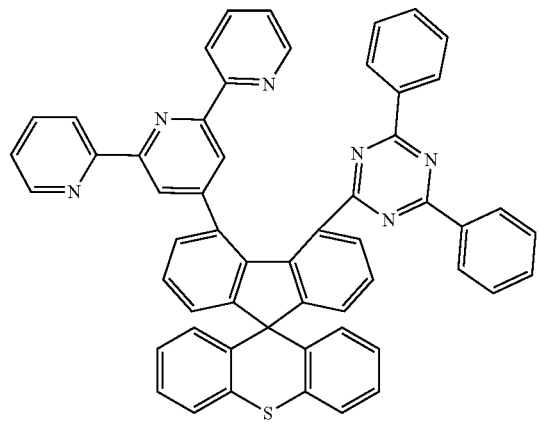
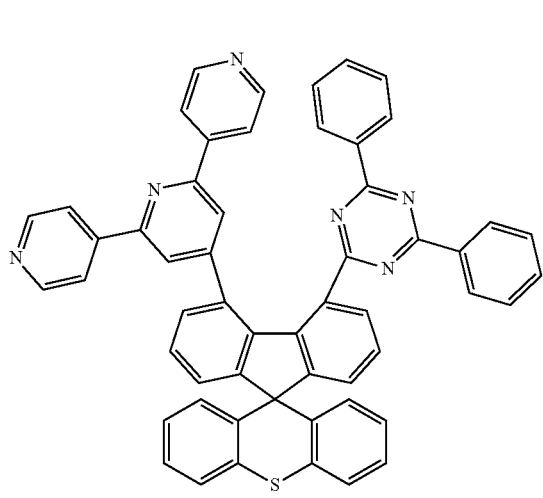
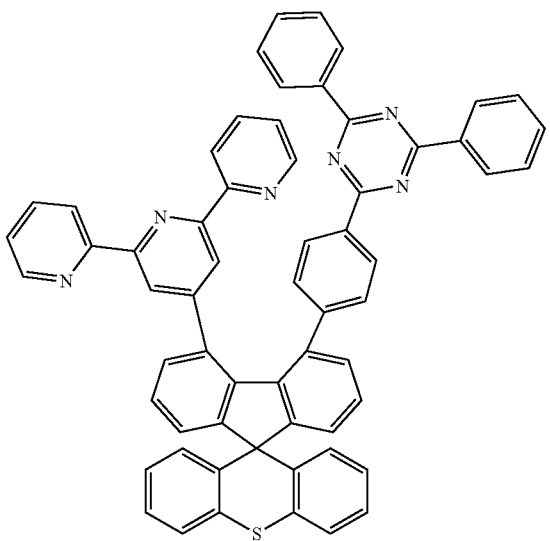

-continued
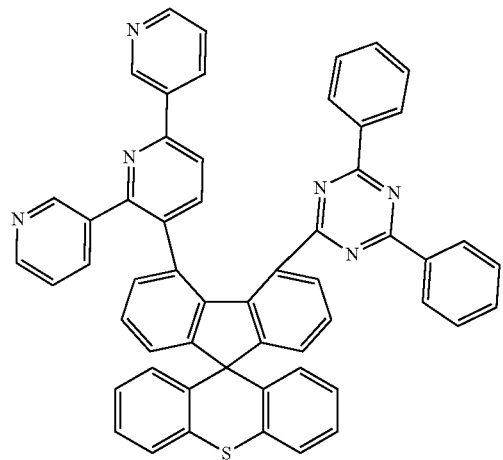
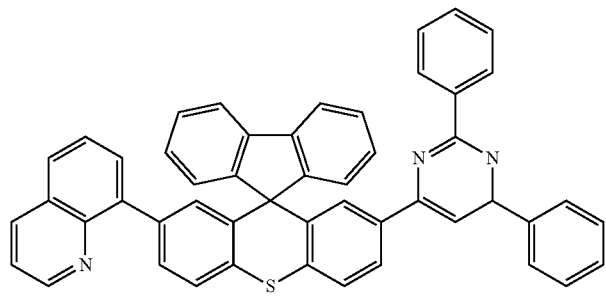
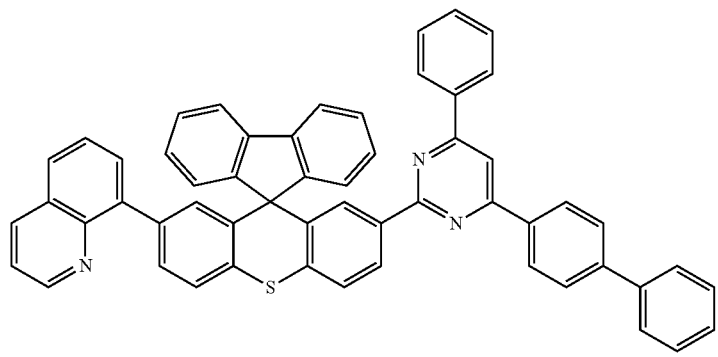
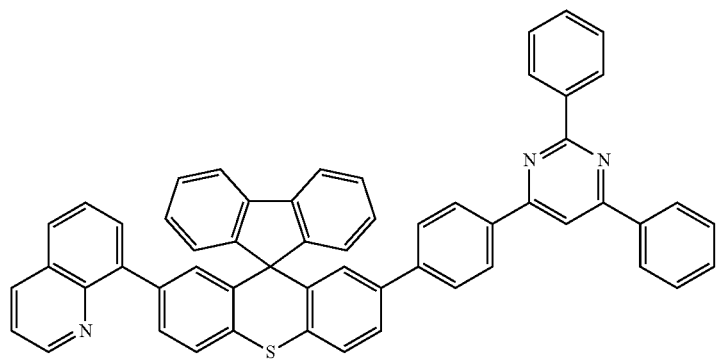

-continued
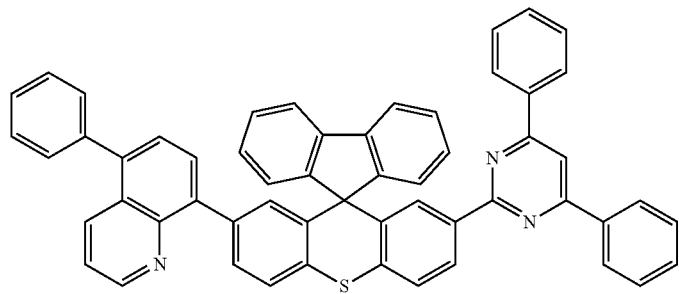
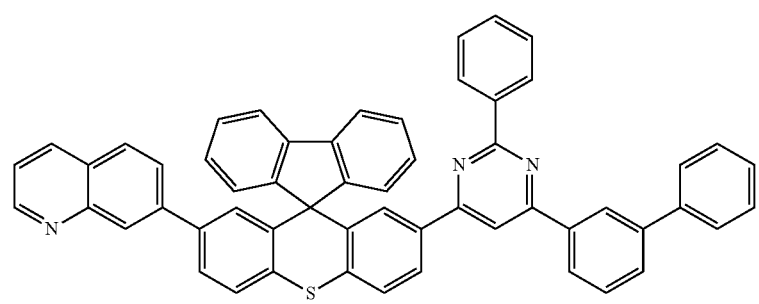
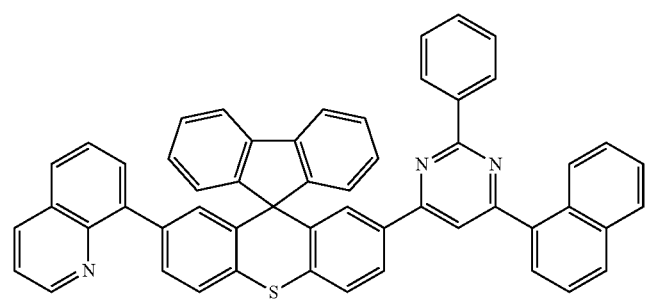
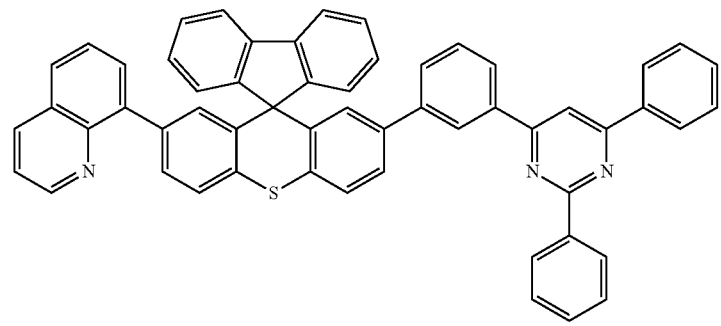
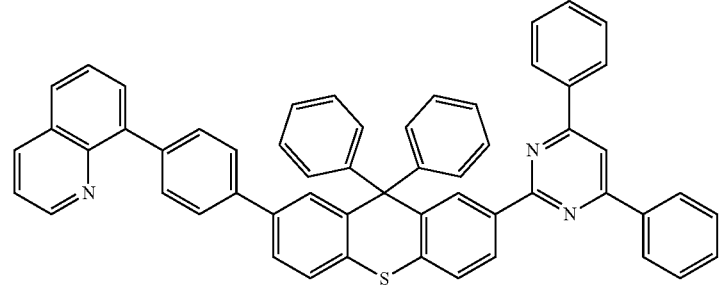

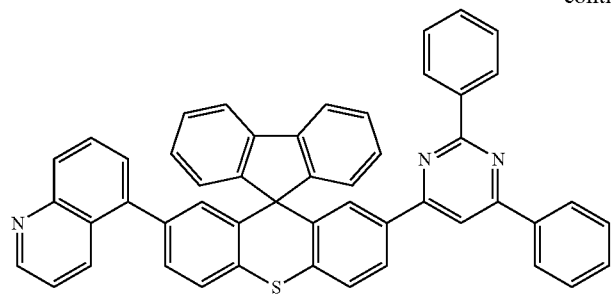
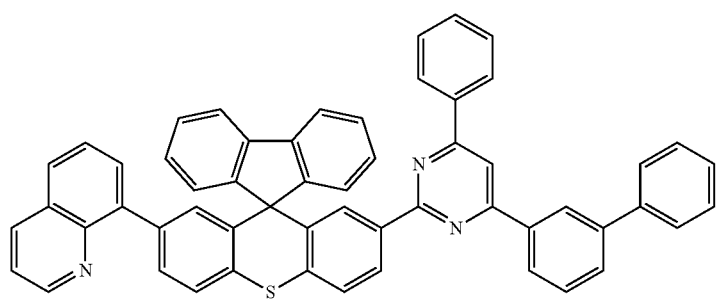
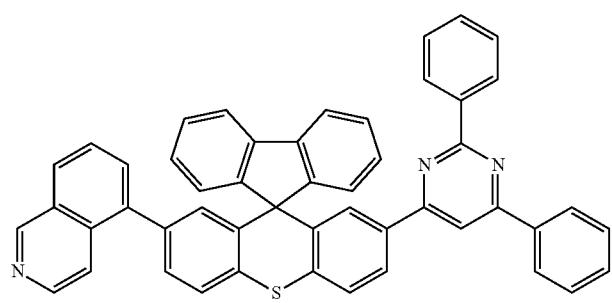
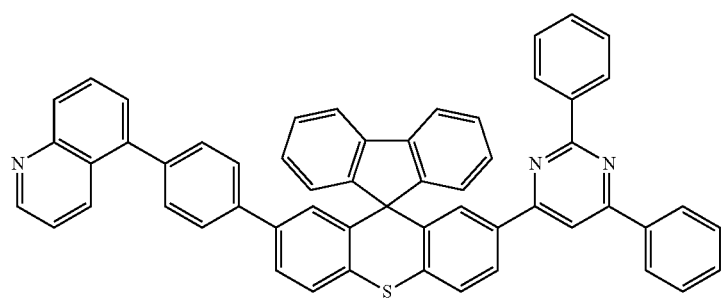
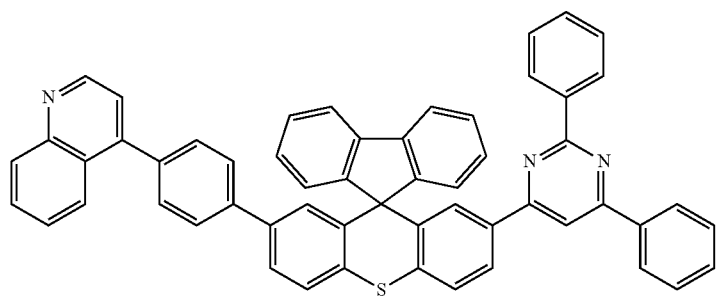

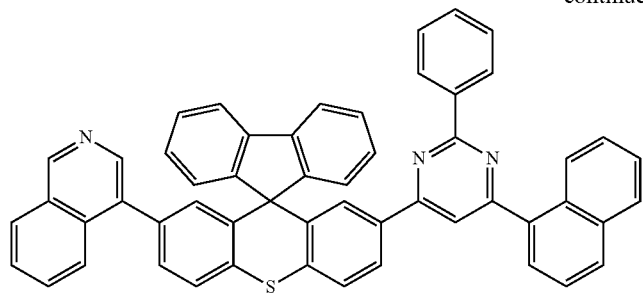
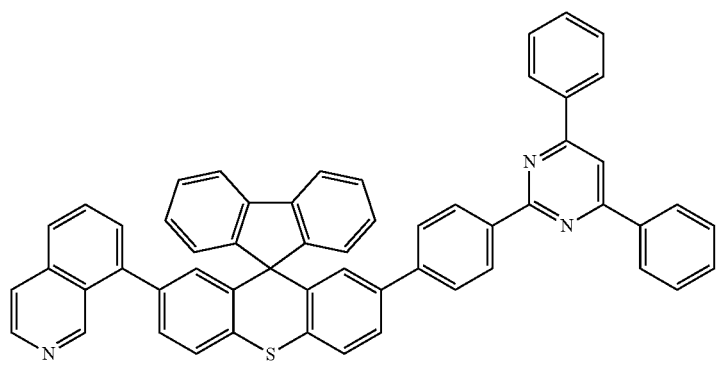
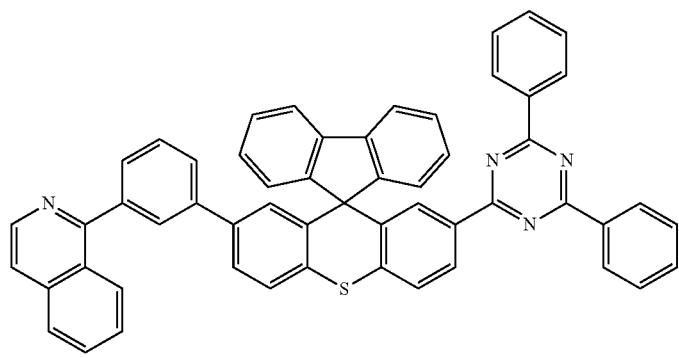
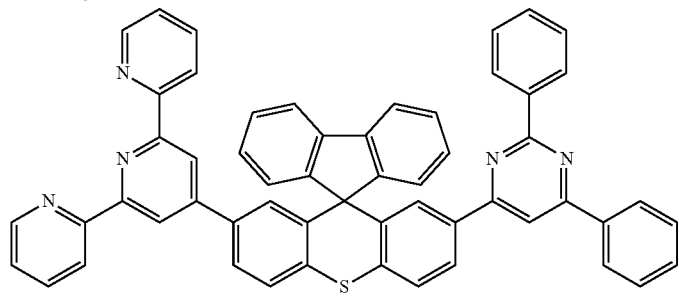
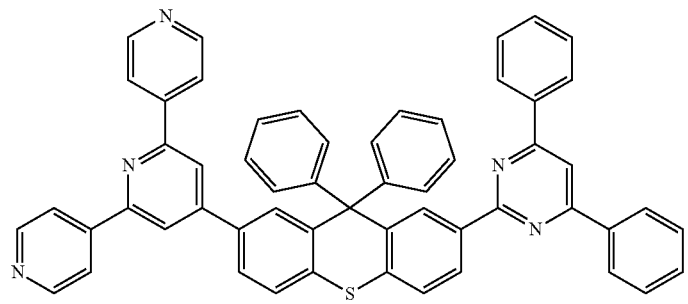

-continued
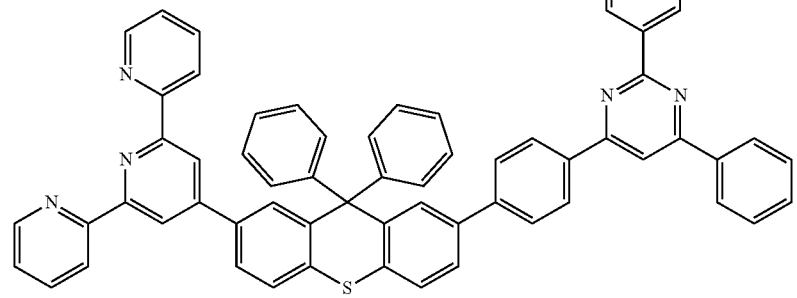
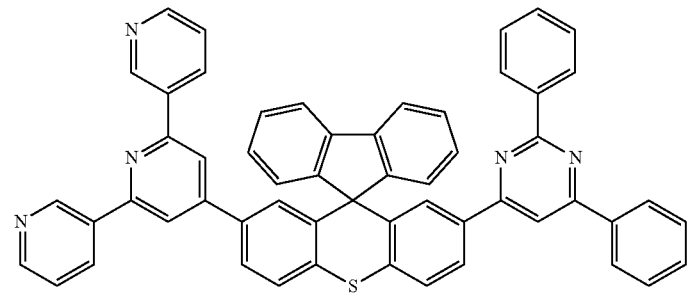
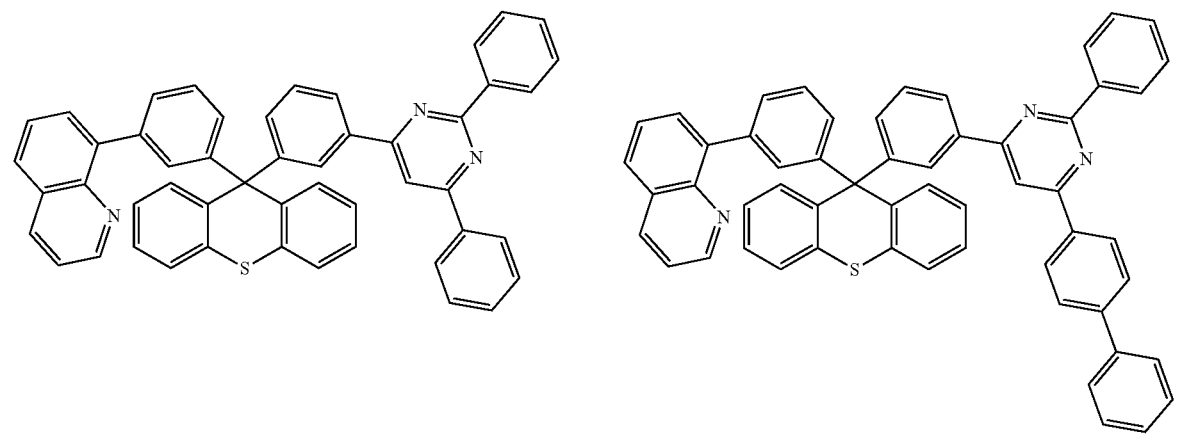
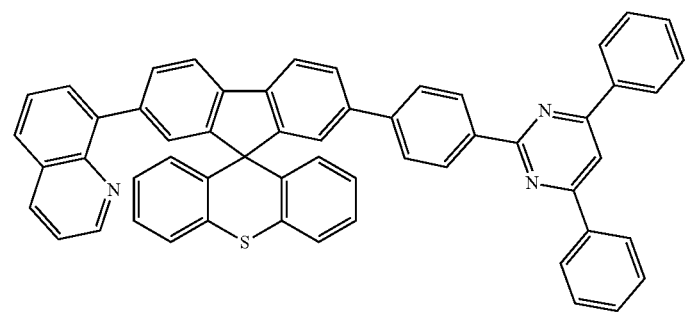
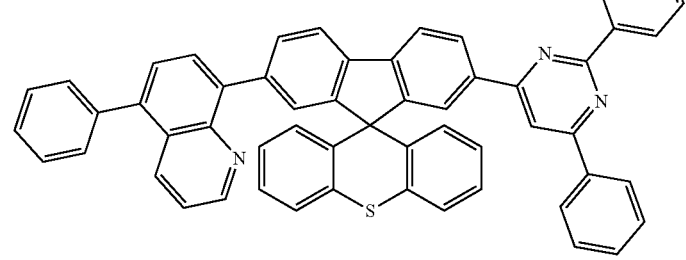

-continued
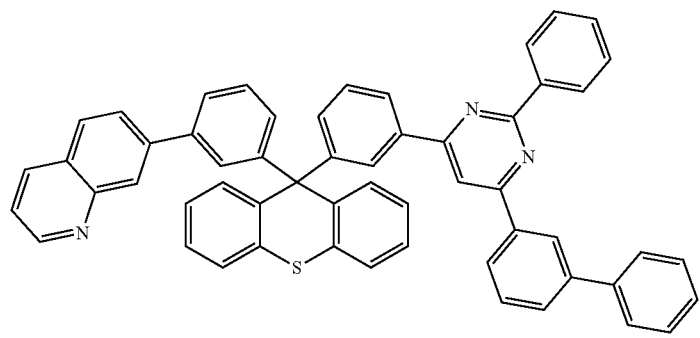
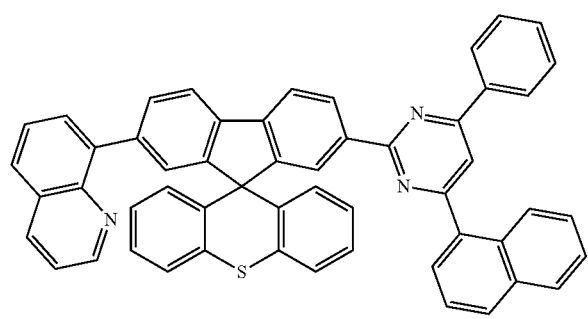
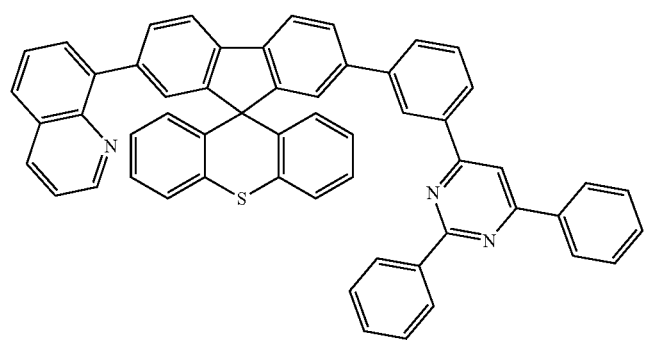
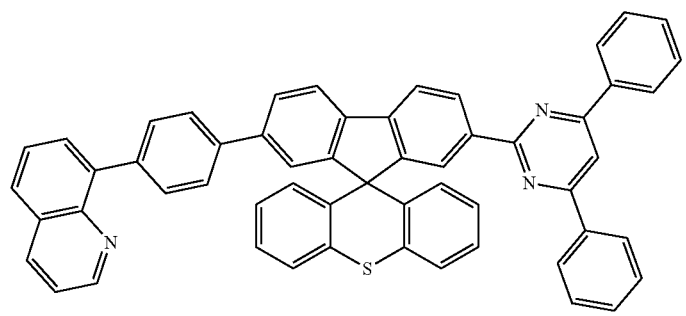
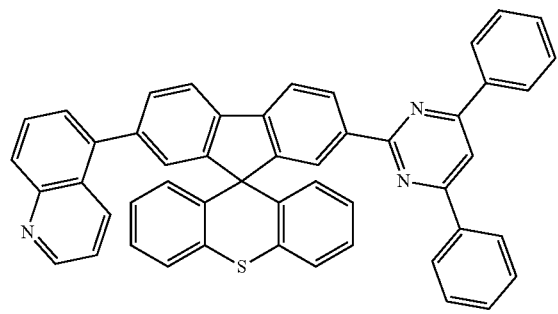

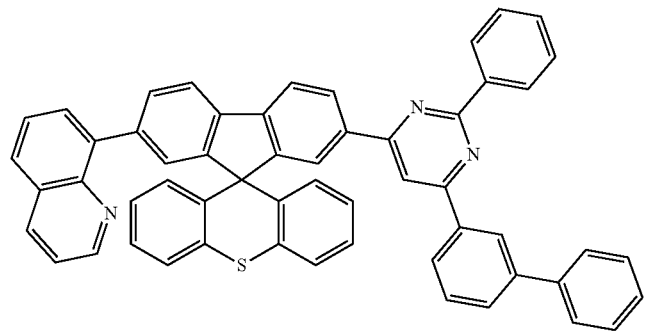
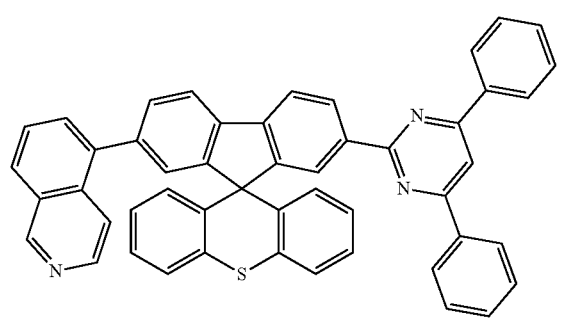
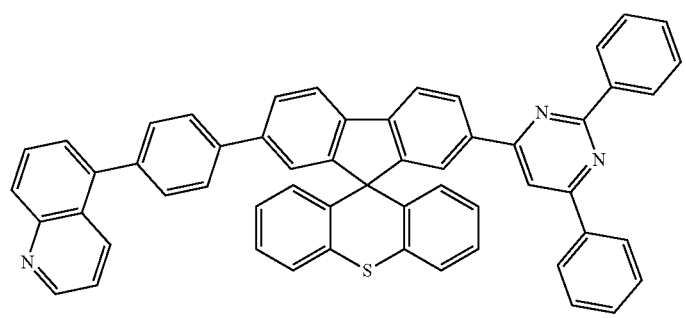
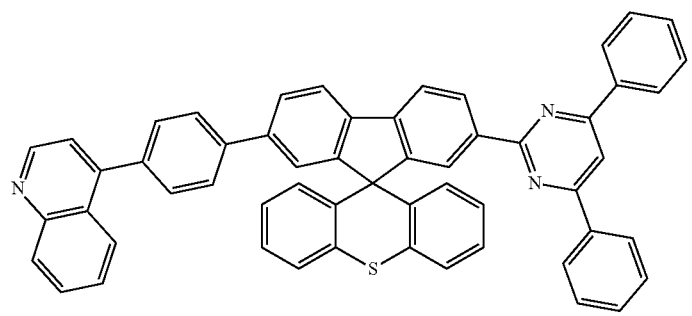
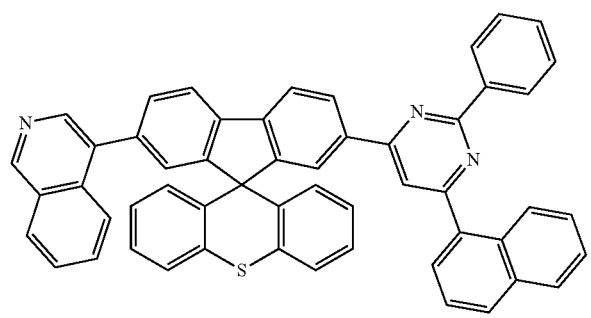

-continued
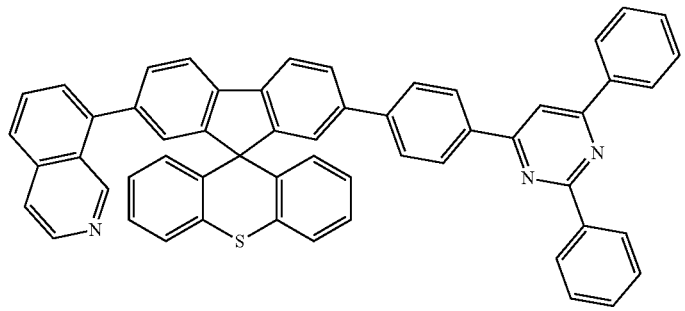
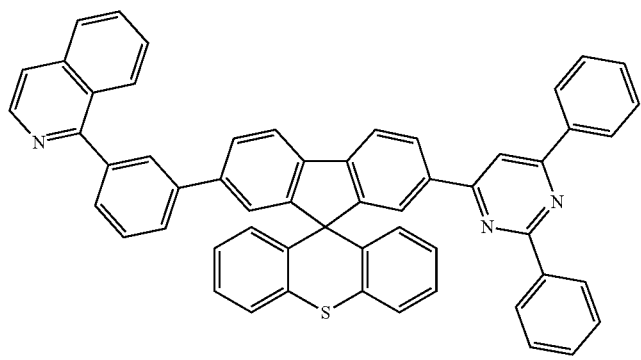
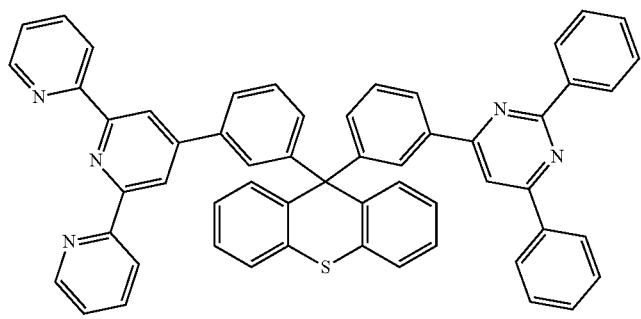
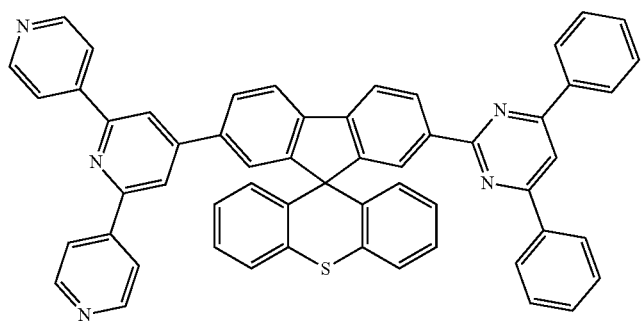
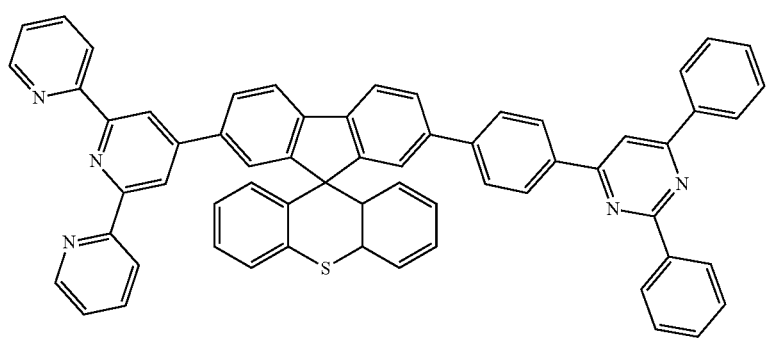

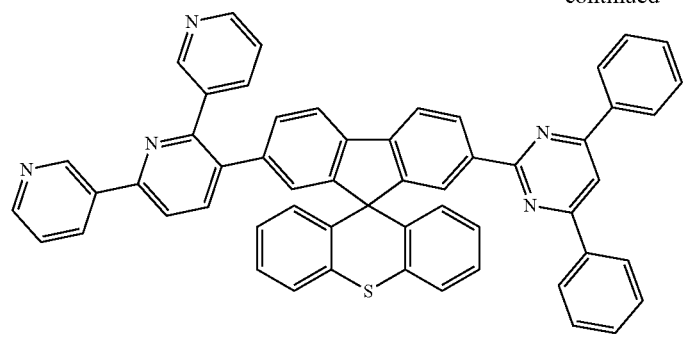
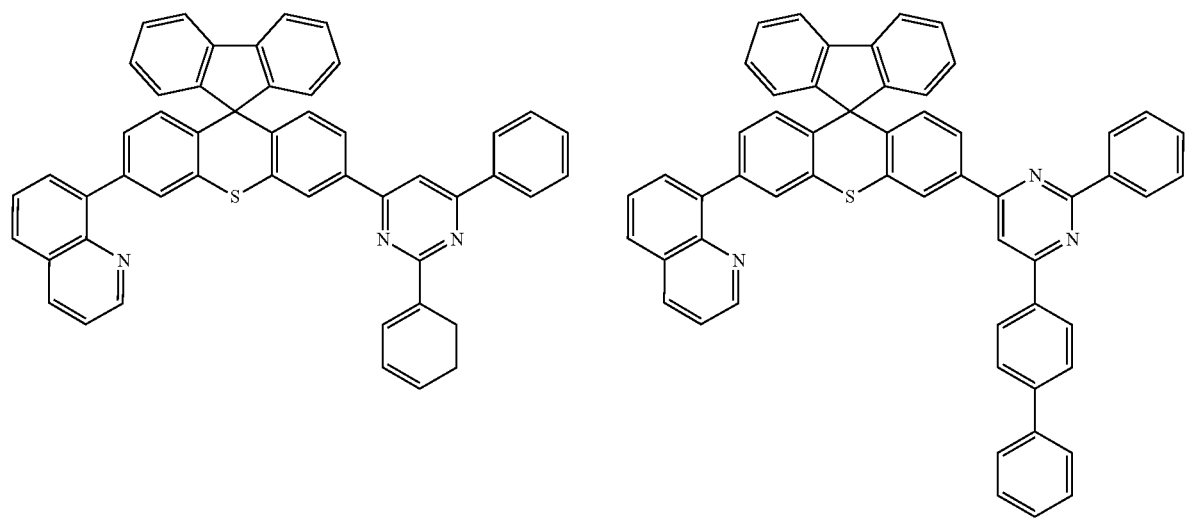
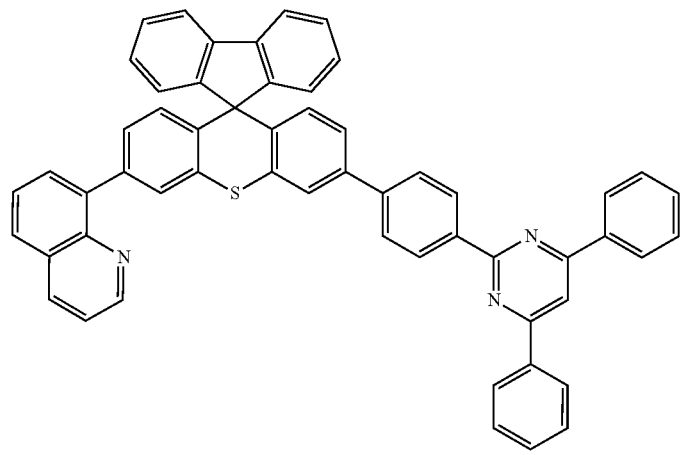
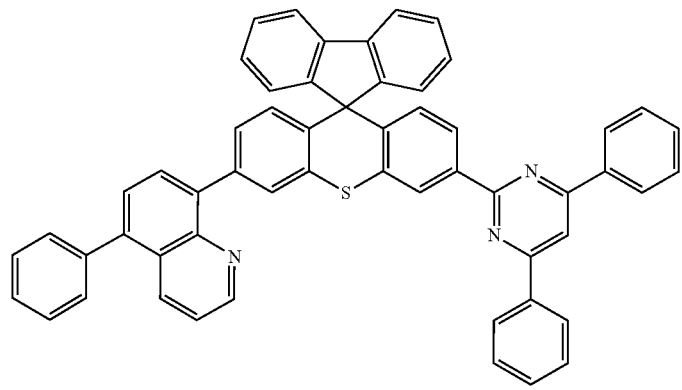

311
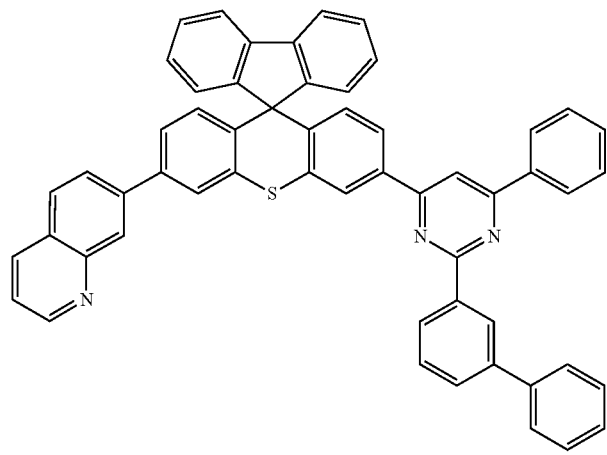
312
-continued
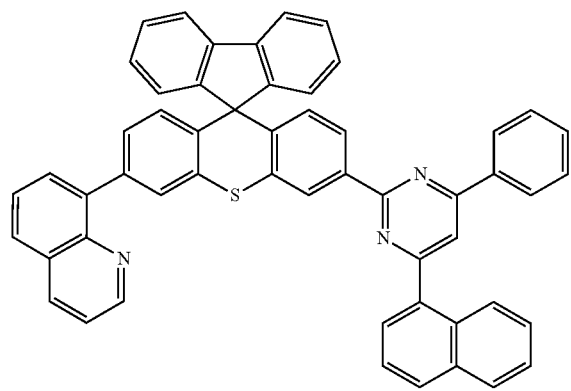
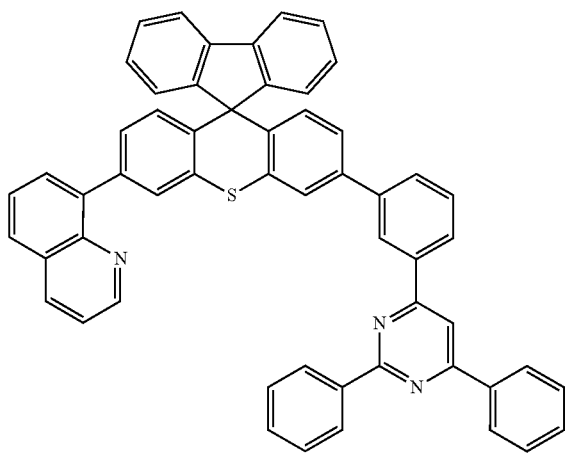
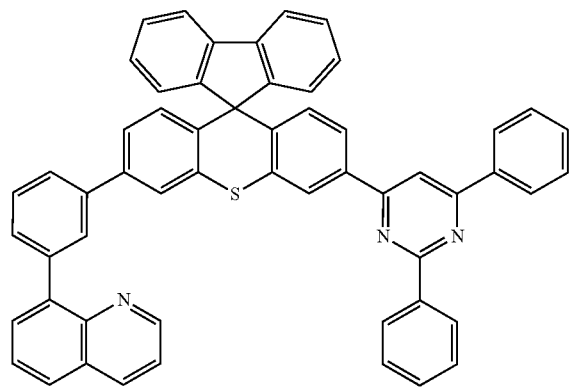
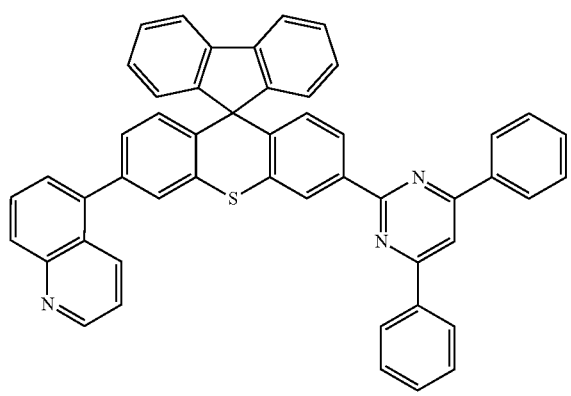

-continued
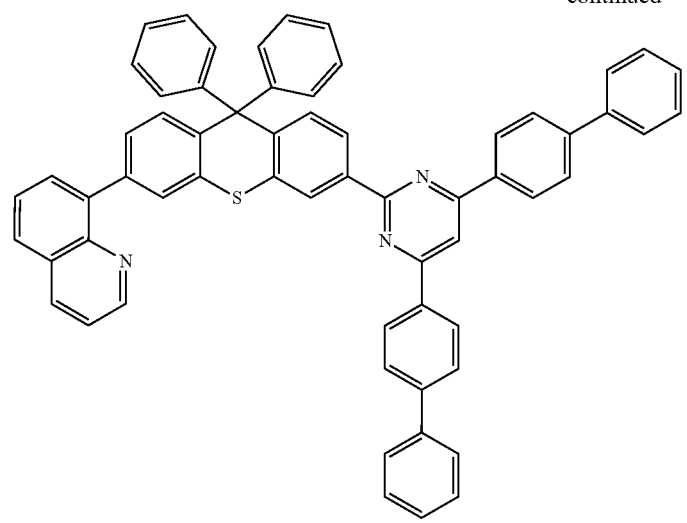
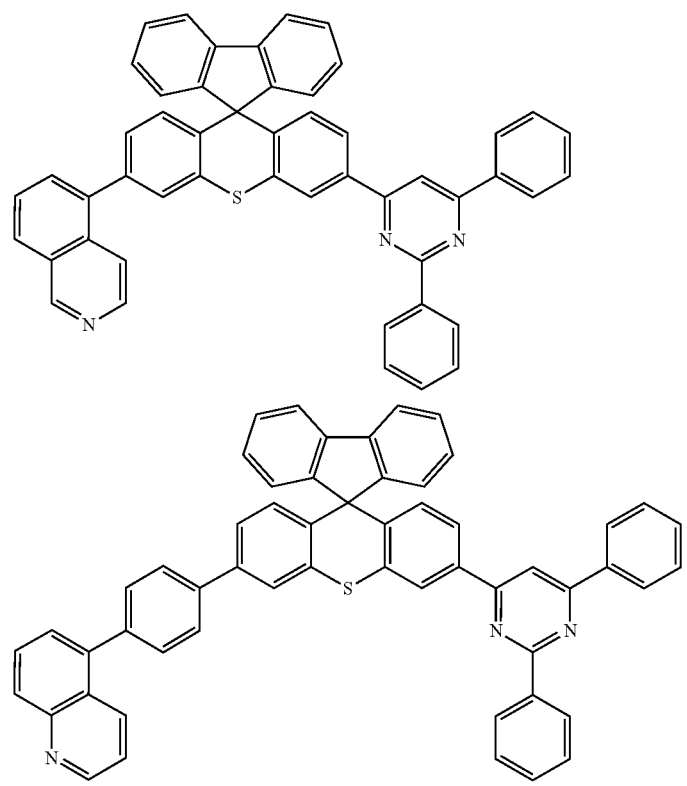
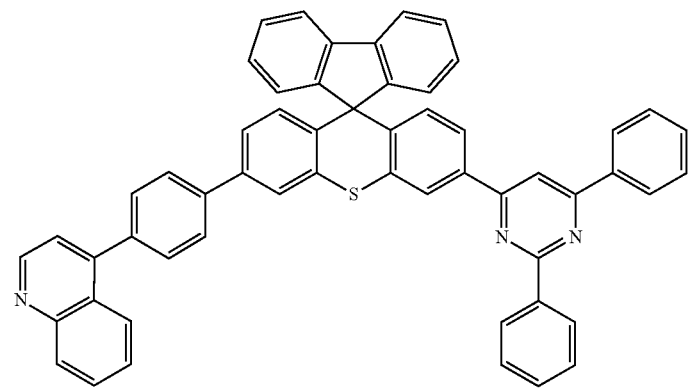

315
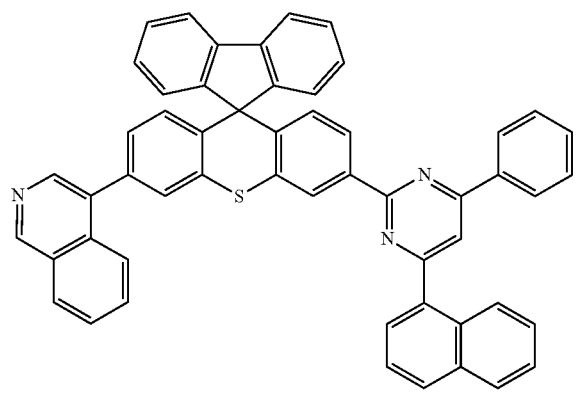
316
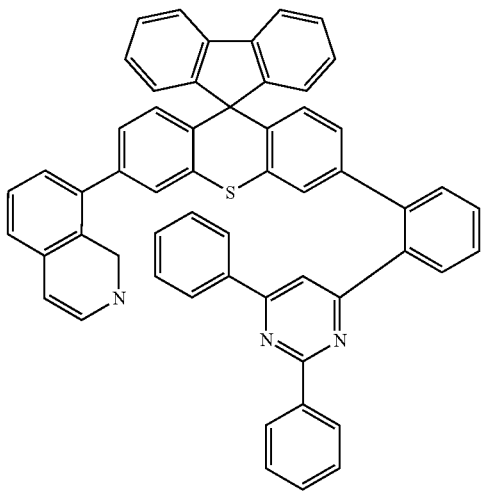
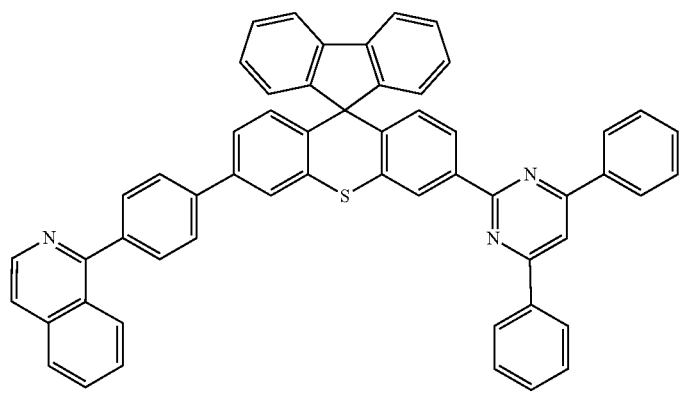
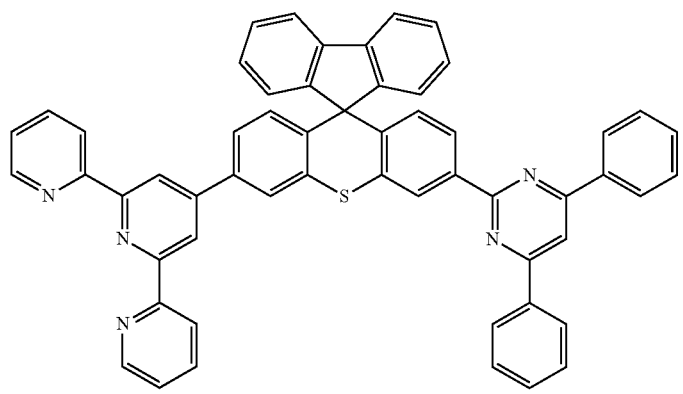
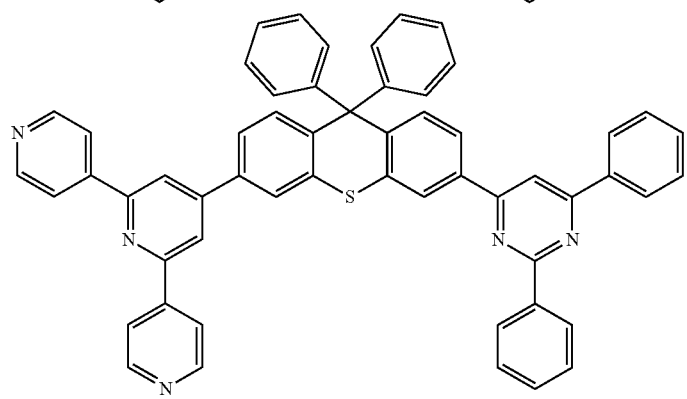

317
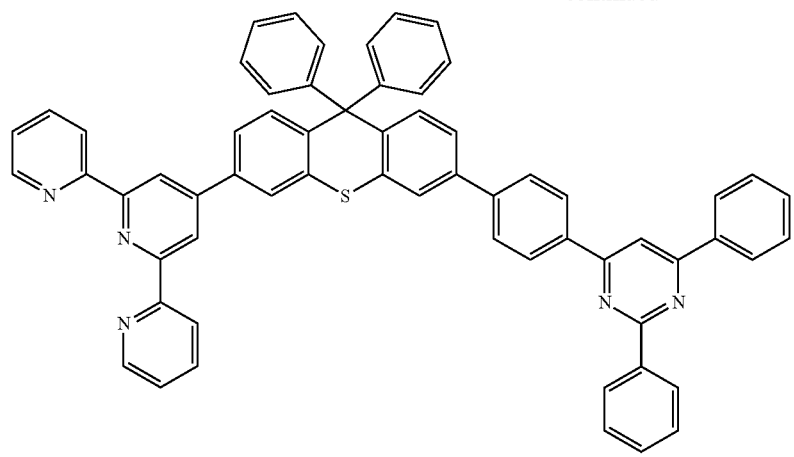
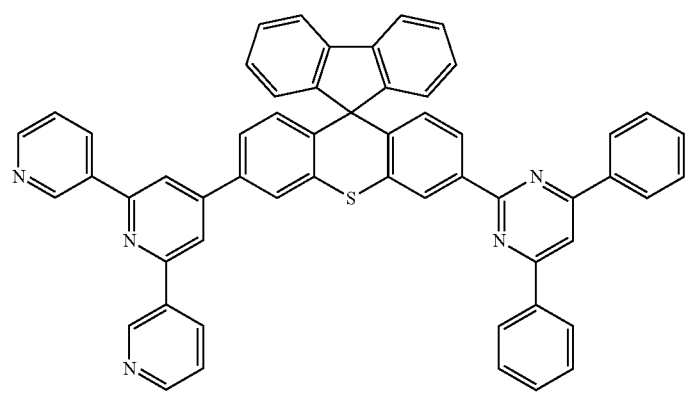
318
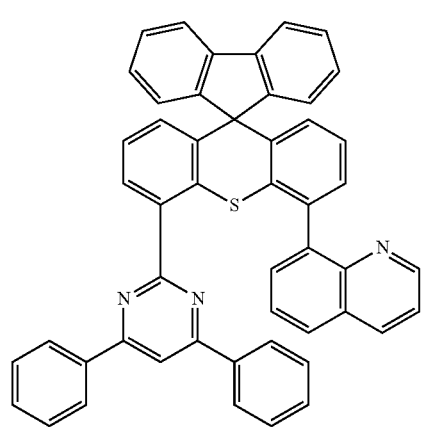
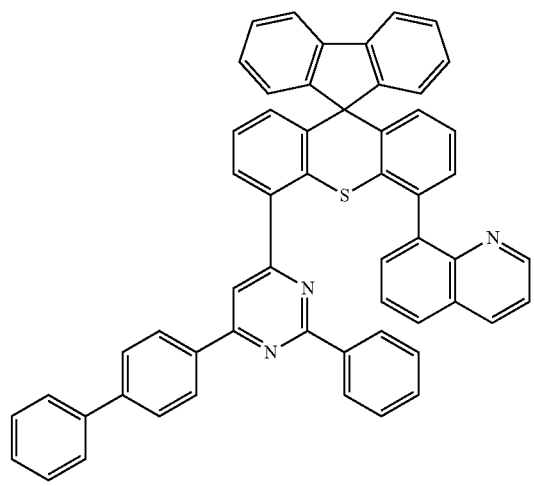

-continued
319
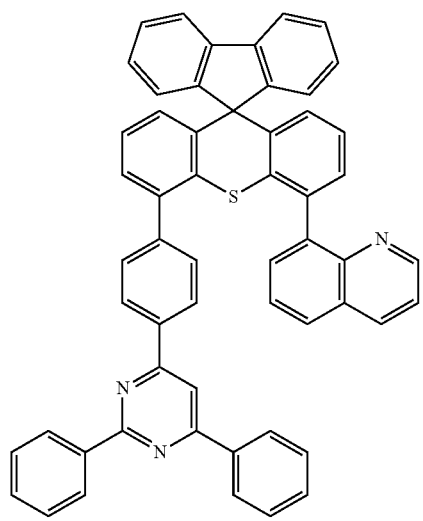
320
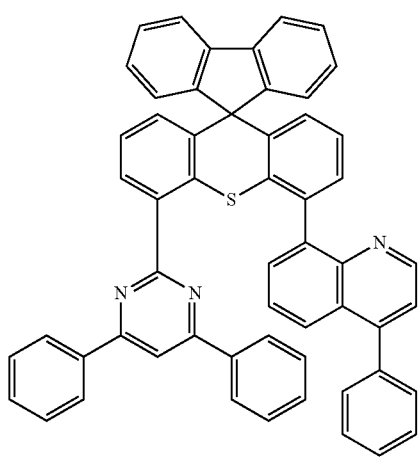
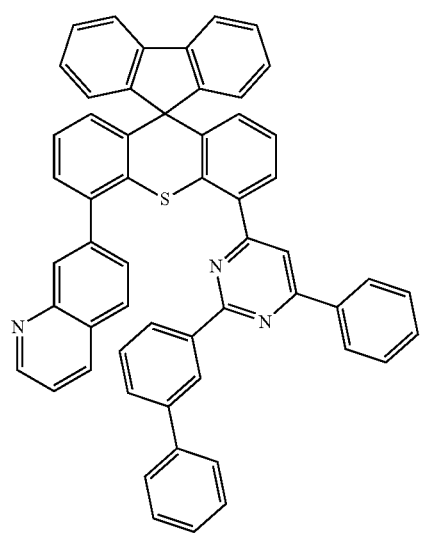
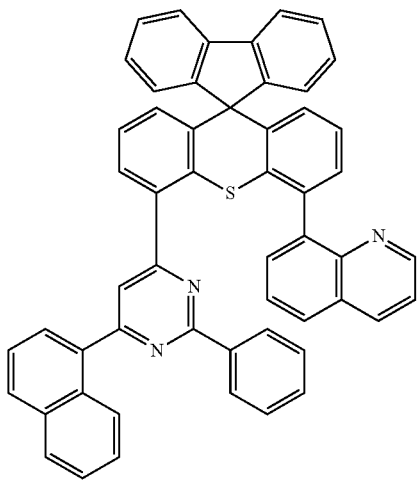
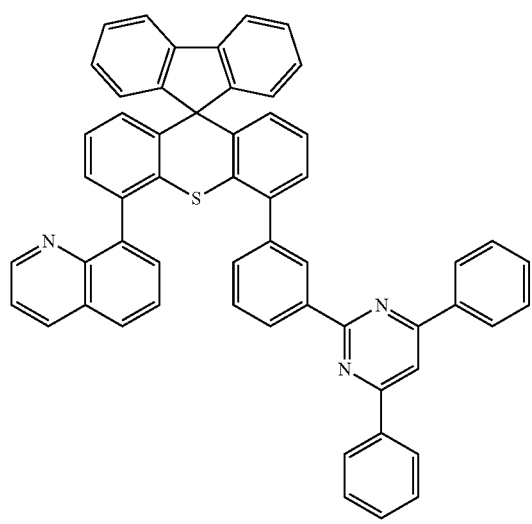
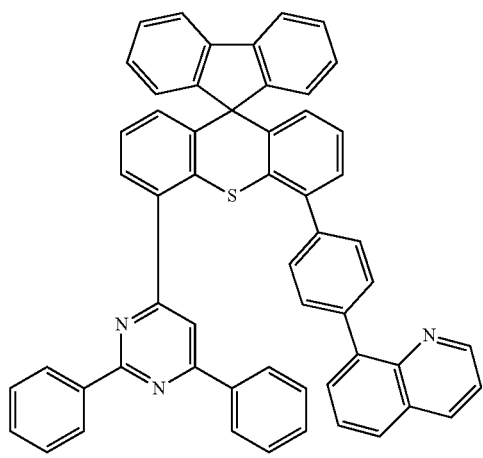

-continued
321
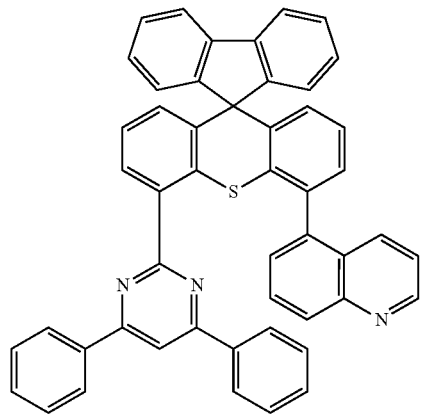
322
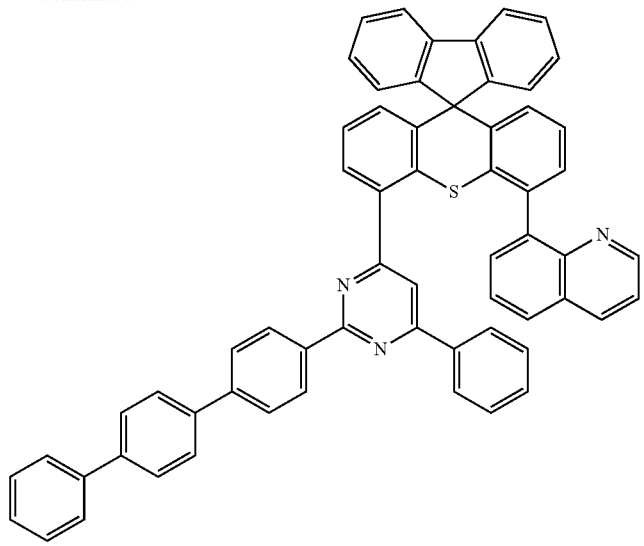
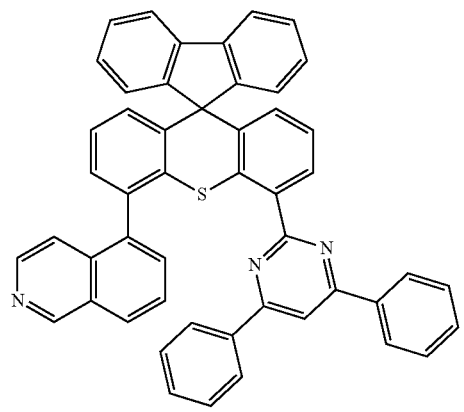
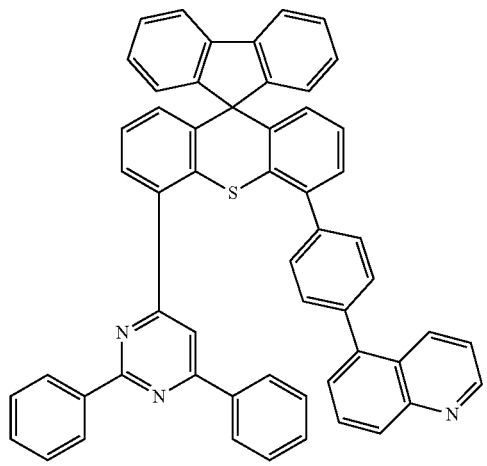
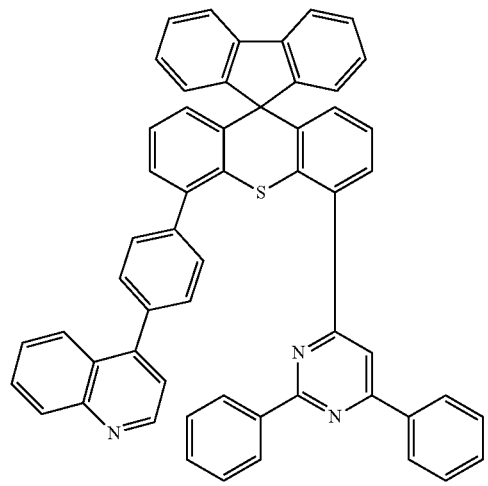
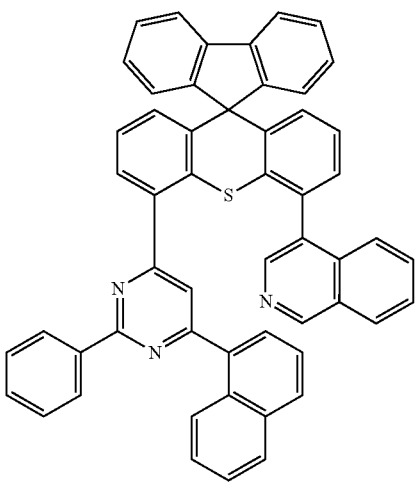

323 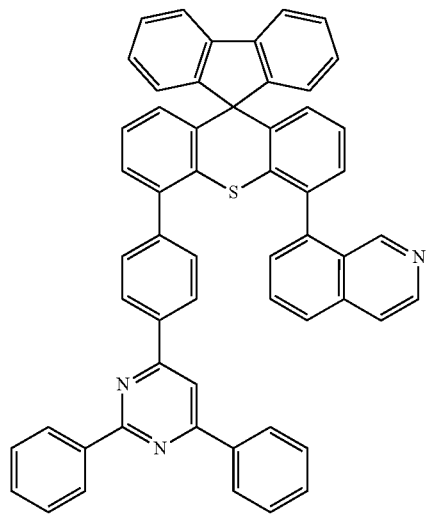
324 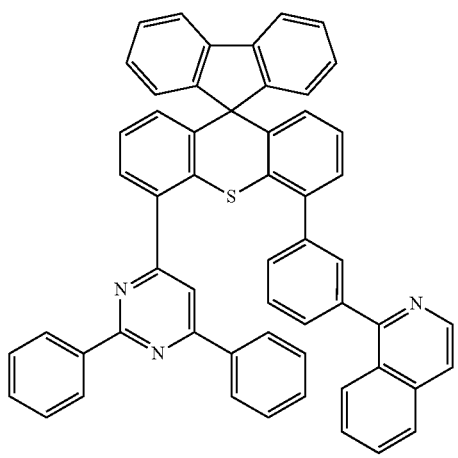
-continued
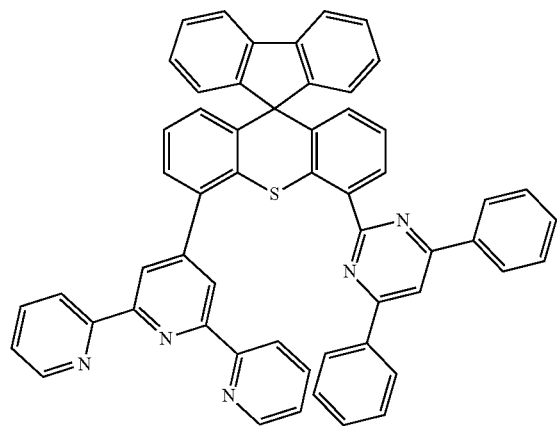
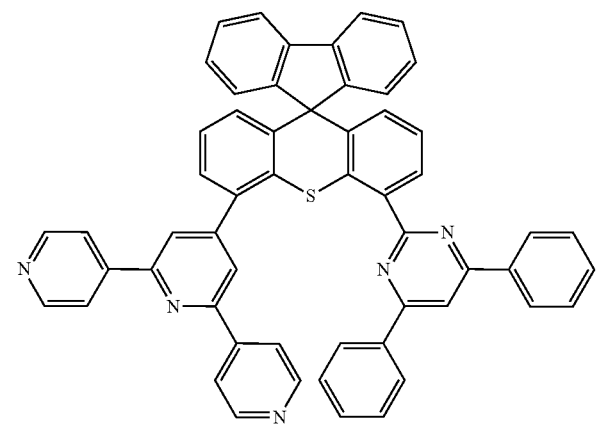
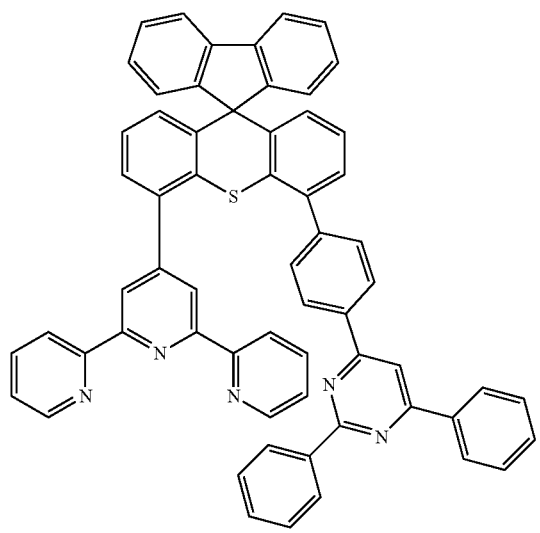
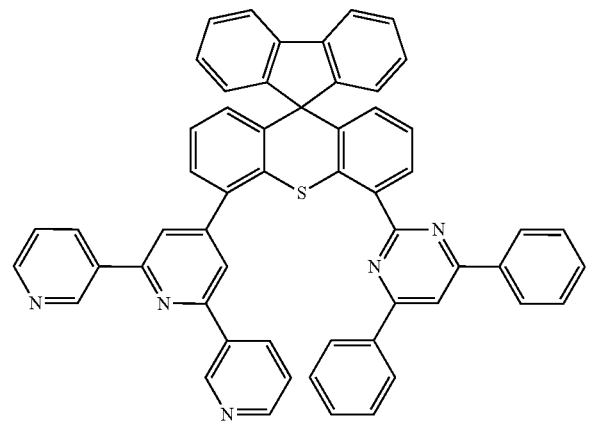

| 325 | 326 |
|---|---|
| 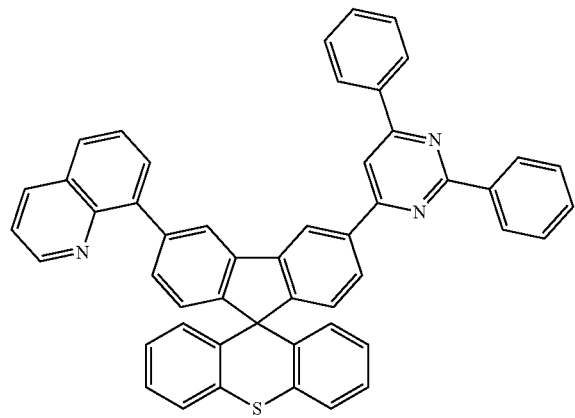 | 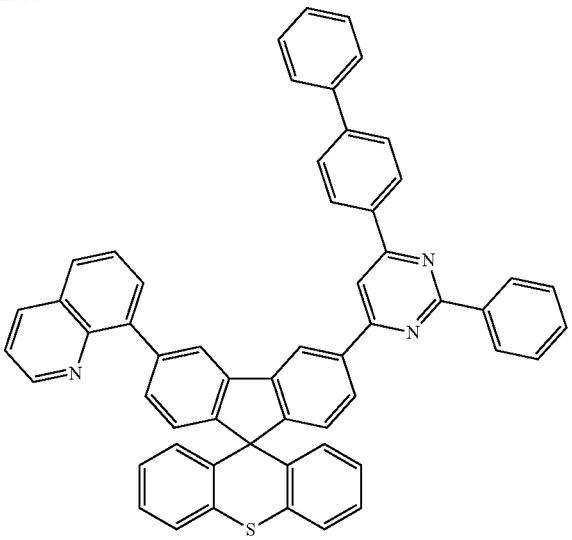 |
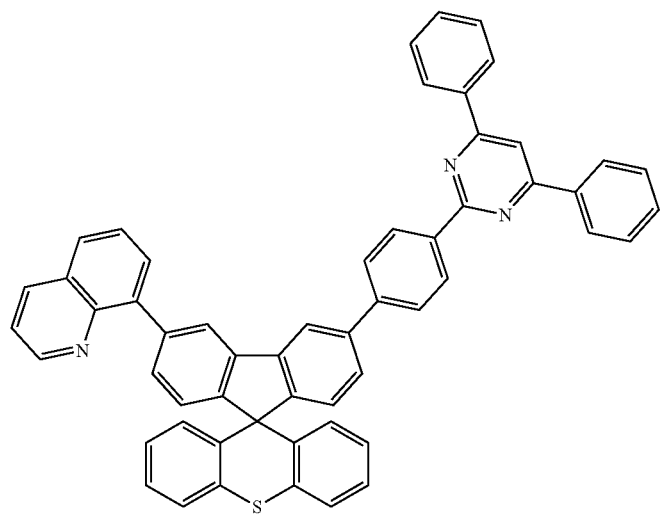
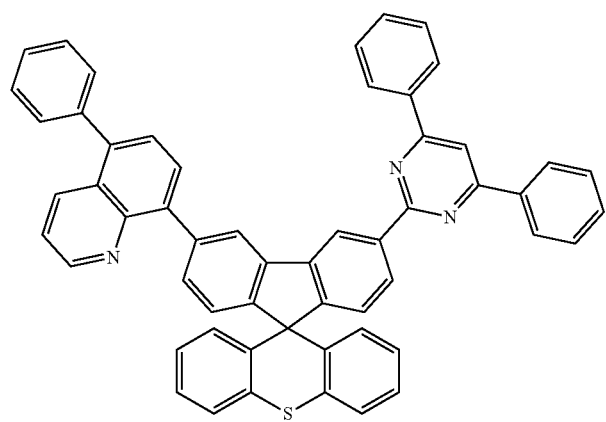

327 328
-continued
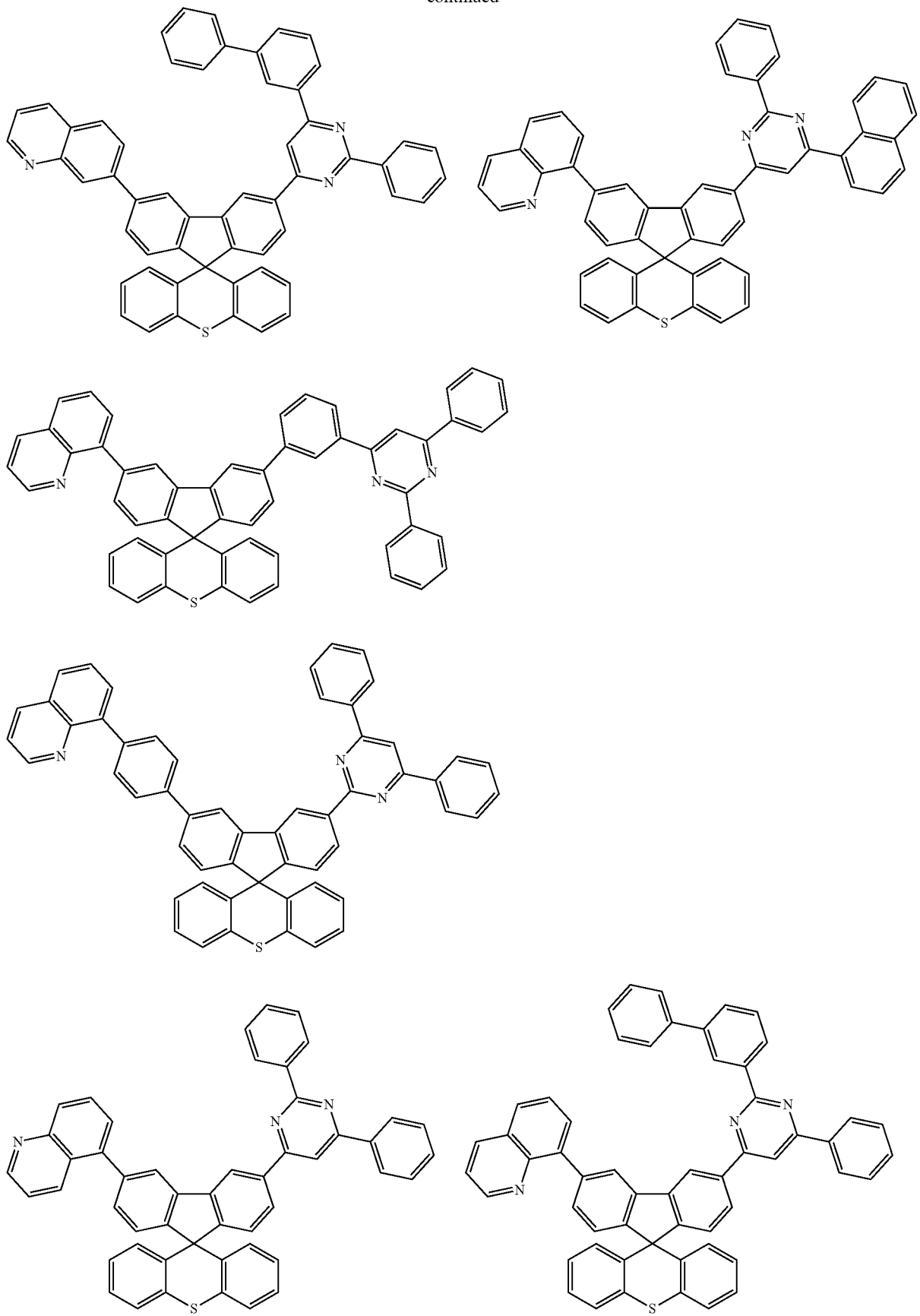

-continued
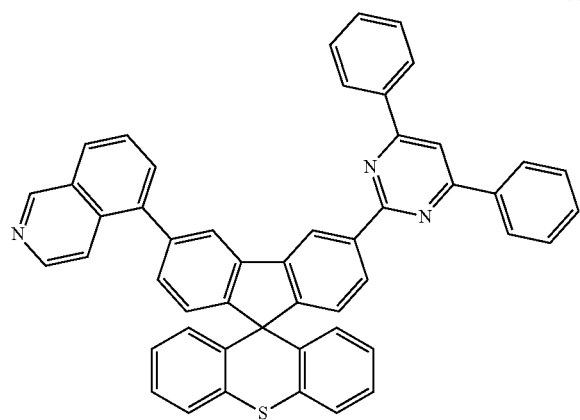
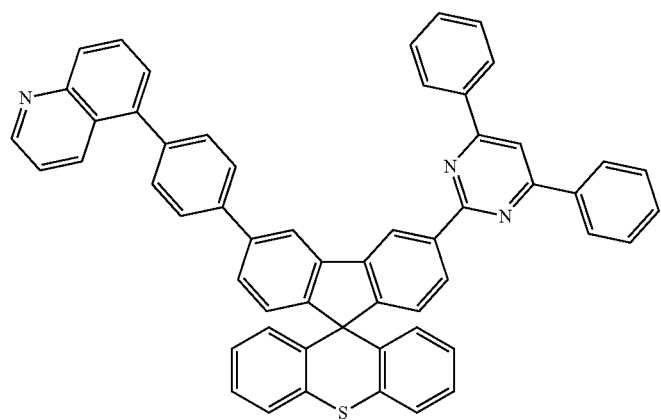
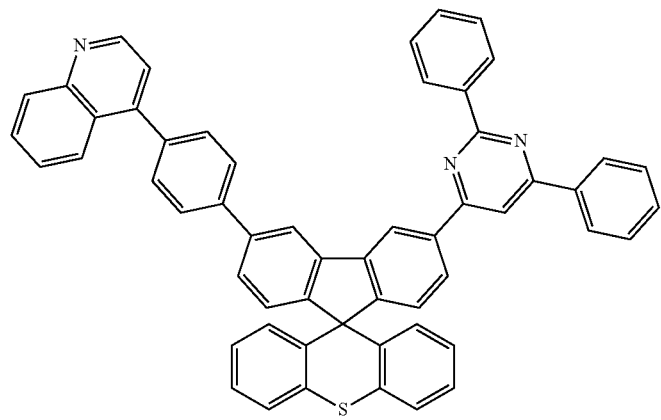
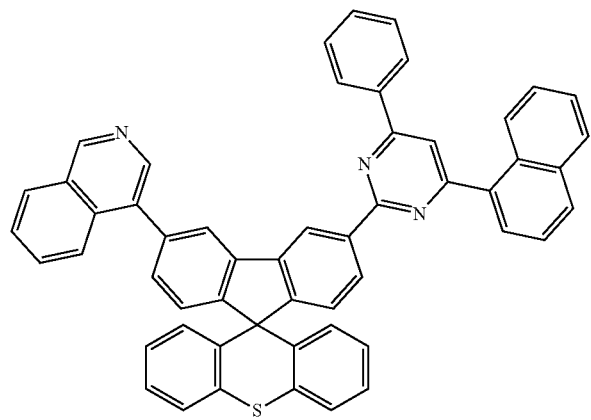

-continued
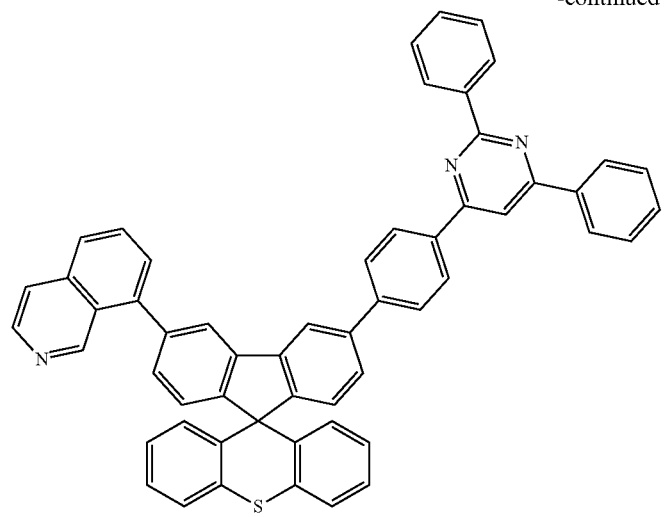
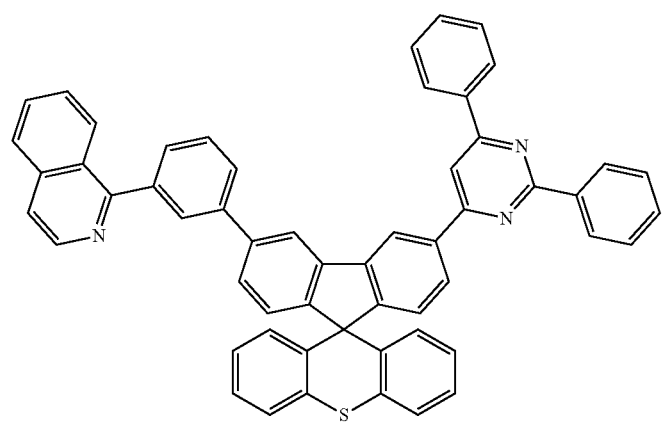
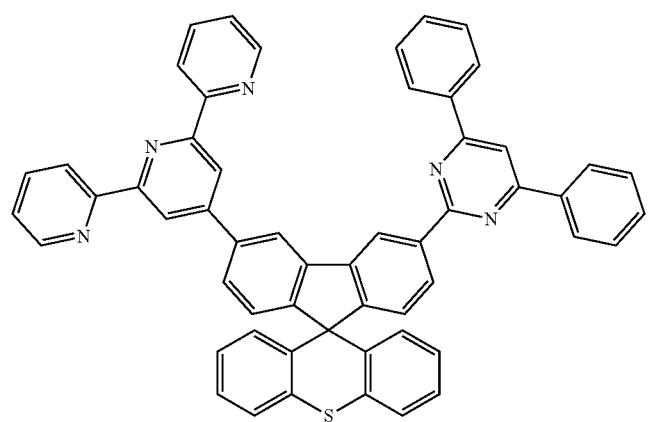

333
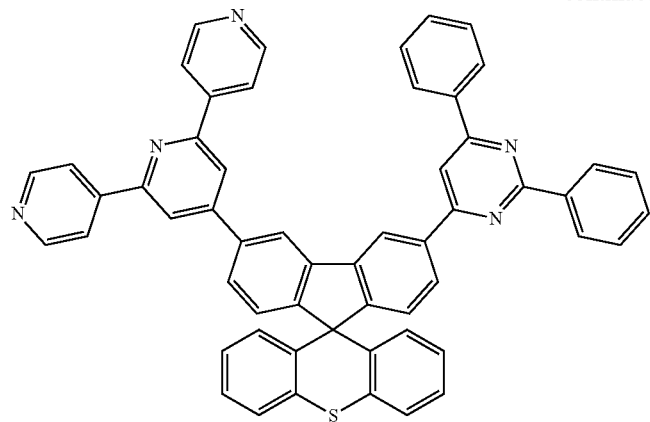
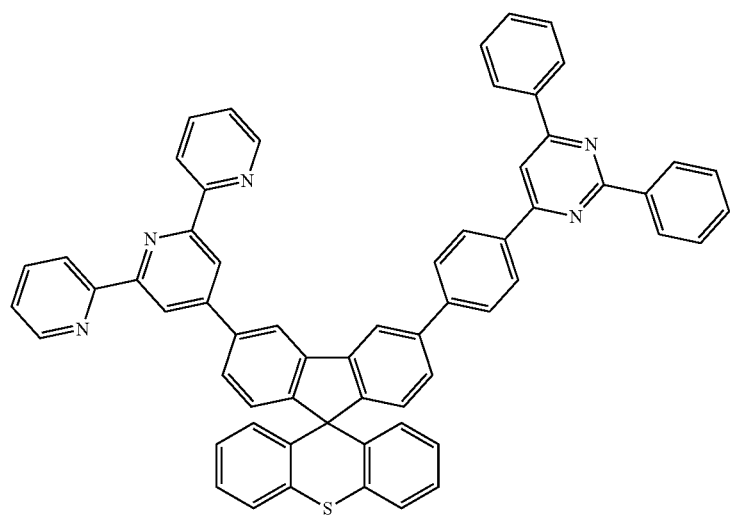
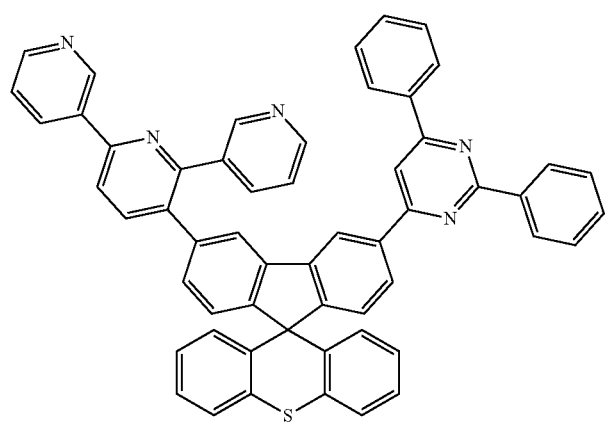
-continued
334
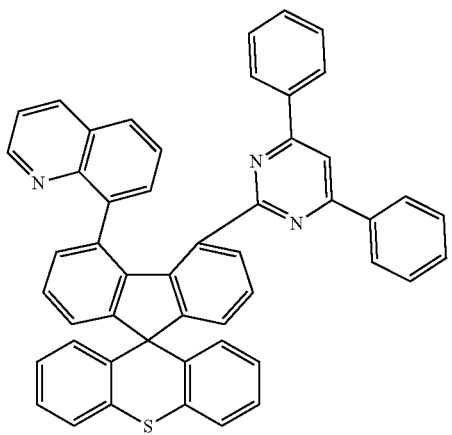

335
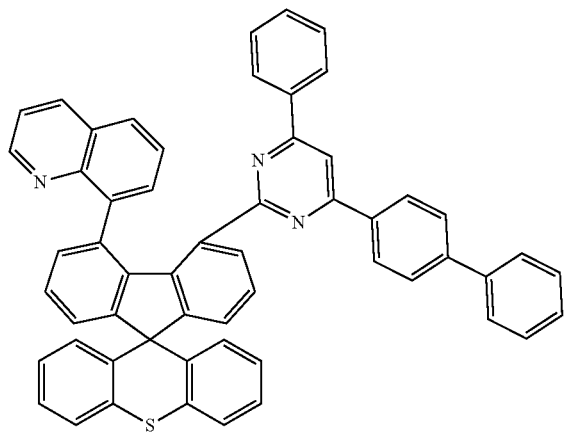
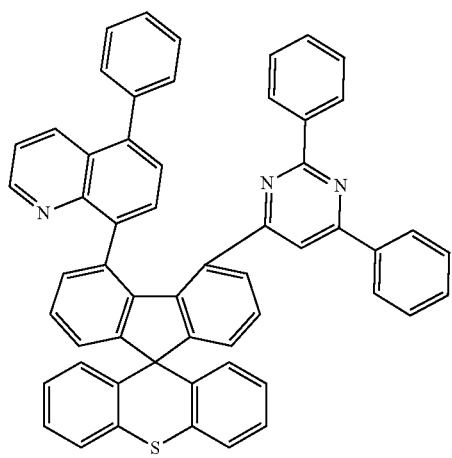
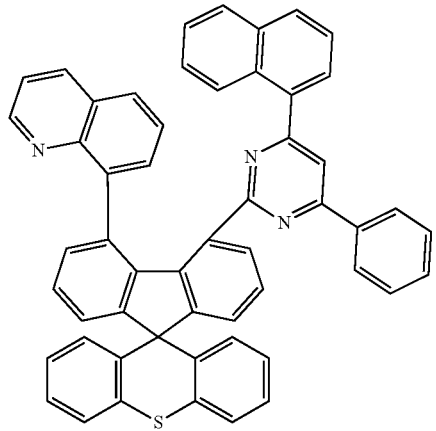
336
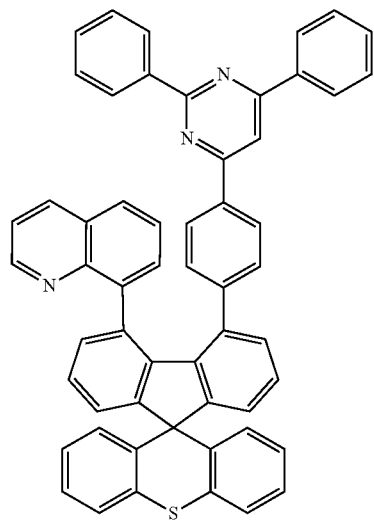
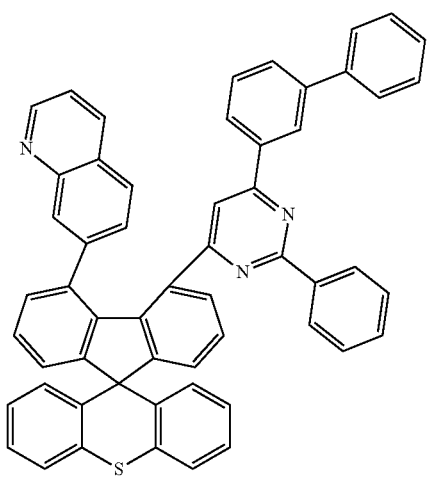
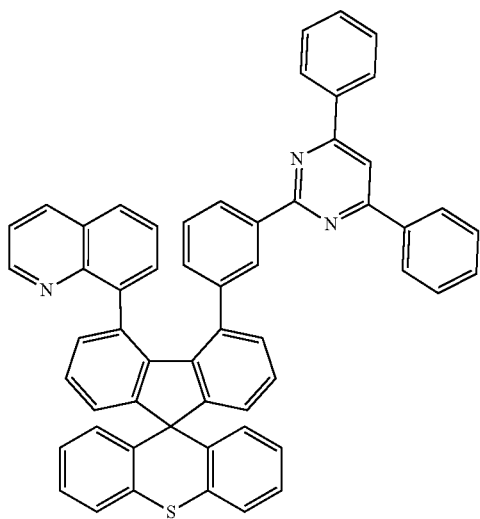

337
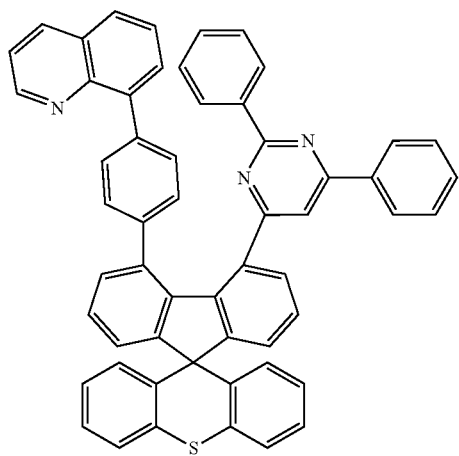
338
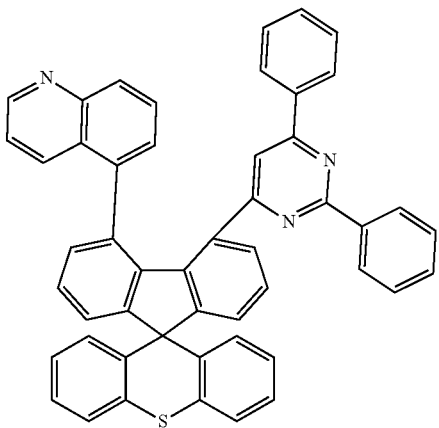
-continued
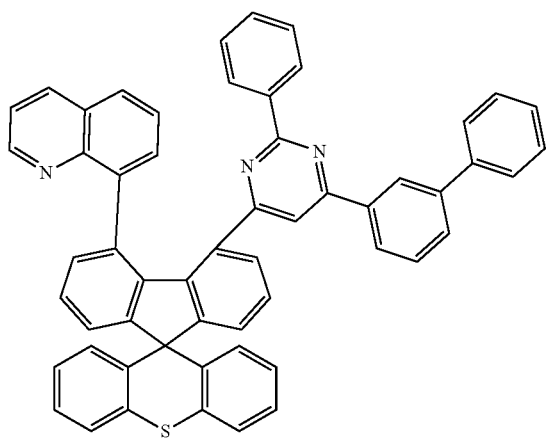
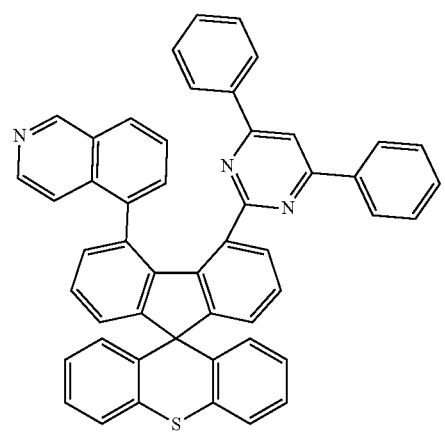
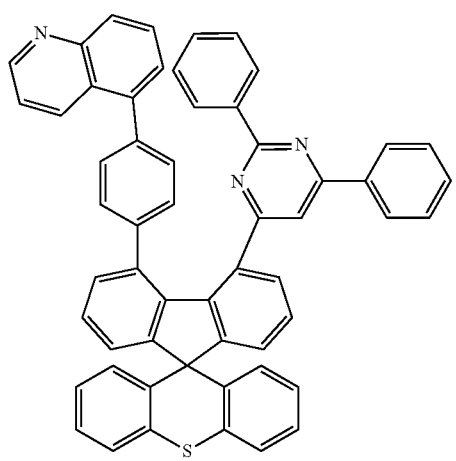
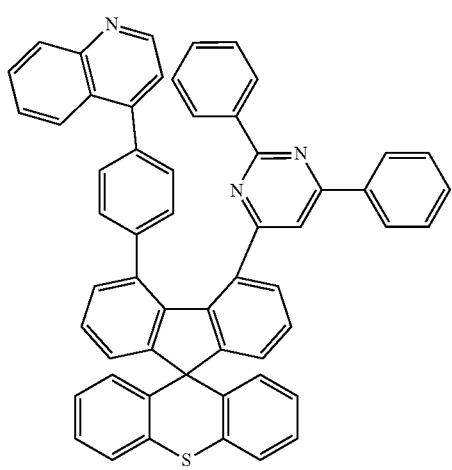

-continued
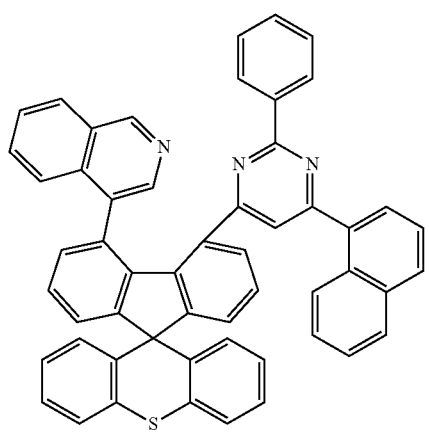
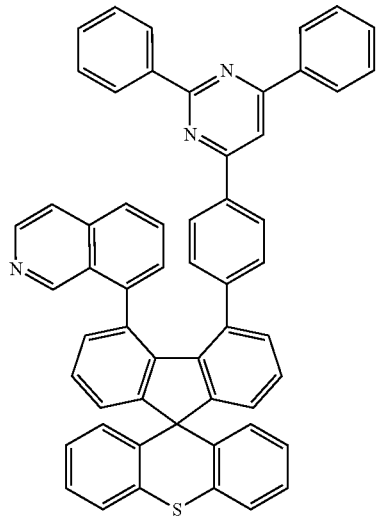
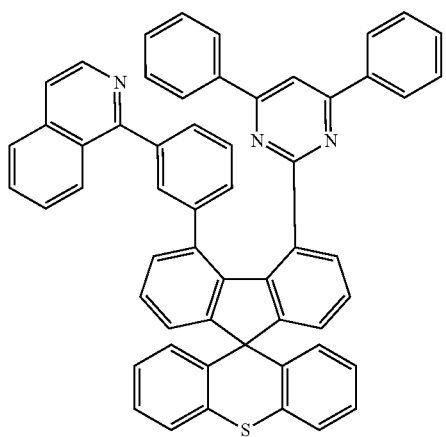
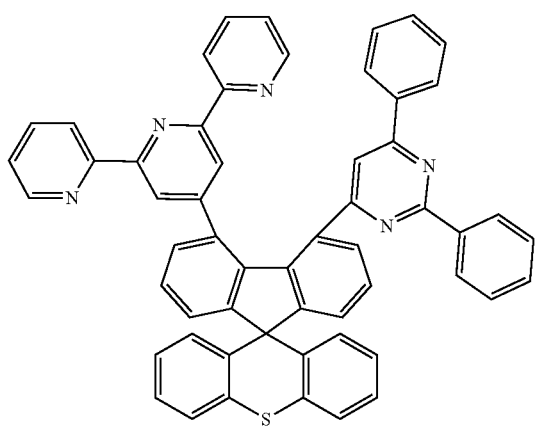
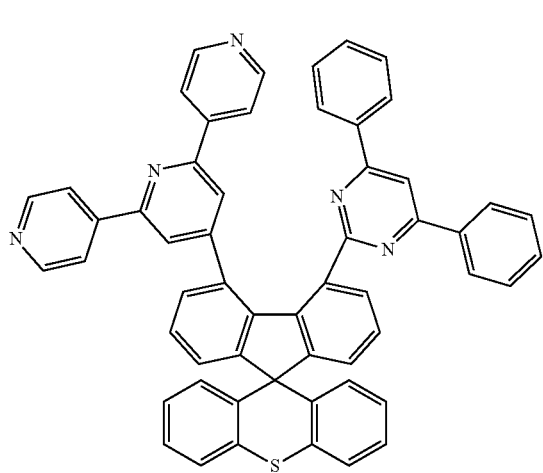
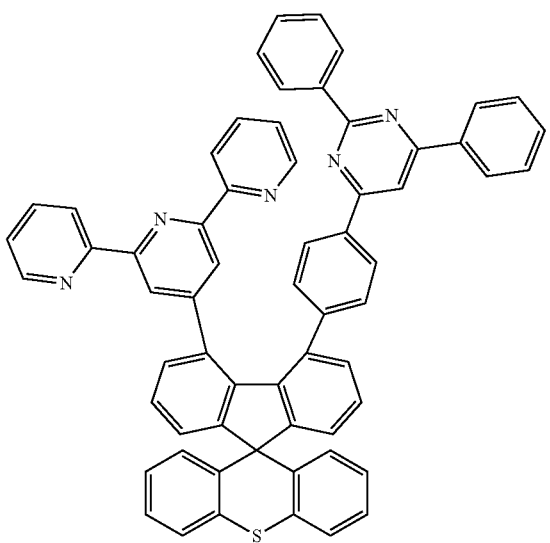

-continued

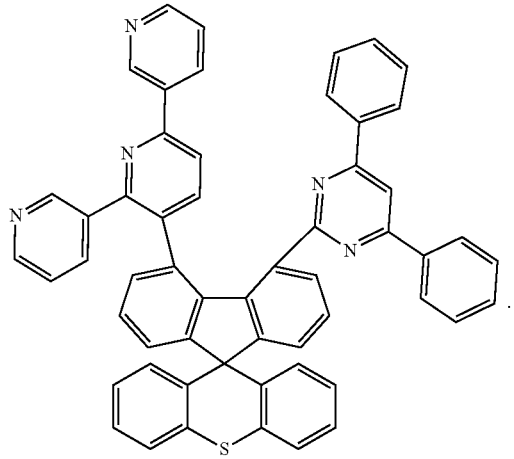

13. An organic light emitting device comprising:
a first electrode;
a second electrode provided opposite to the first electrode; and
one or more organic material layers provided between the first electrode and the second electrode,
wherein one or more layers of the organic material layers include the heterocyclic compound of claim 1.

14. The organic light emitting device of claim 13, wherein the organic material layer includes an electron injection layer, an electron transfer layer, or a layer carrying out electron injection and electron transfer at the same time, and the electron injection layer, the electron transfer layer, or the layer carrying out electron injection and electron transfer at the same time includes the heterocyclic compound.

15. The organic light emitting device of claim 13, wherein the organic material layer includes a hole blocking layer, and the hole blocking layer includes the heterocyclic compound.

16. The organic light emitting device of claim 13, wherein the organic material layer includes an electron control layer, and the electron control layer includes the heterocyclic compound.

* * * * *

UNITED STATES PATENT AND TRADEMARK OFFICE
CERTIFICATE OF CORRECTION

| | | |
|---|---|---|
| PATENT NO. | : 11,367,836 B2 | Page 1 of 9 |
| APPLICATION NO. | : 16/606707 | |
| DATED | : June 21, 2022 | |
| INVENTOR(S) | : Dong Uk Heo et al. | |

It is certified that error appears in the above-identified patent and that said Letters Patent is hereby corrected as shown below:

In the Claims

In Claim 12, at Column 187, please replace the 4th Structure, Lines 47-57:

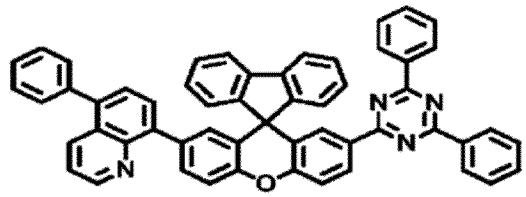

In Claim 12, at Column 188, please replace the 5th Structure, Lines 40-50:

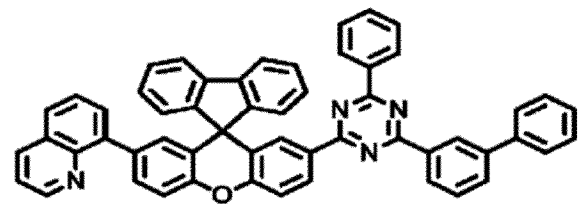

In Claim 12, at Column 190, please replace the 1st Structure, Lines 1-10:

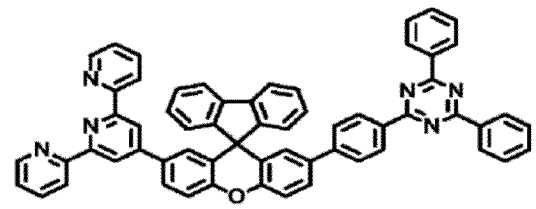

Signed and Sealed this
Second Day of August, 2022

Katherine Kelly Vidal
*Director of the United States Patent and Trademark Office*

In Claim 12, at Column 190, please replace the 2nd Structure, Lines 11-20:
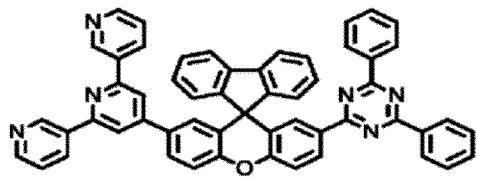
In Claim 12, at Column 190, please replace 4th Structure, Lines 32-47:
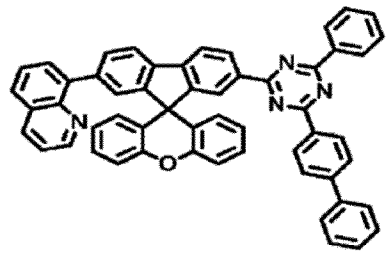
In Claim 12, at Column 190, please replace 5th Structure, Lines 47-57:
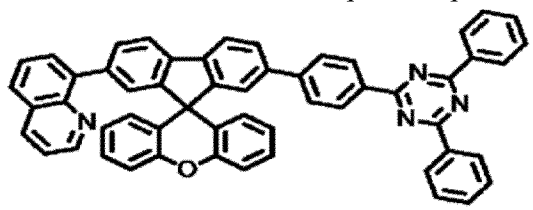
In Claim 12, at Column 190, please replace the 6th Structure, Lines 58-67:
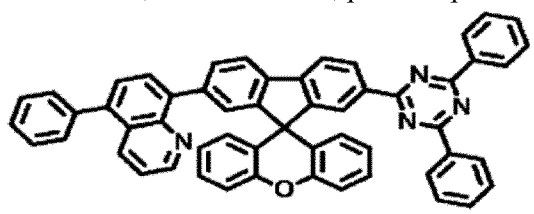
In Claim 12, at Column 192, please replace the 3rd Structure, Lines 26-35:
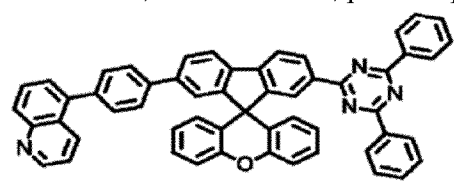
In Claim 12, at Column 192, please replace the 4th Structure, Lines 36-45:
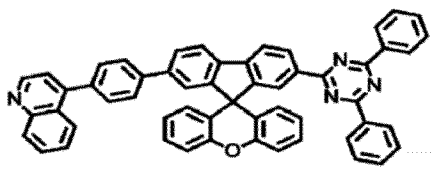

In Claim 12, at Column 201, please replace the 1st Structure, Lines 1-20:
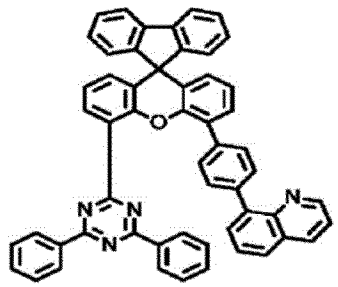
In Claim 12, at Column 205, please replace the 2nd Structure, Lines 20-40:
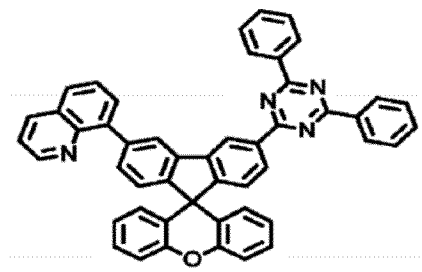
In Claim 12, at Column 207, please replace the 2nd Structure, Lines 15-30:
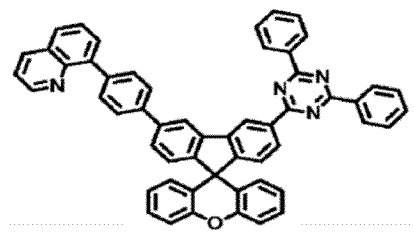
In Claim 12, at Column 207, please replace the 3rd Structure, Lines 31-47:
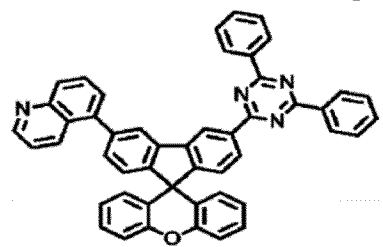
In Claim 12, at Column 208, please replace the 4th Structure, Lines 51-66:
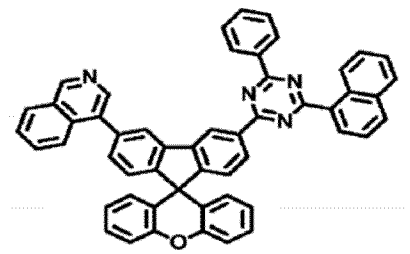

In Claim 12, at Column 209, please replace the 1st Structure, Lines 1-18:
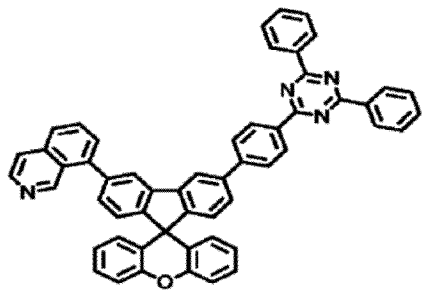
In Claim 12, at Column 209, please replace the 2nd Structure, Lines 20-34:
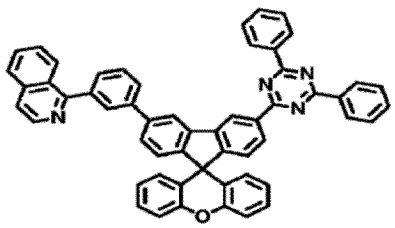
In Claim 12, at Column 209, please replace the 3rd Structure, Lines 36-51:
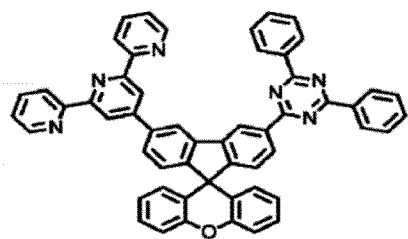
In Claim 12, at Column 209, please replace the 4th Structure, Lines 52-66:
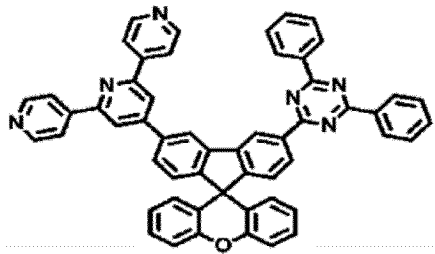
In Claim 12, at Column 215, please replace the 3rd Structure, Lines 48-66:
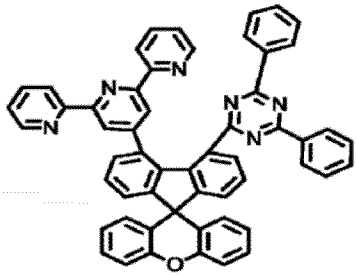

In Claim 12, at Column 216, please insert the missing structure following the first structure ending at Line 20:
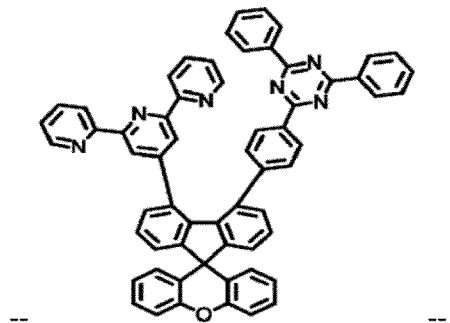
-- --
In Claim 12, at Column 218, please replace the 5th Structure, Lines 48-56:
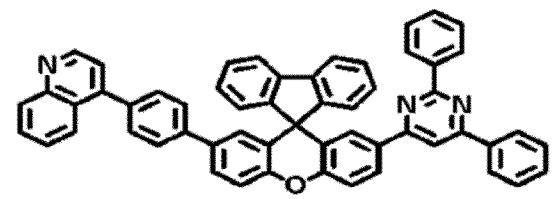
In Claim 12, at Column 231, please replace the 1st Structure, Lines 1-17:
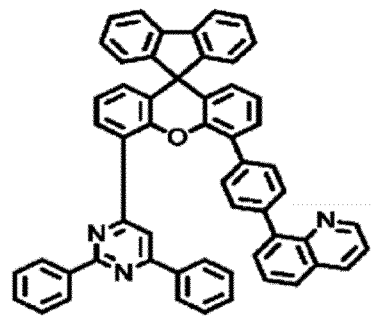
In Claim 12, at Column 249, please replace the 2nd Structure:
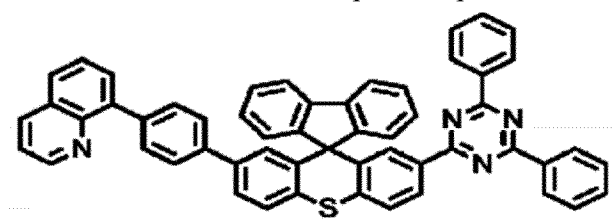
In Claim 12, at Column 253, please replace the 2nd Structure:
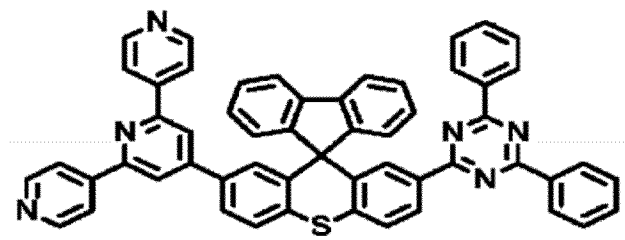

In Claim 12, at Column 253, please replace the 3rd Structure:
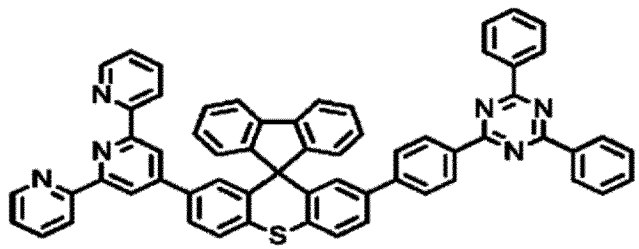
In Claim 12, at Column 253, please replace the 5th Structure:
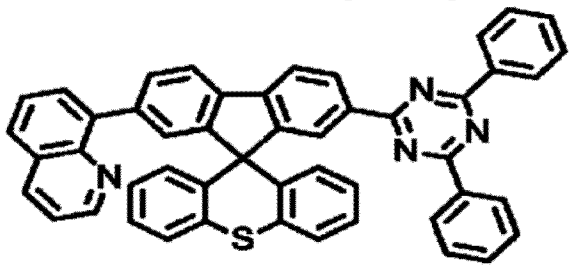
In Claim 12, at Column 254, please replace the 6th Structure - the only structure appearing at the bottom:
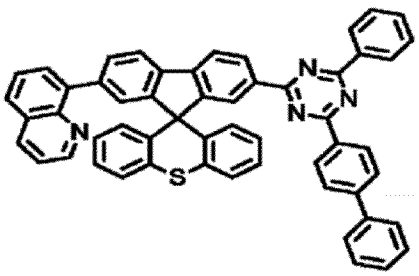
In Claim 12, at Column 255, please replace the 3rd Structure:
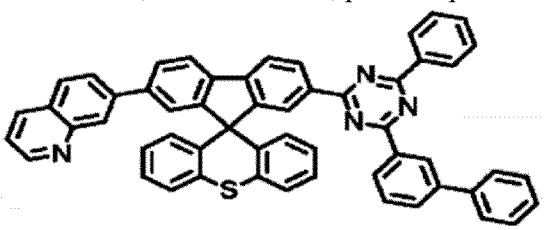
In Claim 12, at Column 259, please replace the 5th Structure:
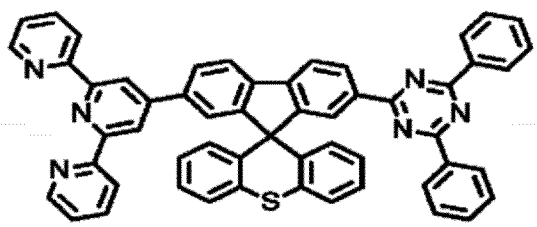

CERTIFICATE OF CORRECTION (continued)
U.S. Pat. No. 11,367,836 B2

In Claim 12, at Column 265, please replace the 2nd Structure:

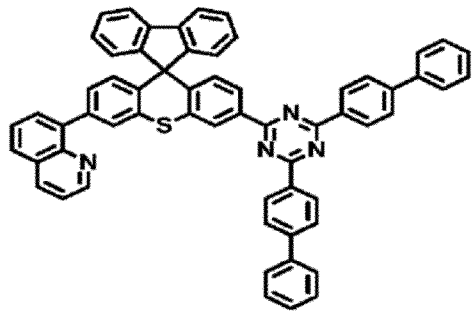

In Claim 12, at Column 269, please replace the 1st Structure:

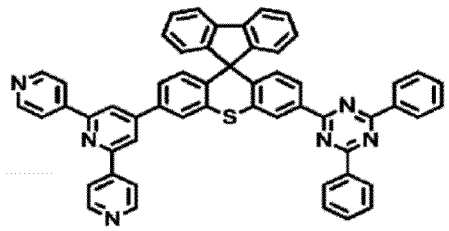

In Claim 12, at Column 269, please replace the 2nd Structure:

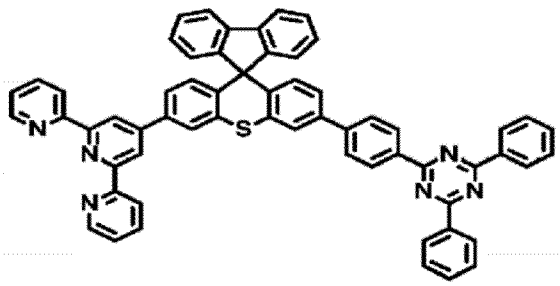

In Claim 12, at Column 295, please replace the 5th Structure:

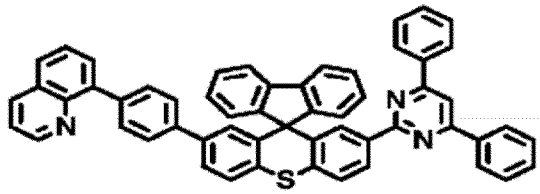

In Claim 12, at Column 299, please replace the 3rd Structure:

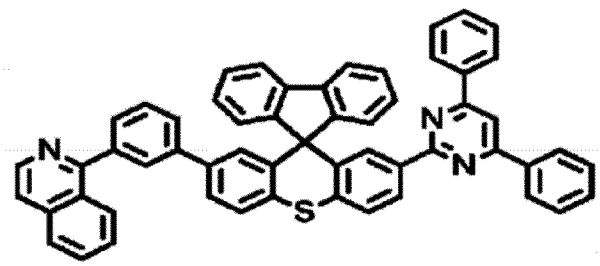

CERTIFICATE OF CORRECTION (continued)
U.S. Pat. No. 11,367,836 B2

In Claim 12, at Column 299, please replace the 5th Structure:

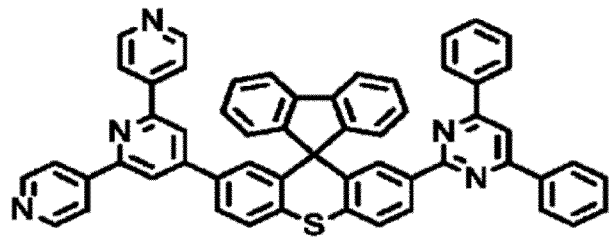

In Claim 12, at Column 301, please replace the 1st Structure:

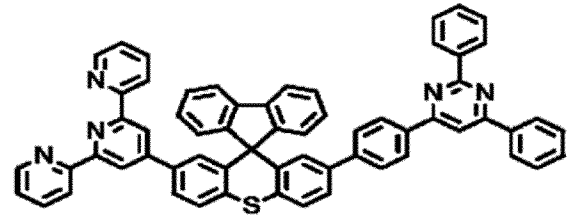

In Claim 12, at Column 301, please replace the 3rd Structure:

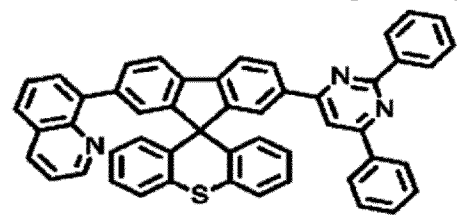

In Claim 12, at Column 302, please replace the only structure appearing half way down the page:

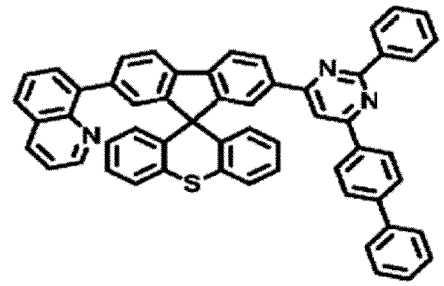

In Claim 12, at Column 303, replace the 1st Structure: